United States Patent
Hanson et al.

(10) Patent No.: US 8,642,554 B2
(45) Date of Patent: Feb. 4, 2014

(54) SMAC MIMETIC DIMERS AND TRIMERS USEFUL AS ANTI-CANCER AGENTS

(75) Inventors: Gunnar Hanson, Chapel Hill, NC (US); Haizhou Sun, Dallas, TX (US)

(73) Assignee: Joyant Pharmaceuticals, Inc., Dallas, TX (US)

( * ) Notice: Subject to any disclaimer, the term of this patent is extended or adjusted under 35 U.S.C. 154(b) by 1699 days.

(21) Appl. No.: 12/101,733

(22) Filed: Apr. 11, 2008

(65) Prior Publication Data

US 2009/0104151 A1    Apr. 23, 2009

Related U.S. Application Data

(60) Provisional application No. 60/911,472, filed on Apr. 12, 2007, provisional application No. 60/952,493, filed on Jul. 27, 2007.

(51) Int. Cl.
*A61K 38/00* (2006.01)
*A61P 43/00* (2006.01)

(52) U.S. Cl.
USPC .......................................................... 514/18.9

(58) Field of Classification Search
None
See application file for complete search history.

(56) References Cited

U.S. PATENT DOCUMENTS

| | | | |
|---|---|---|---|
| 4,261,989 A | | 4/1981 | Sasaki et al. |
| 5,387,584 A | | 2/1995 | Schnur |
| 5,624,677 A | | 4/1997 | El-Rashidy et al. |
| 5,932,566 A | | 8/1999 | Schnur et al. |
| 6,916,846 B2 | * | 7/2005 | Farrar et al. .................. 514/457 |
| 7,579,320 B2 | * | 8/2009 | Boudreault et al. ........... 514/1.1 |
| 2005/0197403 A1 | | 9/2005 | Harran et al. |
| 2006/0014700 A1 | | 1/2006 | Cohen et al. |
| 2006/0025347 A1 | | 2/2006 | Condon et al. |

FOREIGN PATENT DOCUMENTS

| | | |
|---|---|---|
| WO | WO-02/36075 | 5/2002 |
| WO | WO-03/086470 | 10/2003 |
| WO | WO-2005/028434 | 3/2005 |
| WO | WO-2005/094818 | 10/2005 |
| WO | WO-2005/097791 | 10/2005 |
| WO | WO-2006/069063 | 6/2006 |

OTHER PUBLICATIONS

Bockbrader et al., Oncogene (2005) 24:7381-7388.
Cheung et al., Bioorg. Med. Chem. Lett. (2005) 15:3338-3343.
Chiosis et al., ACS Chem. Biol. (2006) 1(5):279-284.
Du et al., Cell (2000) 102:33-43.
Li et al., Science (2004) 305:1471-1474.
Makin et al., Cell Tissue Res. (2000) 301(1):143-152.
Marusawa et al., Bioorg. Med. Chem. (2002) 1399-1415.
Moulin et al., J. Amer. Chem. Soc. (2005) 127:6999-7004.
Soga et al., Curr. Cancer Drug Targets (2003) 3:359-369.
Verhagen et al., Cell (2000) 102:43-53.
Vucic et al., Biochem. J. (2005) 385(1):11-20.
Yamamoto et al., Angew. Chem. (2003) 42:1280-1284.
International Search Report for PCT/US08/60140, mailed on Jul. 15, 2008, 3 pages.
Written Opinion of the International Searching Authority for PCT/US08/60140, mailed on Jul. 15, 2008, 5 pages.

* cited by examiner

*Primary Examiner* — Cecilia J Tsang
*Assistant Examiner* — Randall L Beane
(74) *Attorney, Agent, or Firm* — Richard Aron Osman

(57) ABSTRACT

The invention provides small molecule mimics of the Smac peptide that are dimer-like or trimer-like compounds having two or three amide-containing domains connected by a linker. These compounds are useful to promote apoptosis. The invention includes pharmaceutical compositions comprising such compounds and methods to use them to treat conditions including cancer and autoimmune disorders.

3 Claims, No Drawings

US 8,642,554 B2

SMAC MIMETIC DIMERS AND TRIMERS USEFUL AS ANTI-CANCER AGENTS

CROSS-REFERENCE TO RELATED APPLICATIONS

This application claims priority from U.S. Provisional Application Ser. No. 60/911,472, filed 12 Apr. 2007; and U.S. Provisional Application Ser. No. 60/952,493, filed 27 Jul. 2007. The content of each of these documents is incorporated by reference herein in its entirety.

TECHNICAL FIELD

The field of the invention is dimer- and trimer-like small molecule promoters of apoptosis. The compounds of the invention have a linking group that connects two or three binding domains, each of which contains two essential amide groups. These compounds mimic the activity of the protein known as Smac, and are thereby able to promote the initiation of apoptosis. The compounds are therefore useful in treating conditions where initiating apoptosis is desirable, such as in pathological cells or tissues.

BACKGROUND ART

Apoptosis plays a central role in the development and homeostasis of all multi-cellular organisms. Abnormal inhibition of apoptosis is a hallmark of cancer and autoimmune diseases, whereas excessive activation of cell death is implicated in neuro-degenerative disorders such as Alzheimer's disease. Pro-apoptotic chemotherapeutic drugs provide a recent approach to overcoming the clinical problem of drug resistance; see, e.g. Makin et al., *Cell Tissue Res.* (July 2000) 301(1):143-152 ("Apoptosis and cancer chemotherapy").

The mechanism of apoptosis is conserved across species and executed with a cascade of sequential activation of proteases called caspases. Once activated, these caspases are responsible for proteolytic cleavage of a broad spectrum of cellular targets that ultimately lead to cell death. IAPs (inhibitor-of-apoptosis proteins) regulate apoptosis by inhibiting caspases; and a protein called Smac ('Smac' stands for second mitochondria-derived activator of caspases, and is a mitochondrial protein) binds to and inhibits IAPs, and thereby promotes caspase activation.

The protein Smac has been shown to inhibit a wide variety of IAPs, and is believed to be a key regulator of apoptosis in mammals. See Du, et al., *Cell* (2000) 102:33-43; Verhagen et al., *Cell* (2000) 102:43-53; and Vucic et al., *Biochem. J.* (2005) 385(1):11-20. N-terminal Smac-derived peptides and mimetics have been shown to similarly inhibit IAPs, and promote caspase activation. IAPs are components of TNFR (tumor necrosis factor receptor), so IAP inhibitors can divert TNFR signaling from an NfkB-mediated pro-inflammatory signal, to an anti-inflammatory apoptotic signal.

Defective apoptosis regulation can confer resistance to many current treatment protocols, leading to tumor growth. This may occur as a result of overexpression of IAPs, which inhibit the caspases that would otherwise initiate apoptosis. Alternatively, deregulation can occur as a result of underproduction of the Smac peptides that act to inhibit IAP activity. Deficiency of Smac can thus allow IAP to prevent apoptosis from occurring when it should, and a Smac mimetic like the present compounds can replace the activity of Smac and thus promote desired apoptosis.

Debatin, et al., WO 03/086470, describes Smac-peptides as therapeutic agents useful against cancer and autoimmune diseases; they are reported to act by sensitizing the cells toward TRAIL-induced or anticancer drug-induced apoptosis. (TRAIL stands for TNF related apoptosis-inducing ligand). See also Li, et al., *Science* (3 Sep. 2004) 305:1471-14744. Debatin provides in vivo evidence that Smac induces the eradication of certain tumors such as glioblastoma tumor models in animals when administered in combination with TRAIL. According to Debatin, aggressive cancer phenotypes, which result from deregulation of signaling pathways, commonly fail to undergo apoptosis when they otherwise would, allowing rapid and abnormal tissue growth. Bockbrader, et al., disclose efficacy of Smac mimic compounds on breast cancer cell lines when used in conjunction with TRAIL or etoposide, or when used in cells that express TRAIL at relatively high levels. *Oncogene* (2005) 24:7381-7388.

Similarly, according to Debatin, defects in apoptosis regulation play a key role in the pathogenesis of autoimmune disorders, including lupus erythematodes disseminatus and rheumatoid arthritis. Accordingly, compounds that mimic the activity of Smac can treat some of the effects of such conditions.

A recent U.S. Patent Application, US 2005/0197403, describes dimeric compounds with good activity as promoters of apoptosis. The compounds have two amide-containing groups linked by a linker that is broadly described. Another U.S. Patent Application, US 2006/0025347, describes small molecule compounds having activity related to promotion of apoptosis. However, while the latter reference mentions that dimeric compounds can be used, none of the compounds it discloses have a dimeric structure, nor is there any indication of what type of dimers to explore.

Several recent patent applications, for example, US 2006/0025347, US 2005/0197403, WO 2006/069063, US 2006/0014700, WO 2005/094818, and WO 2005/097791, each of which is incorporated herein by reference in its entirety, disclose monomeric IAP inhibitors, but do not describe dimeric structures.

DISCLOSURE OF THE INVENTION

The present invention relates to novel compounds having apoptosis promoting effects that, without being bound by theory, appear to originate in their ability to mimic Smac. These compounds are believed to bind to two or three separate domains in the baculovirus inhibitory repeat (BIR) domain within the proteins referred to as IAP (inhibitor-of-apoptosis) proteins, which regulate apoptosis by inhibiting caspases. The compounds are dimer- or trimer-like, in that they possess two or three structurally similar binding domains. In many embodiments, each binding domain includes a ring that is substituted by at least one aryl-containing group —W—X, —X'—X' or —W"—X". These binding domains are linked by a linking group, and while similar, the domains need not be identical. In certain embodiments, the binding domains are the same, so the molecule is symmetric about its linking group.

In one aspect, the invention provides a compound of formula (I):

or a pharmaceutically acceptable salt or hydrate form thereof, wherein b is 0 or 1;

each Q, Q' and Q", if present, independently represents —O— or —NR²—, where each R² is independently H, optionally substituted C1-C8 alkyl or optionally substituted C1-C8 heteroalkyl; or —CH₂—, —CH(OR)—, —CH(R)—, —CH₂O—, —CH(R)O— or —(CH₂)₄NH—, wherein R is H, $C_1$-$C_4$ alkyl or $C_1$-$C_4$ heteroalkyl; or one or more of Q, Q' and Q" may be a bond when L comprises a ring;

L represents an optionally substituted C1-C24 hydrocarbyl linker, optionally containing from 1-8 heteroatoms selected from N, O and S, which linker is 1-18 atoms in length when counted along the shortest path between Q and Q', or Q and Q", or Q' and Q"; and each D, D' and D", if present, is independently selected from the group consisting of

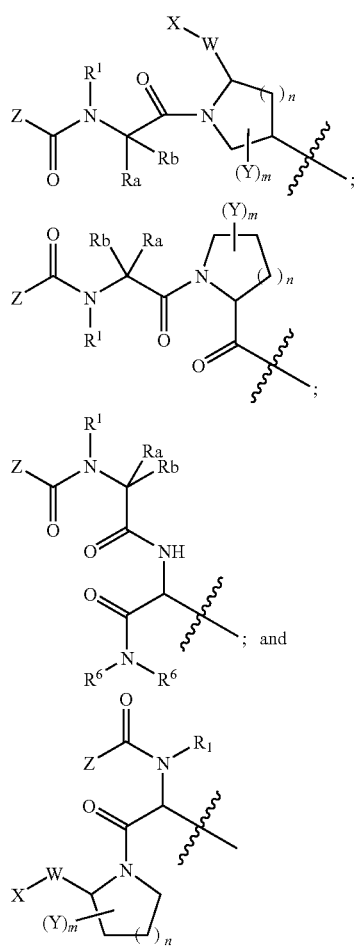

wherein each $R_a$ and $R_b$ is independently H, or C1-C8 alkyl, C2-C8 alkenyl or C2-C8 alkynyl, or a heteroform of one of these, each of which may be optionally substituted; or is optionally substituted phenyl;

each $R^1$ is independently H or optionally substituted C1-C8 alkyl;

each Z independently represents an optionally substituted C1-C6 aminoalkyl group.

each Y, where present, independently represents C1-C8 alkyl, =O, OR, NR₂, OC(O)R, NRC(O)R, NRSO₂R or COOR, wherein each R is independently H, C1-C8 alkyl or C1-C8 heteroalkyl, and wherein two Y groups can cyclize to form a 3-6 membered ring that can be saturated, unsaturated or aromatic, and which ring may include a heteroatom selected from O, S and N as a ring member and may be optionally substituted;

each W, where present, independently represents an optionally substituted C1-C6 alkylene or C1-C6 heteroalkylene;

each X, where present, independently represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

each n, where present, is independently 0-3;

each m, where present, is independently 0-4; and each $R^6$, where present, is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring;

with the proviso that, when b is 0, D and D' are not both of the formula

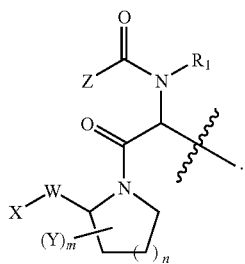

In some embodiments, of formula (I), when b is 0, D and D' are not both of the formula

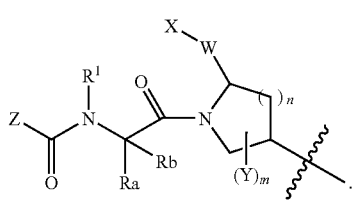

In another aspect, the invention provides a compound of formula (IA):

or a pharmaceutically acceptable salt or hydrate form thereof, wherein b is 0 or 1;

each Q, Q' and Q", if present, independently represents —O— or —NR²—, where each R² is independently H, optionally substituted C1-C8 alkyl or optionally substituted C1-C8 heteroalkyl; or —CH$_2$—, —CH(OR)—, —CH(R)—, —CH$_2$O—, —CH(R)O— or —(CH$_2$)$_4$NH—, wherein R is H, C$_1$-C$_4$ alkyl or C$_1$-C$_4$ heteroalkyl; or one or more of Q, Q' and Q" may be a bond when L comprises a ring;

L represents an optionally substituted C1-C24 hydrocarbyl linker, optionally containing from 1-8 heteroatoms selected from N, O and S, which linker is 1-18 atoms in length when counted along the shortest path between Q and Q', or Q and Q", or Q' and Q"; and each D, D' and D", if present, is independently selected from the group consisting of

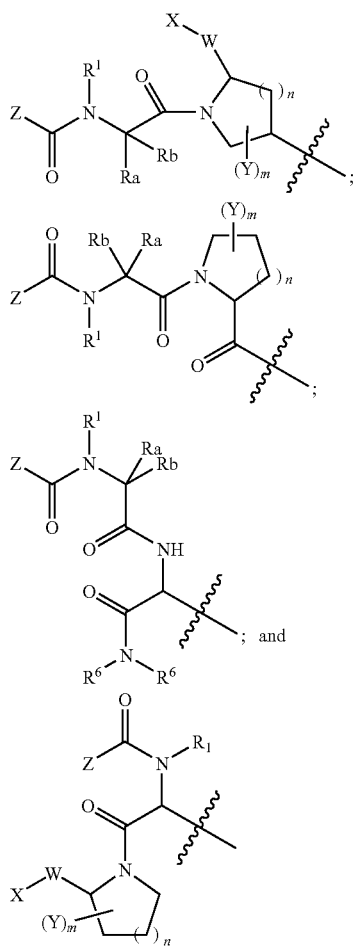

wherein each R$_a$ and R$_b$ is independently H, or C1-C8 alkyl, C2-C8 alkenyl or C2-C8 alkynyl, or a heteroform of one of these, each of which may be optionally substituted;

each R$^1$ is independently H or optionally substituted C1-C8 alkyl;

each Z independently represents an optionally substituted C1-C6 aminoalkyl group.

each Y, where present, independently represents C1-C8 alkyl, =O, OR, NR$_2$, OC(O)R, NRC(O)R, NRSO$_2$R or COOR, wherein each R is independently H, C1-C8 alkyl or C1-C8 heteroalkyl, and wherein two Y groups can cyclize to form a 3-6 membered ring that can be saturated, unsaturated or aromatic, and which ring may include a heteroatom selected from O, S and N as a ring member and may be optionally substituted;

each W, where present, independently represents an optionally substituted C1-C6 alkylene or C1-C6 heteroalkylene;

each X, where present, independently represents an optionally substituted C$_5$-C$_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

each n, where present, is independently 0-3;

each m, where present, is independently 0-4; and each R$^6$, where present, is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring;

with the proviso that, when b is 0, D and D' are not both of the formula

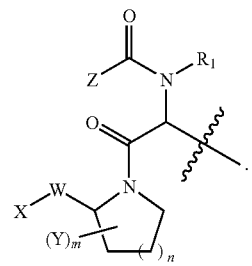

In another aspect, the invention provides a compound of formula (II)

$$D-U \qquad (II)$$

or a pharmaceutically acceptable salt or hydrate form thereof;

wherein D is selected from the group consisting of

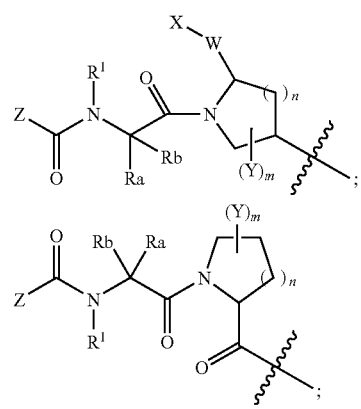

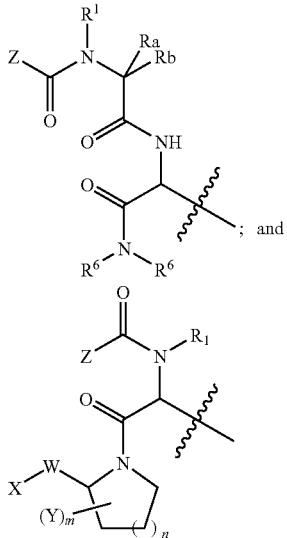
; and

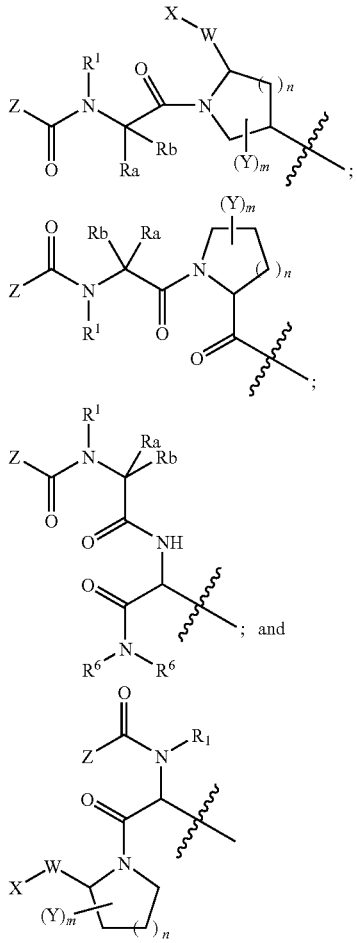

wherein each $R_a$ and $R_b$ is independently H, or C1-C8 alkyl, C2-C8 alkenyl or C2-C8 alkynyl, or a heteroform of one of these, each of which may be optionally substituted; or optionally substituted phenyl;

$R^1$ is independently H or optionally substituted C1-C8 alkyl;

Y, where present, independently represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl, and wherein two Y groups can cyclize to form a 3-6 membered ring that can be saturated, unsaturated or aromatic, and which ring may include a heteroatom selected from O, S and N as a ring member and may be optionally substituted;

W, where present, independently represents an optionally substituted C1-C6 alkylene or C1-C6 heteroalkylene;

X, where present, independently represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

each n, where present, is independently 0-3;

each m, where present, is independently 0-4; and each $R^6$, where present, is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring;

Z is an optionally substituted C1-C6 aminoalkyl group wherein the amine may be in a protected or unprotected form; and U represents —$OR^8$, —$OC(O)R^8$, —$OSO_2R^8$, C=O, —$OC(O)OR^8$, —$COOR^8$, —$NR^8_2$, azido or halo, where each $R^8$ is independently H, or C1-C8 alkyl, C1-C8 alkenyl, C1-C8 alkynyl, C5-C12 aryl, C5-C21 arylalkyl, or a heteroform of one of these, each of which may be optionally substituted; or C1-C8 alkyl, C2-C8 alkenyl, C2-C8 alkynyl, C5-C12 aryl or C5-C21 arylalkyl, or a heteroform of one of these, each of which may be optionally substituted.

In another aspect, the invention provides a compound of formula (IIA)

$$D\text{-}U \qquad (IIA)$$

or a pharmaceutically acceptable salt or hydrate form thereof;

wherein D is selected from the group consisting of wherein each $R_a$ and $R_b$ is independently H, or C1-C8 alkyl, C2-C8 alkenyl or C2-C8 alkynyl, or a heteroform of one of these, each of which may be optionally substituted;

$R^1$ is independently H or optionally substituted C1-C8 alkyl;

Y, where present, independently represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl, and wherein two Y groups can cyclize to form a 3-6 membered ring that can be saturated, unsaturated or aromatic, and which ring may include a heteroatom selected from O, S and N as a ring member and may be optionally substituted;

W, where present, independently represents an optionally substituted C1-C6 alkylene or C1-C6 heteroalkylene;

X, where present, independently represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

each n, where present, is independently 0-3;

each m, where present, is independently 0-4; and each $R^6$, where present, is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring;

Z is an optionally substituted C1-C6 aminoalkyl group wherein the amine may be in a protected or unprotected form; and U represents —$OR^8$, —$OC(O)R^8$, —$OSO_2R^8$, C=O, —$OC(O)OR^8$, —$COOR^8$, —$NR^8_2$, azido or halo, where each $R^8$ is independently H, or C1-C8 alkyl, C1-C8 alkenyl, C1-C8 alkynyl, C5-C12 aryl, C5-C21 arylalkyl, or a heteroform of one of these, each of which may be optionally substituted; or C1-C8 alkyl, C2-C8 alkenyl, C2-C8 alkynyl, C5-C12 aryl or C5-C21 arylalkyl, or a heteroform of one of these, each of which may be optionally substituted.

In another aspect, the invention provides a compound of formula (1):

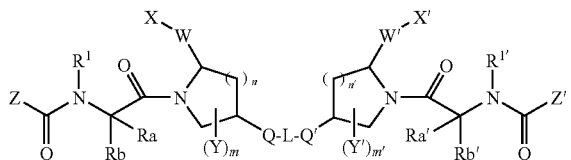

(1)

or a pharmaceutically acceptable salt or hydrate form thereof, wherein each $R_a$, $R_{a'}$, $R_b$ and $R_{b'}$ is independently H, or C1-C8 alkyl, C2-C8 alkenyl or C2-C8 alkynyl, or a heteroform of one of these, each of which may be optionally substituted; or is optionally substituted phenyl;

each Y and Y' independently represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl, and wherein two Y or Y' groups can cyclize to form a 3-6 membered ring that can be saturated, unsaturated or aromatic, and which ring may include a heteroatom selected from O, S and N as a ring member and may be optionally substituted;

each W and W' independently represents an optionally substituted C1-C6 alkylene or C1-C6 heteroalkylene;

each X and X' independently represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —O— or —$NR^2$—, where each $R^2$ is independently H, or optionally substituted C1-C8 alkyl, or optionally substituted C1-C8 heteroalkyl; or one or both of Q and Q' may be a bond when L comprises a ring;

each n and n' is independently 0-3;

each m and m' is independently 0-4;

each $R^1$ and $R^{1'}$ is independently H or optionally substituted C1-C8 alkyl;

each Z and Z' independently represents an optionally substituted C1-C6 aminoalkyl group; and L represents an optionally substituted C1-C24 hydrocarbyl linker, optionally containing from 1-8 heteroatoms selected from N, O and S, which linker is 1-18 atoms in length when counted along the shortest path between Q and Q'.

In another aspect, the invention provides a compound of formula (1A):

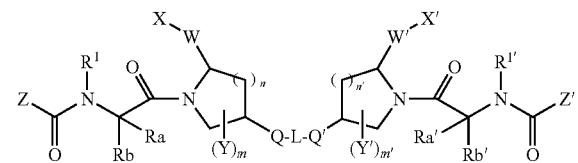

(1A)

or a pharmaceutically acceptable salt or hydrate form thereof, wherein each $R_a$, $R_{a'}$, $R_b$ and $R_{b'}$ is independently H, or C1-C8 alkyl, C2-C8 alkenyl or C2-C8 alkynyl, or a heteroform of one of these, each of which may be optionally substituted;

each Y and Y' independently represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl, and wherein two Y or Y' groups can cyclize to form a 3-6 membered ring that can be saturated, unsaturated or aromatic, and which ring may include a heteroatom selected from O, S and N as a ring member and may be optionally substituted;

each W and W' independently represents an optionally substituted C1-C6 alkylene or C1-C6 heteroalkylene;

each X and X' independently represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —O— or —$NR^2$—, where each $R^2$ is independently H, or optionally substituted C1-C8 alkyl, or optionally substituted C1-C8 heteroalkyl; or one or both of Q and Q' may be a bond when L comprises a ring;

each n and n' is independently 0-3;

each m and m' is independently 0-4;

each $R^1$ and $R^{1'}$ is independently H or optionally substituted C1-C8 alkyl;

each Z and Z' independently represents an optionally substituted C1-C6 aminoalkyl group; and L represents an optionally substituted C1-C24 hydrocarbyl linker, optionally containing from 1-8 heteroatoms selected from N, O and S, which linker is 1-18 atoms in length when counted along the shortest path between Q and Q'.

In another aspect, the invention provides a compound of formula (2):

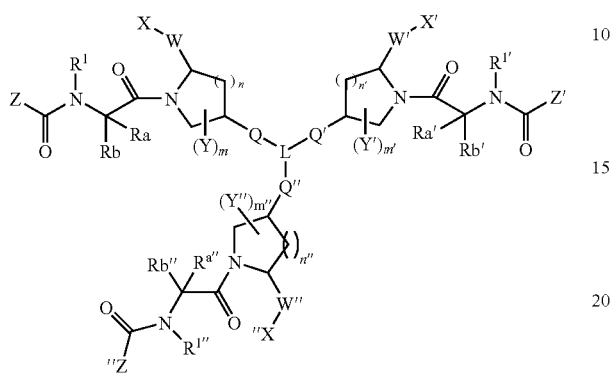

(2)

or a pharmaceutically acceptable salt or hydrate form thereof, wherein each $R_a$, $R_{a'}$, $R_{a''}$, $R_b$, $R_{b'}$ and $R_{b''}$ is independently H, or C1-C8 alkyl, C2-C8 alkenyl or C2-C8 alkynyl, or a heteroform of one of these, each of which may be optionally substituted; or is optionally substituted phenyl;

each Y, Y' and Y" independently represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl, and wherein two Y or Y' groups can cyclize to form a 3-6 membered ring that can be saturated, unsaturated or aromatic, and which ring may include a heteroatom selected from O, S and N as a ring member and may be optionally substituted;

each W, W' and W" independently represents an optionally substituted C1-C6 alkylene or C1-C6 heteroalkylene;

each X, X' and X" independently represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, W' or W", provided that each X, X' and X" comprises at least one aryl or heteroaryl ring;

each Q, Q' and Q" independently represents —O— or —$NR^2$—, where each $R^2$ is independently H, optionally substituted C1-C8 alkyl or optionally substituted C1-C8 heteroalkyl; or one or more of Q, Q' and Q" may be a bond when L comprises a ring;

each n, n' and n" is independently 0-3;

each m, m' and m" is independently 0-4;

each $R^1$, $R^{1'}$ and $R^{1''}$ is independently H or optionally substituted C1-C8 alkyl;

each Z, Z' and Z" is independently an optionally substituted C1-C6 aminoalkyl group; and L represents a C1-C24 hydrocarbyl linker, optionally containing from 1-8 heteroatoms selected from N, O and S, which linker is 1-18 atoms in length when counted along the shortest path between Q and Q', and which linker may be optionally substituted.

In another aspect, the invention provides a compound of formula (3A):

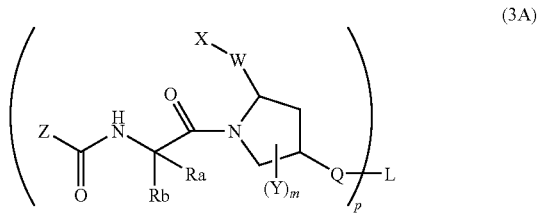

(3A)

or a pharmaceutically acceptable salt or hydrate form thereof, wherein $R_a$ is H and $R_b$ is $R^5$;

$R^5$ is H, or C1-C8 alkyl, C2-C8 alkenyl, C2-C8 alkynyl, or phenyl, each of which may be optionally substituted;

each Y represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl;

W represents an optionally substituted C1-C6 alkylene or C1-C6 heteroalkylene;

X represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

Q represents —O— or —$NR^2$—, where each $R^2$ is independently H, or optionally substituted C1-C8 alkyl, or optionally substituted C1-C8 heteroalkyl; or Q may be a bond when L comprises a ring;

m is 0-4;

p is 2-3;

Z represents an optionally substituted C1-C6 aminoalkyl group; and

L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In preferred embodiments of formula (3A), Z is a C1-C6 aminoalkyl group of the formula —$CH(R^3)NR^4_2$, where $R^3$ is H, or an optionally substituted C1-C8 alkyl or optionally substituted C1-C8 heteroalkyl.

In other embodiments, $R^3$ can cyclize with $R^4$ on an adjacent nitrogen atom to form an optionally substituted azacyclic group having 5-10 ring members, which azacyclic group may be saturated, unsaturated or aromatic, and may contain 1-2 additional heteroatoms selected from N, O and S as a ring member.

In some embodiments of formula (3A), each $R^4$ is independently H, or an optionally substituted C1-C8 alkyl or optionally substituted C1-C8 heteroalkyl, and the two $R^4$ groups on one nitrogen can cyclize to form an optionally substituted azacyclic group having 5-10 ring members, which azacyclic group may be saturated, unsaturated or aromatic, and may contain 1-2 additional heteroatoms selected from N, O and S as a ring member.

In another aspect, the invention provides a compound of formula (3):

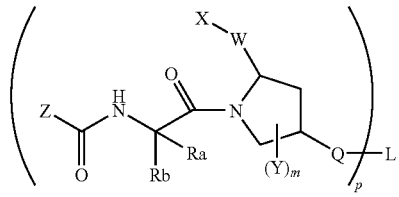

or a pharmaceutically acceptable salt or hydrate form thereof,
wherein R⁵ is H, or C1-C8 alkyl, C2-C8 alkenyl or C2-C8 alkynyl, each of which may be optionally substituted;
each Y represents C1-C8 alkyl, =O, OR, NR₂, OC(O)R, NRC(O)R, NRSO₂R or COOR, wherein each R is independently H, C1-C8 alkyl or C1-C8 heteroalkyl;
W represents an optionally substituted C1-C6 alkylene or C1-C6 heteroalkylene;
X represents an optionally substituted C₅-C₂₀ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;
Q represents —O— or —NR²—, where each R² is independently H, or optionally substituted C1-C8 alkyl, or optionally substituted C1-C8 heteroalkyl; or Q may be a bond when L comprises a ring;
m is 0-4;
p is 2-3;
Z represents an optionally substituted C1-C6 aminoalkyl group; and
L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In yet another aspect, the invention provides a compound of formula (4):

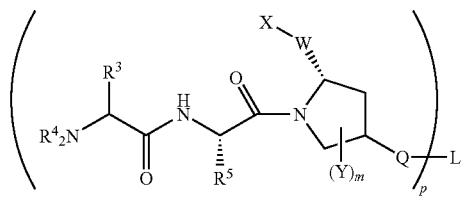

or a pharmaceutically acceptable salt or hydrate form thereof,
wherein R⁵ is H, or C1-C8 alkyl, C2-C8 alkenyl, C2-C8 alkynyl, or phenyl, each of which may be optionally substituted;
each Y represents C1-C8 alkyl, =O, OR, NR₂, OC(O)R, NRC(O)R, NRSO₂R or COOR, wherein each R is independently H, C1-C8 alkyl or C1-C8 heteroalkyl;
W represents an optionally substituted C1-C6 alkylene or C1-C6 heteroalkylene;
X represents an optionally substituted C₅-C₂₀ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;
Q represents —O— or —NR²—, where each R² is independently H, optionally substituted C1-C8 alkyl or optionally substituted C1-C8 heteroalkyl; or Q may be a bond when L comprises a ring;
m is 0-4;
p is 2 or 3;
R³ is H, or an optionally substituted C1-C8 alkyl or optionally substituted C1-C8 heteroalkyl, and R³ can cyclize with R⁴ on an adjacent nitrogen atom to form an optionally substituted azacyclic group having 5-10 ring members, which azacyclic group may be saturated, unsaturated or aromatic, and may contain 1-2 additional heteroatoms selected from N, O and S as a ring member;
each R⁴ is independently H, or an optionally substituted C1-C8 alkyl or optionally substituted C1-C8 heteroalkyl, and the two R⁴ groups on one nitrogen can cyclize to form an optionally substituted azacyclic group having 5-10 ring members, which azacyclic group may be saturated, unsaturated or aromatic, and may contain 1-2 additional heteroatoms selected from N, O and S as a ring member; and
L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In still another aspect, the invention provides a compound of formula (5):

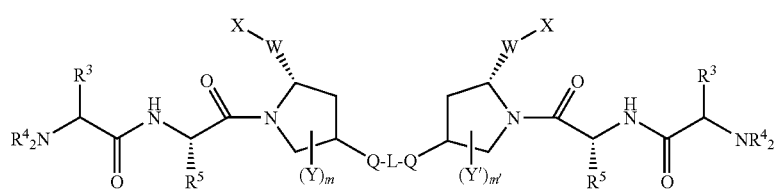

or a pharmaceutically acceptable salt or hydrate form thereof, $R^5$ is H, or C1-C8 alkyl, C2-C8 alkenyl, C2-C8 alkynyl, or phenyl, each of which may be optionally substituted;

each Y represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl;

W represents an optionally substituted C1-C6 alkylene or C1-C6 heteroalkylene;

X represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

Q represents —O— or —$NR^2$—, where each $R^2$ is independently H, optionally substituted C1-C8 alkyl or optionally substituted C1-C8 heteroalkyl; or Q may be a bond when L comprises a ring;

m is 0-4;

$R^3$ is H, or an optionally substituted C1-C8 alkyl or optionally substituted C1-C8 heteroalkyl, and $R^3$ can cyclize with $R^4$ on an adjacent nitrogen atom to form an optionally substituted azacyclic group having 5-10 ring members, which azacyclic group may be saturated, unsaturated or aromatic, and may contain 1-2 additional heteroatoms selected from N, O and S as a ring member;

each $R^4$ is independently H, or an optionally substituted C1-C8 alkyl or C1-C8 heteroalkyl group, and the two $R^4$ groups on one nitrogen can cyclize to form an optionally substituted azacyclic group having 5-10 ring members, which azacyclic group may be saturated, unsaturated or aromatic, and may contain 1-2 additional heteroatoms selected from N, O and S as a ring member;

L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In another aspect, the invention provides a monomer of formula (6), and methods of using them for the preparation of compounds of formula (1)-(5), (7)-(9), (1A) and (3A):

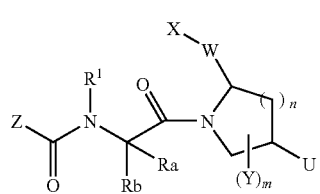

(6)

or a pharmaceutically acceptable salt or hydrate form thereof, wherein each $R_a$ and $R_b$ is independently H, or C1-C8 alkyl, C2-C8 alkenyl or C2-C8 alkynyl, or a heteroform of one of these, each of which may be optionally substituted; or is optionally substituted phenyl;

each Y independently represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl, and wherein two Y groups can cyclize to form a 3-6 membered ring that can be saturated, unsaturated or aromatic, and which ring may include a heteroatom selected from O, S and N as a ring member and may be optionally substituted;

W represents an optionally substituted C1-C6 alkylene or C1-C6 heteroalkylene;

X represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

n is 0-3;

m is 0-4;

$R^1$ is H or optionally substituted C1-C8 alkyl;

Z is an optionally substituted C1-C6 aminoalkyl group; and

U represents —$OR^8$, —$OC(O)R^8$, —$OSO_2R^8$, C=O, —$OC(O)OR^8$, —$COOR^8$, —$NR^8_2$, azido or halo, where each $R^8$ is independently H, or C1-C8 alkyl, C1-C8 alkenyl, C1-C8 alkynyl, C5-C12 aryl, C5-C21 arylalkyl, or a heteroform of one of these, each of which may be optionally substituted; or C1-C8 alkyl, C2-C8 alkenyl, C2-C8 alkynyl, C5-C12 aryl or C5-C21 arylalkyl, or a heteroform of one of these, each of which may be optionally substituted.

In another aspect, the invention provides a compound of formula (7):

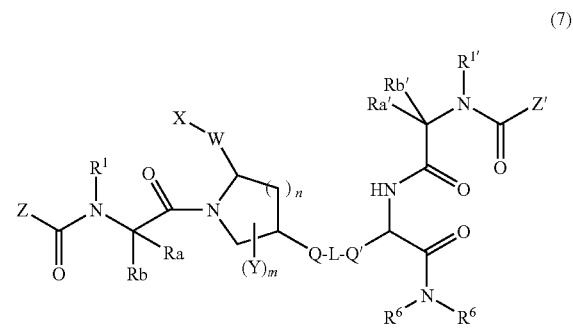

(7)

or a pharmaceutically acceptable salt or hydrate form thereof, wherein each $R_a$, $R_{a'}$, $R_b$ and $R_{b'}$ is independently H or C1-C8 alkyl, C2-C8 alkenyl or C2-C8 alkynyl, or a heteroform of one of these, each of which may be optionally substituted; or is optionally substituted phenyl;

each Y independently represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl, and wherein two Y groups can cyclize to form a 3-6 membered ring that can be saturated, unsaturated or aromatic, and which ring may include a heteroatom selected from O, S and N as a ring member and may be optionally substituted;

W represents an optionally substituted C1-C6 alkylene or C1-C6 heteroalkylene;

X represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that X comprises at least one aryl or heteroaryl ring;

Q represents —O— or —NR²—, where R² is H, C1-C8 alkyl or C1-C8 heteroalkyl, each of which may be optionally substituted;

Q' represents —CH₂—, —CH(OR)—, —CH(R)—, —CH₂O—, —CH(R)O— or —(CH₂)₄NH—, wherein R is H, C₁-C₄ alkyl or C₁-C₄ heteroalkyl;

or one or both of Q and Q' can be a bond where L comprises a ring;

n is 0-3;

m is 0-4;

each $R^1$ and $R^{1'}$ is independently H or optionally substituted C1-C8 alkyl;

each $R^6$ is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring;

each Z and Z' independently represents an optionally substituted C1-C6 aminoalkyl group; and L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In another aspect, the invention provides a compound of formula (8):

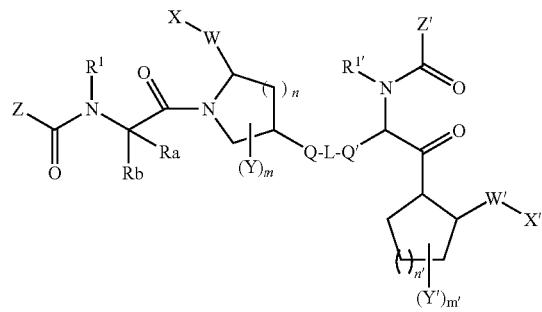

(8)

or a pharmaceutically acceptable salt or hydrate form thereof, wherein each $R_a$, and $R_b$ is independently H, or C1-C8 alkyl, C2-C8 alkenyl or C2-C8 alkynyl, or a heteroform of one of these, each of which may be optionally substituted; or is optionally substituted phenyl;

each Y and Y' independently represents C1-C8 alkyl, =O, OR, NR₂, OC(O)R, NRC(O)R, NRSO₂R or COOR, wherein each R is independently H, C1-C8 alkyl or C1-C8 heteroalkyl, and wherein two Y or Y' groups on one azacyclic ring can cyclize to form a 3-6 membered ring that can be saturated, unsaturated or aromatic, and which ring may include a heteroatom selected from O, S and N as a ring member and may be optionally substituted;

each W and W' independently represents an optionally substituted C1-C6 alkylene or C1-C6 heteroalkylene;

each X and X' independently represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

Q represents —O— or —NR²—, where R² is H, C1-C8 alkyl or C1-C8 heteroalkyl, each of which may be optionally substituted;

Q' represents —CH₂—, —CH(OR)—, —CH(R)—, —CH₂O—, —CH(R)O— or —(CH₂)₄NH—, wherein R is H, C1-C4 alkyl or C1-C4 heteroalkyl;

or one or both of Q and Q' can be a bond where L comprises a ring;

each n and n' is 0-3;

each m and m' is 0-4;

each $R^1$ and $R^{1'}$ is independently H or optionally substituted C1-C8 alkyl;

each Z and Z' independently represents an optionally substituted C1-C6 aminoalkyl group; and L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In another aspect, the invention provides a compound of formula (9):

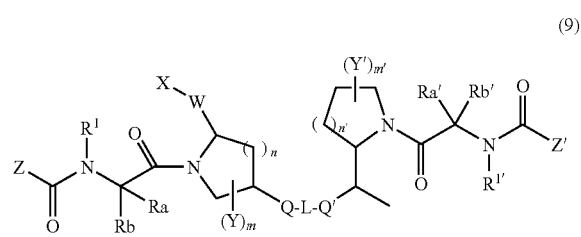

(9)

or a pharmaceutically acceptable salt or hydrate form thereof, wherein each $R_a$, $R_{a'}$, $R_b$ and $R_{b'}$ is independently H or C1-C8 alkyl, C2-C8 alkenyl or C2-C8 alkynyl, or a heteroform of one of these, each of which may be optionally substituted; or is optionally substituted phenyl;

each Y and Y' independently represents C1-C8 alkyl, =O, OR, NR₂, OC(O)R, NRC(O)R, NRSO₂R or COOR, wherein each R is independently H, C1-C8 alkyl or C1-C8 heteroalkyl, and wherein two Y groups can cyclize to form a 3-6 membered ring that can be saturated, unsaturated or aromatic, and which ring may include a heteroatom selected from O, S and N as a ring member and may be optionally substituted;

W represents an optionally substituted C1-C6 alkylene or C1-C6 heteroalkylene;

X represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that X comprises at least one aryl or heteroaryl ring;

each Q and Q' independently represents —O— or —NR²—, where R² is H, C1-C8 alkyl, C1-C8 alkenyl, or C1-C8 alkynyl, or a heteroform of one of these, each of which may be optionally substituted; or one or both of Q and Q' can be a bond where L comprises a ring;

each n and n' is 0-3;

each m and m' is 0-4;

each $R^1$ and $R^{1'}$ is independently H or optionally substituted C1-C8 alkyl;

each Z and Z' independently represents an optionally substituted C1-C6 aminoalkyl group; and L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In another aspect, the invention provides compounds of formula (10):

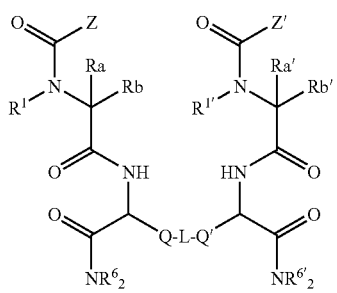

(10)

or a pharmaceutically acceptable salt or hydrate form thereof, wherein each $R_a$, $R_{a'}$, $R_b$ and $R_{b'}$ is independently H or C1-C8 alkyl, C2-C8 alkenyl or C2-C8 alkynyl, or a heteroform of one of these, each of which may be optionally substituted; or is optionally substituted phenyl;

each $R^1$ and $R^{1'}$ is independently H or optionally substituted C1-C8 alkyl;

each $R^6$ and $R^{6'}$ is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring;

each Q and Q' independently represents —$CH_2$—, —CH(OR)—, —CH(R)—, —$CH_2$O—, —CH(R)O— or —$(CH_2)_4$NH—, wherein R is H, $C_1$-$C_4$ alkyl or $C_1$-$C_4$ heteroalkyl; or one or both of Q and Q' can be a bond where L comprises a ring;

each Z and Z' independently represents an optionally substituted C1-C6 aminoalkyl group; and L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In another aspect, the invention provides compounds of formula (11):

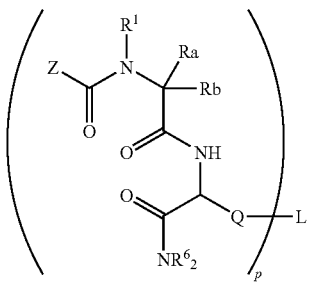

(11)

or a pharmaceutically acceptable salt or hydrate form thereof, wherein p is 2-3;

wherein $R_a$ and $R_b$ are independently H or C1-C8 alkyl, C2-C8 alkenyl or C2-C8 alkynyl, or a heteroform of one of these, each of which may be optionally substituted; or is optionally substituted phenyl;

$R^1$ is H or optionally substituted C1-C8 alkyl;

each $R^6$ is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring;

Q represents —$CH_2$—, —CH(OR)—, —CH(R)—, —$CH_2$O—, —CH(R)O— or —$(CH_2)_4$NH—, wherein R is H, $C_1$-$C_4$ alkyl or $C_1$-$C_4$ heteroalkyl; or Q can be a bond when L comprises a ring;

Z is an optionally substituted C1-C6 aminoalkyl group; and

L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In another aspect, the invention provides compounds of formula (12):

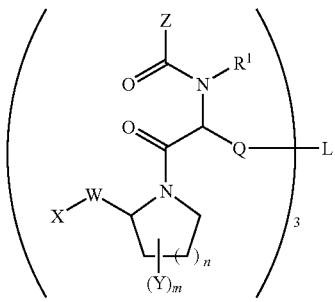

(12)

or a pharmaceutically acceptable salt or hydrate form thereof, $R^1$ is H or optionally substituted C1-C8 alkyl;

Y represents C1-C8 alkyl, =O, OR, $NR_2$, OC(O)R, NRC(O)R, $NRSO_2$R or COOR, wherein each R is independently H, or C1-C8 alkyl or C1-C8 heteroalkyl, each of which may be optionally substituted;

W represents C=O, C=S, or an optionally substituted C2-C6 alkylene or optionally substituted C2-C6 heteroalkylene;

X represents an optionally substituted C5-C20 ring system comprising at least one aromatic ring and up to four heteroatoms selected from N, O and S as a ring member, and can represent either a single 5-15 membered cyclic group or two 5-10 membered cyclic groups that are both attached to the same atom of W, provided that X comprises at least one aryl or heteroaryl ring;

Q represents —CH$_2$—, —CH(OR)—, —CH(R)—, —CH$_2$O—, —CH(R)O—, or —(CH$_2$)$_4$NH—, wherein R is H, or C$_1$-C$_4$ alkyl or C$_1$-C$_4$ heteroalkyl; or Q can be a bond where L comprises a ring;

n is 0-3;

m is 0-4;

Z represents an optionally substituted C1-C6 aminoalkyl group; and

L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In another aspect, the invention provides compounds of formula (13):

(13)

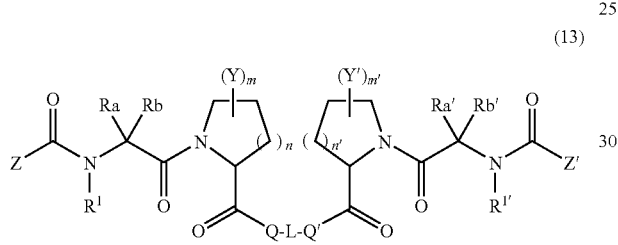

or a pharmaceutically acceptable salt or hydrate form thereof, wherein each R$_a$, R$_{a'}$, R$_b$ and R$_{b'}$ is independently H or C1-C8 alkyl, C2-C8 alkenyl or C2-C8 alkynyl, or a heteroform of one of these, each of which may be optionally substituted; or is optionally substituted phenyl;

each R$^1$ and R$^{1'}$ is independently H or optionally substituted C1-C8 alkyl;

each Y and Y' independently represents C1-C8 alkyl, =O, OR, NR$_2$, OC(O)R, NRC(O)R, NRSO$_2$R or COOR, wherein each R is independently H, or C1-C8 alkyl or C1-C8 heteroalkyl, each of which may be optionally substituted;

each Q and Q' independently represents —O— or —NR$^2$—, where R$^2$ is H, C1-C8 alkyl, C1-C8 alkenyl, or C1-C8 alkynyl, or a heteroform of one of these, each of which may be optionally substituted; or one or both of Q and Q' can be a bond where L comprises a ring;

each n and n' is 1-3;

each m and m' is 0-4;

each Z and Z' independently represents an optionally substituted C1-C6 aminoalkyl group; and L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In one aspect, the invention provides compounds of formula (13A):

(13A)

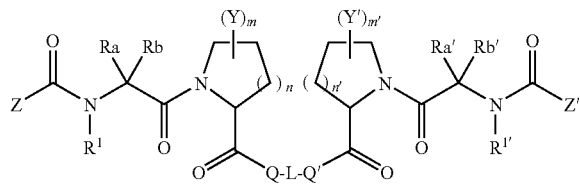

or a pharmaceutically acceptable salt or hydrate form thereof, and including any stereoisomeric forms thereof;

wherein each Y and Y' independently represents an optionally substituted C1-C8 alkyl, C5-C12 aryl, C5-C20 arylalkyl, or a heteroform of one of these; or is =O, OR, SR, S(O)R, SO$_2$R, SO$_2$NR$_2$, NR$_2$, OC(O)R, NRC(O)R, NRCOOR, NRC(O)NR$_2$, NRSO$_2$R, CN, C(O)NR$_2$, C(O)R, COOR, NO$_2$ or halo, wherein each R is independently H, C$_1$-C$_8$ alkyl, C5-C12 aryl or C5-C20 arylalkyl, or a heteroform of one of these each of which may be optionally substituted;

or is any other substituent suitable for an alkyl group;

and wherein two Y or Y' groups on the same ring can cyclize to form a 3-6 membered ring that can be saturated, unsaturated or aromatic, and which ring may include one heteroatom selected from O, S and N as a ring member and may be optionally substituted;

each R$^1$ and R$^{1'}$ is independently H or optionally substituted C1-C8 alkyl;

each R$_a$, R$_{a'}$, R$_b$ and R$_{b'}$ is independently H, or C1-C8 alkyl, C3-C7 cycloalkyl, C2-C8 alkenyl, C2-C8 alkynyl, C5-C12 aryl, C5-C20 arylalkyl, or a heteroform of one of these, each of which may be optionally substituted; or R$_a$ and R$_b$, or R$_{a'}$ and R$_{b'}$ may be taken together with the carbon atom to which they are attached to form an optionally substituted 3-7 membered ring, optionally containing one heteroatom selected from N, O and S as a ring member;

Q is —O— or —NR$^2$—, and Q' is —O— or —NR$^{2'}$—; wherein Q and Q' are independently selected, and where each R$^2$ and R$^{2'}$ is H, C1-C8 alkyl, C1-C8 alkenyl, or C1-C8 alkynyl, or a heteroform of one of these, each of which may be optionally substituted; or one or both of Q and Q' can be a bond where L comprises a ring;

each n and n' is independently 1-3;

each m and m' is independently 0-4;

each Z and Z' independently represents an optionally substituted C1-C6 aminoalkyl group; and L represents an optionally substituted C1-C24 hydrocarbyl linker, optionally containing from 1-8 heteroatoms selected from N, O and S, which linker is 1 to 18 atoms in length when counted along the shortest path between Q and Q';

with the proviso that L does not comprise a disulfide bond.

In another aspect, the invention provides a compound of formula (13B):

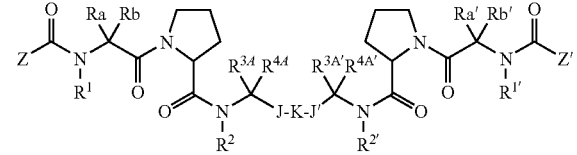

or a pharmaceutically acceptable salt or hydrate form thereof; and including any stereoisomeric forms thereof;

wherein each Y and Y' independently represents an optionally substituted C1-C8 alkyl, C5-C12 aryl, C5-C20 arylalkyl, or a heteroform of one of these; or is =O, OR, SR, S(O)R, SO$_2$R, SO$_2$NR$_2$, NR$_2$, OC(O)R, NRC(O)R, NRCOOR, NRC(O)NR$_2$, NRSO$_2$R, CN, C(O)NR$_2$, C(O)R, COOR, NO$_2$ or halo, wherein each R is independently H, C$_1$-C$_8$ alkyl, C5-C12 aryl or C5-C20 arylalkyl, or a heteroform of one of these; or is any other substituent suitable for an alkyl group;

and wherein two Y or Y' groups on the same ring can cyclize to form a 3-6 membered ring that can be saturated, unsaturated or aromatic, and which ring may include one heteroatom selected from O, S and N as a ring member and may be optionally substituted;

each m and m' is independently is 0-4;

each n and n' is independently 0-3;

each $R^1$, $R^2$, $R^{1'}$ and $R^{2'}$ is independently H or optionally substituted C1-C8 alkyl;

each $R_a$, $R_{a'}$, $R_b$, $R_{b'}$, $R^{3A}$, $R^{3A'}$, $R^{4A}$ and $R^{4A'}$ is independently H, or C1-C8 alkyl, C3-C7 cycloalkyl, C2-C8 alkenyl, C2-C8 alkynyl, C5-C12 aryl, C5-C20 arylalkyl, or a heteroform of one of these, each of which may be optionally substituted; or $R_a$ and $R_b$, $R_{a'}$ and $R_{b'}$, $R^{3A}$ and $R^{4A}$, or $R^{3A'}$ and $R^{4A'}$ may be taken together with the carbon atom to which they are attached to form an optionally substituted 3-7 membered ring, optionally containing one heteroatom selected from N, O and S as a ring member;

each Z and Z' is independently an optionally substituted C1-C6 aminoalkyl;

each J and J' independently represents —CH$_2$—, —CH(OR')—, —CH(R')—, —(CH$_2$)$_r$G-, —CH(R')G— or —CR'=CR'— or —C≡C—, wherein r is 1-4, each G is independently O, NR', or S, and wherein each R' is independently H, or C$_1$-C$_8$ alkyl or C$_1$-C$_8$ heteroalkyl; or one or both of J and J' can be a bond where K comprises a ring; and K represents an optionally substituted C1-C20 hydrocarbyl linker, optionally containing from 1-6 heteroatoms selected from N, O and S, which linker is 1 to 14 atoms in length when counted along the shortest path between J and J';

with the proviso that K does not comprise a disulfide bond.

In another aspect, the invention provides a compound of formula (2):

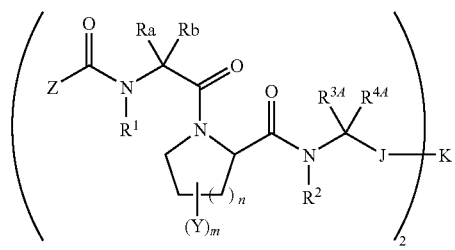

(13C)

or a pharmaceutically acceptable salt or hydrate form thereof; and including any stereoisomeric forms thereof;

wherein each Y independently represents an optionally substituted C1-C8 alkyl, C5-C12 aryl, C5-C20 arylalkyl, or a heteroform of one of these; or is =O, OR, SR, S(O)R, SO$_2$R, SO$_2$NR$_2$, NR$_2$, OC(O)R, NRC(O)R, NRCOOR, NRC(O)NR$_2$, NRSO$_2$R, CN, C(O)NR$_2$, C(O)R, COOR, NO$_2$ or halo, wherein each R is independently H, C1-C8 alkyl, C5-C12 aryl or C5-C20 arylalkyl, or a heteroform of one of these; or is any other substituent suitable for an alkyl group;

m is 0-4;

n is 0-3;

each $R^1$ and $R^2$ is independently H or optionally substituted C1-C4 alkyl;

each $R_a$, $R_b$, $R^{3A}$ and $R^{4A}$ is independently H, or C1-C8 alkyl, C3-C7 cycloalkyl, C2-C8 alkenyl, C2-C8 alkynyl, C5-C12 aryl, C5-C20 arylalkyl, or a heteroform of one of these, each of which may be optionally substituted;

Z is a 1-aminoalkyl group represented by the formula —CH($R^3$)NR$^4$$_2$;

each $R^4$ is independently H, or an optionally substituted C$_1$-C$_8$ alkyl or C$_1$-C$_8$ heteroalkyl group, and the two $R^4$ groups on one nitrogen can cyclize to form an optionally substituted 3-8 membered azacyclic ring, which azacyclic ring may be saturated, unsaturated or aromatic, and may contain 1-2 additional heteroatoms selected from N, O and S as ring members;

each $R^3$ is H, or an optionally substituted C$_1$-C$_8$ alkyl or C$_1$-C$_8$ heteroalkyl group, and $R^3$ can cyclize with $R^4$ on an adjacent nitrogen atom to form an optionally substituted 3-8 membered azacyclic ring, which azacyclic ring may be saturated, unsaturated or aromatic, and may contain 1-2 additional heteroatoms selected from N, O and S as ring members;

J is selected from the group consisting of —CH$_2$—, —CH(R')—, —(CH$_2$)$_r$G-, and —CH(R')G-, wherein r is 1-4, each G is independently O or NR', and wherein each R' is independently H or C1-C4 alkyl; or J can be a bond where K comprises a ring; and K represents a C1-C10 alkylene, C3-C10 cycloalkylene, C2-C10 alkenylene, C2-C10 alkynylene, C5-C12 arylene, or C5-C20 arylalkylene, C5-C20 arylalkenylene or C5-C20 arylalkynylene linker, or a heteroform of one of these, each of which may be optionally substituted;

with the proviso that K does not comprise a disulfide bond.

In a further aspect, the invention provides a compound of formula (13D):

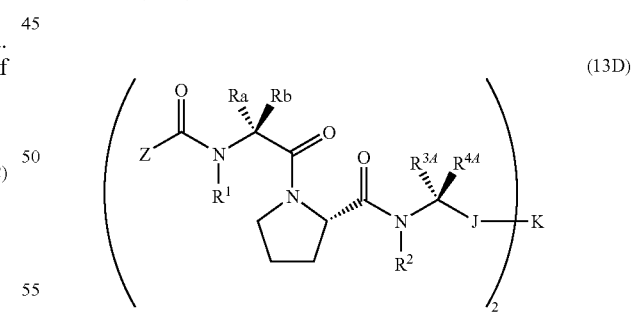

(13D)

or a pharmaceutically acceptable salt or hydrate form thereof;

wherein each $R^1$ and $R^2$ is independently H or methyl;

$R_a$ and $R^{3A}$ are H;

each $R_b$ and $R^{4A}$ is independently H, or C1-C8 alkyl, C3-C7 cycloalkyl, C2-C8 alkenyl, C2-C8 alkynyl, C5-C12 aryl, C5-C20 arylalkyl, or a heteroform of one of these, each of which may be optionally substituted;

Z is a 1-aminoalkyl group represented by the formula —CH($R^3$)NR$^4$$_2$;

each R³ and R⁴ is independently H or C1-C4 alkyl;

J is selected from the group consisting of —CH₂—, —CH(R')—, —(CH₂)ᵣG-, and —CH(R')G-, wherein r is 1-4, each G is independently O or NR', and wherein each R' is independently H or C1-C4 alkyl; or J can be a bond where K comprises a ring; and K represents a C1-C10 alkylene, C3-C10 cycloalkylene, C2-C10 alkenylene, C2-C10 alkynylene, C5-C12 arylene, or C5-C20 arylalkylene, C5-C20 arylalkenylene or C5-C20 arylalkynylene linker, or a heteroform of one of these, each of which may be optionally substituted;

with the proviso that K does not comprise a disulfide bond.

In another aspect, the invention provides a compound selected from the group consisting of:

Q represents —O— or —NR²—, where R² is H, C1-C8 alkyl or C1-C8 heteroalkyl, each of which may be optionally substituted; or Q can be a bond where L comprises a ring;

Z is an optionally substituted C1-C6 aminoalkyl group; and

L represents a C1-C₁₄ alkylene, C1-C₁₄ alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In another aspect, the invention provides compounds of formula (15):

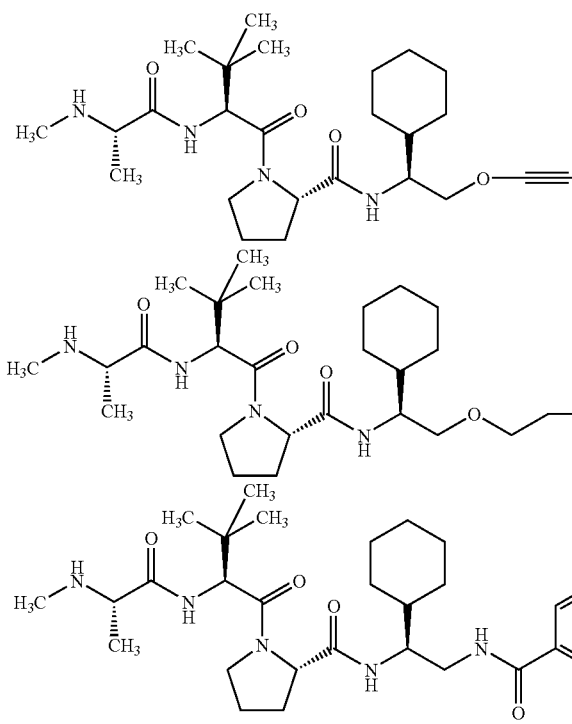

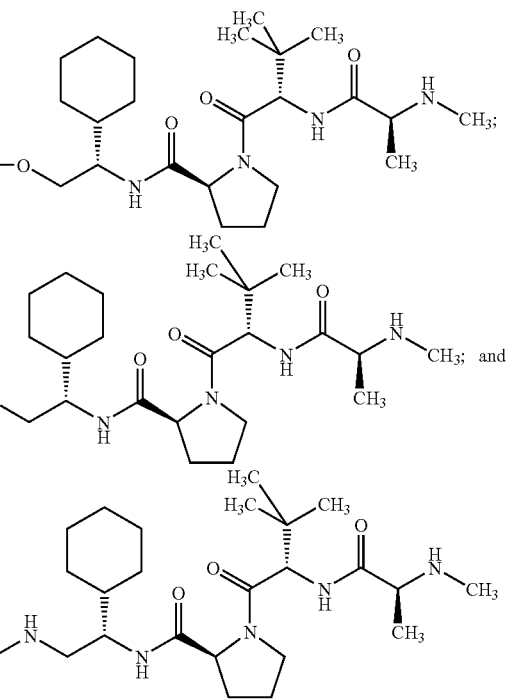

or a pharmaceutically acceptable salt or hydrate form thereof.

In another aspect, the invention provides compounds of formula (14):

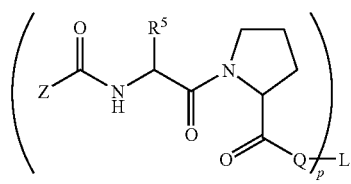

(14)

or a pharmaceutically acceptable salt or hydrate form thereof, wherein p is 2 or 3;

R⁵ is H, C1-C8 alkyl, C2-C8 alkenyl, C2-C8 alkynyl, or phenyl, each of which may be optionally substituted;

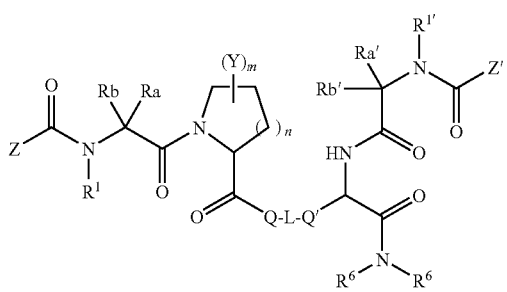

(15)

or a pharmaceutically acceptable salt or hydrate form thereof, wherein $R_a$ and $R_b$ are independently H or C1-C8 alkyl, C2-C8 alkenyl or C2-C8 alkynyl, or a heteroform of one of these, each of which may be optionally substituted; or is optionally substituted phenyl;

each $R^1$ and $R^{1'}$ is independently H or optionally substituted C1-C8 alkyl;

each $R^6$ is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring;

Y represents C1-C8 alkyl, =O, OR, $NR_2$, OC(O)R, NRC(O)R, $NRSO_2R$ or COOR, wherein each R is independently H, or C1-C8 alkyl or C1-C8 heteroalkyl, each of which may be optionally substituted;

Q represents —O— or —$NR^2$—, where $R^2$ is H, optionally substituted C1-C8 alkyl or optionally substituted C1-C8 heteroalkyl;

Q' represents —$CH_2$—, —CH(OR)—, —CH(R)—, —$CH_2$O—, —CH(R)O— or —$(CH_2)_4$NH—, wherein R is H, $C_1$-$C_4$ alkyl or $C_1$-$C_4$ heteroalkyl;

or one or both of Q and Q' can be a bond when L comprises a ring;

n is 1-3;

m is 0-4;

each Z and Z' independently represents an optionally substituted C1-C6 aminoalkyl group; and L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In another aspect, the invention provides compounds of formula (16):

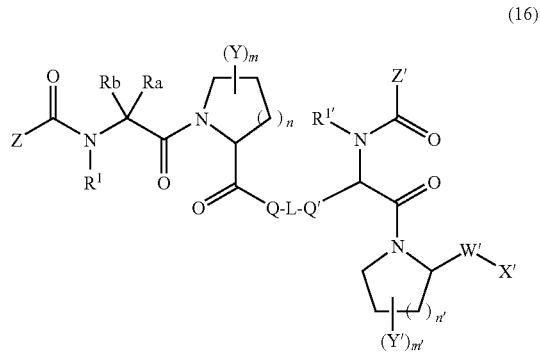

(16)

or a pharmaceutically acceptable salt or hydrate form thereof, wherein $R_a$ and $R_b$ are independently H or C1-C8 alkyl, C2-C8 alkenyl or C2-C8 alkynyl, or a heteroform of one of these, each of which may be optionally substituted; or is optionally substituted phenyl;

each $R^1$ and $R^{1'}$ is independently H or optionally substituted C1-C8 alkyl;

each $R^6$ is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring;

each Y and Y' independently represents C1-C8 alkyl, =O, OR, $NR_2$, OC(O)R, NRC(O)R, $NRSO_2R$ or COOR, wherein each R is independently H, or C1-C8 alkyl or C1-C8 heteroalkyl, each of which may be optionally substituted;

W' represents an optionally substituted $C_1$-$C_6$ alkylene or $C_1$-$C_6$ heteroalkylene;

X' represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W', provided that X' comprises at least one aryl or heteroaryl ring;

Q represents —O— or —$NR^2$—, where $R^2$ is H, optionally substituted C1-C8 alkyl or optionally substituted C1-C8 heteroalkyl;

Q' represents —$CH_2$—, —CH(OR)—, —CH(R)—, —$CH_2$O—, —CH(R)O— or —$(CH_2)_4$NH—, wherein R is H, $C_1$-$C_4$ alkyl or $C_1$-$C_4$ heteroalkyl;

or one or both of Q and Q' can be a bond when L comprises a ring;

each n and n' is 1-3;

each m and m' is 0-4;

each Z and Z' independently represents an optionally substituted C1-C6 aminoalkyl group; and L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

In another aspect, the invention provides monomers of formula (17) and methods of using them for the preparation of compounds of formula (7), (10)-(11) and (15):

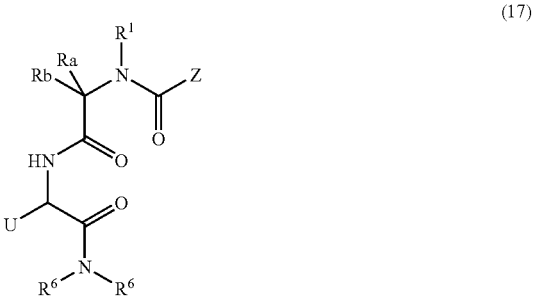

(17)

or a pharmaceutically acceptable salt or hydrate form thereof, wherein $R_a$ and $R_b$ are independently H or C1-C8 alkyl, C2-C8 alkenyl or C2-C8 alkynyl, or a heteroform of one of these, each of which may be optionally substituted; or is optionally substituted phenyl;

$R^1$ is H or optionally substituted C1-C8 alkyl;

each $R^6$ is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring;

U represents —$OR^8$, —$OC(O)R^8$, —$OSO_2R^8$, C=O, —$OC(O)OR^8$, —$COOR^8$, —$NR^8_2$, azido or halo, where each $R^8$ is independently H, or C1-C8 alkyl, C1-C8 alkenyl, C1-C8 alkynyl, C5-C12 aryl, C5-C21 arylalkyl, or a heteroform of one of these, each of which may be optionally substituted; or C1-C8 alkyl, C2-C8 alkenyl, C2-C8 alkynyl, C5-C12 aryl or C5-C21 arylalkyl, or a heteroform of one of these, each of which may be optionally substituted; and Z is an optionally substituted C1-C6 aminoalkyl group wherein the amine may be in a protected or unprotected form.

In another aspect, the invention provides a monomer of formula (18) and methods of using them for the preparation of compounds of formula (8), (12) and (16):

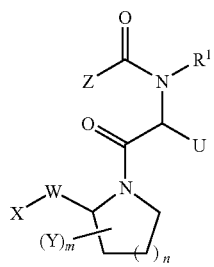

(18)

or a pharmaceutically acceptable salt or hydrate form thereof; and including any stereoisomeric forms thereof;
wherein $R^1$ is H or optionally substituted C1-C8 alkyl;
Y represents C1-C8 alkyl, =O, OR, $NR_2$, OC(O)R, NRC(O)R, $NRSO_2R$ or COOR, wherein each R is independently H, or C1-C8 alkyl or C1-C8 heteroalkyl, each of which may be optionally substituted; and wherein two Y groups can cyclize to form a 3-6 membered ring that can be saturated, unsaturated or aromatic, and which ring may include a heteroatom selected from O, S and N as a ring member and may be substituted;
W represents C=O, C=S, or an optionally substituted C2-C6 alkylene or C2-C6 heteroalkylene;
X represents an optionally substituted C5-C20 ring system comprising at least one aromatic ring and up to four heteroatoms selected from N, —O and S as a ring member, and can represent either a single 5-15 membered cyclic group or two 5-10 membered cyclic groups that are both attached to the same atom of W, provided that each X comprises at least one aryl or heteroaryl ring;
n is 0-3;
m is 0-4;
U represents —$OR^8$, —$OC(O)R^8$, —$OSO_2R^8$, C=O, —$OC(O)OR^8$, —$COOR^8$, —$NR^8_2$, azido or halo, where each $R^8$ is independently H, or C1-C8 alkyl, C1-C8 alkenyl, C1-C8 alkynyl, C5-C12 aryl, C5-C21 arylalkyl, or a heteroform of one of these, each of which may be optionally substituted; or C1-C8 alkyl, C2-C8 alkenyl, C2-C8 alkynyl, C5-C12 aryl or C5-C21 arylalkyl, or a heteroform of one of these, each of which may be optionally substituted; with the proviso that U is not isopropyl; and Z is an optionally substituted C1-C6 aminoalkyl group wherein the amine may be in a protected or unprotected form.

In another aspect, the invention provides monomers of formula (19) and methods of using them for the preparation of compounds of formula (9) and (13)-(16):

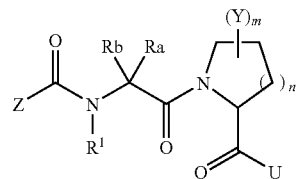

(19)

or a pharmaceutically acceptable salt or hydrate form thereof,
wherein $R_a$ and $R_b$ are independently H or C1-C8 alkyl, C2-C8 alkenyl or C2-C8 alkynyl, or a heteroform of one of these, each of which may be optionally substituted; or is optionally substituted phenyl;
$R^1$ is H or optionally substituted C1-C8 alkyl;
Y represents C1-C8 alkyl, =O, OR, $NR_2$, OC(O)R, NRC(O)R, $NRSO_2R$ or COOR, wherein each R is independently H, or C1-C8 alkyl or C1-C8 heteroalkyl, each of which may be optionally substituted; and wherein two Y groups can cyclize to form a 3-6 membered ring that can be saturated, unsaturated or aromatic, and which ring may include a heteroatom selected from O, S and N as a ring member and may be substituted;
n is 1-3;
m is 0-4;
U represents —$OR^8$, —$OC(O)R^8$, —$OSO_2R^8$, C=O, —$OC(O)OR^8$, —$COOR^8$, —$NR^8_2$, azido or halo, where each $R^8$ is independently H, or C1-C8 alkyl, C1-C8 alkenyl, C1-C8 alkynyl, C5-C12 aryl, C5-C21 arylalkyl, or a heteroform of one of these, each of which may be optionally substituted; or C1-C8 alkyl, C2-C8 alkenyl, C2-C8 alkynyl, C5-C12 aryl or C5-C21 arylalkyl, or a heteroform of one of these, each of which may be optionally substituted; and Z is an optionally substituted C1-C6 aminoalkyl group wherein the amine may be in a protected or unprotected form.

In another aspect, the invention provides monomers of formula (19A) and methods of using them for the preparation of compounds of formula (13A)-(13D):

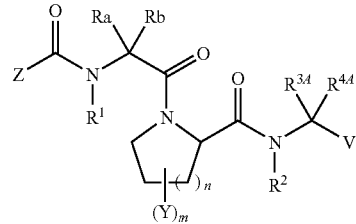

(19A)

or a pharmaceutically acceptable salt or hydrate form thereof; and including any stereoisomeric forms thereof;
wherein each Y independently represents an optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, OC(O)R, NRC(O)R, NRCOOR, $NRC(O)NR_2$, $NRSO_2R$, CN, $C(O)NR_2$, C(O)R, COOR, $NO_2$ or halo, wherein each R is independently H, C1-C8 alkyl, C5-C12 aryl or C5-C20 arylalkyl, or a heteroform of one of these; or is any other substituent suitable for an alkyl group;

and wherein two Y groups on the same ring can cyclize to form a 3-6 membered ring that can be saturated, unsaturated or aromatic, and which ring may include one heteroatom selected from O, S and N as a ring member and may be optionally substituted;

m is 0-4;

n is 0-3;

each $R^1$ and $R^2$ is independently H or optionally substituted C1-C8 alkyl;

each $R_a$, $R_b$ $R^{3A}$ and $R^{4A}$ is independently H, or C1-C8 alkyl, C3-C7 cycloalkyl, C2-C8 alkenyl, C2-C8 alkynyl, C5-C12 aryl, C5-C20 arylalkyl, or a heteroform of one of these, each of which may be optionally substituted; or $R_a$ and $R_b$, or $R^{3A}$ and $R^{4A}$ may be taken together with the carbon atom to which they are attached to form an optionally substituted 3-7 membered ring, optionally containing one heteroatom selected from N, O and S as a ring member;

V represents a C1-C8 alkyl, C1-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl or C5-C20 heteroarylalkyl, each of which may be optionally substituted with —$OR^9$, —OC(O)$R^9$, —$OSO_2R^9$, C=O, —OC(O)$OR^9$, —COO$R^9$, —$NR^9{}_2$, azido or halo, where each $R^9$ is independently H, or C1-C8 alkyl, C1-C8 alkenyl, C1-C8 alkynyl, C5-C12 aryl, C5-C21 arylalkyl, or a heteroform of one of these, each of which may be optionally substituted; and Z is an optionally substituted C1-C6 aminoalkyl group wherein the amine may be in a protected or unprotected form.

The compounds of the invention synergize with TRAIL (TNF-related apoptosis inducing ligand), with etoposide, with TRAIL-related substances including a TRAIL receptor antibody or TNF-α, and with anti-cancer drugs to overcome the apoptosis-inhibiting activity of caspase inhibiting proteins. Without being bound by theory, the present compounds are believed to act by binding to IAP, thus preventing IAP from binding to and inhibiting caspases. This frees the caspases to initiate apoptosis. Accordingly, the compounds of the invention can promote apoptosis in cells that are abnormally resistant to it, which are typically pathogenic cells.

For example, compounds of the invention induce apoptosis in glioblastoma cell culture, typically at picomolar concentrations. The compounds provide new adjuvant chemotherapeutics for cancers, particularly those that resist programmed cell death by over-expressing IAP proteins. The compounds are stable, protease resistant, and freely membrane permeant. The compounds are not by themselves cytotoxic, however, they are believed to operate by overcoming protective mechanisms that some pathogenic cells such as cancer cells use to prevent apoptosis.

Accordingly, the invention also provides methods and compositions for enhancing apoptosis of pathogenic cells using pro-apoptotic dimer-like or trimer-like small molecules that are referred to as Smac mimetics. The invention also includes pharmaceutical compositions comprising at least one compound of any of formulae (1)-(5) and (7)-(16) admixed with at least one pharmaceutically acceptable excipient. Also included are pharmaceutical compositions comprising at least one compound of formulae (I), (IA), (1A), (3A) and (13A)-(13D) admixed with at least one pharmaceutically acceptable excipient.

Compounds of the invention are useful for the treatment or amelioration of cancer, inflammation, or autoimmune disorders. Provided herein are methods for the use of a dimeric or trimeric SMAC mimetic compound for the treatment or amelioration of cancer, inflammation, or an autoimmune disorder, wherein the dimeric or trimeric SMAC mimetic compound is a compound as defined in any one of formulae (I), (IA), (1), (1A), (2)-(5), (7)-(13), (13A), and (14)-(16). In other embodiments, the invention provides methods for the use of the compounds of the dimeric and trimeric SMAC mimetics of the present invention for enhancing or inducing apoptosis. In another aspect, the invention provides pharmaceutical compositions comprising a dimeric or trimeric SMAC mimetic compound, useful for the treatment or amelioration of cancer, inflammation, or an autoimmune disorder, and at least one pharmaceutically acceptable excipient, wherein the dimeric or trimeric SMAC mimetic compound is a compound as defined in any one of formulae (I), (IA), (1), (1A), (2)-(5), (7)-(13), (13A), and (14)-(16)

In some embodiments, the pharmaceutical compositions further include at least one additional cancer therapeutic whose activity is synergized or potentiated by the Smac mimetic activity of the compounds of the invention. Examples of such additional cancer therapeutics include, without limitation, antimetabolites (e.g. cytarabine, fludaragine, 5-fluoro-2'-deoxyuridine, gemcitabine, hydroxyurea and methotrexate), DNA active agents (e.g. bleomycin, chlorambucil, cisplatin and cyclophosphamide), intercalating agents (e.g. adriamycin and mitoxantrone), protein synthesis inhibitors (e.g. L-asparaginase, cycloheximide and puromycin); topoisomerase inhibitors of Type I class (e.g. camptothecin, topotecan and irinotecan) and Type II class (e.g. etoposide, teniposide anthraquinones, anthracyclines and podophyllotoxin), microtubule inhibitors (e.g. docetaxel, paclitaxel, colcemid, colchicines, vinblastine and vincristine), kinase inhibitors (e.g. flavopiridol, staurosporin and hydroxystaurosporine), drugs that affect Hsp90 (e.g. geldanomycin and geldanomycin derivatives, radicicol, purine derivatives and antibodies or antibody fragments that selectively bind to Hsp90), and/or radiation therapy. In some embodiments, the additional cancer therapeutic agent is TRAIL, etoposide, a TRAIL receptor antibody, a Hsp90 inhibitor, TNF-α or TNF-β.

The general method for enhancing or inducing apoptosis comprises the step of contacting a cell with an effective amount of a Smac mimetic compound, optionally followed by the step of detecting, directly, indirectly or inferentially, a resultant increase in apoptosis of the target cells. It may also include a step of identifying or diagnosing a subject in need of such treatment, particularly a subject having one of the conditions described herein as being treated or alleviated by a Smac mimetic.

In preferred embodiments, the cells are in situ in an individual diagnosed as in need of an apoptosis promoting treatment, and the contacting step is effected by administering to the individual a pharmaceutical composition including a therapeutically effective amount of the Smac mimetic, wherein the individual may be subject to concurrent or antecedent radiation or chemotherapy for treatment of a neoproliferative pathology. In particular embodiments, the pathogenic cells are of a tumor, such as glioblastoma, astrocytoma, breast cancer, prostate cancer, lung cancer, pancreatic cancer, gastric cancer, colon cancer, ovarian cancer, renal cancer, hepatoma, melanoma, lymphoma, or sarcoma.

In additional embodiments, the target cells are pro-inflammatory cells or cells of tissue subject to pathogenic inflammation and/or autoimmunity. A wide variety of diseases involve such pathogenic inflammation, including rheumatoid arthritis, diabetes, asthma, lupus, myasthenia gravis, Graves disease, inflammatory bowel disease (e.g. Crohn's disease, ulcerative colitis and related conditions), pelvic inflammatory diseases, chronic obstructive pulmonary disease (COPD), chronic bronchitis, pneumoconiosis, pulmonary emphysema, interstitial lung fibrosis, allergic rhinitis (hay fever), inflammatory cardiovascular diseases (e.g. congestive heart failure and ischemia/reperfusion injuries), atherosclerosis (including coronary artery disease), stroke, neurodegenerative diseases, such as Alzheimer's disease, multiple sclerosis and amyotrophic lateral sclerosis (ALS), neuroinflammatory diseases, organ transplant rejection, autoimmune hematological disorders, psoriasis, sclerodoma, chronic active hepatitis, primary biliary cirrhosis, glomerulonephritis, uveitis and keratoconjunctivitis.

The subject compositions encompass pharmaceutical compositions containing a therapeutically effective amount of an active, dimer-like or trimer-like Smac mimetic as described above in dosage form, and a pharmaceutically acceptable carrier. In some embodiments, such compositions also contain an additional therapeutic agent, such as an antineoproliferative chemotherapeutic agent, in addition to the Smac mimetic.

MODES OF CARRYING OUT THE INVENTION

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" dimer includes one of more dimers.

As used herein, a "therapeutically effective amount" is an amount required to produce a desired therapeutic effect in a tissue, system, animal, or human, that is being sought, e.g., by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, "subject" refers to a human or animal subject. In certain preferred embodiments, the subject is human.

As used herein, "hydrocarbyl residue" refers to a residue which contains only carbon and hydrogen, unless otherwise provided. The residue may be aliphatic or aromatic, straight-chain, cyclic, branched, saturated or unsaturated, or any combination of these. The hydrocarbyl residue, when so stated, however, may contain heteroatoms in addition to or instead of the carbon and hydrogen members of the hydrocarbyl group itself. Thus, when specifically noted as containing or optionally containing heteroatoms, the hydrocarbyl group may contain one or more heteroatoms as indicated within the "backbone" of the hydrocarbyl residue, and when optionally substituted, the hydrocarbyl residue may also have one or more carbonyl groups, amino groups, hydroxyl groups and other suitable substituents as further described herein in place of one or more hydrogens of the parent hydrocarbyl residue.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, tert-butyl, cyclohexyl, cyclopentylethyl, 2-propenyl, 3-butynyl, and the like. The total number of carbon atoms in each such group is sometimes described herein, e.g., when the group can contain up to ten carbon atoms it may be described as 1-10C or as C1-C10 or as $C_{1-10}$. When heteroatoms (typically N, O and S) are allowed to replace carbon atoms of an alkyl, alkenyl or alkynyl group, as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and they are included within the term "alkynyl" when they contain at least one carbon-carbon triple bond.

Alkyl, alkenyl and alkynyl groups are often substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C5-C12 aryl, or C5-C12 heteroaryl, and each R is optionally substituted with one or more groups selected from halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR' and $NO_2$, wherein each R' is independently H, C1-C8 alkyl, C2-C8 heteroalkyl, C1-C8 acyl, C2-C8 heteroacyl, C5-C12 aryl or C5-C12 heteroaryl. Alkyl, alkenyl and alkynyl groups can also be substituted by C1-C8 acyl, C2-C8 heteroacyl, C5-C12 aryl or C5-C12 heteroaryl, each of which can be substituted by the substituents that are appropriate for the particular group.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one or more heteroatoms selected from O, S and N and combinations thereof, within the backbone residue; thus at least one carbon atom of a corresponding alkyl, alkenyl, or alkynyl group is replaced by one of the specified heteroatoms to form a heteroalkyl, heteroalkenyl, or heteroalkynyl group. Preferably, each heteroalkyl, heteroalkenyl and heteroalkynyl group contains only 1-2 heteroatoms as part of the skeleton of backbone of the heteroalkyl group, i.e., not including substituents that may be present.

The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. Where such groups contain N, the nitrogen atom may be present as NH or it may be optionally substituted if the heteroalkyl or similar group is described as optionally substituted. Where such groups contain S, the sulfur atom may optionally be oxidized to SO or $SO_2$ unless otherwise indicated. For reasons of chemical stability, it is also understood that, unless otherwise specified, such groups do not include more than two contiguous heteroatoms as part of the heteroalkyl chain, although an oxo group may be present on N or S as in a nitro or sulfonyl group. Thus —C(O)NH$_2$ can be a C2 heteroalkyl group substituted with =O; and —SO$_2$NH— can be a C2 heteroalkylene, where S replaces one carbon, N replaces one carbon, and S is substituted with two =O groups.

While "alkyl" as used herein includes cycloalkyl and cycloalkylalkyl groups, the term "cycloalkyl" may be used herein to specifically describe a carbocyclic non-aromatic group that is connected via a ring carbon atom, and "cycloalkylalkyl" may be used to describe a carbocyclic non-aromatic group that is connected to the base molecule through an alkyl linker. Similarly, "heterocyclyl" may be used to describe a non-aromatic cyclic group that contains at least one heteroatom as a ring member and that is connected to the molecule via a ring atom of the cyclic group, which may be C or N; and "heterocyclylalkyl" may be used to describe such a group that is connected to another molecule through an alkyl linker. The sizes and substituents that are suitable for the cycloalkyl, cycloalkylalkyl, heterocyclyl, and heterocyclylalkyl groups are the same as those described above for alkyl groups. The size of a cycloalkylalkyl or heterocyclylalkyl group describes the total number of carbon atoms or of carbon atoms plus heteroatoms that replace carbon atoms of an alkyl, alkenyl, alkynyl, cycloalkyl, or alkylenyl portion. As used herein, these terms also include rings that contain a double bond or two, as long as the ring is not aromatic. As used herein, cycloalkyl may also include bridged carbocyclic ring systems, such as the adamantyl ring system.

As used herein, "acyl" encompasses groups comprising an alkyl, alkenyl, alkynyl, aryl or arylalkyl radical attached at one of the two available valence positions of a carbonyl carbon atom, e.g., —C(=O)R where R is an alkyl, alkenyl, alkynyl, aryl, or arylalkyl group, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings.

Typical heteroaromatic systems include monocyclic C5-C6 aromatic groups such as pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, and tetrazolyl rings, and the fused bicyclic moieties formed by fusing one of these monocyclic groups with a phenyl ring or with any of the heteroaromatic monocyclic groups to form a C8-C12 bicyclic group such as indolyl, benzimidazolyl, indazolyl, benzotriazolyl, isoquinolinyl, quinolinyl, benzothiazolyl, benzofuranyl, benzothienyl, benzisoxazolyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity, even though it may be fused to a non-aromatic ring, such as tetrahydronaphthyl, indanyl, fluorenyl, and the like. Typically, the ring systems contain 5-12 ring member atoms. Preferably the monocyclic heteroaryl groups contain 5-6 ring members, and the bicyclic heteroaryls contain 8-12 ring members.

Aryl and heteroaryl moieties may be optionally substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCOOR, NRCOR, CN, COOR, CONR$_2$, OOCR, —C(O)R, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C21 arylalkyl, or C5-C21 heteroarylalkyl, and each R is optionally substituted as described above for alkyl groups.

Preferred optional substituents when present on an aryl or heteroaryl ring include optionally halogenated alkyl (C1-C4), optionally halogenated alkoxy (C1-C4), halo, —NH$_2$, —OH, —CN, —NO$_2$, and NR$_2$, where each R is independently H or C1-4 alkyl.

The substituent groups on an aryl or heteroaryl group may of course be further substituted with the groups described herein as suitable for each type of group that comprises the substituent. Thus, for example, an arylalkyl substituent may be optionally substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety.

An aryl or heteroaryl ring in an arylalkyl or heteroarylalkyl group may be optionally substituted with the same substituents described above for aryl groups. Preferably, an arylalkyl group includes a phenyl ring optionally substituted with the groups defined above for aryl groups and a C1-C8 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane.

Similarly, a heteroarylalkyl group preferably includes a C5-C6 monocyclic heteroaryl group that is optionally substituted with the groups described above as substituents typical on aryl groups and a C1-C8 alkylene that is unsubstituted or is substituted with one or two C1-C4 alkyl groups or heteroalkyl groups, or it includes an optionally substituted phenyl ring or C5-C6 monocyclic heteroaryl and a C1-C8 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-14 and preferably n is 1-8, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. However, for clarity, a three-atom linker that is an alkylene group, for example, refers to a divalent group in which the available valences for attachment to other groups are separated by three atoms such as —$(CH_2)_3$—, i.e., the specified length represents the number of atoms linking the attachment points rather than the total number of atoms in the hydrocarbyl group: —C(Me)$_2$- would thus be a one-atom linker, since the available valences are separated by only one atom. Where an alkylene group is substituted, the substituents include those typically present on alkyl groups as described herein, thus —C(=O)— is an example of a one-carbon substituted alkylene. Where it is described as unsaturated, the alkylene group may contain one or more double or triple bonds, and may be referred to as alkenylene group if it contains at least one carbon-carbon double bond, or as an alkynylene group if it contains at least one carbon-carbon triple bond.

"Heteroalkylene" as used herein is defined similarly to the corresponding alkylene groups, but the 'hetero' terms refer to groups that contain one or more heteroatoms selected from O, S and N and combinations thereof, within the backbone residue; thus at least one carbon atom of a corresponding alkylene group is replaced by one of the specified heteroatoms to form a heteroalkylene group. Thus, —C(=O)NH— is an example of a two-carbon substituted heteroalkylene, where N replaces one carbon, and C is substituted with a =O group.

"Arylene" as used herein refers to divalent or trivalent aromatic or heteroaromatic ring systems that are bonded to their attachment points through a bond.

"Arylalkylene" as used herein refers to divalent or trivalent aromatic and heteroaromatic ring systems which are bonded to their attachment points through alkylene linking groups, including substituted or unsubstituted, saturated or unsaturated, cyclic and acyclic linkers. In some embodiments, the alkylene linking group is unsaturated, and may be referred to as arylalkenylene group if it contains at least one carbon-carbon double bond, or as an arylalkynylene group if it contains at least one carbon-carbon triple bond. Typically the alkylene linker is C1-C8 alkylene or a heteroform thereof. These linkers may also include a carbonyl group, thus making them able to provide substituents such as an acyl or heteroacyl moiety. For example, $CH_2)_2C(O)$—Ar—$C(O)(CH_2)_2$— and —$CH_2$—Ar—$CH_2$— are examples of arylalkylene groups.

"Heteroarylalkylene" as used herein is defined similarly to the corresponding arylalkylene group, but contains one or more heteroatoms, selected from O, S and N and combinations thereof, within the alkylene residue or the aromatic ring; thus at least one carbon atom of a corresponding alkylene group or one carbon atom of the aromatic ring is replaced by one of the specified heteroatoms to form a heteroarylalkylene group. For example, —$(CH_2)_2$NHC(O)—Ar—C(O)NH$((CH_2)_2$— and —$CH_2$-pyridyl-$CH_2$— are examples of heteroarylalkylene groups.

In general, any alkyl, alkenyl, alkynyl, acyl, or aryl or arylalkyl group or any heteroform of one of these groups that is contained in a substituent may itself be optionally substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not intended to be included. However, alkyl substituted by halo, aryl, heteroaryl, amino, hydroxy, alkoxy (C1-C4 alkyl), =O, =S, and the like would be included within the scope of the invention, and the atoms of these substituent groups are not counted in the number used to describe the alkyl, alkenyl, etc. group that is being described.

Where no number of substituents is specified, each such alkyl, alkenyl, alkynyl, acyl, or aryl group may be optionally substituted with a number of substituents according to its available valences and in accord with known principles of chemical stability; in particular, any of these groups may be optionally substituted with fluorine atoms at any or all of the available valences on carbon atoms, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that, unless otherwise specified, no more than two N, O or S atoms are ordinarily connected sequentially, except where an oxo group is attached to N or S to form a nitro or sulfonyl group.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Halo", as used herein includes fluoro, chloro, bromo and iodo. Fluoro and chloro are often preferred.

"Amino" as used herein refers to NH$_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding type of group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, an 'azacyclic' group refers to a heterocyclic group containing at least one nitrogen as a ring atom, wherein the group is attached to the base molecule through a nitrogen atom of the azacyclic ring. Typically these azacyclic groups are 3-8 membered monocyclic rings or 8-12 membered bicyclic fused ring systems. An azacyclic group having more than four ring members can optionally include one additional heteroatom selected from N, O and S, and an azacyclic group having more than six ring members can optionally include one or two additional heteroatoms selected from N, O and S. Typically, an azacyclic group is non-aromatic, and such azacyclic groups can optionally be substituted with substituents that are suitable for alkyl groups. Typical examples of azacyclic groups include pyrrolidine, pyrrolidinone, piperidine, morpholine, thiomorpholine, and piperazine. In certain embodiments, an azacyclic group can be aromatic, provided that at least one ring nitrogen atom is in a five membered ring so the nitrogen can serve as the point of attachment to the base molecule. Examples of aromatic systems that can be azacyclic groups include pyrrole, imidazole, pyrazole, triazole or indole.

The invention provides dimer-like and trimer-like compounds of formulae (I) and (IA) that possess two or three structurally similar binding domains. In many embodiments, each binding domain includes a monocyclic or fused bicyclic ring system that is substituted by at least one aryl-containing group, —W—X. These binding domains are linked by a linking group, and while similar, the domains need not be identical. In certain embodiments of formula (I), each binding domain is the same, so the molecule is symmetric about its linking group.

The apoptosis-promoting compounds of formula (I) where b is 0 are sometimes described herein as 'dimers'. These 'dimers' include both symmetric dimers formed containing two identical monomers of, e.g., formula (6), or formula (17), or formula (18), or formula (19), as well as unsymmetrical dimers. The unsymmetrical dimers may contain two non-identical monomers of a single class (e.g., both are compounds of formula (6)), or they may contain monomers selected from different classes, e.g., a monomer of formula (6) with a monomer of formula (17) or (18) or (19).

In other embodiments, the apoptosis-promoting compounds of formula (I) are sometimes described herein as 'trimers', when b is 1. These 'trimers' include both symmetric trimers formed containing three identical monomers of, e.g., formula (6), or formula (17), or formula (18), or formula (19), as well as unsymmetrical trimers. The unsymmetrical trimers may contain three non-identical monomers of a single class (e.g., all are compounds of formula (6)), or they may contain monomers selected from one or two or three different classes, e.g., one or two monomers of formula (6) with one or more monomers of formula (17) or (18) or (19).

In compounds of formula (I), two or three amide-containing binding domains, D, D' and D", are linked together by a linkage depicted as Q-L-Q', when b is 0, or Q-L(-Q")-Q", when b is 1:

$$D\text{-}Q\text{-}L\text{-}Q'\text{-}D' \atop [Q''\text{-}D'']_b.$$  (I)

As further described herein for specific embodiments, this linkage can comprise numerous alternatives that can include a chain that may be substituted and may be saturated or unsaturated; it may also include a combination of cyclic and acyclic features. In frequent embodiments, L represents an optionally substituted C1-C24 hydrocarbyl linker, optionally containing from 1-8 heteroatoms selected from N, O and S, which linker is 1-18 atoms in length when counted along the shortest path between Q and Q', or Q and Q", or Q' and Q".

In compounds of formula (I), each Q, Q' and Q", where present, independently represents —O— or —NR$^2$—, where each R$^2$ is independently H, optionally substituted C1-C8 alkyl or optionally substituted C1-C8 heteroalkyl; or —CH$_2$—, —CH(OR)—, —CH(R)—, —CH$_2$O—, —CH(R)O— or —(CH$_2$)$_4$NH—, wherein R is H, C$_1$-C$_4$ alkyl or C$_1$-C$_4$ heteroalkyl; or one or more of Q, Q' and Q" may be a bond when L comprises a ring.

Each amide-containing binding domain, D, D' and D", where present, is independently selected from the group consisting of

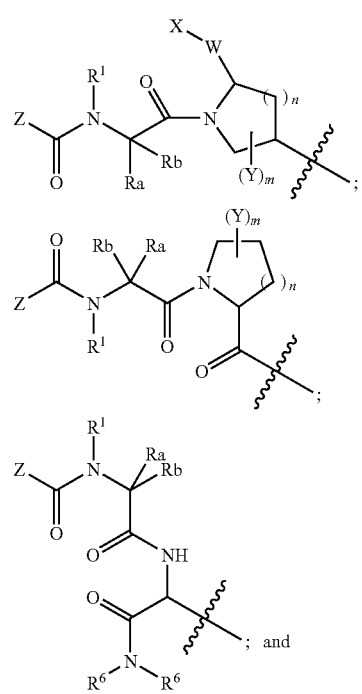

-continued

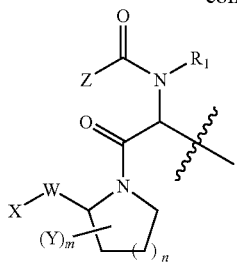

wherein each $R_a$, $R_b$, $R^1$, Z, Y, W, X, n, m, and $R^6$ are as further defined herein;

with the proviso that, when b is 0, D and D' are not both of the formula

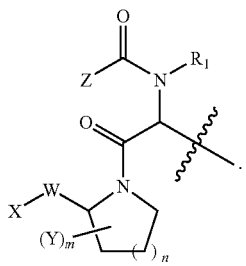

In some embodiments, of formula (I), when b is 0, D and D' are not both of the formula

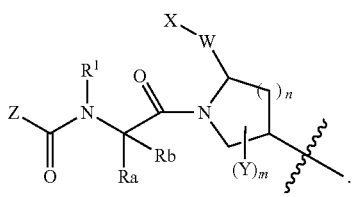

In compounds of formula (I) where b is 0, the amide binding domains D and D' may be the same or different. In certain embodiments, they are different, meaning that their backbone structures are different. In other embodiments of formula (I), the amide binding domains D and D' are the same, meaning that their backbone structures are the same, although they may be differentially substituted. In further embodiments, amide binding domains D and D' may be identical, comprising identical backbone structures, and bearing identical substituents.

In preferred embodiments of formulae (I), when b is 0, both D and D' are of the formula

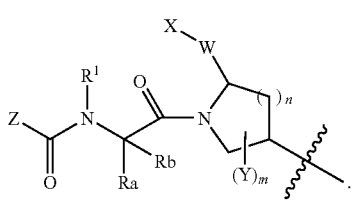

In compounds of formula (I) where b is 1, the amide binding domains D, D' and D" may be the same or different. In certain embodiments, they are different, meaning that the backbone structures of one or more of D, D' and D" are different. In other embodiments of formula (I) where b is 1, the amide binding domains D, D' and D" are the same, meaning that their backbone structures are the same, although they may be differentially substituted. In further embodiments, amide binding domains D, D' and D" may comprise identical backbone structures, bearing identical substituents.

In some embodiments of formula (I), each $R_a$ and $R_b$ is independently H, or C1-C8 alkyl, C2-C8 alkenyl or C2-C8 alkynyl, or a heteroform of one of these, each of which may be optionally substituted; or is optionally substituted phenyl. Each $R^1$ is independently H or optionally substituted C1-C8 alkyl, and each n, where present, is independently 0-3. In preferred embodiments, each $R^1$ is H and n is 1.

Each Z in compounds of formula (I) independently represents an optionally substituted C1-C6 aminoalkyl group. In frequent embodiments, each Z represents a 1-aminoalkyl substituent. In certain preferred embodiments, Z represents a group of the formula —CH($R^3$)$NR^4_2$, where $R^3$ and $R^4$ are as further described herein. In more preferred embodiments, each of $R^3$ and $R^4$ is independently selected from H and C1-C4 alkyl. In particularly preferred embodiments, one $R^4$ is H and the other is methyl.

Where present, each Y in compounds of formula (I) independently represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl, and wherein two Y groups can cyclize to form a 3-6 membered ring that can be saturated, unsaturated or aromatic, and which ring may include a heteroatom selected from O, S and N as a ring member and may be optionally substituted. Each m, where present, is independently 0-4; in many embodiments, m is 0 or 1, and each Y, where present, is the same.

In compounds of formula (I), each W, where present, independently represents an optionally substituted C1-C6 alkylene or C1-C6 heteroalkylene. In certain preferred embodiments, W comprises an amide moiety. Each X, where present, independently represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring. In specific embodiments, X represents a phenyl ring, or two phenyl rings attached to the same atom of W, or a tetrahydronaphthyl or indanyl ring system, each of which may be optionally substituted.

In compounds of formula (I), each $R^6$, where present, is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring. In certain embodiments, each $R^6$ independently represents H, methyl, or optionally substituted benzyl, phenethyl, diphenylmethyl, pyridylmethyl, or pyridylethyl. In specific embodiments, one $R^6$ is H, and the other represents an optionally substituted tetrahydronaphthyl, indanyl or fluorenyl ring system attached to nitrogen through an open valence on the saturated ring.

The same groups described herein for formula (I) are also suitable for formula (IA).

In compounds of formula (1), two amide-containing domains are linked together by a linkage depicted as -Q-L-

Q'-. This linkage can comprise numerous alternatives that can include a chain that may be optionally substituted and/or unsaturated; it may also include a combination of cyclic and acyclic features.

In many embodiments of formula (1), L represents a C1-C24 hydrocarbyl linker, optionally containing from 1-8 heteroatoms selected from N, O and S. In compounds of formula (1), L represents a linker between Q and Q' that is 1-18 atoms in length when counted along the shortest path (by atom count) between Q and Q'. L may be optionally substituted as described herein with substituents that are suitable for its structure.

In some embodiments, L is an optionally substituted and/or unsaturated C1-C14 alkylene or C1-C14 heteroalkylene. For example, L may represent a C1-C14 alkylene, C1-C14 alkenylene, C1-C14 alkynylene linker, or a heteroform of one of these, each of which may be optionally substituted. In frequent embodiments, L is substituted with one or more carbonyl substituents (=O), to form a linker comprising one or more acyl groups.

In certain embodiments, L is symmetric about its central atom (if the chain connecting the two available valences is an odd number of atoms in length) or its central bond (if the chain connecting the two available valences is an even number of atoms in length). In some embodiments, L is 2-8 atoms in length, counting along the shortest path between Q and Q'. In certain embodiments, L can also include one or more heteroatoms selected from N, O and S, but does not include a disulfide linkage.

In compounds of formula (1), L can be substituted by substituents including rings, and it can comprise one or more rings as part of the linkage that connects Q and Q' together. Where L comprises at least one ring that is part of or is fused to the shortest path (by atom count) connecting Q and Q', Q and/or Q' in formula (1) can be a bond as well as any of the other structures described herein for Q and Q'. Where L comprises a ring, the ring(s) may be cycloalkyl, heterocyclyl, aryl, or heteroaryl, and may be further substituted. Such rings may be alternatively referred to herein as carbocyclic, heterocyclic, aromatic or heteroaromatic, each of which may be optionally substituted.

Such rings can be connected to Q and/or Q' (or, where Q and/or Q' represents a bond, the rings can be connected by the bond Q or Q' directly to the carbon to which Q or Q' is attached), at any ring position, and it may be attached either directly or through an optionally substituted intervening alkylene or heteroalkylene group, provided the shortest path (by atom counting) between Q and Q' is 1-18 atoms in length, and preferably 2-8 atoms in length. For example, L could be a 1,3-disubstituted aryl or heteroaryl linker, or a buten-1,4-diyl linker.

Frequently, the ring which is part of L is substituted by carboxy groups which form the point of attachment to Q or Q', such that an ester or amide linkage is formed by the bond between Q/Q' and L.

In preferred embodiments, L comprises an optionally substituted 5- or 6-membered aromatic or heteroaromatic ring. In specific embodiments, L comprises at least one optionally substituted phenyl, pyrazole or triazole ring.

In some embodiments, L comprises an optionally substituted phenyl or pyridyl ring that may be 1,2-disubstituted, or 1,3-disubstituted, or 1,4-disubstituted, by the groups Q and Q', which may be directly attached to the ring or may be separated from the ring by one or more atoms that are included in L. In other embodiments, L comprises an optionally substituted pyrazinyl, triazinyl, pyrazolyl, or thiophenyl ring, each of which may be optionally substituted. In further embodiments, L comprises at least one optionally substituted triazole ring that is part of the linker between Q and Q'.

Rings which comprise part of the linker, L, may be optionally substituted to the extent such substitution makes chemical sense. Preferred optional substituents when present on a ring which comprises part of L include alkyl (C1-C4), alkoxy (C1-C4), —CF$_3$, —OCF$_3$, halo, —OH, —NO$_2$, —CN, or NR$_2$, where each R is independently H or C1-C4 alkyl.

In certain embodiments of formula (1), L comprises an optionally substituted arylene or arylalkylene group, or a heteroform of one of these, to which Q and Q' are attached. For example, L can be —CH$_2$—Ar—CH$_2$—, —C(O)—Ar—C(O)—, —SO$_2$—Ar—SO$_2$—, —C(O)—Ar— or —Ar—, where Ar represents an optionally substituted 5- or 6-membered aromatic or heteroaromatic ring. In some embodiments, L comprises a phenyl ring that may be 1,2-disubstituted, or 1,3-disubstituted, or 1,4-disubstituted by the groups Q and Q', which may be directly attached to the ring or may be separated from the ring by one or more atoms that are included in L. In other embodiments, L comprises an optionally substituted 5- or 6-membered heteroaryl ring, which may contain from 1-4 heteroatoms selected from N, O and S as a ring member. In further embodiments, L comprises an optionally substituted C3-C10 cycloalkylene ring.

In certain embodiments, L comprises one or more triazole rings which may be directly attached to the azacyclic core through the bond Q and/or Q' or which may be attached through an alkylene or heteroalkylene linker. In specific embodiments, L comprises two triazole rings each attached directly to an azacyclic core through the bonds Q and Q', wherein the two triazole rings are separated by an optionally substituted, saturated or unsaturated alkylene or heteroalkylene group, or by an arylene moiety.

In certain embodiments of formula (1), -Q-L-Q'- represents a structure selected from the following group:

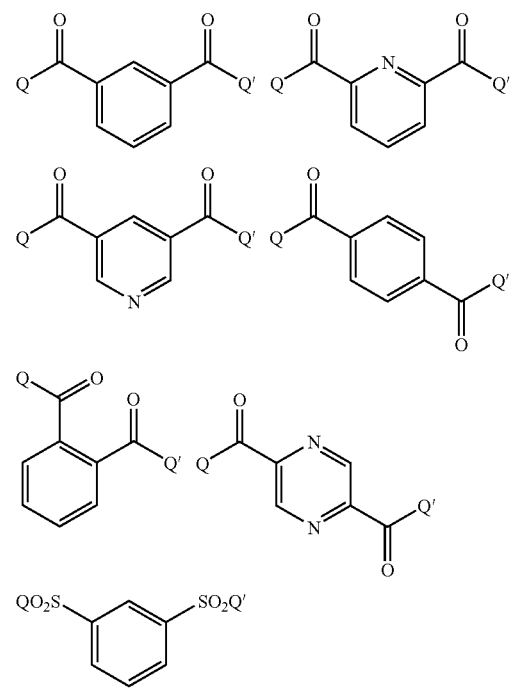

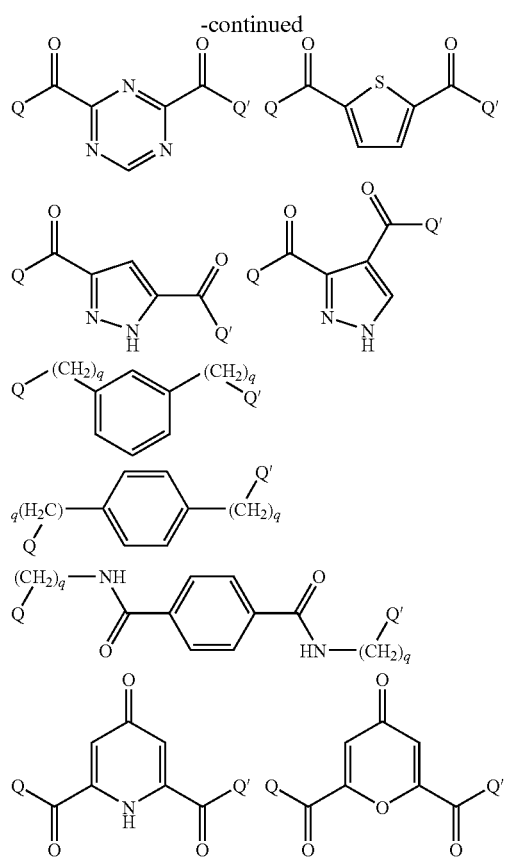

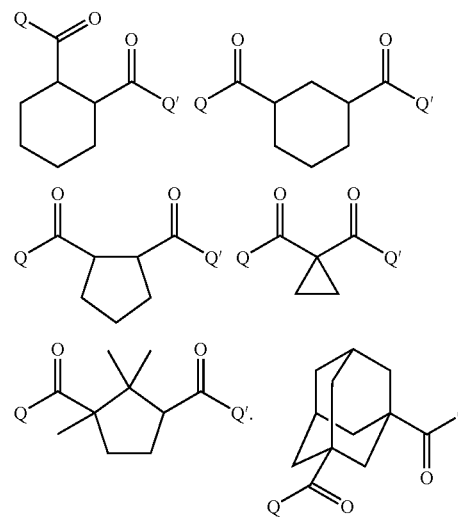

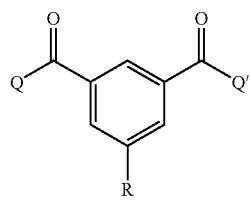

wherein each q is independently 0-8, and each aromatic, heteroaromatic and heterocyclic ring is optionally substituted. In certain embodiments, the ring that comprises part of L is substituted with one or more substituents selected from the group consisting of —OH, —OMe, halo, $NO_2$ or $NH_2$.

In particular embodiments, -Q-L-Q'- represents a structure

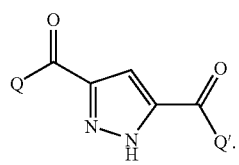

wherein R is —OH, —OMe, halo, $NO_2$ or $NH_2$. In certain preferred embodiments, R is OH, OMe or $NH_2$.

In other preferred embodiments, -Q-L-Q'- represents a structure

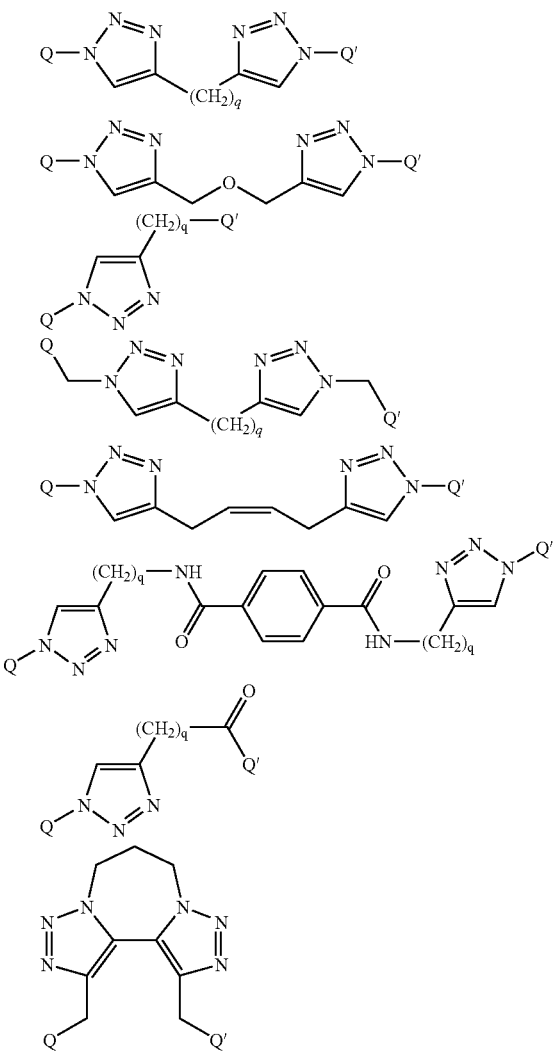

In other embodiments, -Q-L-Q'- represents a structure selected from the following group:

In still further embodiments, -Q-L-Q'- represents a structure selected from the following group:

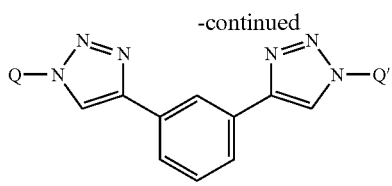

wherein each q is independently 0-8, and each aryl or heteroaryl ring and alkylene group is optionally substituted.

In other embodiments, L comprises an optionally substituted C1-C14 alkylene or C1-C14 heteroalkylene which may be saturated or unsaturated. For example, L can be —(CH$_2$)$_q$— where q is 1-8, and may be optionally substituted with groups suitable for an alkyl group. In certain embodiments, the alkylene chain is substituted with one or two carbonyl oxygens (=O). When L is unsaturated, it is sometimes a C1-C14 alkenylene or C1-C14 alkynylene linker. For example, L can be 1,4-but-2-enylene (—CH$_2$—CH=CH—CH$_2$—); 1,10-deca-4,6-diynylene (—(CH$_2$)$_3$C≡C—C≡C(CH$_2$)$_3$—; 1,7-hepta-1,3-diynylene (—C≡C—C≡C(CH$_2$)$_3$—; or an optionally substituted version of one of these. L can also include one or more heteroatoms, for example, it can be —CH$_2$—O—CH$_2$— or —(CH$_2$)$_2$NHC(O)ArC(O)NH(CH$_2$)$_2$— or a substituted version of one of these.

In some embodiments, -Q-L-Q'- represents a structure selected from the following group:

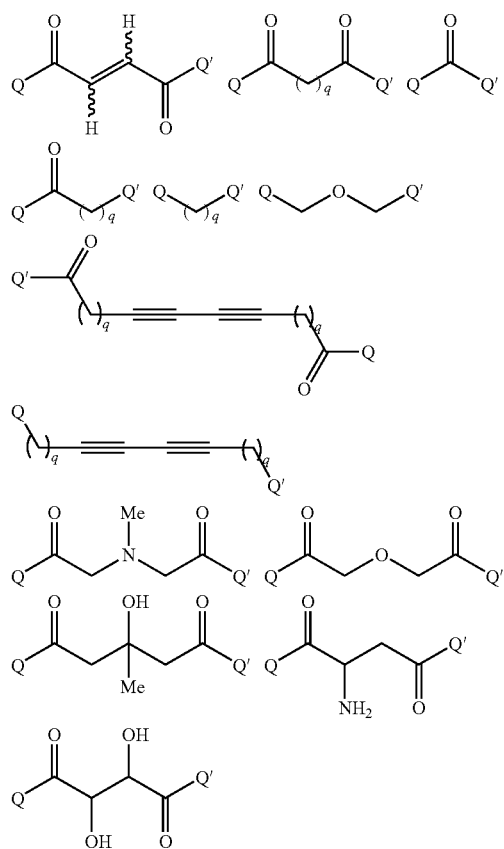

wherein each q is independently 0-8, and each alkylene group may be optionally substituted.

The same groups described here for L in compounds of formula (1) are also suitable for L in compounds of formulae (I), (IA), (1A), (2)-(5), (7)-(16), (3A) and (13A).

In compounds of formula (1), each Q and Q' may independently represent —O— or —NR$^2$—, where each R$^2$ is independently H, or a C1-C4 alkyl. In some embodiments, Q and Q' are the same. In specific embodiments, each Q and Q' is —NH—. In other embodiments, each Q and Q' may independently represent a bond when L comprises a ring. In specific embodiments, each Q and Q' independently represents a bond when L comprises at least one triazole ring.

The same groups described here for Q and Q' in compounds of formula (1) are also suitable for Q, Q', and Q", if present, in compounds of formulas (2)-(5), (9) and (13), and for Q in compounds of formulas (7)-(8) and (14)-(16).

In compounds of formula (1), n and n' can independently be 0-3, and in some embodiments n and n' are the same. In certain embodiments, n and n' are each selected from 1 and 2 and can be the same or different; in specific embodiments, n and n' are both 1.

In compounds of formula (1), each of (Y)$_m$ and (Y')$_{m'}$ represents one or more substituents optionally present on the nitrogen-containing ring, and each of m and m' is 0-4. In compounds of formula (1), each of the nitrogen-containing rings may be differently substituted. Each Y and Y' is independently selected from the substituents described herein as suitable for alkyl groups. For example, each Y and Y' may independently represent C1-C8 alkyl, =O, OR, NR$_2$, OC(O)R, NRC(O)R, NRSO$_2$R or COOR, wherein each R is independently H, C1-C8 alkyl or C1-C8 heteroalkyl. In certain embodiments, two Y or Y" groups on a single nitrogen-containing ring groups may cyclize to form a saturated, unsaturated or aromatic ring having 3-6 ring members and optionally containing one heteroatom (N, O or S) as a ring member, and such ring embodiments may be optionally substituted with suitable substituents as described herein.

In certain embodiments of formula (1), m and m' are the same. In many embodiments, each of m and m' is either 0 or 1. Specific embodiments include m=m'=1 and m=m'=0. In some embodiments where m and m' are 1, each of Y and Y' are the same.

The groups described herein for Y and Y' in compounds of formula (1) are also suitable for Y, Y', and Y''', where present, in compounds of formulas (1A), (3A), (2)-(9), (12)-(13), (15)-(16), and (18)-(19). In such compounds, each of m, m' and m", where present, are 0-4.

In compounds of formula (1), each R$_a$, R$_{a'}$, R$_b$ and R$_{b'}$ is independently H, C1-C8 alkyl, C2-C8 alkenyl, or C2-C8 alkynyl, or a heteroform of one of these, each of which may be optionally substituted; or is optionally substituted phenyl. In some embodiments, one of R$_a$ and R$_b$ is H, and the other is C1-C4 alkyl, C2-C4 alkenyl, C2-C4 alkynyl and one of R$_{a'}$ and R$_{b'}$ is H, and the other is C1-C4 alkyl, C2-C4 alkenyl, or C2-C4 alkynyl. In other embodiments, one of R$_a$ and R$_b$ is H, and the other is cyclohexyl or optionally substituted phenyl.

For compounds of formula (1), each R$^1$ and R$^{1'}$ is independently H or optionally substituted C1-C8 alkyl; in preferred embodiments, R$^1$ and R$^{1'}$ are H.

Each of Z and Z' in compounds of formula (1) is independently an optionally substituted C1-C6 aminoalkyl group. This can be a C1-C6 alkyl group that is substituted with at least one amine group and is optionally substituted with one or more other groups suitable as substituents for an alkyl group. In some embodiments, Z and Z' can be a 1-aminoalkyl group such as a 1-aminomethyl or 1-aminoethyl or 1-aminopropyl, where the amine group is substituted with one or two optionally substituted C1-C8 alkyl groups, and may also be substituted with a C1-C8 acyl or heteroacyl group. In a typical embodiment, each of Z and Z' is 1-aminopropyl, or 1-aminoethyl, or aminomethyl, or 1-methylaminopropyl, or 1-methylaminoethyl. Alternatively, Z or Z' can be 1-ethylaminomethyl or 1-ethylaminoethyl. In certain embodiments, Z and Z' are the same. Where Z or Z' has a chiral center adjacent to the carbonyl to which it is connected, the chiral center may have either the (R) or the (S) configuration. For specific embodiments, it is sometimes preferably in the (S) absolute configuration. In specific embodiments, Z is a group of the formula —CH($R^3$)$NR^4_2$, as further described herein.

The same groups described for Z and Z' in compounds of formula (1) are suitable for Z, Z' and Z", where present, in compounds of formulae (1A), (2)-(3) and (6)-(17).

In compounds of formula (1), each W and W' independently represents an optionally substituted C1-C6 alkylene or C1-C6 heteroalkylene linker to which X or X' is attached. Each of W and W' in formula (1) is independently selected, so they can be the same or different. In some embodiments, W and W' are the same; in many embodiments, each of W and W' is substituted with =O. In certain embodiments, each of W and W' may be represented as —C(O)NR(CHR)p—, where each p is 0-2, and each R is independently H, or C1-C4 alkyl or C1-C4 heteroalkyl.

Each of X and X' in compounds of formula (1) represents a C5-C20 ring system comprising at least one aryl or heteroaryl group and up to four heteroatoms selected from N, O and S as a ring member, and can be a single 5-15 membered cyclic group or it can be two 5-10 membered cyclic groups that are both attached to a single atom of W or W'. Each of these cyclic groups can be a single ring, a fused ring system, or linked rings such as a biaryl group. Optionally, each X and X' can be substituted and can include up to four heteroatoms selected from O, N and S. Thus, by way of example, each X and X' can comprise an aryl or heteroaryl ring, which can be monocyclic or bicyclic, provided at least one ring of a bicyclic group is aromatic, or it can represent two 5-10 membered cyclic group provided that at least one of them comprises an aryl or heteroaryl ring.

In specific embodiments, each X and X' independently comprises an optionally substituted phenyl ring; or two phenyl rings on one atom of W or W', which can be substituted on one or both phenyl rings; or each X and X' can independently comprise a fused ring system having two aromatic rings or having a saturated 5-6 membered ring fused to a 5-6 membered aryl ring, each of which can be substituted on either or both rings. X and X' are independently selected, and may be the same or different. In specific embodiments, X and X' are sometimes the same.

When X and/or X' comprises a 5 or 6 membered saturated ring fused to a 5 or 6 membered aryl ring, in some embodiments, X is attached to W through an atom in the saturated ring. In specific embodiments, each X and X' is independently a tetrahydronaphthyl, indanyl or fluorenyl ring system linked to nitrogen of W or W' through an open valence on the saturated ring of the tetrahydronaphthyl, indanyl or fluorenyl ring system. In certain embodiments, X comprises one or two aryl rings, preferably one or two phenyl rings; and each aryl ring is attached to W through a terminal carbon atom of W. For example, in some embodiments, —W—X comprises an arylalkyl group, such as benzyl, 1-phenylethyl, or diphenylmethyl.

The aryl or heteroaryl ring in any of these embodiments may be optionally substituted. Preferred substituents when present on an aryl or heteroaryl ring that is part of X or X' include C1-C4 alkyl, C1-4 heteroalkyl, C1-C4 alkenyl, C1-4 heteroalkenyl, C1-C4 alkynyl, C1-4 heteroalkynyl, OR, $NR_2$, SR, S(O)R, $SO_2R$, C(O)R, C5-12 aryl, C5-12 heteroaryl, C5-12 arylalkyl, C5-12 heteroarylalkyl, and halo, where each R is independently H, or C1-C4 alkyl, C1-C4 heteroalkyl, C5-C12 aryl, C5-C12 heteroaryl, C5-C12 arylalkyl, or C5-C12 heteroarylalkyl, each of which may be further substituted with groups suitable for its structure; and wherein any alkyl or arylalkyl substituent may be optionally fluorinated on the alkyl portion. More preferred substituents when present on an aryl or heteroaryl ring that is part of X include C1-4 alkyl, C1-4 alkoxy, $CF_3$, $OCF_3$, halo, $NO_2$, CN, and $NR_2$, where each R is independently H or C1-4 alkyl.

In particular embodiments of the compounds of the invention, —W—X and X'—X' represent a group of the form —C(O)NR(CHR)$_p$X or —C(O)NR(CHR)$_p$X', where each p is 0-2, and each R is independently H or a C1-C8 alkyl group. In certain embodiments, p is 0 or 1, and each R may be H or methyl. In some embodiments, —W—X and X'—X' are the same, though they can be different. In preferred embodiments, each X and X' independently comprises one or two phenyl groups, or a tetrahydronaphthyl, indanyl or fluorenyl ring system linked to nitrogen of W through an open valence on the saturated ring of the tetrahydronaphthyl, indanyl or fluorenyl ring system.

In preferred embodiments of the compounds of the invention, —W—X and X'—X' represent a group of the form —C(O)NH(CHR)Ph', where R is H or Me, and Ph' is optionally substituted phenyl. In other preferred embodiments, —W—X and X'—X' represent a group of the form —C(O)NHCH(Ph')$_2$, where Ph' is optionally substituted phenyl. In further preferred embodiments, —W—X and X'—X' represent a group of the form —C(O)NH—Ar', where Ar' represents a tetrahydronaphthyl ring system, preferably bonded to the amide nitrogen through one of the atoms in the saturated ring.

The same groups described for W, W', X and X' in compounds of formula (1) are suitable for W, W', W", X, X' and X", where present, in compounds of formulae (1A), (2)-(9), (12), (16) and (18).

The same groups described here for compounds of formula (1) are also suitable for compounds of formulae (I), (IA), (1A), (2)-(5), (7)-(16), (3A) and (13A).

In compounds of formula (2), three amide-containing domains are linked together by a linkage depicted as Q-L(-Q")-Q', wherein L is defined as above for compounds of formula (1). In many embodiments, L comprises a C5-C12 arylene or C5-C21 arylalkylene group, or a heteroform of one of these, each of which may be optionally substituted. In preferred embodiments, L comprises a tri-substituted 5- or 6-membered aryl or heteroaryl ring. In specific embodiments, Q-L(-Q")-Q' represents a structure selected from the following group:

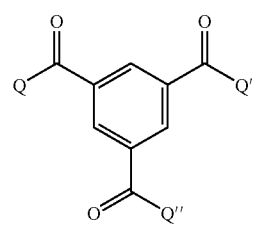

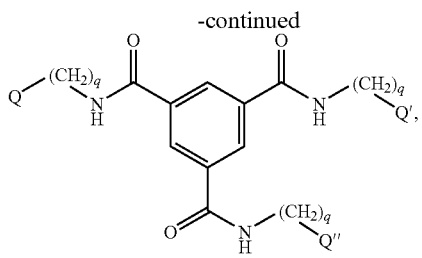

wherein each q is independently 0-8, and each phenyl ring is optionally substituted with 1-2 groups selected from C1-C4 alkyl, C1-C4 alkoxy, $CF_3$ and halo.

In compounds of formula (2), each Q, Q' and Q" may independently represent —O— or $NR^2$—, where each $R^2$ is independently H or a C1-C8 alkyl, or C1-C8 heteroalkyl, which may be optionally substituted. In some embodiments, each of Q, Q' and Q" may independently be a bond when L comprises a ring. In certain embodiments, Q, Q' and Q" are the same. In specific embodiments, each of Q, Q' and Q" is —NH—. In other specific embodiments, each of Q, Q' and Q" represents a bond. In specific embodiments, each of Q, Q" and Q' is a bond when L comprises one or more triazole rings.

In compounds of formula (2), n, n' and n" can independently be 0-3, and in some embodiments n, n' and n" are the same. In specific embodiments, each of n, n' and n" is 1.

In compounds of formula (2), $(Y)_m$, $(Y')_{m'}$ and $(Y")_{m"}$, where present, are defined as described above for compounds of formula (1). Each of m, m' and m", where present, may be 0-4. In some embodiments of formula (2), each of m, m' and m" is the same. In certain embodiments, each of m, m' and m" is 0. Where any of m, m' or m" is other than zero, each Y, Y' and Y" present is independently selected from the substituents suitable for alkyl groups as described above.

In compounds of formula (2), each $R_a$, $R_{a'}$, $R_{a"}$, $R_b$, $R_{b'}$ and $R_{b"}$ is independently H or C1-C8 alkyl, which may be optionally substituted. In some embodiments, $R_a$, $R_{a'}$ and $R_{a"}$ are H and $R_b$, $R_{b'}$ and $R_{b"}$ are C1-C8 alkyl. Each $R^1$, $R^{1'}$ and $R^{1"}$ is independently selected from H and C1-C8 alkyl; in preferred embodiments, each $R^1$, $R^{1'}$ and $R^{1"}$ is H.

Each of Z, Z' and Z" in compounds of formula (2) is independently an optionally substituted (C1-C6) aminoalkyl group, as described for formula (1). In some embodiments, Z, Z' and Z" can be a 1-aminoalkyl group such as the groups described above for formula (1). In a typical embodiment, each of Z, Z' and Z" is 1-aminopropyl, or 1-aminoethyl, or aminomethyl, or 1-methylaminopropyl, or 1-methylaminoethyl, or methylaminomethyl. Alternatively, each Z, Z' and Z" can be 1-ethylaminomethyl or 1-ethylaminoethyl. In certain embodiments, Z, Z' and Z" are the same. Where Z, Z' or Z" has a chiral center adjacent to the carbonyl to which it is connected, the chiral center may have either the (R) or the (S) configuration. For specific embodiments, it is sometimes preferably in the (S) configuration.

In compounds of formula (2), each W, W' and W'" independently represents an optionally substituted C1-C6 alkylene or C1-C6 heteroalkylene linker to which X, X' or X" is attached. In some embodiments, W, W' and W" are the same; in many embodiments, each of W, W' and W" is substituted with C=O. In certain embodiments, each of W, W' and W" may be represented as —C(O)NR(CHR)p-, where each p is 0-2, and each R is independently H, or C1-C4 alkyl or C1-C4 heteroalkyl.

Each of X, X' and X" in compounds of formula (2) represents an optionally substituted C5-C20 ring system comprising at least one aryl or heteroaryl group having up to four heteroatoms selected from O, N and S as a ring member, as described for groups X and X' in formula (1). In preferred embodiments, each of X, X' and X" comprises an optionally substituted phenyl ring; or two phenyl rings, each of which may be optionally substituted, on one atom of W, W' or W"; or each of X, X' and X" comprises a tetrahydronaphthyl, indanyl or fluorenyl group, each of which can be optionally substituted on either or both rings.

When X, X' or X" comprises a 5 or 6 membered saturated ring fused to a 5 or 6 membered aryl ring, in some embodiments, each X, X' or X" is attached to W, W' or W" through an atom in the saturated ring. The aryl or heteroaryl ring in any of these embodiments may be optionally substituted, with groups described as preferred substituents when present on an aryl ring that is part of X or X' for compounds for formula (1). In some embodiments, substituents on an aryl or heteroaryl ring that is part of X, X' or X" include methyl, methoxy, trifluoromethyl and halo. X, X' and X" in formula (2) can be the same or different; in some embodiments they are the same.

In some embodiments of formula (2), each of —W—X, —W'—X' and —W"—X" represents a group of the form —C(O)NR(CHR)$_p$X, where p is 0-2, X represents one or two phenyl groups, tetrahydronaphthyl, indanyl or fluorenyl, each of which may be optionally substituted, and R is independently H or a C1-C8 alkyl group. In certain embodiments, q is 0 or 1, and each R may be H or methyl. In specific embodiments, each of —W—X, X'—X' and —W"-X" is the same and represents a group of the form —C(O)NR(CHR)$_p$X, where p is 0, X is tetrahydronaphthyl and each R is H.

Compounds of formula (3A) contain two or three amino acid-derived binding domains that have the same formula, but may differ in stereochemistry. For compounds of formula (3A), p is 2 or 3, and m, Q, L, W, X, Y and Z are as described for compounds formula (1) and/or (2). In compounds of formula (3A), $R_a$ is H, and $R_b$ is $R^5$, where $R^5$ is H, or C1-C8 alkyl, C2-C8 alkenyl, C2-C8 alkynyl, or phenyl, each of which may be optionally substituted. In preferred embodiments of formula (3A), p is 2. In many embodiments, L in compounds of formula (3A) represents a C1-C14 alkylene, C1-C14 alkenylene, or C1-C14 alkynylene linker, or a heteroform of one of these, each of which may be optionally substituted. In other embodiments of formula (3A), L represents a C5-C12 arylene, C5-C21 arylalkylene, C5-C21 arylalkenylene, or C5-C21 alkynylene linker, or a heteroform of one of these, each of which may be optionally substituted.

Compounds of formula (3) contain two or three amino acid-derived binding domains that have the same formula, but may differ in stereochemistry. For compounds of formula (3), p is 2 or 3, and m, Q, L, W, X, Y and Z are as described for compounds formula (1) and/or (2). In preferred embodiments of formulae (3), p is 2. In many embodiments, L in compounds of formulae (3)-(5) represents a C1-C14 alkylene, C1-C14 alkenylene, or C1-C14 alkynylene linker, or a heteroform of one of these, each of which may be optionally substituted. In other embodiments of formulae (3)-(5), L represents a C5-C12 arylene, C5-C21 arylalkylene, C5-C21 arylalkenylene, or C5-C21 alkynylene linker, or a heteroform of one of these, each of which may be optionally substituted.

Compounds of formula (4) contain two or three amino acid-derived binding domains that have the same formula and stereochemistry. For compounds of formula (4), p is 2 or 3, and m, Q, L, W, X, and Y are as described for compounds formula (1) and/or (2). In preferred embodiments of formula (4), p is 2.

Compounds of formula (5) contain two amino acid-derived binding domains that have the same formula and opposite stereochemistry. For compounds of formula (5), m, Q, L, W, X, and Y are as described for compounds formula (1) and/or (2).

For compounds of formula (3)-(5), $R^5$ is H, or C1-C8 alkyl, C1-C8 alkenyl, C1-C8 alkynyl, or phenyl, each of which may be optionally substituted. In certain embodiments, $R^5$ is selected from methyl, ethyl, n-propyl, isopropyl, cyclopropyl, n-butyl, isobutyl, sec-butyl, tert-butyl, propyn-3-yl, cyclohexyl, or phenyl.

For compounds of formula (3)-(5), m is 0-4. Frequently, m is 0 or 1, and where m is 1, Y is often =O, C1-C4 alkyl or C1-C4 alkoxy. In preferred embodiments, Q is —NH— or a bond.

In many embodiments of formulas (3)-(5), W is an amide linker. In certain embodiments, —W—X represents —C(O)NR(CHR)$_p$X, where p is 0, 1 or 2 and each R is H or a C1-C4 alkyl group. In specific embodiments, —X represents an optionally substituted phenyl ring, or two phenyl rings attached to the same atom of W, each of which may be optionally substituted, or is a tetrahydronaphthyl, indanyl group or fluorenyl group linked to a nitrogen atom of W through an open valence on the saturated ring of the tetrahydronaphthyl, indanyl or fluorenyl ring system.

$R^3$ in formula (4) or (5) can be H or an optionally substituted C1-C8 alkyl or optionally substituted C1-C8 heteroalkyl group, and can optionally cyclize with a group $R^4$ if an $R^4$ is other than H. In certain preferred embodiments, $R^3$ is H or a C1-C4 alkyl group such as methyl, ethyl or propyl.

Each $R^4$ in formula (4) or (5) is independently H or an optionally substituted C1-C8 alkyl or optionally substituted C1-C8 heteroalkyl. If two $R^4$ groups other than H are present on one nitrogen atom, they can optionally cyclize to form an optionally substituted azacyclic group having 5-10 ring members, which azacyclic ring may be saturated, unsaturated or aromatic, and may contain 1-2 additional heteroatoms selected from N, O and S, as further described herein. In certain preferred embodiments, each $R^4$ is independently H or a C1-C4 alkyl group, such as methyl, ethyl or propyl.

In another aspect, the invention relates to monomers of formula (II), useful for the preparation of the dimers and trimers of the invention. A suitable monomer is a molecule that can be readily covalently linked to a second or third monomer molecule which may be identical or different, to form a dimer, trimer, dimer-like or trimer-like Smac mimetic compound as described above. Accordingly, compounds encompassed in the present invention include dimer, trimer, dimer-like and trimer-like molecules and monomeric intermediates useful for the synthesis of such dimeric and trimeric compounds. Also provided are methods of synthesizing such dimer, trimer, dimer-like and trimer-like molecules from monomeric intermediates.

The invention provides monomers of formula (II)

D-U  (II)

wherein D is selected from the group consisting of

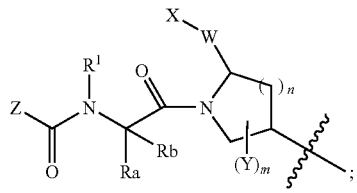

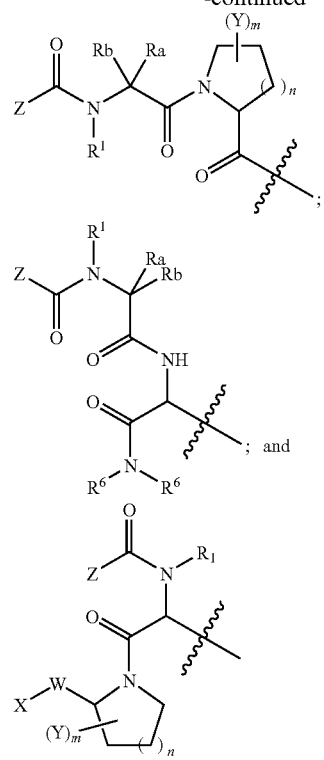

wherein each $R_a$, $R_b$, $R^1$, Y, W, X, n, m, and $R^6$ are as further defined herein for compounds of formula (I), and Z is an optionally substituted C1-C6 aminoalkyl group wherein the amine may be in a protected or unprotected form.

U in compounds of formula (II) preferably comprises at least one functional group that can be used to connect the monomer directly to another monomer, or that is capable of undergoing reaction with another molecule that will be used to connect two or more monomers, each having a group U present that can be linked together using conventional transformations. Monomers of formula (II) may be linked together directly or by reaction with an additional component that forms part of the linker, L.

Thus, U represents at least one functional group capable of undergoing chemical reaction with another molecule. For example, U can represent a functional group such as —OR$^8$, —OC(O)R$^8$, —OSO$_2$R$^8$, C=O, —OC(O)OR$^8$, —COOR$^8$, —NR$^8$$_2$, azido or halo, or the like, where each R$^8$ is independently H, or C1-C8 alkyl, C1-C8 alkenyl, C1-C8 alkynyl, C5-C12 aryl, C5-C21 arylalkyl, or a heteroform of one of these, each of which may be optionally substituted. Alternatively, U can be an optionally substituted C1-C8 alkyl, C2-C8 alkenyl, C2-C8 alkynyl group, C5-C20 aryl or C5-C20 arylalkyl group, or a heteroform of one of these.

In some embodiments, U represents a C1-C8 alkyl or C5-C12 aryl group substituted with halo, azide, —COOH, —NH$_2$, —OH, or —OSO$_2$R, where R is C1-C4 alkyl, CF$_3$, or optionally substituted phenyl; in other embodiments, U comprises a terminal alkene or a terminal alkyne. In certain preferred embodiments, U is —NH$_2$, azide, —CH$_2$C≡CH, —NH(CH$_2$)$_r$C≡CH or NHC(O)(CH$_2$)$_r$C≡CH, where r is 1-2, —CH(R)OCH$_2$C≡CH, where R is H or methyl, or U is (CH$_2$)$_t$Ar, where t is 0 or 1 and Ar represents a phenyl ring substituted with halo, —OH or —OTf.

Such monomers may undergo chemical reaction using conditions well known in the art to connect a monomer containing such a functional group U to another molecule. The following examples are included for illustrative purposes only and are not intended to represent or limit the scope of the subject matter claimed herein. A person of skill in the art would understand that a wide variety of chemical reactions would be suitable to provide the compounds of the invention.

In some embodiments, monomers undergoing dimerization or trimerization contain different functional groups, U. In other embodiments, the functional groups, U, in monomers undergoing dimerization or trimerization are the same.

Where the functional groups, U, are different, they sometimes represent a monomer in which U comprises a primary or secondary amine and a monomer containing a carboxylic acid or acyl halide, which undergo an acylation or amide coupling reaction to form an amide-linked dimer. In other embodiments, an azide containing monomer can undergo cycloaddition with a monomer in which U comprises an alkyne to form a dimer wherein the linker comprises at triazole ring.

In certain embodiments, the functional groups, U, are the same. For example, two amine containing monomers of formula (II) may undergo reaction with a diacid, which may be optionally activated as a diacyl halide, mixed anhydride, activated ester, a bis-sulfonyl halide, or the like, to provide a dimer wherein L comprises a bis-amide or bis-sulfonamide linkage. In other embodiments, three amine containing monomers may react with a triacid, triacyl halide or tris-sulfonyl halide, to give trimeric compounds. In still other embodiments, two monomers containing a terminal alkyne can undergo copper catalyzed cross-coupling reaction to give a linker comprising a bis-acetylene moiety, or two terminal alkene containing monomers may undergo dimerization via an olefin metathesis reaction. In further embodiments, two azide containing monomers can undergo reaction with a bis-acetylene containing molecule to form a dimer wherein the linker comprises two triazole rings. In additional embodiments, two monomers containing a terminal alkyne can react with a third molecule containing a bis-azide to form a dimer wherein the linker comprises two triazole rings.

Compounds of formulae (6) and (17)-(19) and (19A) represent specific embodiments of monomers of formula (II) which are useful for the preparation of dimer, trimer, dimer-like or trimer-like compounds.

U in compounds of formula (6) represents at least one functional group such as —$OR^8$, —$OC(O)R^8$, —$OSO_2R^8$, $C=O$, —$OC(O)OR^8$, —$COOR^8$, —$NR^8_2$, azido or halo, or the like, where each $R^8$ is independently H, or C1-C8 alkyl, C1-C8 alkenyl, C1-C8 alkynyl, C5-C12 aryl, C5-C21 arylalkyl, or a heteroform of one of these, each of which may be optionally substituted; or C1-C8 alkyl, C2-C8 alkenyl, C2-C8 alkynyl, C5-C12 aryl or C5-C21 arylalkyl, or a heteroform of one of these, each of which may be optionally substituted. In other embodiments, U can be an optionally substituted C1-C8 alkyl, C2-C8 alkenyl, C2-C8 alkynyl group, C5-C20 aryl or C5-C20 arylalkyl group, or a heteroform of one of these. In preferred embodiments, U is —$NH_2$, azide, or —$NH(CH_2)_rC\equiv CH$ or $NHC(O)(CH_2)_rC\equiv CH$, where r is 1-2.

Monomers of formula (6) may be linked together directly or by reaction with an additional component that forms part of the linker, L. In frequent embodiments, the linker comprises one or more carboxylate groups such that an ester or amide linkage is formed by the bond Q-L and/or Q'-L.

In compounds of formula (6), n, m, $R_a$, $R_b$, $R^1$, W, X, Y and Z are as described for compounds of any of formulae (1)-(5) and (3A). In many embodiments of formula (6), Z represents a protected amine. One of skill in the art would appreciate that appropriate amine protecting groups may vary depending on the functionality present in the particular monomer. Suitably protected amines may include, for example, carbamates (e.g. tert-butoxycarbonyl, benzyloxycarbonyl, fluorenylmethyloxycarbonyl, allyloxycarbonyl or (trialkylsilyl)ethoxy-carbonyl), carboxamides (e.g. formyl, acyl or trifluoroacetyl), sulfonamides, phthalimides, Schiff base derivatives, and the like.

Two monomers may be brought together by reaction with a third molecule containing at least two reactive centers, such as the reaction of two amine containing monomers with carbonyldiimidazole to form a urea-containing linkage; the reaction of two amine containing monomers with a diacid or diacyl halide to form a bis-amide containing linkage; the reaction of two amine containing monomers with a bis-sulfonyl halide to form a bis-sulfonamide linkage; or the reaction of two azido containing monomers with a bis-acetylene compound to form a dimer wherein Q and Q' represent a bond and L comprises two triazole rings.

Alternatively, three monomers may be brought together by reaction with a fourth molecule containing at least three reactive centers to form a trimer or trimer-like molecule. For example, reaction of three amine containing monomers with, e.g. 1,3,5-tricarboxybenzene, or an activated form thereof, can be used to form a trimeric molecule wherein each binding domain is attached to the 1,3,5-tricarboxybenzene linker through an amide bond.

When an unsymmetrical dimer of formula (1) is desired, two monomers having complementary functional groups can be combined. For example, cycloaddition of a monomer containing an azide to an alkyne-containing monomer may be used to provide dimers wherein the linking group comprises a triazole ring.

For compounds of formula (7)-(19), each of m, m', n, n' $R_a$, $R_{a'}$, $R_b$, $R_{b'}$, $R^1$, $R^{1'}$, W, W', X, X' Y, Z, and Z', where present, are as described for compounds of formulae (1)-(5). In many embodiments, where present, n is 1 and m is 0 or 1. Where m is 1, Y is frequently =O. In preferred embodiments, $R^1$ and $R^{1'}$ are H.

For compounds of formula (19A), each of m, m', n, n' $R_a$, $R_{a'}$, $R_b$, $R_{b'}$, $R^1$, $R^{1'}$, W, W', X, X' Y, Z, and Z', where present, are as described for compounds of formulae (1)-(5). In many embodiments, where present, n is 1 and m is 0 or 1. Where m is 1, Y is frequently =O. In preferred embodiments, $R^1$ and $R^{1'}$ are H.

In certain embodiments of formula (7)-(9), (12) and (16), —W— and/or —W'—, where present, represent a group of the form —C(O)NR(CHR)$_p$—, where each p is 0-2, and each R is independently H, or C1-C4 alkyl or C1-C4 heteroalkyl. In certain embodiments, p is 0 or 1, and each R may be H or methyl. In some embodiments, —W—X and —X'—X' are the same. In preferred embodiments, each X and X' is independently one or two phenyl groups, each of which may be optionally substituted, or is a tetrahydronaphthyl, indanyl or fluorenyl ring system linked to nitrogen of W or W' through an open valence on the saturated ring of the tetrahydronaphthyl, indanyl or fluorenyl ring system.

For compounds of formula (7), (10)-(11), (15) and (17), where present, each $R^6$ and/or $R^{6'}$ is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring. In preferred embodiments, one of $R^6$ and $R^{6'}$ is H, and the other is a tetrahydronaphthyl, indanyl or fluorenyl ring system attached to the nitrogen atom through an open valence on the saturated ring.

For compounds of formula (7)-(16), L represents a C1-C14 alkylene, C5-C20 arylene or C5-C20 arylalkylene linker, or a heteroform of one of these, each of which may be optionally substituted, and wherein the alkylene portion may be saturated or unsaturated. L may be optionally substituted with substituents suitable for its nature, and may include a combination of cyclic and acyclic features. In some embodiments, L comprises at least one ring that is part of or is fused to the linker that forms the shortest path between any two Q and/or Q'. Such rings may be saturated, unsaturated or aromatic, and may contain from 1-3 heteroatoms selected from the group consisting of N, O and S. In certain embodiments, L is symmetric about its central atom (if the chain connecting the two available valences is an odd number of atoms in length) or its central bond (if the chain connecting the two available valences is an even number of atoms in length). Frequently, L is 3-6 atoms in length, counting along the shortest path between Q and Q'. L can also include one or more heteroatoms selected from N, O and S, but does not include a disulfide linkage. The same groups are suitable for compounds of formula (13A).

For compounds of formula (7) and (8), Q represents —O— or —NR$^2$—, where R$^2$ is independently H, or optionally substituted C1-C8 or optionally substituted C1-C8 heteroalkyl; and Q' represents —CH$_2$—, —CH(OR)—, —CH(R)—, —CH$_2$O—, —CH(R)O— or —(CH$_2$)$_4$NH—, wherein R is H, C1-C4 alkyl or C1-C4 heteroalkyl. In certain embodiments, Q and/or Q' can independently be a bond when L comprises a ring.

In some embodiments of formulas (7) and (8), Q is a bond where L comprises a triazole ring. In other embodiments, Q is —NH—, and L represents an optionally substituted C1-C8 alkylene linker, which may be saturated or unsaturated. In certain embodiments, Q' is —CH$_2$— and L represents an optionally substituted C2-C8 alkylene linker, which may be saturated or unsaturated. In further embodiments, Q' is a bond where L comprises an aryl ring.

In certain embodiments of formula (7) and (8), L represents an optionally substituted C2-C8 alkynylene linker. For example, L can be an optionally substituted bis-acetylenic linker, such as —(CH$_2$)$_q$—C≡C—C≡C—(CH$_2$)$_q$— or —C≡C—C≡C—(CH$_2$)$_q$C(O)— where q is 0-5, or an arylalkynyl linker, such as -Ph-C≡C—(CH$_2$)$_q$— where q is 0-5. In other embodiments, L comprises a triazole ring.

For compounds of formula (9), each of Q and Q' independently represents —O— or —NR$^2$—, where R$^2$ is independently H, or optionally substituted C1-C8 or optionally substituted C1-C8 heteroalkyl; or one or both of Q and Q' can be a bond where L comprises a ring. In certain embodiments, Q represents a bond where L comprises a triazole ring.

In compounds of formula (10), each of Q and Q' independently represents —CH$_2$—, —CH(OR)—, —CH(R)—, —CH$_2$O—, —CH(R)O— or —(CH$_2$)$_4$NH—, wherein R is H, C$_1$-C$_4$ alkyl or C$_1$-C$_4$ heteroalkyl. In certain embodiments, Q and/or Q' can independently be a bond when L comprises a ring. In some embodiments Q and Q' are —CH$_2$— and L is a C5-C12 arylene or C5-C20 arylalkylene linker, or a heteroform of one of these, each of which may be optionally substituted.

In certain embodiments of formula (10), Q and/or Q' represent —CH$_2$— and L represents an optionally substituted C1-C8 alkylene or C1-C8 heteroalkylene linker, which may be saturated or unsaturated. In other embodiments, Q and/or Q' represent a bond when L comprises an aryl ring. In further embodiments, Q and/or Q' represent —(CH$_2$)$_4$NH— and L comprises one or more amide groups.

For compounds of formula (10), each R$^6$ and/or R$^{6'}$ is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring. In preferred embodiments, one of R$^6$ and R$^{6'}$ is H, and the other is a tetrahydronaphthyl, indanyl or fluorenyl ring system attached to the nitrogen atom through an open valence on the saturated ring.

For compounds of formula (11), p is 2 or 3, and Q, L and R$^6$ are as described for compounds of formula (10). In some embodiments, p is 3 and L comprises a tri-substituted phenyl ring.

For compounds of formula (12), Q is represents —CH$_2$—, —CH(OR)—, —CH(R)—, —CH$_2$O—, —CH(R)O— or —(CH$_2$)$_4$NH—, wherein R is H, C1-C4 alkyl or C1-C4 heteroalkyl. In certain embodiments, Q can independently be a bond when L comprises a ring. In preferred embodiments, Q is —(CH$_2$)$_4$NH— and L comprises a tri-substituted phenyl ring.

For compounds of formula (13), each of Q and Q' independently represents —O— or —NR$^2$—, where R$^2$ is independently H, or optionally substituted C1-C8 alkyl, C1-C8 heteroalkyl, C2-C8 alkenyl, C2-C8 heteroalkenyl, C2-C8 alkynyl or C2-C8 heteroalkynyl; or one or both of Q and Q' can be a bond where L comprises a ring. In certain embodiments, Q and Q' are the same. In preferred embodiments, each of Q and Q' represents —NH— or —N(Me)- where L comprises one or more triazole rings. The same groups are suitable for compounds of formula (13A).

For compounds of formula (14), p is 2 or 3. In certain embodiments, R$^5$ is C1-C8 alkyl or C1-C8 heteroalkyl. In preferred embodiments, R$^5$ is tert-butyl. In some embodiments of formula (14), L is an optionally substituted and/or unsaturated C1-C14 alkylene or C5-C20 arylalkylene linker, or a heteroform of one of these. In certain embodiments, L comprises one or more triazole rings. In some embodiments, Q is —NR$^2$—, wherein R$^2$ is H or methyl.

In compounds of formula (13A), two amide-containing binding domains are linked together by a linkage depicted as Q-L-Q'. As further described herein for specific embodiments, this linkage can comprise numerous alternatives that can include a chain that may be substituted and may be saturated or unsaturated; it may also include a combination of cyclic and acyclic features.

In some embodiments of formula (13A), L represents an optionally substituted C1-C24 hydrocarbyl linker, optionally containing from 1-8 heteroatoms selected from N, O and S, which linker is 1-18 atoms in length when counted along the shortest path between Q and Q'.

In certain embodiments, L is a C1-C12 alkylene, C3-C12 cycloalkylene, C2-C12 alkenylene, or C2-C12 alkynylene linker, or a heteroform of one of these, each of which may be optionally substituted. In frequent embodiments, L is an optionally substituted acyclic C1-C12 alkylene, which may be saturated or unsaturated (i.e., an alkenylene or alkynylene).

In certain embodiments, such alkylene linker is preferably unsaturated, and may be an alkynylene linker. In some embodiments, L is symmetric, and frequently L is 6-10 atoms in length, counting along the shortest path (by atom count) between Q and Q'. In certain embodiments, L can also include one or more heteroatoms selected from N, O and S, but does not include a disulfide linkage.

L can be substituted by substituents including rings, and it can comprise one or more rings as part of the linkage that connects Q and Q' together. Where L comprises at least one ring that is part of or is fused to the shortest path (by atom count) connecting Q and Q', Q and/or Q' in formula (13A) can be a bond as well as any of the other structures described herein for Q and Q'.

Where L comprises a ring, the ring(s) may be carbocyclic, heterocyclic, aromatic or heteroaromatic, each of which may be optionally substituted. Such rings can be connected to Q and/or Q' (or, where Q and/or Q' represent a bond, the rings can be connected by the bond Q or Q' directly to the carbon to which Q/Q' are attached), at any ring position, and may be attached either directly or through an intervening alkylene or heteroalkylene group, provided the shortest path (by atom counting) between Q and Q' consists of 1-18 atoms, and preferably 1-14 atoms or 1-10 atoms.

Rings which comprise part of the linker, L, may be optionally substituted to the extent such substitution makes chemical sense. Preferred optional substituents when present on a ring which comprises part of L include alkyl (C1-C4), alkoxy (C1-C4), —CF$_3$, —OCF$_3$, halo, —OH, —NO$_2$, —CN, or NR$_2$, where R is H or C1-C4 alkyl.

Alternatively, L can be a saturated or unsaturated arylalkylene linker, comprised of an aryl ring and an alkylene group, or an aryl ring and two alkylene groups combined, each of which may be optionally substituted. For example, it can be —CH$_2$—Ar—, —(CH$_2$)$_2$—Ar—(CH$_2$)$_2$—, —C(O)—Ar—C(O)—, or —CH$_2$—Ar—C≡C—, where Ar represents a 5- or 6-membered aromatic or heteroaromatic ring. L can also include one or more heteroatoms, for example, it can be —CH$_2$—Ar—O— or —NH—Ar—CH$_2$— or a substituted version of one of these.

In compounds of formula (13A), Q is —O— or —NR$^2$—, and Q' is —O— or —NR$^2$—, where Q and Q' are independently selected, and each R$^2$ and R$^{2'}$ is independently H, or C1-C8 alkyl, C1-C8 alkenyl, or C1-C8 alkynyl, or a heteroform of one of these, each of which may be optionally substituted; or one or both of Q and Q' can be a bond where L comprises a ring;

In preferred embodiments, Q and Q' are —NR$^2$— and —NR$^{2'}$—, respectively, where each R$^2$ and R$^{2'}$ is independently H, or C1-C8 alkyl, C1-C8 alkenyl, or C1-C8 alkynyl, or a heteroform of one of these, each of which may be optionally substituted.

In compounds of formula (13A), each R$^1$ and R$^{1'}$ is independently H or optionally substituted C1-C8 alkyl, preferably C1-C4 alkyl. In certain embodiments, each R$^1$ and R$^{1'}$ is independently H or methyl.

In formula (13A), each R$_a$, R$_b$, R$_{a'}$ and R$_{b'}$ is independently H, or C1-C8 alkyl, C3-C7 cycloalkyl, C2-C8 alkenyl, C2-C8 alkynyl, C5-C12 aryl, C5-C20 arylalkyl, or a heteroform of one of these, each of which may be optionally substituted. In certain embodiments, the two R-groups on one carbon atom, i.e., R$_a$ and R$_b$, or R$_{a'}$ and R$_{b'}$, may be taken together with the carbon atom to which they are attached to form an optionally substituted 3-7 membered ring, optionally containing one heteroatom selected from N, O and S as a ring member.

Each Z and Z' in compounds of formula (13A) independently represents an optionally substituted C1-C6 aminoalkyl group. In frequent embodiments, each Z and Z' represents a 1-aminoalkyl substituent. In some embodiments, Z and Z' may comprise an optionally protected amino group. Amino groups in Z and Z' may be suitably protected as, for example, carbamates (e.g. tert-butoxycarbonyl, benzlyoxycarbonyl, fluorenylmethyloxy-carbonyl, allyloxycarbonyl or (trialkylsilyl)ethoxycarbonyl), carboxamides (e.g. formyl, acyl or trifluoroacetyl), sulfonamides, phthalimides, Schiff base derivatives, and the like.

In preferred embodiments, each Z and Z' represents a 1-aminoalkyl substituent of the formula —CH(R$^3$)NR$^4$$_2$, wherein R$^3$ and R$^4$ are as further described herein.

In some such embodiments, each R$^4$ is independently H, or an optionally substituted C$_1$-C$_8$ alkyl or optionally substituted C$_1$-C$_8$ heteroalkyl group, and the two R$^6$ groups on one nitrogen can cyclize to form an optionally substituted 3-8 membered azacyclic ring, which azacyclic ring may be saturated, unsaturated or aromatic, and may contain 1-2 additional heteroatoms selected from N, O and S as ring members.

Each R$^3$ is H, or an optionally substituted C$_1$-C$_8$ alkyl or optionally substituted C$_1$-C$_8$ heteroalkyl group, and R$^3$ can cyclize with R$^4$ on an adjacent nitrogen atom to form an optionally substituted 3-8 membered azacyclic ring, which azacyclic ring may be saturated, unsaturated or aromatic, and may contain 1-2 additional heteroatoms selected from N, O and S as ring members. In preferred embodiments, each R$^3$ and R$^4$ is independently H or C1-C4 alkyl.

In compounds of formula (13A), where present, each Y and Y' independently represents an optionally substituted C1-C8 alkyl, C5-C12 aryl, C5-C20 arylalkyl, or a heteroform of one of these; or is =O, —OR, —SR, —S(O)R, —SO$_2$R, —SO$_2$NR$_2$, —NR$_2$, —OC(O)R, —NRC(O)R, —NRCOOR, —NRC(O)NR$_2$, —NRSO$_2$R, —CN, —C(O)NR$_2$, —C(O)R, —COOR, —NO$_2$ or halo, wherein each R is independently H, C$_1$-C$_8$ alkyl, C5-C12 aryl or C5-C20 arylalkyl, or a heteroform of one of these; or is any other substituent suitable for an alkyl group; and wherein two Y or Y' groups on the same ring can cyclize to form a 3-6 membered ring that can be saturated, unsaturated or aromatic, and which ring may include one heteroatom selected from O, S and N as a ring member and may be substituted.

Each m and m' in compounds of formula (13A) is independently 0-4, and each n and n' is independently 0-3. In frequent embodiments, each of n and n' is 1, and each m and m' is 0 or 1, and Y and Y', if present, are the same.

In a particularly preferred embodiment of formula (13A), Q and Q' are —NR$^2$— and —NR$^2$—, respectively, and L represents an optionally substituted C1-C24 hydrocarbyl linker of the formula —C(R$^{3,4}$R$^{4,4}$)-J-K-J'—C(R$^{3,4'}$R$^{4,4'}$)—, optionally containing from 1-8 heteroatoms selected from N, O and S, wherein R$^{3,4}$, R$^{4,4}$, R$^{3,4'}$, R$^{4,4'}$ J, J' and K are as further described herein for compounds of formula (13B)-(13D).

In certain embodiments, the compounds of the invention have the formula (13B). In compounds of formula (13B), each of Y, Y', m, m', n, n', R$_a$, R$_{a'}$, R$_b$, R$_{b'}$, R$^1$, R$^{1'}$, Z and Z' are as described for formula (13A). In compounds of formula (13B), Q and Q' in formula (13A) are —NR$^2$— and —NR$^{2'}$—, respectively, and L represents a linker having the formula —C(R$^{3,4}$R$^{4,4}$)-J-K-J'-C(R$^{3,4'}$R$^{4,4'}$)—, as described herein.

In compounds of formula (13B), the linkage described as J-K-J' can comprise numerous alternatives that can include a chain that may be substituted and may be saturated or unsaturated; it may also include a combination of cyclic and acyclic features.

In compounds of formula (13B), K represents an optionally substituted C1-C20 hydrocarbyl linker, optionally containing from 1-6 heteroatoms selected from N, O and S, which linker is 1-14 atoms in length when counted along the shortest path between J and J'. In some embodiments, K is symmetric, and frequently L is 6-10 atoms in length, counting along the shortest path (by atom count) between J and J'. In certain embodiments, K can also include one or more heteroatoms selected from N, O and S, but does not include a disulfide linkage.

In some embodiments of formula (13B), K represents a C1-C10 alkylene, C3-C10 cycloalkylene, C2-C10 alkenylene, C2-C10 alkynylene, C5-C12 arylene, C5-C20 arylalkylene, C5-C20 arylalkenylene or C5-C20 arylalkynylene linker, or a heteroform of one of these, each of which may be optionally substituted; with the proviso that K does not comprise a disulfide bond.

For example, K can be —$(CH_2)_k$— where k is 1-8, and may be optionally substituted with groups suitable for an alkyl group. Some saturated embodiments of K include 1,3-propylene, 1,4-butylene, 1,5-pentylene and 1,6-hexylene, or 1,4-cyclohexylene, each of which can be substituted. In certain embodiments, the alkylene chain is substituted with one or two carbonyl oxygens (=O).

When K is unsaturated, it is sometimes a C2-C1 alkenylene or C2-C1 alkynylene linker. Some unsaturated embodiments of K include 1,4-but-2-enylene (—$CH_2$—CH=CH—$CH_2$—), 1,4-buta-1,3-dienylene (—CH=CH—CH=CH); 1,4-buta-1,3-diynylene (—C≡C—C≡C—); or an optionally substituted version of one of these. K can also include one or more heteroatoms selected from N, O and S. When K is substituted, it is frequently substituted with one or two =O, halo, C1-C4 alkyl, —OR or —$NR_2$, where R is H or C1-C4 alkyl.

K can be substituted by substituents including rings, and it can comprise one or more rings as part of the linkage that connects J and J' together. Where K comprises at least one ring that is part of or is fused to the shortest path (by atom count) connecting J and J', J and/or J' in formula (13B) can be a bond as well as any of the other structures described herein for J and J'.

Where K comprises a ring, the ring(s) may be carbocyclic, heterocyclic, aromatic or heteroaromatic, each of which may be optionally substituted. Such rings can be connected to J and/or J' (or, where J and/or J' represent a bond, the rings can be connected by the bond J or J' directly to the carbon to which they are attached), at any ring position, and may be attached either directly or through an intervening alkylene or heteroalkylene group, provided the shortest path (by atom counting) between J and J' consists of 1-14 atoms, and preferably 1-10 atoms or 1-8 atoms.

In certain embodiments, K comprises at least one carbocyclic, heterocyclic, aromatic or heteroaromatic ring that is part of or is fused to the linker which forms the shortest path between J and J'. In specific embodiments, K comprises at least one optionally substituted phenyl or triazole ring.

In some embodiments, K comprises a phenyl or pyridyl ring that may be 1,2-disubstituted, or 1,3-disubstituted, or 1,4-disubstituted, by the groups J and J', which may be directly attached to the ring or may be separated from the ring by one or more atoms that are included in K.

In compounds of formula (13B), each of J and J' independently represents —$CH_2$—, —CH(OR')—, —CH(R')—, —$(CH_2)_rG$-, —CH(R')G-, or —CR'=CR'— or —C≡C—, wherein r is 1-4, each G is independently O, NR', or S, and wherein each R' is independently H, or C1-C8 alkyl or C1-C8 heteroalkyl; or one or both of J and J' can be a bond where K comprises a ring.

In preferred embodiments, each J and J' is independently selected from the group consisting of —$CH_2$—, —CH(R')—, —$(CH_2)_rG$-, and —CH(R')G-, wherein r is 1-4, each G is independently O or NR', and wherein each R' is independently H or C1-C4 alkyl.

In particularly preferred embodiments, each of J and J' is independently —$CH_2$—, —$CH_2O$— or —$CH_2N(R')$—, where R' is H or methyl.

In compounds of formula (13B), each $R^1$ and $R^{1'}$ is independently H or optionally substituted C1-C8 alkyl, preferably C1-C4 alkyl. In certain embodiments, each $R^1$ and $R^{1'}$ is independently H or methyl.

In formula (13B), each $R_a$, $R_b$, $R_{a'}$ and $R_{b'}$ is independently H, or C1-C8 alkyl, C3-C7 cycloalkyl, C2-C8 alkenyl, C2-C8 alkynyl, C5-C12 aryl, C5-C20 arylalkyl, or a heteroform of one of these, each of which may be optionally substituted. In certain embodiments, the two R-groups on one carbon atom, i.e., $R_a$ and $R_b$, or $R_{a'}$ and $R_{b'}$, may be taken together with the carbon atom to which they are attached to form an optionally substituted 3-7 membered ring, optionally containing one heteroatom selected from N, O and S as a ring member.

In compounds of formula (13B), each $R^2$ and $R^{2'}$ is independently H or optionally substituted C1-C8 alkyl, preferably C1-C4 alkyl. In preferred embodiments, each $R^2$ and $R^{2'}$ is independently H or methyl.

Each $R^3$, $R^{4A}$, $R^{3A'}$ and $R^{4A'}$ in formula (13B) is independently H, or C1-C8 alkyl, C3-C7 cycloalkyl, C2-C8 alkenyl, C2-C8 alkynyl, C5-C12 aryl, C5-C20 arylalkyl, or a heteroform of one of these, each of which may be optionally substituted. In certain embodiments, the two R-groups on one carbon atom, i.e., $R^{3A}$ and $R^{4A}$, or $R^{3A'}$ and $R^{4A'}$ may be taken together with the carbon atom to which they are attached to form an optionally substituted 3-7 membered ring, optionally containing one heteroatom selected from N, O and S as a ring member.

Each Z and Z' in compounds of formula (13B) independently represents an optionally substituted C1-C6 aminoalkyl group. In frequent embodiments, each Z and Z' represents a 1-aminoalkyl substituent. In certain embodiments, each Z and Z' represents a group of the formula —$CH(R^3)NR^4_2$, wherein $R^3$ and $R^4$ are as described for preferred embodiments of formula (13A).

In some such embodiments, each $R^4$ is independently H, or an optionally substituted $C_1$-$C_8$ alkyl or optionally substituted $C_1$-$C_8$ heteroalkyl group, and the two $R^4$ groups on one nitrogen can cyclize to form an optionally substituted 3-8 membered azacyclic ring, which azacyclic ring may be saturated, unsaturated or aromatic, and may contain 1-2 additional heteroatoms selected from N, O and S as ring members.

Each $R^3$ is H, or an optionally substituted $C_1$-$C_8$ alkyl or optionally substituted $C_1$-$C_8$ heteroalkyl group, and $R^3$ can cyclize with $R^4$ on an adjacent nitrogen atom to form an optionally substituted 3-8 membered azacyclic ring, which azacyclic ring may be saturated, unsaturated or aromatic, and may contain 1-2 additional heteroatoms selected from N, O and S as ring members. In preferred embodiments, each $R^3$ and $R^4$ is independently H or C1-C4 alkyl.

In specific embodiments, each $R^3$ and $R^4$ is independently H or C1-C4 alkyl. In preferred embodiments, each $R^4$ is independently H or methyl, and $R^3$ is selected from methyl, ethyl, n-propyl, isopropyl, cyclopropyl, n-butyl, isobutyl, sec-butyl, and tert-butyl.

In compounds of formula (13B), where present, each Y and Y' is defined as for formula (13A), each m and m' is independently 0-4, and each n and n' is independently 0-3. In frequent embodiments, each of n and n' is 1, each m and m' is 0 or 1, and Y and Y', if present, are the same.

In other embodiments, the compounds of the invention have the formula (13C), wherein each Y, m, n, $R_a$, $R_b$, $R^1$, $R^2$, $R^{3A}$, $R^{4A}$, J, K and Z is as defined for compounds of formula (13B).

In preferred embodiments of formula (13C), each of $R^1$ and $R^2$ is independently H or methyl, n is 1, and m is 0 or 1. In particularly preferred embodiments, $R_a$ and $R^{3,4}$ are H, and each of $R_b$ and $R^{4,4}$ is independently H, or C1-C8 alkyl, C3-C7 cycloalkyl, C2-C8 alkenyl, C2-C8 alkynyl, C5-C12 aryl, C5-C20 arylalkyl, or a heteroform of one of these, each of which may be optionally substituted.

In compounds of formula (13C), Z is a 1-aminoalkyl group represented by the formula —CH($R^3$)N$R^4{}_2$, wherein $R^3$ and $R^4$ are defined as above. In specific embodiments, each $R^3$ and $R^4$ is independently H or C1-C4 alkyl. In preferred embodiments, each $R^4$ is independently H or methyl, and $R^3$ is selected from methyl, ethyl, n-propyl, isopropyl, cyclopropyl, n-butyl, isobutyl, sec-butyl, and tert-butyl.

In compounds of formula (13C), J is selected from the group consisting of —CH$_2$—, —CH(R')—, —(CH$_2$)$_r$G-, and —CH(R')G-, wherein r is 1-4, each G is independently O or NR', and wherein each R' is independently H or C1-C4 alkyl; or J can be a bond where K comprises a ring.

In preferred embodiments, J is —CH$_2$—, —CH$_2$O— or —CH$_2$N(R')', where R' is H or methyl.

In compounds of formula (13C), K represents a C1-C10 alkylene, C3-C10 cycloalkylene, C2-C10 alkenylene, C2-C10 alkynylene, C5-C12 arylene, C5-C20 arylalkylene, C5-C20 arylalkenylene or C5-C20 arylalkynylene linker, or a heteroform of one of these, each of which may be optionally substituted.

In specific embodiments of formula (13C), K comprises a C1-C6 alkylene, C1-C6 alkenylene, or C1-C6 alkynylene linker. In other embodiments, K is a C5-C12 arylene or a saturated or unsaturated C5-C20 arylalkylene linker. In specific embodiments, K comprises an optionally substituted phenyl or triazole ring.

In some embodiments, the compounds of the invention have the formula (13D), wherein each Z, J and K is as defined for compounds of formula (13B) and (13C).

In compounds of formula (13D), each $R^1$ and $R^2$ is independently H or methyl. In preferred embodiments, each of $R^1$ and $R^2$ is H.

In compounds of formula (13D), each of $R_a$ and $R^{3,4}$ is H, and each $R_b$ and $R^{4,4}$ is independently H, or C1-C8 alkyl, C3-C7 cycloalkyl, C2-C8 alkenyl, C2-C8 alkynyl, C5-C12 aryl, C5-C20 arylalkyl, or a heteroform of one of these, each of which may be optionally substituted. In a preferred embodiment, each of $R_b$ and $R^{4,4}$ is independently a C1-C8 alkyl or C3-C7 cycloalkyl group.

In another aspect, the invention provides monomeric compounds of formulae (19) and (19A), and methods of using them to prepare compounds of formulae (13) and (13B)-(13D). In compounds of formulae (19A), each of Y, m, n, $R_a$, $R_b$, $R^1$, $R^2$, $R^{3,4}$, $R^{4,4}$ and Z is defined as for formula (13B).

In certain embodiments of formula (19A), Z is often a protected amine, as further described herein. One of skill in the art would appreciate that appropriate amine protecting groups may vary depending on the functionality present in the particular monomer. Suitably protected amines may include, for example, carbamates (e.g. tert-butoxycarbonyl, benzlyoxycarbonyl, fluorenylmethyloxycarbonyl, allyloxycarbonyl or (trialkylsilyl)ethoxycarbonyl), carboxamides (e.g. formyl, acyl or trifluoroacetyl), sulfonamides, phthalimides, Schiff base derivatives, and the like.

In compounds of formula (19A), V represents a C1-C8 alkyl, C1-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl or C5-C20 heteroarylalkyl, each of which may be optionally substituted with —OR$^9$, —OC(O)R$^9$, —OSO$_2$R$^9$, C═O, —OC(O)OR$^9$, —COOR$^5$, —NR$^9{}_2$, azido or halo, where each R$^9$ is independently H, or C1-C8 alkyl, C1-C8 alkenyl, C1-C8 alkynyl, C5-C12 aryl, C5-C21 arylalkyl, or a heteroform of one of these, each of which may be optionally substituted.

Preferred substituents when present on V include hydroxyl, optionally substituted amino, azido, alkylsulfonate, arylsulfonate, halo, acyl, carbonyl, and carboxyl. In specific embodiments, V is —CH$_2$OH, —CH$_2$OMs, —CH$_2$NH$_2$, —CH$_2$N$_3$, or —CH$_2$OCH$_2$C≡CH.

For compounds of formulae (15) and (16), Q represents —O— or —NR$^2$—, where R$^2$ is independently H, or optionally substituted C1-C8 or optionally substituted C1-C8 heteroalkyl; and Q' represents —CH$_2$—, —CH(OR)—, —CH(R)—, —CH$_2$O—, —CH(R)O— or —(CH$_2$)$_4$NH—, wherein R is H, C$_1$-C$_4$ alkyl or C$_1$-C$_4$ heteroalkyl. In certain embodiments of formulae (15) and (16), Q and/or Q' can independently be a bond when L comprises a ring. In frequent embodiments, Q represents —NR$^2$—, where R$^2$ is H or methyl. In certain embodiments, Q' is a bond where L comprises a C5-C12 arylene or C5-C12 heteroarylene ring. In other embodiments, Q' is —CH$_2$— and L comprises an optionally substituted C2-C8 alkylene or heteroalkylene group, which may be saturated or unsaturated.

For compounds of formula (17), $R_a$, $R_b$, $R^1$ and Z are as described for compounds of formulae (1)-(5), and $R^6$ is as defined for compounds of formulas (10) and (11). In many embodiments, Z represents a protected C1-C6 aminoalkyl group.

For compounds of formula (18), $R^1$, m, n, W, X, Y and Z are as defined for compounds of formulae (1)-(5). Frequently, Z represents a protected C1-C6 aminoalkyl group.

For compounds of formula (17) and (18), U represents C1-C8 alkyl, C2-C8 alkenyl, C2-C8 alkynyl, C5-C12 aryl, or C5-C21 arylalkyl, or a heteroform of one of these, each of which may be optionally substituted. In some embodiments, U comprises a terminal alkene or terminal alkyne. In preferred embodiments of formula (17) or (18), U is —CH$_2$C≡CH, —CH(R)OCH$_2$C≡CH, where R is H or methyl, or U is (CH$_2$)$_t$Ar, where t is 0 or 1 and Ar represents a phenyl ring substituted with halo, —OH or —OTf.

For compounds of formula (19), $R_a$, $R_b$, $R^1$, m, n, Y and Z are as defined for compounds of formulae (1)-(5), and U is as defined for compounds of formula (6). In preferred embodiments, U is —NH$_2$ or —NH(CH$_2$)$_r$C≡CH where r is 1-2. In frequent embodiments, Z represents a protected C1-C6 aminoalkyl group.

For compounds of formula (19A), $R_a$, $R_b$, $R^1$, m, n, Y and Z are as defined for formula (19), and $R^2$, $R^3$, and $R^4$ are defined as for formula (13B). V in formula (19A) represents a C1-C8 alkyl, C1-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl or C5-C20 heteroarylalkyl, each of which may be optionally substituted with —OR$^9$, —OC(O)R$^9$, —OSO$_2$R$^9$, C═O, —OC(O)OR$^9$, —COOR$^9$, —NR$^9{}_2$, azido or halo, where each R$^9$ is independently H, or C1-C8 alkyl, C1-C8 alkenyl, C1-C8 alkynyl, C5-C12 aryl, C5-C21 arylalkyl, or a heteroform of one of these, each of which may be optionally substituted.

In some embodiments, two or three monomers of formula (6), formula (17), formula (18), formula (19) or formula (19A), which may be the same or different, are reacted to produce dimeric or trimeric Smac inhibitors.

For example, two monomers of formula (17) may be reacted to give a dimer of formula (10) or formula (11), wherein p is 2. For example, two monomers of formula (17) in which U comprises a terminal acetylene moiety may be coupled to form a bis-acetylene linkage. In other embodiments, three monomers of formula (17) may be reacted to give a trimer of formula (11), where p is 3.

In another embodiment, three monomers of formula (18) may be reacted to give a trimer of formula (12). In a further embodiment, two monomers of formula (19) may be reacted to give a dimer of formula (13) or (14). In some such embodiments, each U represents —NH$_2$ or —NH(Me).

As a further example, a monomer of formula (17) or (18) may be reacted with a monomer of formula (6) to provide an unsymmetrical dimer of formula (7) or (8), respectively. For example, an alkyne containing monomer of formula (17) or (18) may be reacted with an azido containing monomer of formula (6) to provide a dimer of formula (7) or (8), wherein L comprises a triazole ring.

In a further example, two monomers of formula (19A) may be reacted to provide a compound of formulae (13B)-(13D).

The compounds of the invention typically contain one or more chiral centers. The invention expressly includes each diastereomer, as well as each enantiomer of each diastereomer of the compounds described and mixtures thereof, particularly racemic mixtures of single diastereomers such as the ones described, and highly enriched enantiomers having an enantiomeric excess (e.e.) of greater than 90% or greater than about 95%. Substituent groups may also include one or more chiral centers, and each enantiomer and diastereomer of these substituents as well as mixtures thereof are all included within the scope of the invention. Similarly, where double bonds are present, the compounds can exist in some cases as either cis or trans isomers; the invention includes each isomer individually as well as mixtures of isomers.

Merely as examples of selected compounds of the invention, Table 3 and Table 4 illustrate a number of compounds of formulae (I) and (IA). These compounds represent selected preferred species, and other species that include combinations of the features in the compounds specifically depicted are also preferred.

The compounds of the invention may be isolated as salts where an ionizable group such as a basic amine or a carboxylic acid is present. The invention includes the salts of these compounds that have pharmaceutically acceptable counterions. Such salts are well known in the art, and include, for example, salts of acidic groups formed by reaction with organic or inorganic bases, and salts of basic groups formed by reaction with organic or inorganic acids, as long as the counterions introduced by the reaction are acceptable for pharmaceutical uses. Examples of inorganic bases with alkali metal hydroxides (e.g., sodium hydroxide, potassium hydroxide, etc.), alkaline earth metal hydroxides (e.g., of calcium, magnesium, etc.), and hydroxides of aluminum, ammonium, etc.

Examples of organic bases that could be used include trimethylamine, triethylamine, pyridine, picoline, ethanolamine, diethanolamine, triethanolamine, dicyclohexylamine, N,N'-dibenzylethylenediamine, etc. Examples of inorganic acids that could be used include hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, methanesulfonic acid, benzenesulfonic acid, p-toluenesulfonic acid, etc. Also included are salts with basic amino acids such as arginine, lysine, ornithine, etc., and salts with acidic amino acids such as aspartic acid, glutamic acid, etc.

The compounds of the invention can be used to prepare pharmaceutical compositions containing at least one compound of any of formulae (I), (IA), (1A), (3A), (1)-(5), (7)-(16), and (13A)-(13D). Such compositions can be optimized for various conditions and routes of administration using guidance that is widely relied on for such purposes including Remington's *Pharmaceutical Sciences*, latest edition, Mack Publishing Co., Easton, Pa., which is incorporated herein by reference. The compositions comprise a compound of the invention admixed with at least one pharmaceutically acceptable excipient, and preferably with at least one such excipient other than water or a solvent such as DMSO.

The compounds of the invention are suitable to treat a wide variety of cancers. In particular, they are suitable to treat neuroblastoma, glioblastoma, breast carcinoma, melanoma, prostate carcinoma, pancreatic carcinoma, hepatocellular carcinoma, colon carcinoma, and small-cell and non-small cell lung carcinoma.

The compounds of the invention are also suitable to treat various autoimmune disorders, particularly rheumatoid arthritis, lupus, vasculitis, glomerulonephritis, type-I diabetes, pernicious anemia, myasthenia gravis, Guillain-Barre syndrome, and infections with autoimmune effects such as AIDS, malaria, Chagas disease, and Lyme disease.

The compounds of the invention are not on their own very cytotoxic: they depend for their activity on potentiation of the effects of other effectors, which may be natural, endogenous substances, or they may be additional therapeutic substances. For example, Smac mimics have been shown to strongly potentiate the activity of TRAIL or etoposide when co-administered. Accordingly, the compounds of the invention may be used in conjunction with or in combination with an additional therapeutic having anticancer effects. Such additional therapeutic can be a drug, or it can be a radiation treatment. Where an additional drug is administered, it is typically one known to have cytostatic, cytotoxic or antineoplastic activity. These agents include, for example, antimetabolites such as cytarabine, fludaragine, 5-fluoro-2'-deoxyuridine, gemcitabine, hydroxyurea, methotrexate; DNA active agents such as bleomycin, chlorambucil, cisplatin, cyclophosphamide, intercalating agents such as adriamycin and mitoxantrone; protein synthesis inhibitors such as L-asparaginase, cycloheximide, puromycin; topoisomerase I inhibitors such as camptothecin or topotecan; topoisomerase II inhibitors such as etoposide and teniposide; microtubule inhibitors such as colcemid, colchicines, paclitaxel, vinblastine and vincristine; and kinase inhibitors such as flavopiridol, staurosporin, and hydroxystaurosporine. Preferred additional drugs for co-administration with the compounds of the invention include those that affect Hsp90 (heat-shock protein 90). Suitable Hsp90 inhibitors include ansamycin derivatives such as geldanomycin and geldanomycin derivatives including 17-(allylamino)-17-desmethoxygeldanamycin (17-AAG), its dihydro derivative, 17-AAGH$_2$, and 17-amino derivatives of geldanamycin such as 17-dimethylaminoethylamino-17-demethoxy-geldanamycin (17-DMAG), 11-oxogeldanamycin, and 5,6-dihydrogeldanamycin, which are disclosed in U.S. Pat. Nos. 4,261,989; 5,387,584; and 5,932,566, each of which is incorporated herein by reference. Other suitable Hsp90 inhibitors include radicicol and oximes and other analogs thereof, disclosed in Soga, et al., *Curr. Cancer Drug Targets* (2003) 3:359-369, and in Yamamoto, et al., *Angew. Chem.* (2003) 42:1280-1284; and in Moulin, et al., *J. Amer. Chem. Soc.* (2005) 127:6999-7004; purine derivatives such as PU3, PU24FCI and PUH64 (see Chiosis et al., *ACS Chem. Biol.* (2006) 1(5):279-284 and those disclosed in PCT Application No. WO 2002/0236075; related heterocyclic derivatives disclosed in PCT Application No. WO 2005/028434; and 3,4-diarylpyrazole compounds disclosed in Cheung, et al., *Bioorg. Med. Chem. Lett.* (2005) 15:3338-3343. Antibodies or antibody fragments that selectively bind to Hsp90 may also be administered as drugs to cause inhibition of Hsp90, and can be used in combination with the compounds of the invention.

Natural effectors such as TRAIL, a TRAIL receptor antibody, and TNF-α and TNF-β can also be administered as drugs for this purpose, and are also preferred, as are active fragments of these peptides.

Where a compound of the invention is utilized to potentiate the effects of another therapeutic, the two agents may be co-administered, or they may be administered separately where their administration is timed so the two agents act concurrently or sequentially. Accordingly, the compositions of the invention include at least one compound of formulae (I), (IA), (1A), (3A), (1)-(5), (7)-(16), and (13A)-(13D) and can optionally include one or more additional cytotoxic or cytostatic therapeutic such as, but not limited to, those disclosed above. Similarly, the methods of the invention include methods wherein a subject diagnosed as in need of treatment for inflammation and/or cancer is treated with at least one compound of the invention, and is simultaneously or concurrently treated with one or more of the additional therapeutic agents described above.

Formulations of the compounds and compositions of the invention may be prepared in a manner suitable for systemic administration or topical or local administration. Systemic formulations include those designed for injection (e.g., intramuscular, intravenous or subcutaneous injection) and those prepared for transdermal, transmucosal, or oral administration. The formulation will generally include a diluent as well as, in some cases, adjuvants, buffers, preservatives and the like. The compounds can be administered also in liposomal compositions or as microemulsions.

Injection methods are sometimes appropriate routes for administration of the compounds for systemic treatments and sometimes also for localized treatments. These include methods for intravenous, intramuscular, subcutaneous, and other methods for internal delivery that bypass the mucosal and dermal barriers to deliver the composition directly into the subject's living tissues.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain minor amounts of nontoxic auxiliary substances such as wetting or emulsifying agents, pH buffering agents and the like, such as, for example, sodium acetate, sorbitan monolaurate, and so forth.

Various sustained release systems for drugs have also been devised and can be utilized with the compounds of the invention. See, for example, U.S. Pat. No. 5,624,677. The present compositions can be utilized in such controlled-release delivery systems where appropriate.

Systemic administration may also include relatively non-invasive methods such as the use of suppositories, transdermal patches, transmucosal delivery and intranasal administration. Oral administration is also suitable for compounds of the invention, which are more robust than the Smac peptide itself and are thus advantageously more orally bioavailable. Suitable forms include syrups, capsules, tablets, and the like as in understood in the art.

Selection of a particular route of administration for a given subject and indication is well within the ordinary level of skill in the art. For example, rectal delivery as a suppository is often appropriate where the subject experiences nausea and vomiting that precludes effective oral delivery. Transdermal patches are commonly capable of delivering a controlled-release dosage over several days or to a specific locus, and are thus suitable for subjects where these effects are desired.

Transmucosal delivery is also appropriate for some of the compositions and methods of the invention. Thus the compositions of the invention may be administered transmucosally using technology and formulation methods that are known in the art.

For administration to animal or human subjects, the dosage of a compound of the invention is typically 10-2400 mg per administration. However, dosage levels are highly dependent on the nature of the condition, the condition of the patient, the judgment of the practitioner, and the frequency and mode of administration. Selection of a dosage of such compounds is within the skill of an ordinary artisan, and may be accomplished by starting at a relatively low dosage and increasing the dosage until an acceptable effect is achieved.

Frequency of administration of the compounds of the invention can also be readily determined by one skilled in the art using well known techniques. For example, the patient may be administered a low dosage of a compound or composition of the invention at a low frequency such as once per day or less often; and the dosage and/or frequency of administration may be systematically increased until a desired effect is achieved in the patient.

Many suitable monomers are readily prepared by known methods, including the extensive body of literature describing synthesis of peptides and peptide mimetics. Examples of the synthesis of certain monomers are included herein. Representative monomers are shown in Table 5.

The invention includes monomers of formula (6) and methods of using such monomers to make compounds of formulas (1)-(5) and (7)-(9). Certain amine and azide containing monomers can be prepared as shown in Schemes 1, 6 and 7. It will be understood that similar monomers possessing different absolute or relative stereochemistry could be made by varying the chirality of the starting materials utilized, or through standard functional group manipulations which are known to those of skill in the art. For example, double-inversion of the 4-hydroxyl substituent on compound I in Scheme 1, e.g., by tosylation, treatment with iodide, followed by displacement with azide anion, would provide an isomer of compound II where the 2- and 4-substituents have the relative trans stereochemistry. Many other suitable monomers can be prepared by methods that are known in the art. A preferred method for making the compounds of formula (1) involves reaction of two monomers of formula (6) with a third molecule containing at least two reactive centers.

For example, compounds of formula (1) where L comprises a bis-amide linker can be prepared by acylation of two amine containing monomers of formula (6) with a diacid, which may be optionally activated as a diacyl halide, mixed anhydride, activated ester, bis-sulfonyl halide, or the like. Such compounds may be symmetrical or unsymmetrical. This reaction is illustrated in Schemes 4 and 6. For compounds of formula (2), three amine containing monomers of formula (6) may be reacted with a triacid derivative, as shown in Scheme 5.

Compounds of formula (1) having a diacetylenic in the linker L can be made, as described by Harran, et al., US 2005/0197403, by dimerizing two acetylenic monomers in the presence of a copper salt.

The acetylenic linking groups can be readily modified to produce other linkers; for example, catalytic hydrogenation of such bis-acetylenic compounds would provide the partially or fully saturated-linker compounds.

The acetylenic linking groups may also undergo cycloaddition reactions. For example, cycloaddition reactions of a bis-acetylenic dimer of formula (1) with an alkyl bis-azide provides fused triazoles.

In addition, two azido monomers of formula (6) may undergo dimerization concomitantly with cycloaddition with a bis-acetylene containing molecule, to form a dimer wherein the linker comprises two triazole rings. Alternatively, an azide containing monomer of formula (6), may undergo cycloaddition with an acetylene containing monomer to form a dimer containing a triazole ring as part of the linker.

A wide variety of methods for forming such dimeric compounds are known in the art, and may be employed with suitably functionalized monomers. For example, hydroxyl substituted aryl or arylalkyl groups may be modified to form aryl triflates or other suitable functional groups, which may undergo cross-coupling reactions, for example with alkynes, to form dimeric structures. One of skill in the art would recognize that such compounds may undergo further chemical transformations, for example, partial or complete hydrogenation to form alkenyl or saturated linkers.

Additionally, hydroxyl or amino substituted monomers may be alkylated, for example with allylic or propargylic halides, to form other linkers or other functionalized monomers. Such monomers can undergo dimerization or trimerization reactions, and may be further modified after dimerization or trimerization Alkylamine containing monomers may undergo dimerization by further reaction at the amine center, for example by N-alkylation, acylation, sulfonylation, or carbamoylation, to produce dimers wherein the linkage represents as Q-L-Q' comprises a substituted amine, or an amide, sulfonamide or urea. In addition, alkylamine monomers may undergo reaction to provide additional monomers containing functional groups suitable for dimerization, for example, by alkylation with propargyl halides to provide acetylene containing monomers.

The invention includes monomers of formula (19A), and methods of using such monomers to make compounds of formulas (13B) to (13D). Certain alcohol and alkynyl containing monomers can be prepared as shown in Scheme 9. Certain amine and azide containing monomers can be prepared as shown in Scheme 10.

Many other suitable monomers can be prepared by methods that are known in the art. One preferred method for making the compounds of formula (13B) involves reaction of two monomers of formula (19A) with a third molecule containing at least two reactive centers.

For example, compounds of formula (13B) where J-K-J' comprises a bis-amide linker can be prepared by acylation of two amine-containing monomers of formula (19A) with a diacid, which may be optionally activated as a diacyl halide, mixed anhydride, activated ester, bis-sulfonyl halide, or the like. Such compounds may be symmetrical or unsymmetrical. This reaction is illustrated in Scheme 10.

Compounds of formula (13B) having a linker K comprising a diacetylenic moiety can be made, as described by Harran, et al., US 2005/0197403, by dimerizing two acetylenic monomers of formula (19A) in the presence of a copper salt, as shown in Scheme 9. The acetylenic linking groups can be readily modified to produce other linkers; for example, catalytic hydrogenation of such bis-acetylenic compounds provides the partially or fully saturated-linker compounds.

The acetylenic linking groups may also undergo cycloaddition reactions. For example, cycloaddition reactions of a bis-acetylenic dimer of formula (13A) with an alkyl bis-azide will provide a linker containing two triazole rings.

In addition, two azido monomers of formula (19A) may undergo dimerization concomitantly with cycloaddition with a bis-acetylene containing molecule, to form a dimer wherein the linker comprises two triazole rings. Alternatively, an azide containing monomer of formula (19A), may undergo cycloaddition with an acetylene containing monomer to form a dimer containing a triazole ring as part of the linker.

Alkylamine containing monomers may undergo dimerization by further reaction at the amine center, for example by N-alkylation, acylation, sulfonylation, or carbamoylation, to produce dimers wherein the linkage represented as J-K-J' comprises a substituted amine, or an amide, sulfonamide or urea.

Preparation of the Compounds of the Invention from Such Precursors can be Achieved using methods known in the art. Accordingly, synthesis of these compounds is within the ordinary skill in the art. Synthetic methods for making selected compounds of the invention are also provided herein.

Synthetic Scheme 1:

Compound II was prepared according to H. Marusawa et al., *Bioorg Med. Chem.* (2002) 1399-1415. II was treated with acid to deprotect the Boc group and coupled to Boc-Tle-OH to make III. By repeating the similar Boc deprotection and coupling steps, Compound IV was synthesized. Hydrolysis of the methyl ester and amide formation gave the corresponding peptide V. The azide group on the 4 position of the proline was reduced to free amine to give compound VI

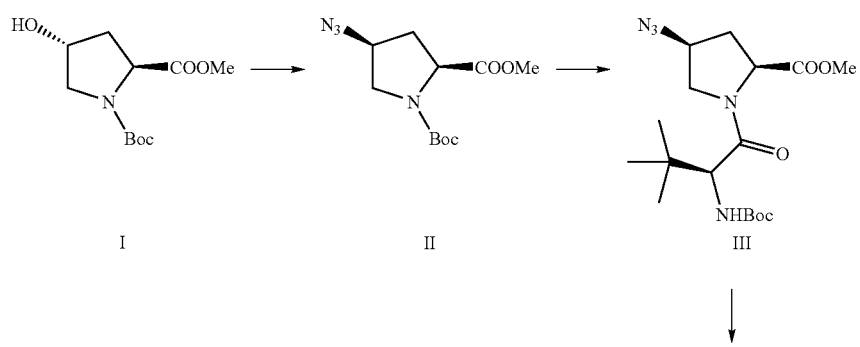

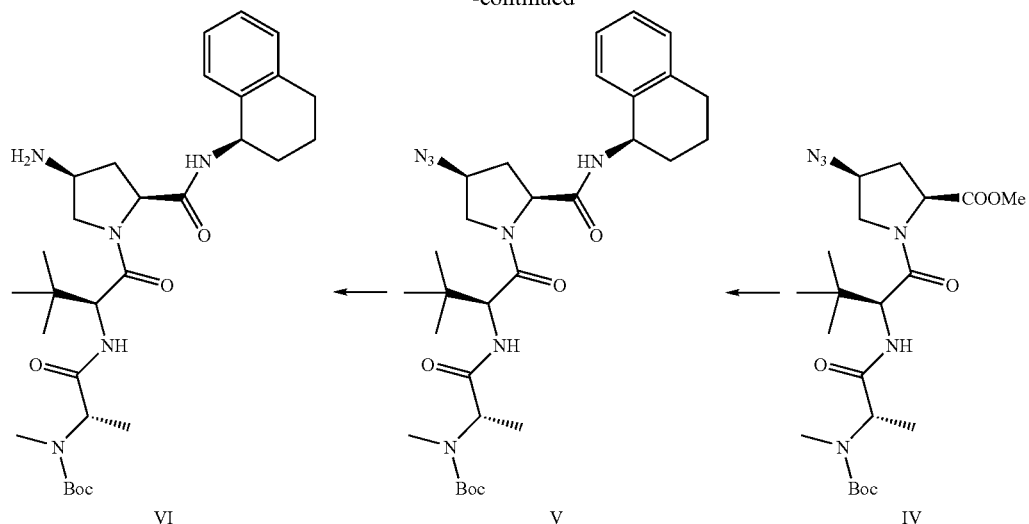

Synthetic Schemes 2-5:

By taking advantage of the copper(I) catalyzed azide-alkyne [3+2]cycloaddition, the compound V was able to be used to synthesize a series of dimerized compounds VII or VIII.

On the other hand, compound VI can be coupled with di-acid or its derivatives by the amide formation reaction to make a number of dimerized compounds IX or trimerized compounds X.

Scheme 2:

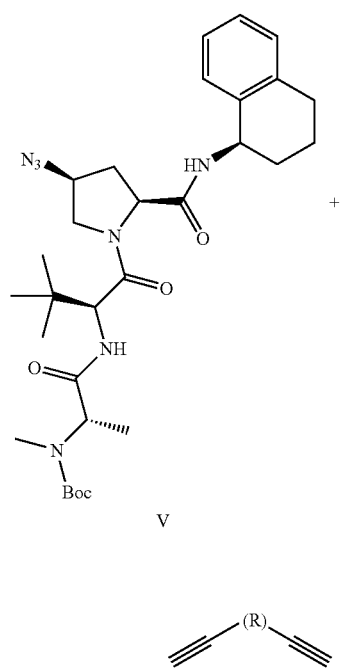

Scheme 3:

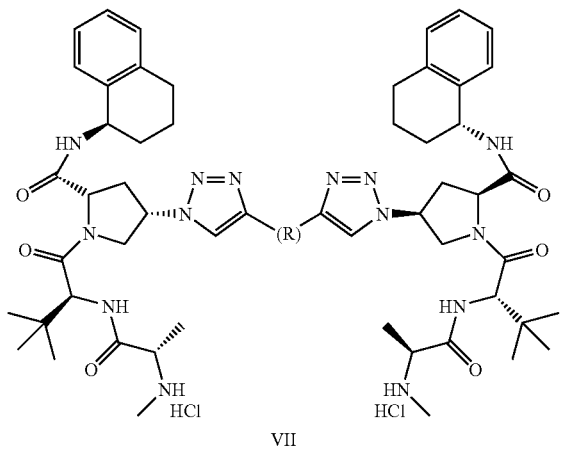

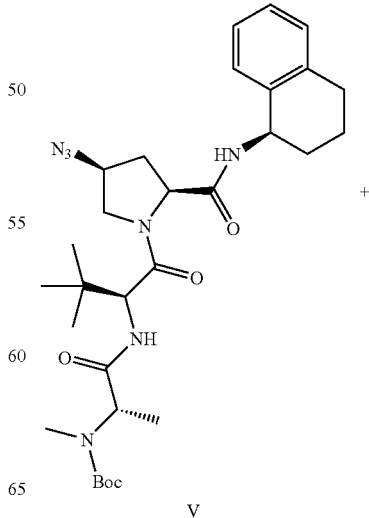

73
-continued
74
-continued
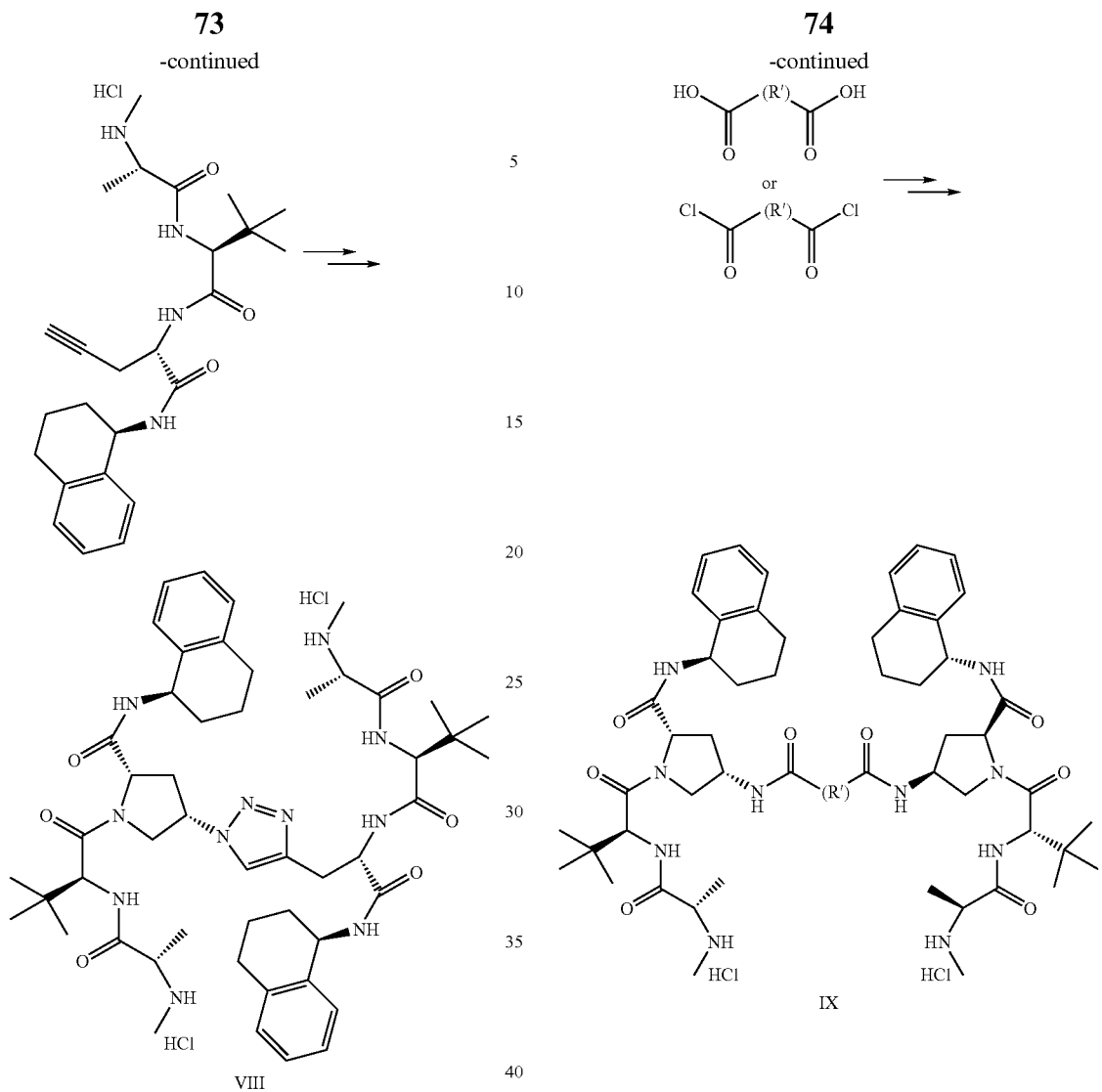
Scheme 4:
Scheme 5:
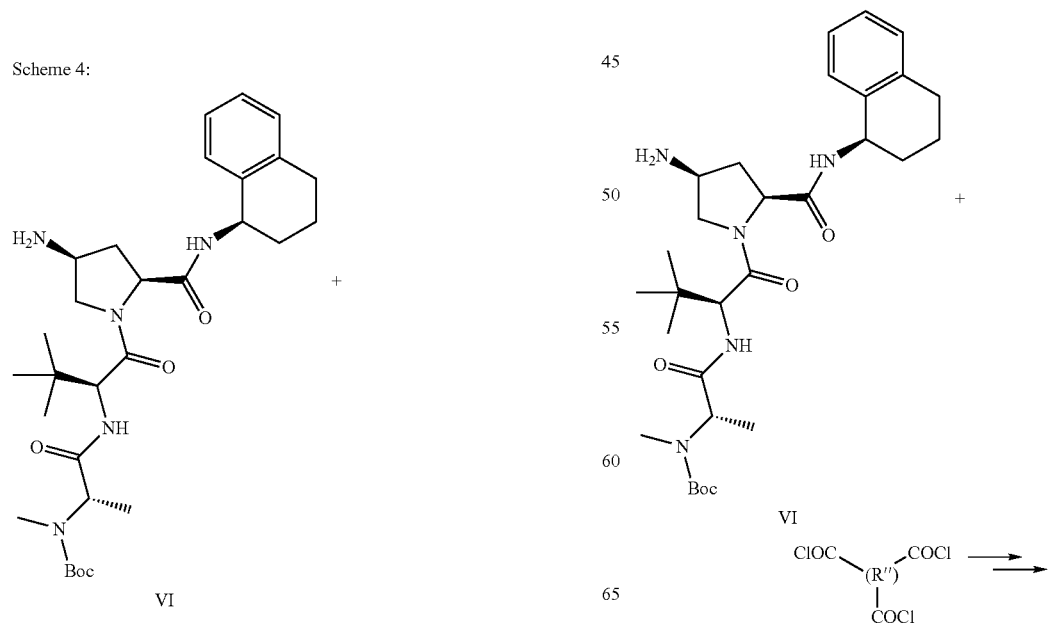

-continued
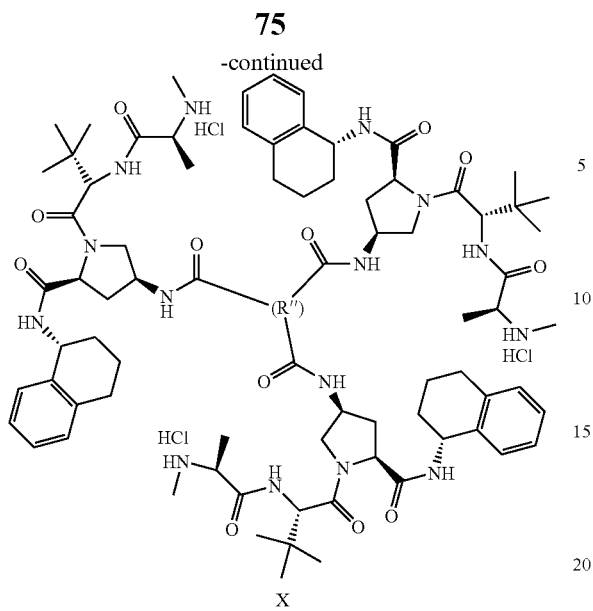
X
Scheme 6:
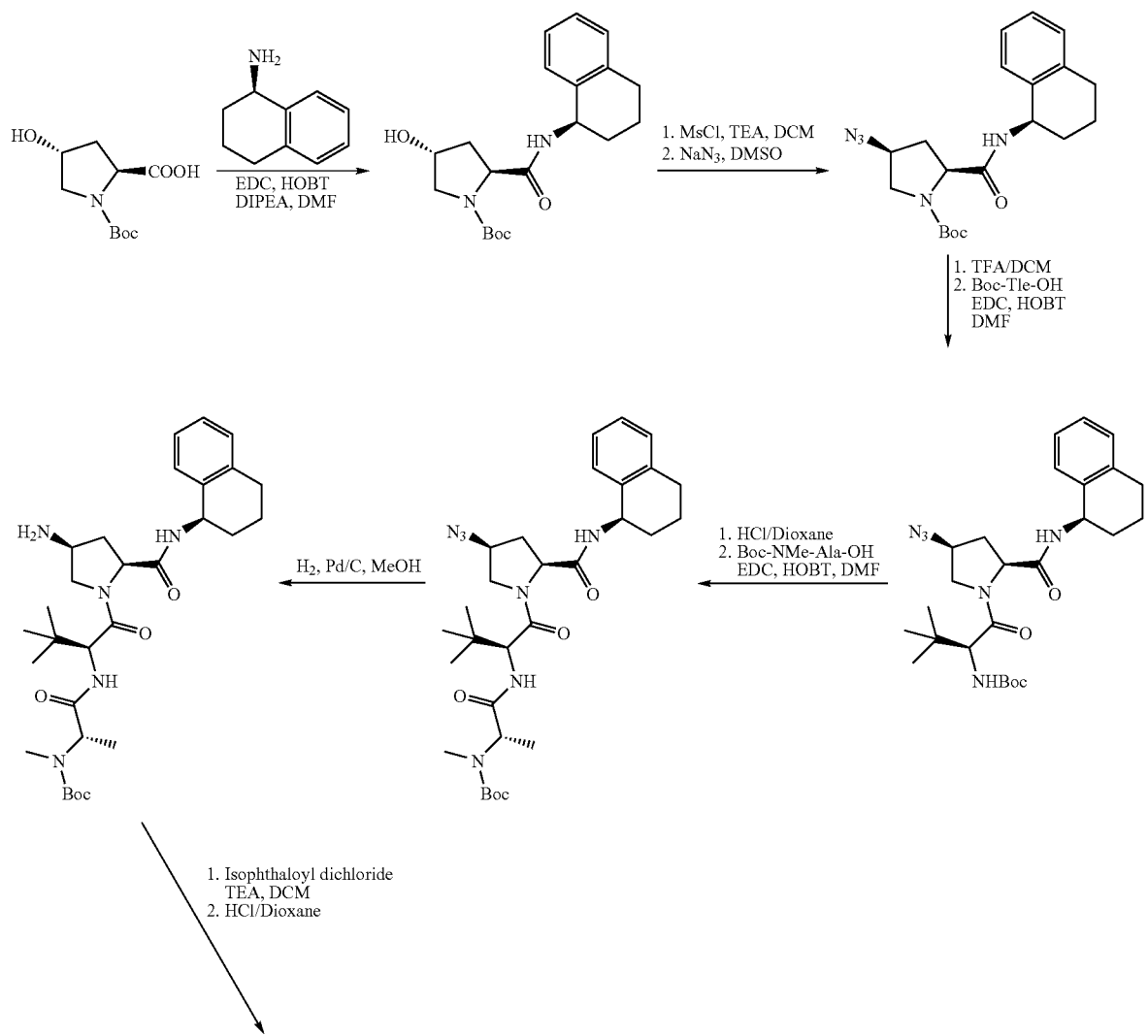

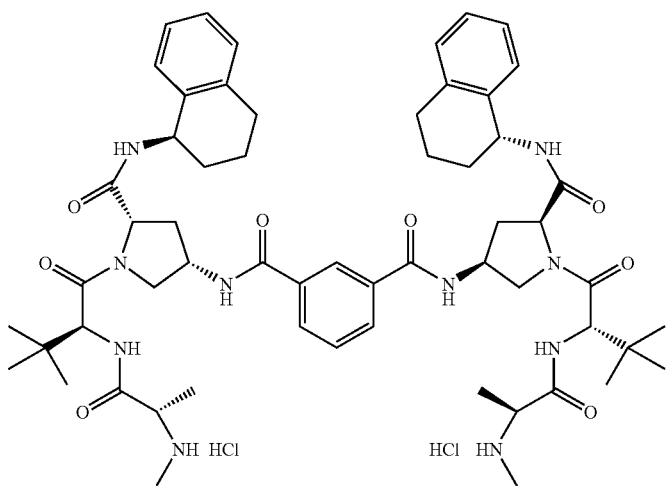
Scheme 7:
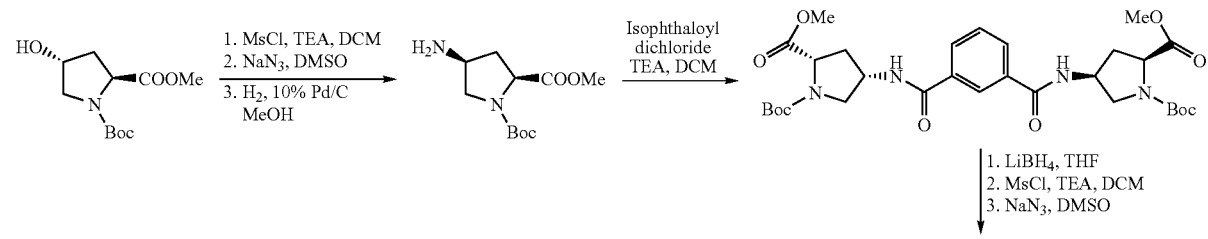
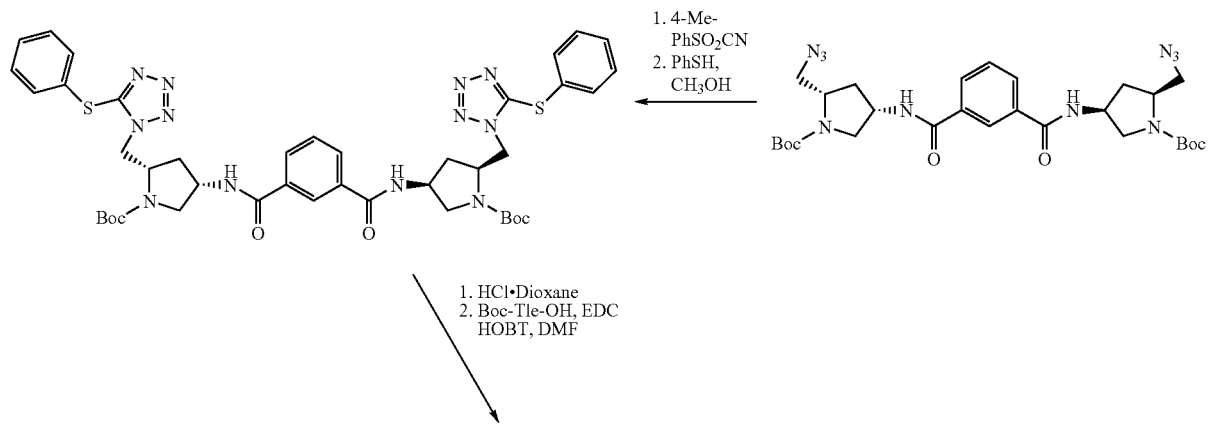

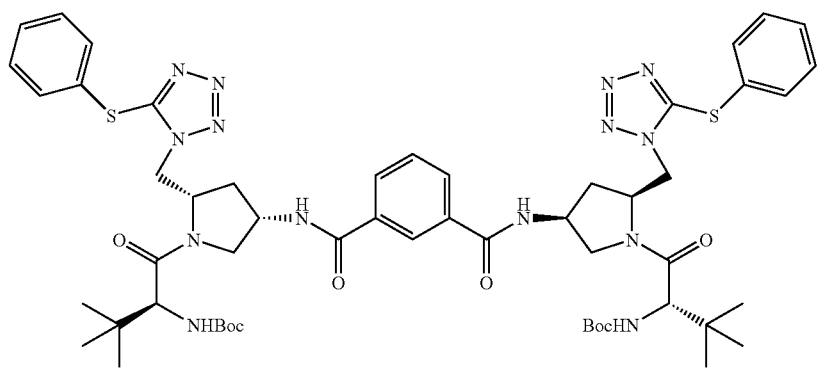

1. HCl·Dioxane
2. Boc-NMe-Ala-OH
   EDC, HOBT, DMF
3. HCl·Dioxane

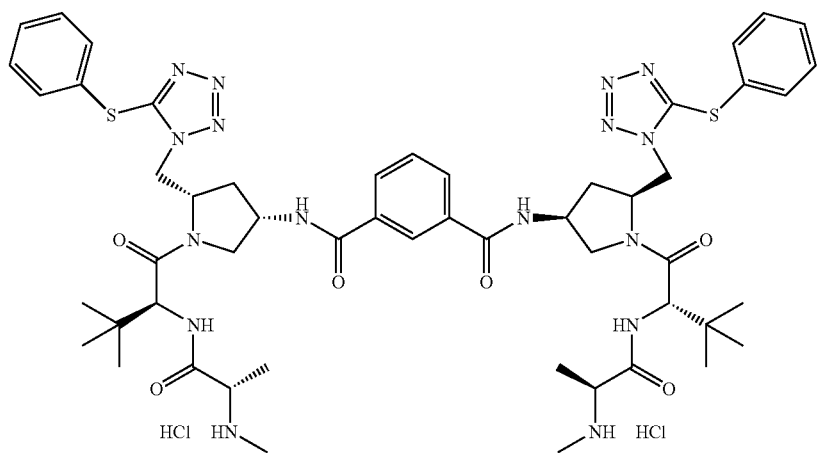

Synthetic Schemes 8-9:

Compounds of formulae (13 and 13A-D) were prepared according to Schemes 8-10. A protected monomer of formula (19) was prepared as shown in Scheme 8. Amide coupling of the free carboxylic acid from Scheme 8 with an amino alkyne derivative provided a monomer of formula (19A). Cross-coupling of two terminal alkyne monomers provided a diynyl linked dimer of formula (13A), which was hydrogenated to give a dimer with a saturate alkylene linker.

81 82
Scheme 8
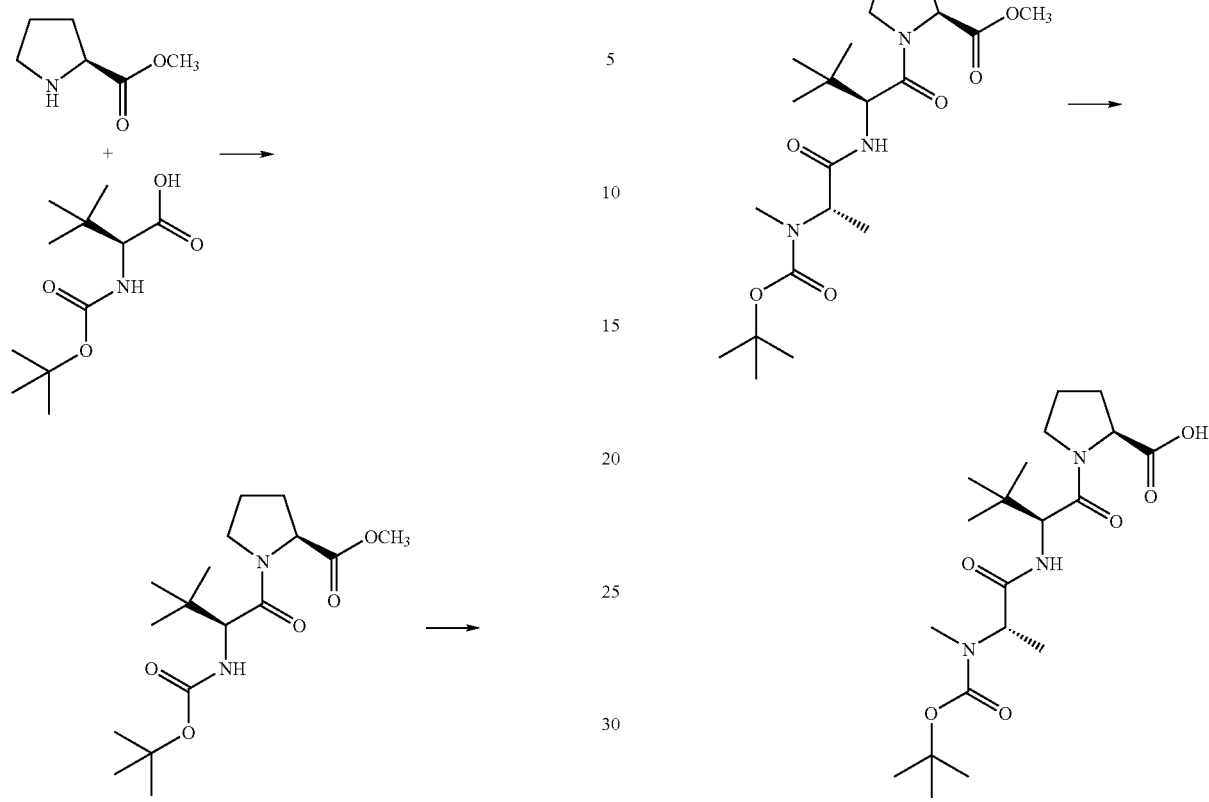
-continued
Scheme 9
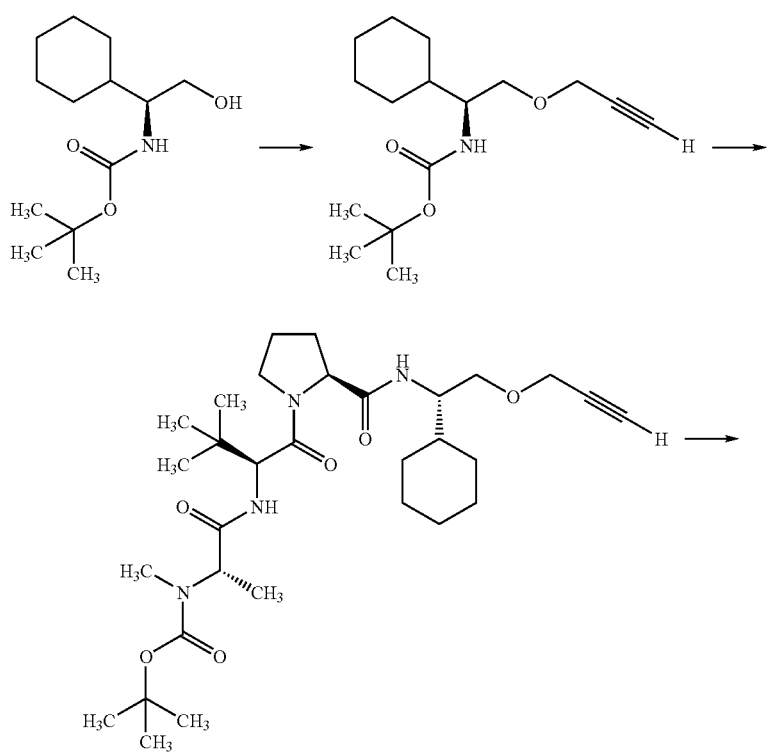

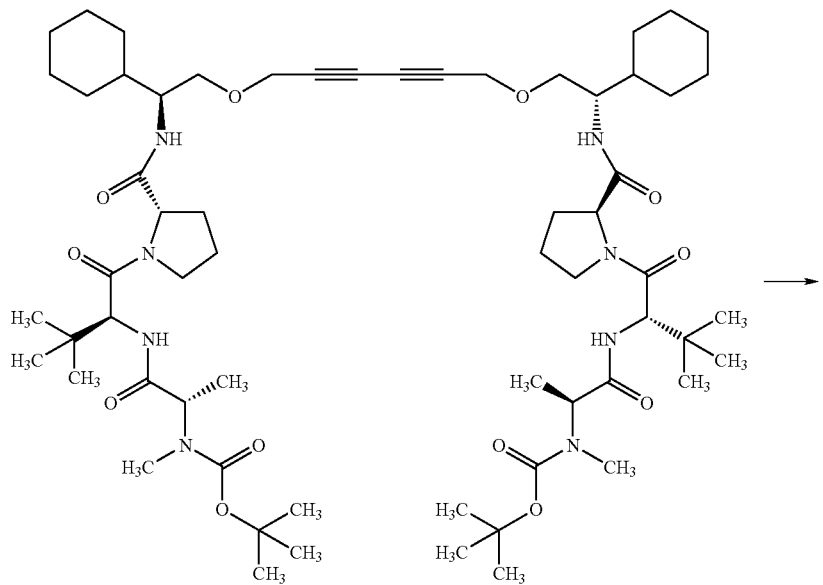
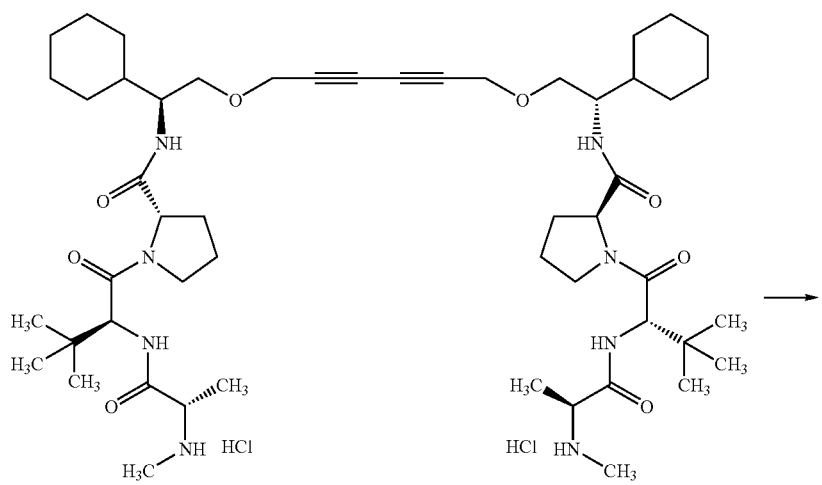
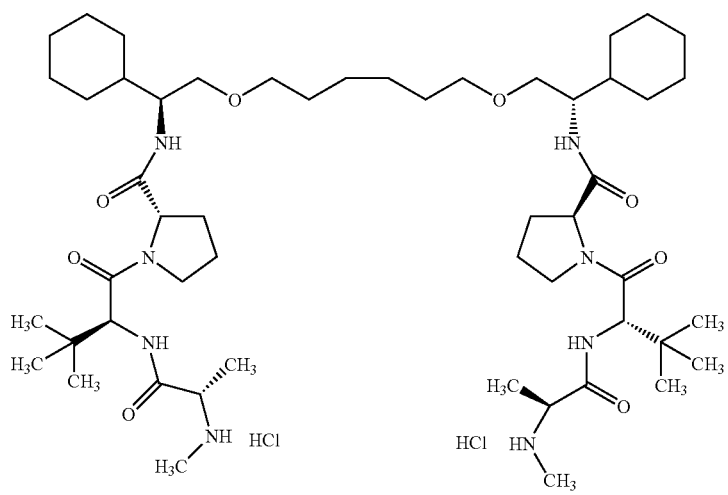

Synthetic Scheme 10:
Scheme 10 describes the preparation of azido-containing monomer of formula (19A), which was reduced to the corresponding amino-containing monomer and dimerized by formation of amide bonds between two monomers units and a benzene dicarboxylic acid, to provide a dimer of formula (13A).
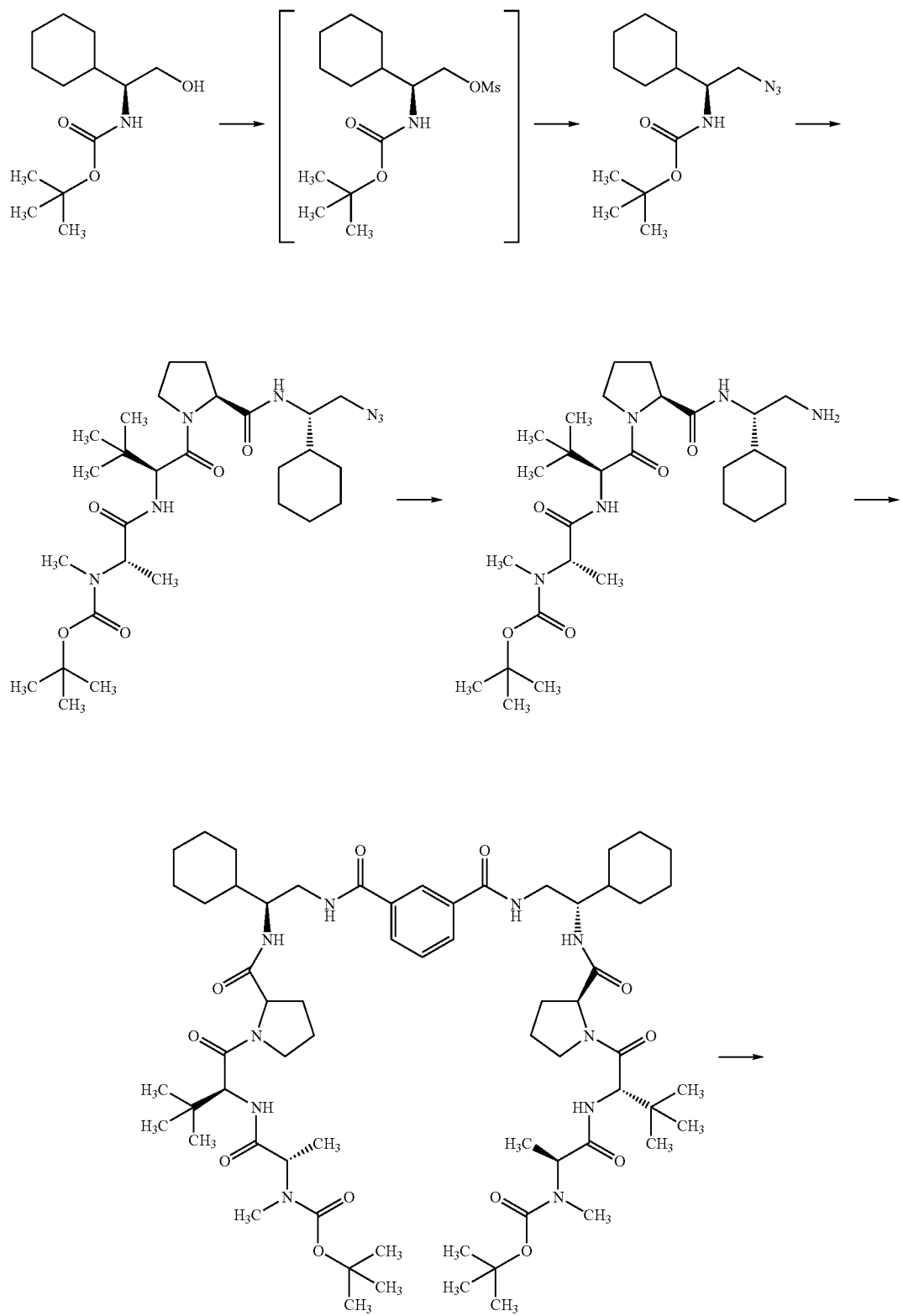

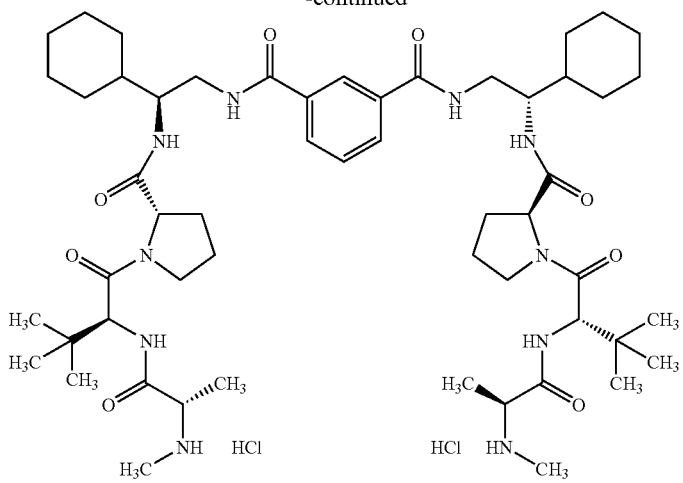
Scheme 11 describes the preparation of the compound 104, described in Examples 43-49.
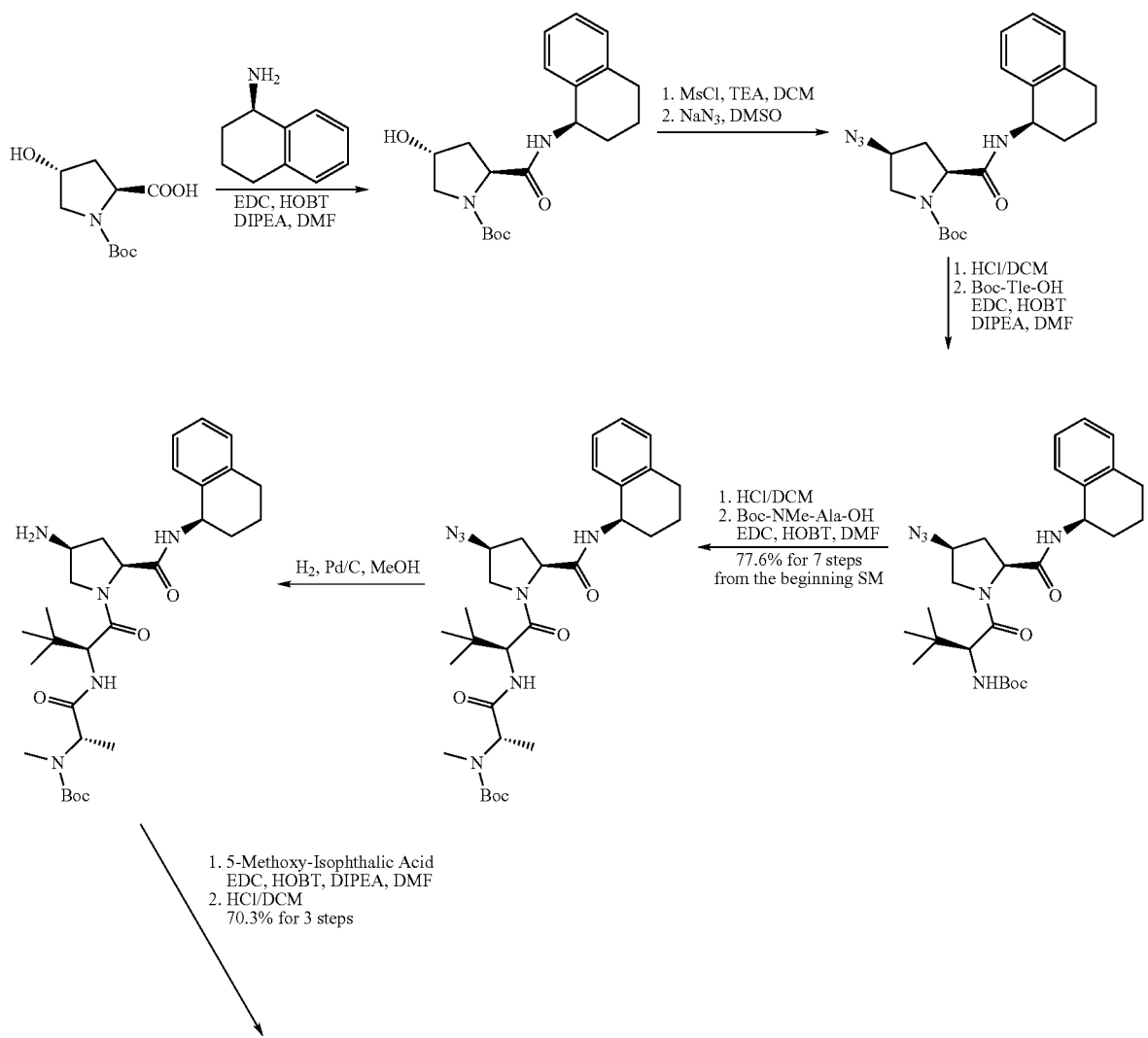

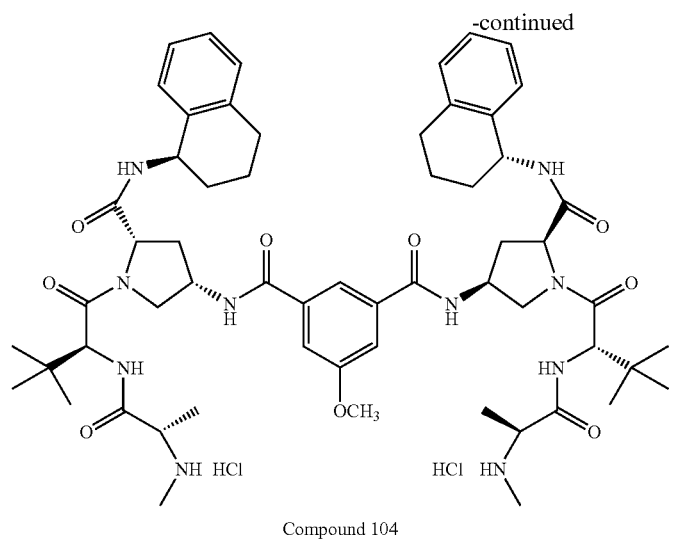
Compound 104
Scheme 12
Scheme 12 describes the synthesis of compound 51, described in Examples 50-56.
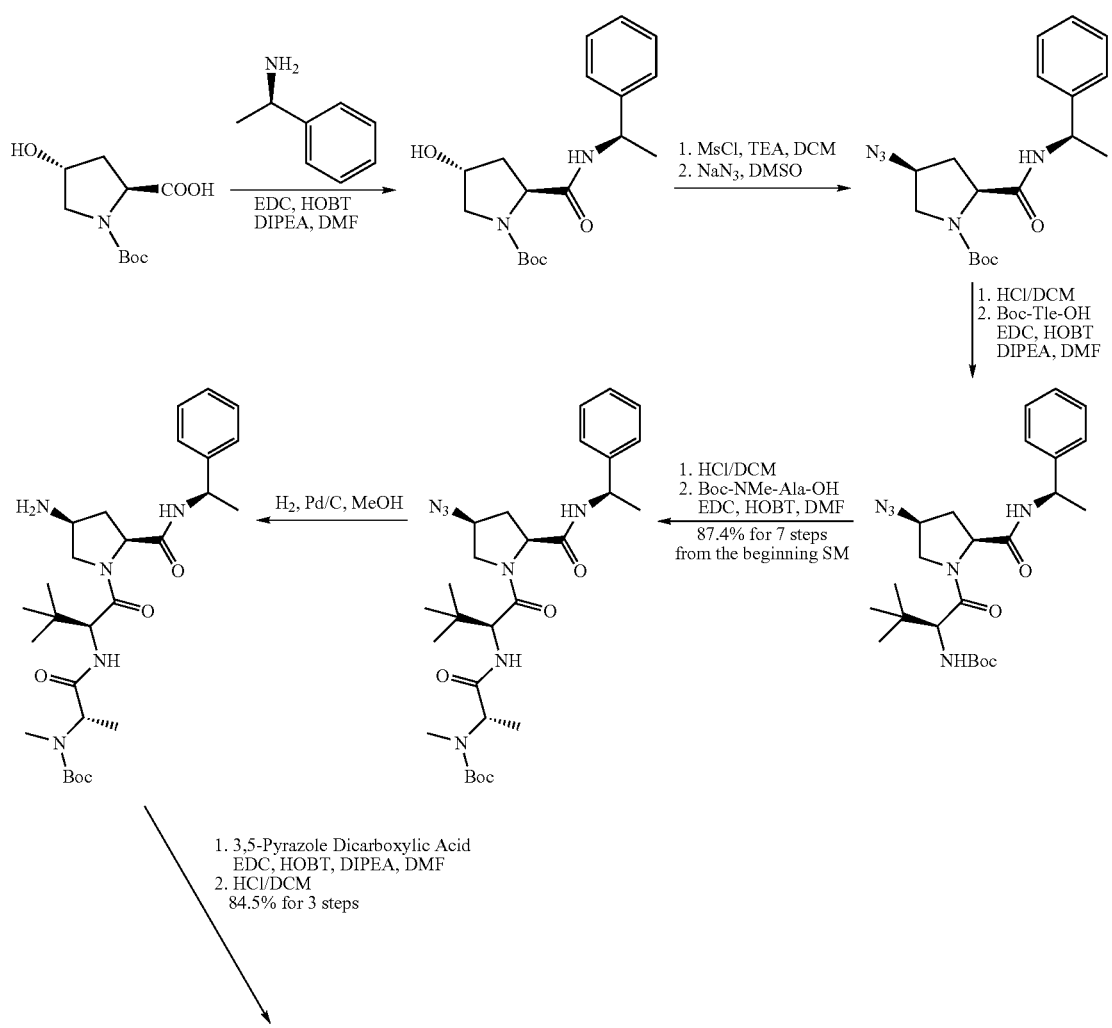

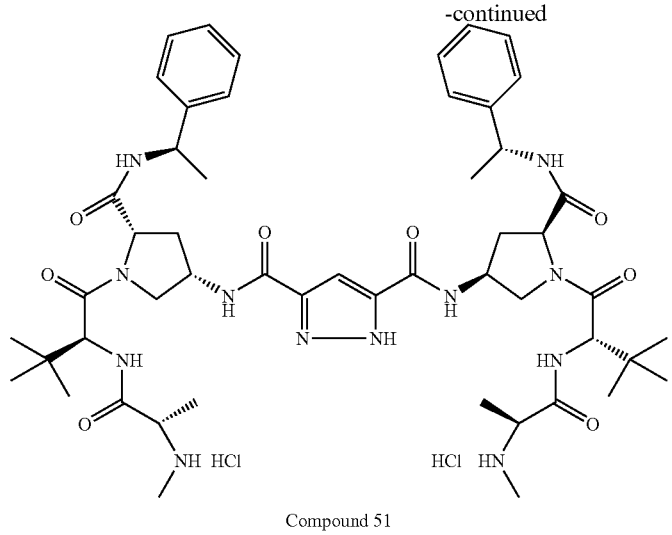
Compound 51
Scheme 13
Scheme 13 describes the synthesis of compound 57, described in Examples 57-63.
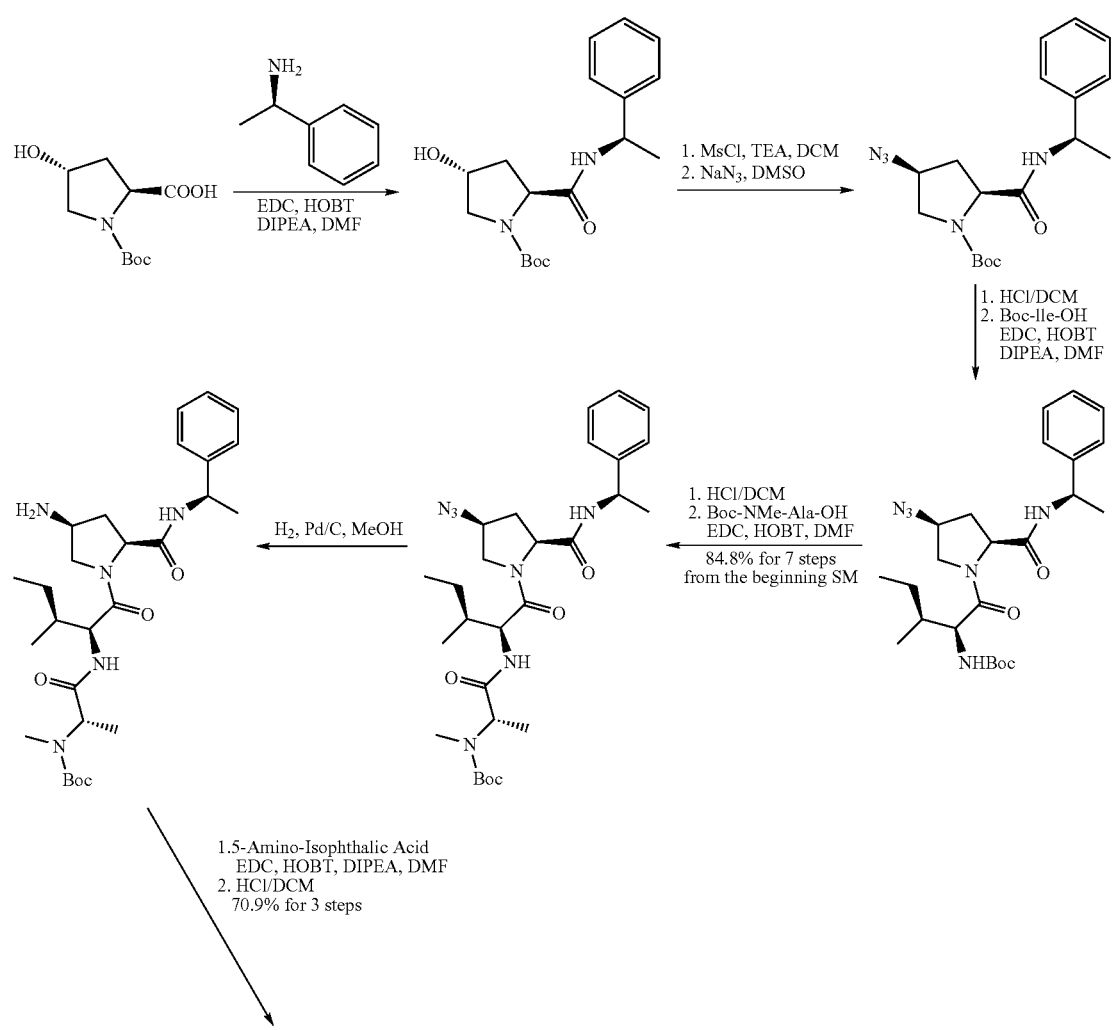

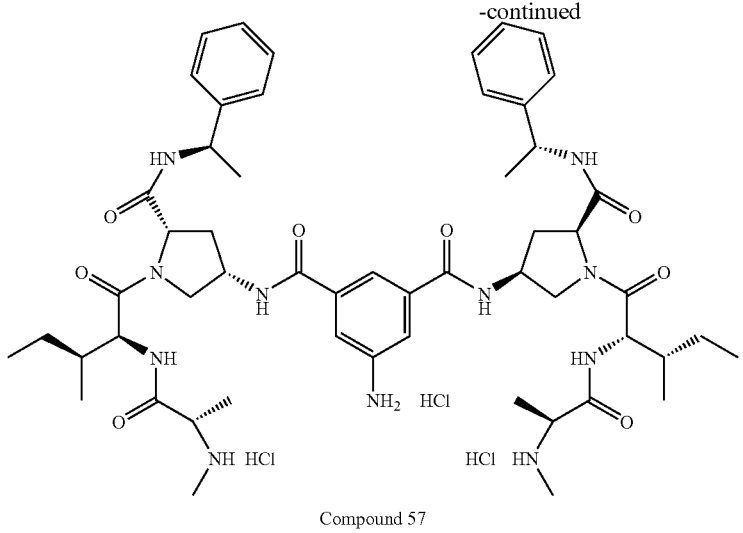
Compound 57
Scheme 14
Scheme 14 describes the synthesis of compound 32, described in Examples 64-70.
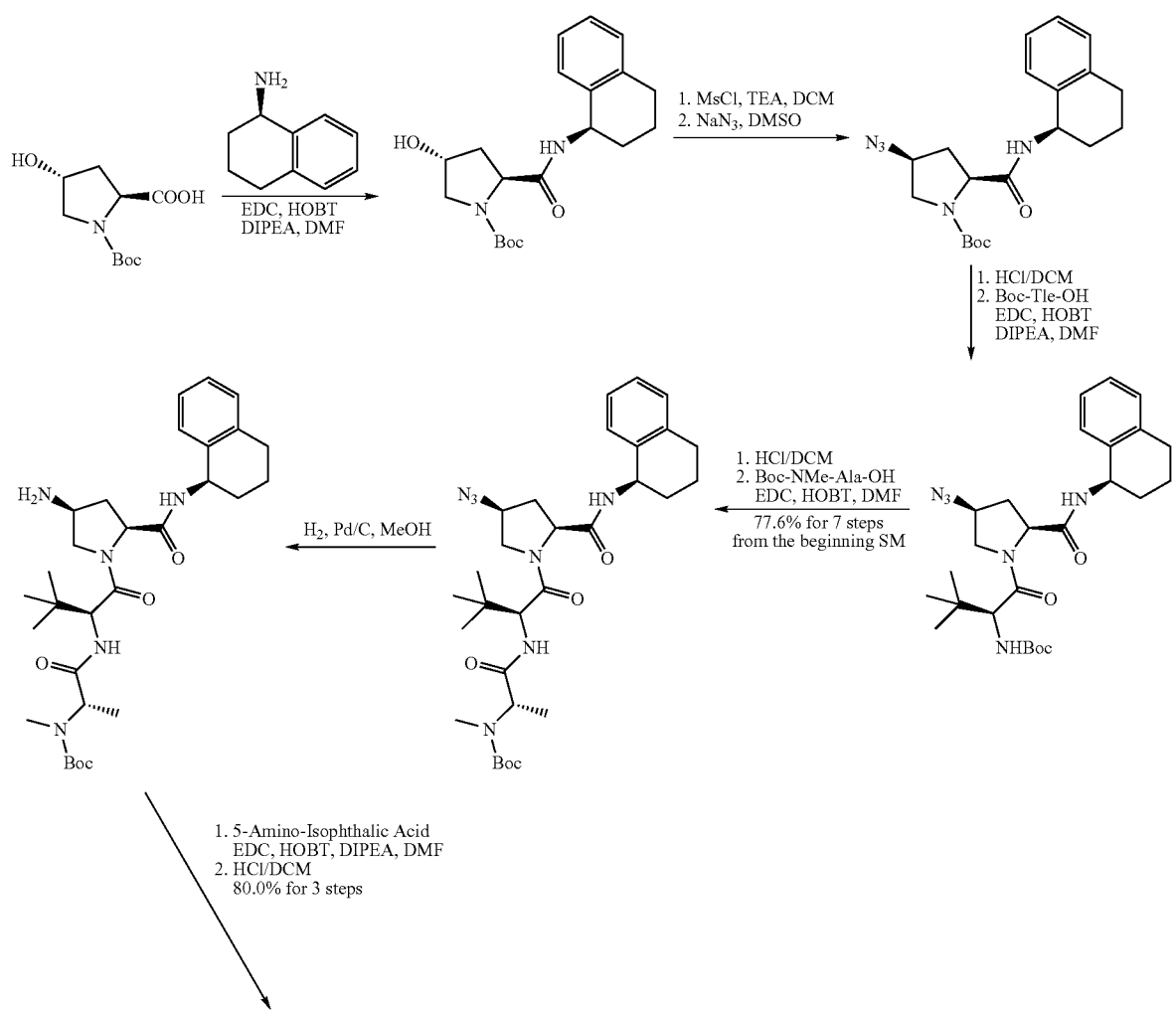

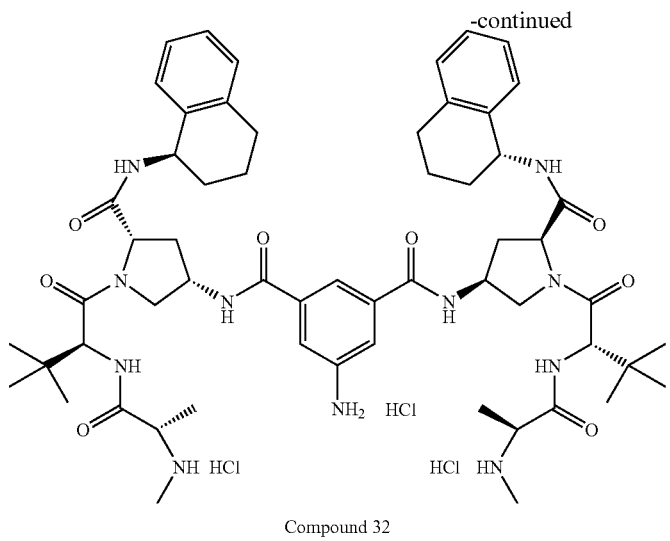

Compound 32

General Methods:

NMR spectra were acquired at a proton frequency 400 MHz. $^1$H chemical shifts are reported with Me$_4$Si (0.00 ppm), CHCl$_3$ (7.24 ppm) or CD$_2$HOD (3.3 ppm) as internal standards. $^{13}$C chemical shifts are reported with CDCl$_3$ (77.23 ppm) or CD$_3$OD (49.00 ppm) as internal standards.

HPLC analysis used an AGILENT® LC/MS instrument (1100 series) with an AGILENT® ECLIPSE™ XBD-C18 column (4.6×150 mm, 5 micron packing) operating at a flow rate of 1.00 mL/min. A linear acetonitrile/water gradient was used, with 0.05% TFA in each solvent. Initial solvent composition was 20% acetonitrile, increasing to 100% acetonitrile over 10 min. After holding at 100% acetonitrile for 5 min., the composition was returned to 20% acetonitrile over 2 min. and held at that composition for 3 min. to complete the cycle. Eluent was monitored by MS, along with UV at 220 and 254 nm.

Standard abbreviations are used throughout the experimental sections and will be understood by one of skill in the art. For example, hydrochloric acid (HCl); lithium hydroxide (LiOH); methanol (MeOH); water (H$_2$O); ethyl acetate (EtOAc); sodium sulfate (Na$_2$SO$_4$); dimethylformamide (DMF); N-Hydroxybenzotriazole (HOBT); diisopropylethylamine (DIPEA); 1-ethyl-3-(3-dimethylaminopropyl)carbodiimide hydrochloride (EDC); sodium bicarbonate (NaHCO$_3$); tert-butoxycarbonyl (Boc); triphenyl phosphine (PPh$_3$); methyl t-butyl ether (MeOtBu); N-methyl morpholine (NMM); copper (I) iodide (CuI); triethylamine (TEA); dichloromethane (DCM); sodium azide (NaN$_3$); trifluoroacetic acid (TFA); palladium on charcoal (Pd/C); lithium borohydride (LiBH$_4$); potassium carbonate (K$_2$CO$_3$); benzenethiol (PhSH); sodium hydride (NaH); copper (II) acetate (Cu(OAc)$_2$); dimethylsulfoxide (DMSO). Amino acids are referred to herein using the standard 3-letter code; e.g., alanine is sometimes referred to herein as Ala, and tert-leucine may be referred to as Tle.

General Procedure A (for Deprotection of Boc):

To a solution of the substrate in methylene chloride was added trifluoroacetic acid (5 eq) at room temperature. The solution was stirred at room temperature for 2-3 hrs and monitored by thin layer chromatography (TLC). After all the starting material has been consumed, the solvents and trifluoroacetic acid were removed under reduced pressure to give the desired product.

General Procedure B (for Deprotection of Boc):

To a solution of the substrate in methylene chloride was added HCl in dioxane (4N, 4 eq) at room temperature. The solution was stirred at room temperature for 1-2 hr and monitored by TLC. After all the starting material has been consumed, the solvents and HCl were removed under reduced pressure. The residue was lyophilized to give the desired product.

General Procedure C (for Hydrolysis of the Methyl Esters):

To a well-stirred solution of the substrate in a mixture of 5:1 MeOH/H$_2$O was added LiOH at 0° C. After stirring for 18 hours, 1N HCl was added until the pH=4. EtOAc was used to extract the product and the combined organic layers were washed with brine and dried over Na$_2$SO$_4$. The solution was concentrated under reduced pressure to give the desired product.

General Procedure D (for Preparation of Amides):

To a well-stirred mixture of the acid (1 eq.) and amine salt (1.1 eq) in DMF at 0° C., were added HOBT (1.1 eq.) and DIPEA (2.25 eq.) in this order. After 5-10 min, EDC (1.1 eq.) was added. The mixture was stirred for 1 hour at 0° C., then slowly warmed up to room temperature and stirred for 18 hours at room temperature. The reaction mixture was concentrated under vacuum. The residue was diluted with EtOAc and washed by HCl solution (1 N), saturated NaHCO$_3$ solution and brine. The organic phase was dried over Na$_2$SO$_4$ and concentrated under reduced pressure to give the desired product.

General Procedure E (for Preparation of Amides):

To a well-stirred mixture of the acid substrate in DMF at 0° C., was added HOBT (1.1 eq), DIPEA (1.5 eq) and EDC (1.1 eq) in this order. After 10 minutes, the free amine substrate (1.1 eq) was added. The mixture was stirred for 1 hour at 0° C., then slowly warmed up to room temperature and stirred for 18 hours at room temperature. The reaction mixture was concentrated under vacuum. The residue was diluted with EtOAc and washed by HCl solution (1 N), saturated NaHCO$_3$ solution and brine. The organic phase was dried over Na$_2$SO$_4$ and concentrated under reduced pressure to give the desired product.

General Description of In Vitro and In Vivo Assays

The in vitro and in vivo activities of the compounds of the invention may be determined using techniques that are known in the art. For example, Bockbrader, et al., *Oncogene* (2005)

24:7381-7388 discloses assays for determination of the effect of Smac mimics using cell culture assays and in vitro assays for caspase activation. Accordingly, in addition to guidance from symptomology, treatment with the compounds, compositions and methods of the invention can be monitored by methods known in the art for determining the effects of Smac mimetic compounds.

The following examples are included for illustrative purposes only and are not intended to represent or limit the scope of the subject matter claimed herein.

EXAMPLE 1

(2S,4S)-methyl 4-azido-1-((S)-2-(tert-butoxycarbonylamino)-3,3-dimethylbutanoyl)pyrrolidine-2-carboxylate

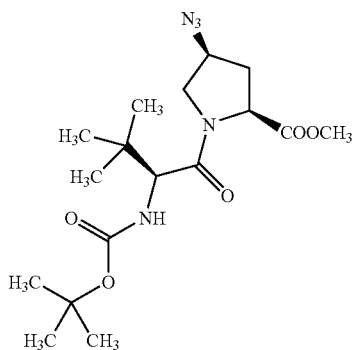 [SMILES: COC(=O)[C@@H]1C[C@H](N=[N+]=[N-])CN1C(=O)[C@@H](NC(=O)OC(C)(C)C)C(C)(C)C]

Compound II was treated with trifluoroacetic acid using the general procedure A to deprotect the BOC group. The resulting trifluoroacetic acid salt was coupled to Boc-Tle-OH using the general procedure D to prepare the title compound of Example 1. $^1$H NMR (CDCl$_3$): consistent with proposed structure.

EXAMPLE 2

(2S,4S)-methyl 4-azido-1-((S)-2-((S)-2-(tert-butoxycarbonyl(methyl)amino)propanamido)-3,3-dimethylbutanoyl)pyrrolidine-2-carboxylate

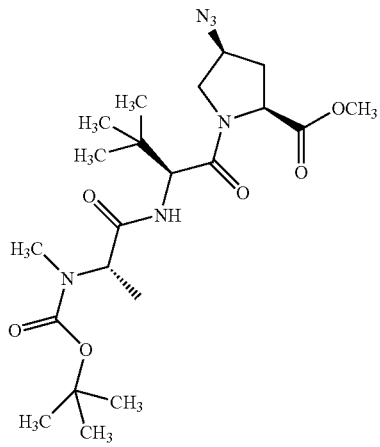 [SMILES: COC(=O)[C@@H]1C[C@H](N=[N+]=[N-])CN1C(=O)[C@@H](NC(=O)[C@H](C)N(C)C(=O)OC(C)(C)C)C(C)(C)C]

The title compound of Example 1 was treated with trifluoroacetic acid using the general procedure A to deprotect the BOC group. The resulting trifluoroacetic acid salt was coupled to Boc-N-Me-Ala-OH using the general procedure D to prepare the title compound of Example 2. $^1$H NMR (CDCl$_3$): consistent with proposed structure.

EXAMPLE 3 tert-butyl (S)-1-((S)-1-((2S,4S)-4-azido-2-((R)-1,2,3,4-tetrahydronaphthalen-1-ylcarbamoyl)pyrrolidin-1-yl)-3,3-dimethyl-1-oxobutan-2-ylamino)-1-oxopropan-2-yl(methyl)carbamate

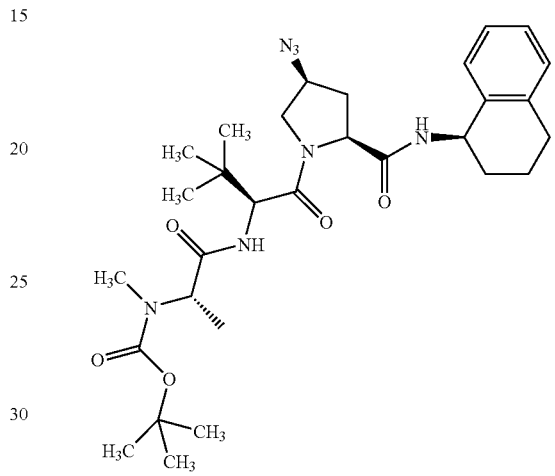

The title compound of Example 2 was treated with LiOH using the general procedure C to hydrolyze the methyl ester. The resulting acid was coupled to (R)-tetrahydro-1-naphthylamine using the general procedure D to prepare the title compound of Example 3. $^1$H NMR (CDCl$_3$): consistent with proposed structure.

EXAMPLE 4 tert-butyl (S)-1-((S)-1-((2S,4S)-4-amino-2-((R)-1,2,3,4-tetrahydronaphthalen-1-ylcarbamoyl)pyrrolidin-1-yl)-3,3-dimethyl-1-oxobutan-2-ylamino)-1-oxopropan-2-yl(methyl)carbamate

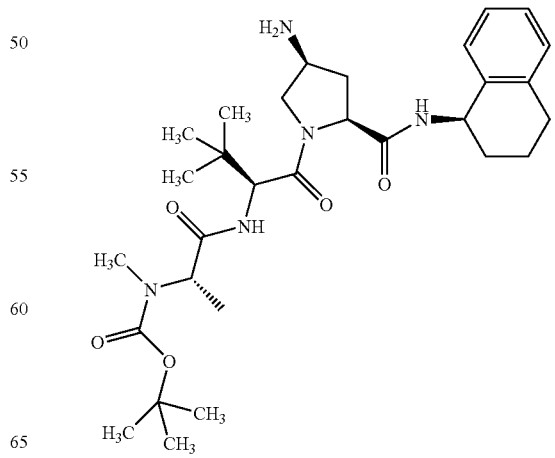

To a solution of the title compound of Example 3 (1.7 g, 2.9 mmol) in 10.6 mL dry THF was added Ph₃P (765 mg, 2.9 mmol) at room temperature. Water (78.3 μL, 4.35 mmol) was added drop wise and the reaction mixture was allowed to stir for 16 hours at room temperature. A 1:1 mixture of water/MeOtBu was added to quench the reaction. The two phases were separated. The aqueous phase was extracted by EtOAc twice, and then the combined organic phase was washed by brine, dried over sodium sulfate and concentrated under reduced pressure. The residue was chromatographed on silica gel, eluting with EtOAc, the 5% to 15% MeOH/methylene chloride to give the title compound as a white foam-like solid. ¹H NMR (CDCl₃): consistent with proposed structure.

EXAMPLE 5

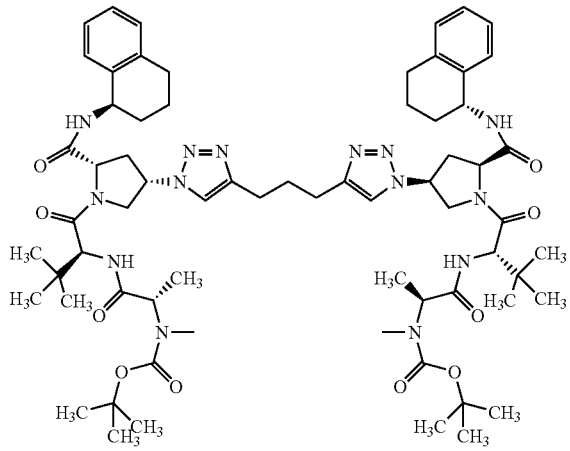 [SMILES: C[C@@H](C(=O)N[C@H](C(=O)N1C[C@@H](n2cc(CCCc3cn([C@H]4C[C@@H](C(=O)N[C@@H]5CCCc6ccccc65)N(C(=O)[C@@H](NC(=O)[C@H](C)N(C)C(=O)OC(C)(C)C)C(C)(C)C)C4)nn3)nn2)C[C@H]1C(=O)N[C@@H]1CCCc2ccccc21)C(C)(C)C)N(C)C(=O)OC(C)(C)C]

The title compound of Example 3 (500 mg, 0.86 mmol) was dissolved in a 1:1 mixture of t-butanol and water (30 mL) at room temperature. NMM (118 μL, 1.08 mmol), CuI (82 mg, 0.43 mmol) and 1,6-heptadiyne (49 μL, 0.43 mmol) were added in this order. The suspension was vigorously stirred at room temperature for 24 hours. The reaction mixture was diluted with MeOH and filtered through a CELITE® pad and rinsed with MeOH. The combined filtrate was concentrated under vacuum. The remaining aqueous solution was extracted by EtOAc three times. The organic phase was dried over sodium sulfate and concentrated under reduced pressure. The residue was chromatographed on silica gel, eluting with EtOAc, then 5% to 10% MeOH/methylene chloride to give the title compound as a white solid. ¹H NMR (CDCl₃): consistent with proposed structure.

EXAMPLE 6

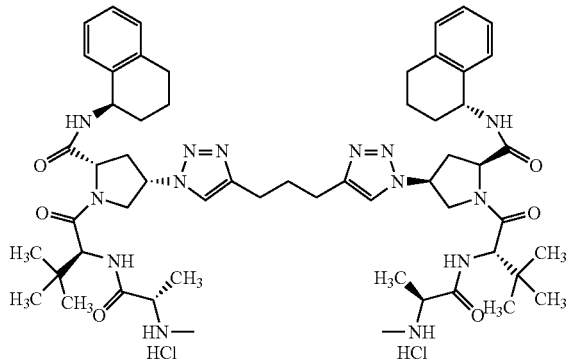 [SMILES: CN[C@@H](C)C(=O)N[C@H](C(=O)N1C[C@@H](n2cc(CCCc3cn([C@H]4C[C@@H](C(=O)N[C@@H]5CCCc6ccccc65)N(C(=O)[C@@H](NC(=O)[C@H](C)NC)C(C)(C)C)C4)nn3)nn2)C[C@H]1C(=O)N[C@@H]1CCCc2ccccc21)C(C)(C)C ; Cl ; Cl]

The title compound of Example 5 (410 mg, 0.33 mmol) in 1 mL methylene chloride was treated with HCl/dioxane (4M, 1.2 mL) using the general procedure B to give the title compound as a white solid. ¹H NMR (CDCl₃): consistent with proposed structure.

EXAMPLE 7

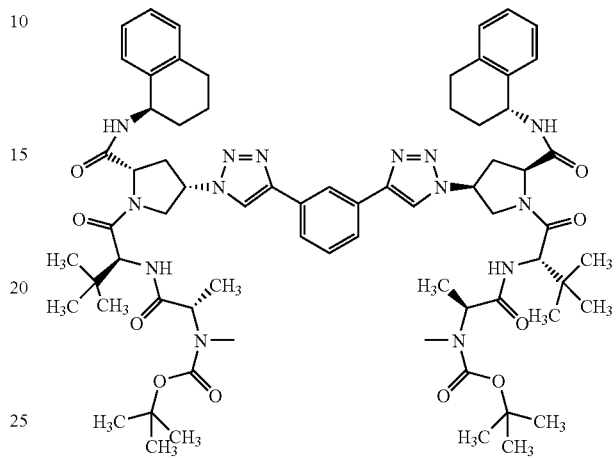

The title compound of Example 3 (500 mg, 0.86 mmol) was dissolved in a 1:1 mixture of t-butanol and water (20 mL) at room temperature. NMM (118 μL, 1.08 mmol), CuI (82 mg, 0.43 mmol) and 1,3-diethynylbenzene (57 μL, 0.43 mmol) were added in this order. The suspension was vigorously stirred at 60° C. for 24 hours. The reaction mixture was diluted with MeOH and filtered through a CELITE® pad and rinsed by MeOH. The combined filtrate was concentrated under vacuum. The remaining aqueous solution was extracted by EtOAc three times. The organic phase was dried over sodium sulfate and concentrated under reduced pressure. The residue was chromatographed on silica gel, eluting with EtOAc, 5% MeOH/EtOAc and then 8% MeOH/methylene chloride to give the title compound as a white solid. ¹H NMR (CDCl₃): consistent with proposed structure.

EXAMPLE 8

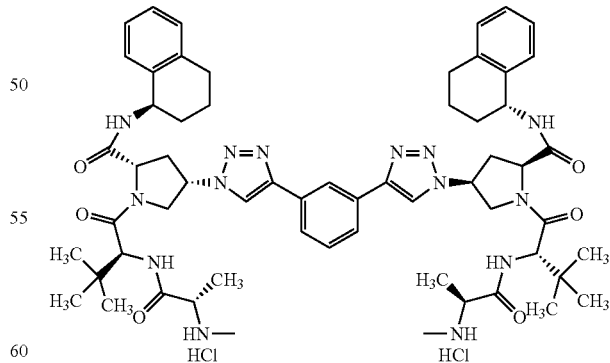

The title compound of Example 5 (468 mg, 0.36 mmol) in 1 mL methylene chloride was treated with HCl/dioxane (4M, 1.2 mL) using the general procedure B to give the title compound as a pale yellow solid. ¹H NMR (CDCl₃): consistent with proposed structure.

EXAMPLE 9

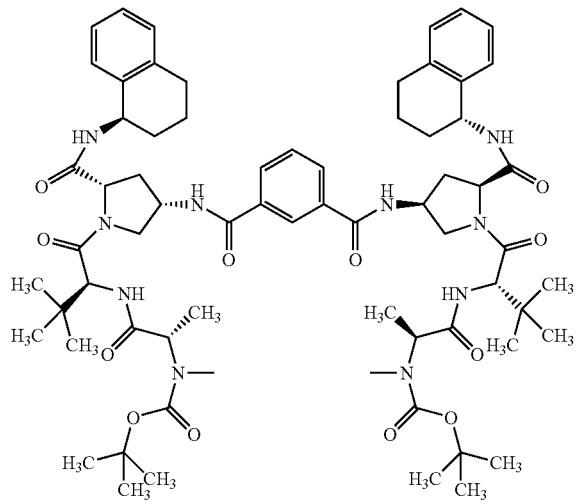 [SMILES: C[C@@H](C(=O)N[C@H](C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)N(C)C(=O)OC(C)(C)C)C(C)(C)C)C3)c2)C[C@H]1C(=O)N[C@@H]1CCCc2ccccc21)C(C)(C)C)N(C)C(=O)OC(C)(C)C]

The title compound of Example 4 (600 mg, 1.08 mmol) was dissolved in methylene chloride (25 mL) at 0° C. TEA (226 μL, 1.62 mmol) was added and the mixture was stirred for 10 min, to which isophthaloyl dichloride (109 mg, 0.54 mmol) was added. The reaction mixture was kept stirring for 1 hour at 0° C., and then slowly warmed up to room temperature and stirred overnight. Water was added to quench the reaction. The two phases were separated and the aqueous phase extracted by methylene chloride twice. The combined organic phase was washed by HCl solution (1M), saturated NaHCO$_3$ solution and brine. The organic phase was dried over sodium sulfate and concentrated under reduced pressure. The residue was chromatographed on silica gel, eluting with EtOAc, the 3% to 10% MeOH/methylene chloride to give the title compound as a white solid. $^1$H NMR (CDCl$_3$): consistent with proposed structure.

EXAMPLE 10

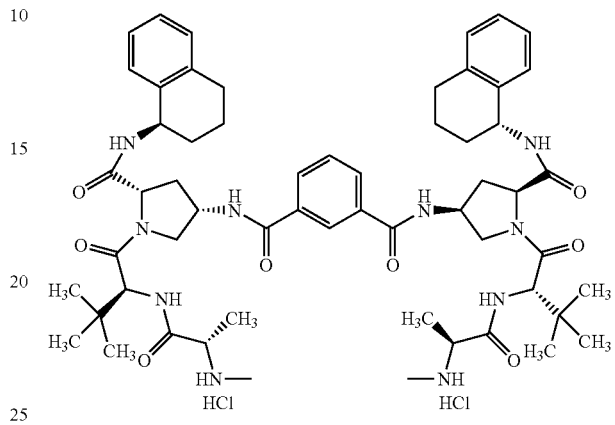

The title compound of Example 9 (632 mg, 0.51 mmol) in 1.5 mL methylene chloride was treated with HCl/dioxane (4M, 2 mL) using the general procedure B to give the title compound as a white solid. $^1$H NMR (CDCl$_3$): consistent with proposed structure.

EXAMPLE 11

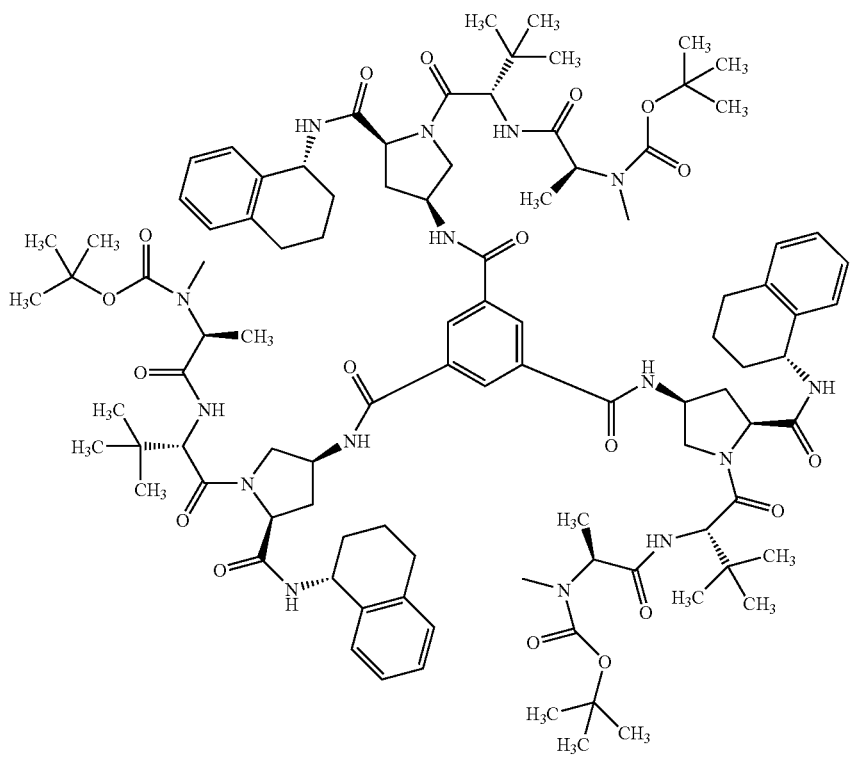 [SMILES: C[C@@H](C(=O)N[C@H](C(=O)N1C[C@@H](NC(=O)c2cc(C(=O)N[C@H]3C[C@@H](C(=O)N[C@@H]4CCCc5ccccc54)N(C(=O)[C@@H](NC(=O)[C@H](C)N(C)C(=O)OC(C)(C)C)C(C)(C)C)C3)cc(C(=O)N[C@H]3C[C@@H](C(=O)N[C@@H]4CCCc5ccccc54)N(C(=O)[C@@H](NC(=O)[C@H](C)N(C)C(=O)OC(C)(C)C)C(C)(C)C)C3)c2)C[C@H]1C(=O)N[C@@H]1CCCc2ccccc21)C(C)(C)C)N(C)C(=O)OC(C)(C)C]

The title compound of Example 4 (400 mg, 0.72 mmol) was dissolved in methylene chloride (15 mL) at 0° C. TEA (125 μL, 0.9 mmol) was added and the mixture was stirred for 10 min, to which 1,3,5-Benzenetricarbonyl trichloride (63 mg, 0.24 mmol) was added. The reaction mixture was kept stirring for 1 hour at 0° C., and then slowly warmed up to room temperature and stirred overnight. The reaction mixture was diluted with 50 mL methylene chloride and then washed by HCl solution (1M), saturated NaHCO$_3$ solution and brine. The organic phase was dried over sodium sulfate and concentrated under reduced pressure. The residue was chromatographed on silica gel, eluting with 2% to 10% MeOH/methylene chloride to give the title compound as a white solid. $^1$H NMR (CDCl$_3$): consistent with proposed structure.

EXAMPLE 12

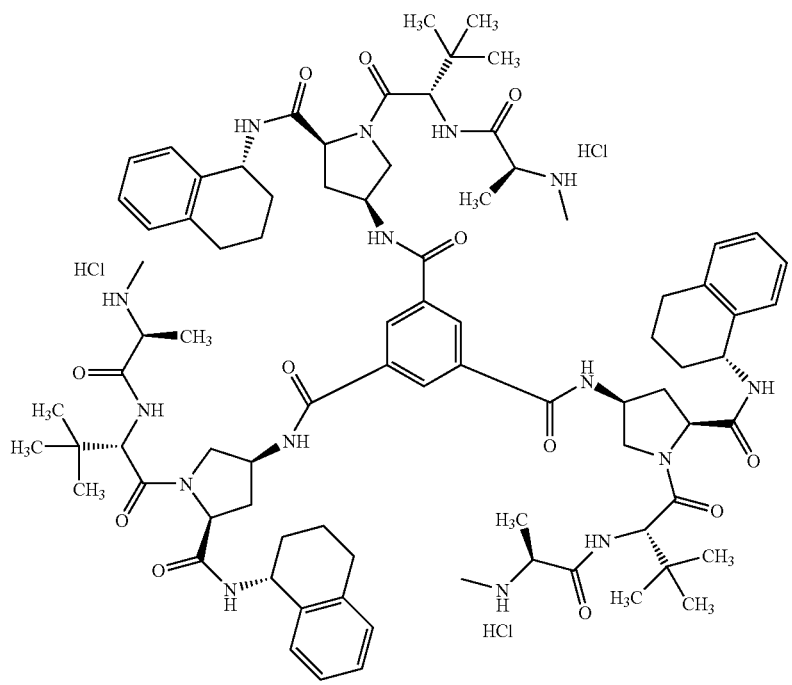 [SMILES: CN[C@@H](C)C(=O)N[C@H](C(=O)N1C[C@@H](NC(=O)c2cc(C(=O)N[C@H]3C[C@@H](C(=O)N[C@@H]4CCCc5ccccc54)N(C(=O)[C@@H](NC(=O)[C@H](C)NC)C(C)(C)C)C3)cc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@@H]1CCCc2ccccc21)C(C)(C)C ; Cl ; Cl ; Cl]

The title compound of Example 11 (410 mg, 0.22 mmol) in 0.5 mL methylene chloride was treated with HCl/dioxane (4M, 0.5 mL) using the general procedure B to give the title compound as a white solid. $^1$H NMR (CDCl$_3$): consistent with proposed structure.

EXAMPLE 13

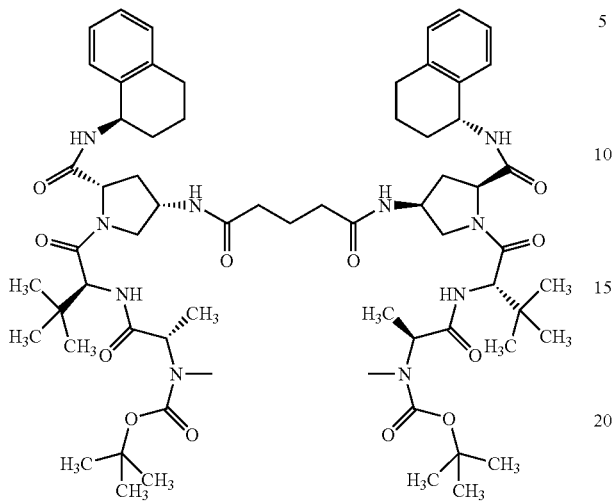

The title compound of Example 4 (80 mg, 0.14 mmol) was dissolved in methylene chloride (4 mL) at 0° C. HOBT (20 mg, 0.15 mmol) and TEA (47 μL, 0.34 mmol) were added, followed by the addition of glutaric acid (8.8 mg, 0.67 mmol). The mixture was stirred for 10 min, to which EDC (28.5 mg, 0.15 mmol) was added. The reaction mixture was kept stirring for 1 hour at 0° C., and then slowly warmed up to room temperature and stirred overnight. The reaction mixture was diluted with 50 mL methylene chloride and then washed by HCl solution (1M), saturated NaHCO$_3$ solution and brine. The organic phase was dried over sodium sulfate and concentrated under reduced pressure. The residue was chromatographed on silica gel, eluting with EtOAc and then 2% to 8% MeOH/methylene chloride to give the title compound as a white solid. $^1$H NMR (CDCl$_3$): consistent with proposed structure.

EXAMPLE 14

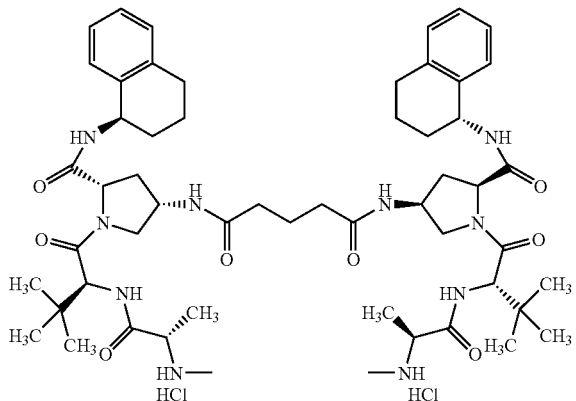 [SMILES: CN[C@@H](C)C(=O)N[C@H](C(=O)N1C[C@@H](NC(=O)CCCC(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl]

The title compound of Example 13 (45 mg, 0.037 mmol) in 0.2 mL methylene chloride was treated with HCl/dioxane (4M, 0.2 mL) using the general procedure B to give the title compound as a white solid. $^1$H NMR (CDCl$_3$): consistent with proposed structure.

EXAMPLE 15

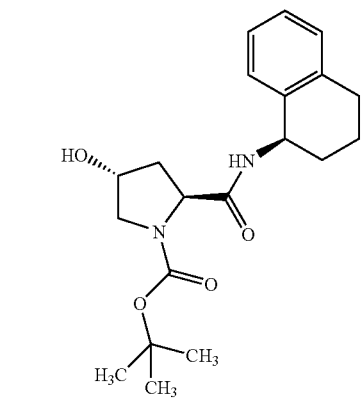 [SMILES: CC(C)(C)OC(=O)N1C[C@H](O)C[C@H]1C(=O)N[C@@H]1CCCc2ccccc21]

Compound 4-trans-hydroxy-(L)-N-Boc-Proline was coupled to (R)-tetrahydro-1-naphthylamine using the general procedure E to prepare the title compound. $^1$H NMR (CDCl$_3$): consistent with proposed structure.

EXAMPLE 16

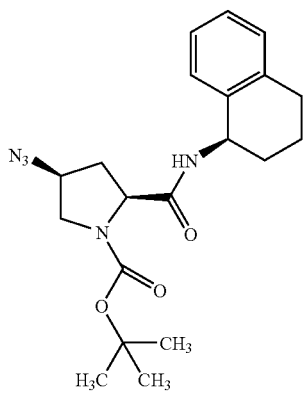 [SMILES: CC(C)(C)OC(=O)N1C[C@@H](N=[N+]=[N-])C[C@H]1C(=O)N[C@@H]1CCCc2ccccc21]

To a solution of the title compound of Example 15 (15.2 g, 42 mmol) in DCM (120 mL) at 0° C., was added TEA (7.7 mL, 55 mmol). MsCl (3.92 mL. 50.6 mmol) was added slowly and the resulting solution was stirred at 0° C. for 5 hours. 50 mL DCM was added. The mixture was washed by HCl solution (1 N), saturated NaHCO$_3$ solution and brine. The organic phase was dried over Na$_2$SO$_4$ and concentrated under reduced pressure to give the crude mesylate as an oil, which was used immediately without further purification. The oil was dissolved in DMSO (180 mL) and NaN$_3$ (5.5 g, 84 mmol) was added. After heating at 90° C. for 8 hours, the solution was cooled to room temperature. Water (100 mL) was added and the mixture was extracted with EtOAc twice. The combined organic phase was washed by brine, dried over Na$_2$SO$_4$ and concentrated under reduced pressure to give the title compound as a white solid. $^1$H NMR (CDCl$_3$): consistent with proposed structure.

EXAMPLE 17

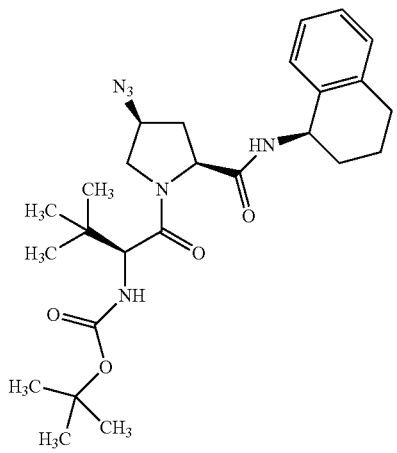 [SMILES: CC(C)(C)OC(=O)N[C@H](C(=O)N1C[C@@H](N=[N+]=[N-])C[C@H]1C(=O)N[C@@H]1CCCc2ccccc21)C(C)(C)C]

The title compound of Example 16 was treated with TFA using the general procedure A to deprotect the BOC group. The resulting TFA salt was coupled to Boc-Tle-OH using the general procedure D to prepare the title compound. $^1$H NMR (CDCl$_3$): consistent with proposed structure.

EXAMPLE 18

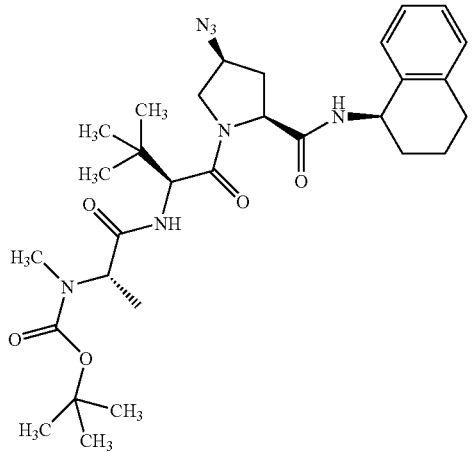 [SMILES: C[C@@H](C(=O)N[C@H](C(=O)N1C[C@@H](N=[N+]=[N-])C[C@H]1C(=O)N[C@@H]1CCCc2ccccc21)C(C)(C)C)N(C)C(=O)OC(C)(C)C]

The title compound of Example 17 was treated with HCl using the general procedure B to deprotect the BOC group. The resulting HCl salt was coupled to Boc-NMe-Ala-OH using the general procedure D to prepare the title compound. $^1$H NMR (CDCl$_3$): consistent with proposed structure.

EXAMPLE 19

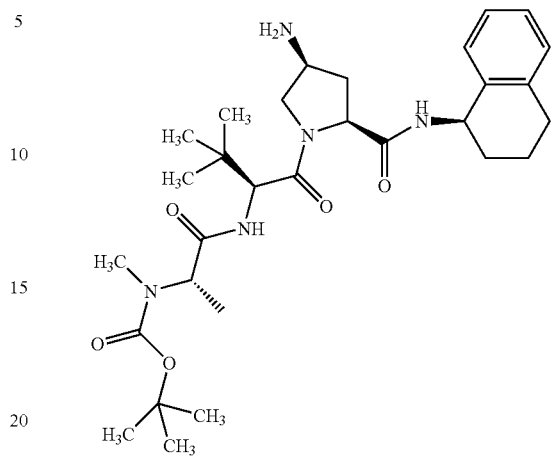

To a solution of the title compound of Example 18 (2.62 g, 4.5 mmol) in 100 mL MeOH, was added 10% Pd/C (262 mg, 10% w/w) at room temperature under N$_2$ atmosphere. The mixture was then charged with a hydrogen balloon and stirred for 8 hours at room temperature. After all the starting material has been consumed, the mixture was filtered through a CELITE® pad and concentrated under reduced pressure to give a white solid as the title compound. $^1$H NMR (CDCl$_3$): consistent with proposed structure.

EXAMPLE 20

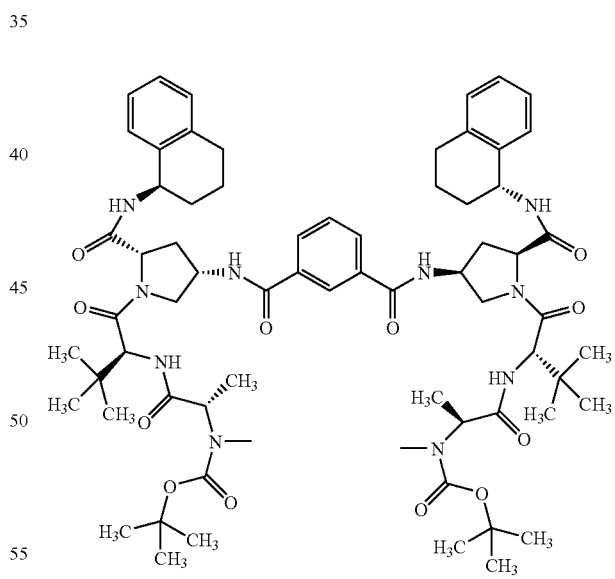

The title compound of Example 19 (600 mg, 1.08 mmol) was dissolved in DCM (25 mL) at 0° C. TEA (226 µL, 1.62 mmol) was added and the mixture was stirred for 10 min, to which isophthaloyl dichloride (109 mg, 0.54 mmol) was added. The reaction mixture was stirred for 1 hour at 0° C., then slowly warmed up to room temperature and stirred overnight. Water was added to quench the reaction. The two phases were separated and the aqueous phase was extracted by DCM twice. The combined organic phase was washed by HCl solution (1M), saturated NaHCO$_3$ solution and brine.

The organic phase was dried over sodium sulfate and concentrated under reduced pressure. The residue was chromatographed on silica gel, eluting with EtOAc, the 3% to 10% MeOH/DCM to give the title compound as a white solid. $^1$H NMR (CDCl$_3$): consistent with proposed structure.

EXAMPLE 21

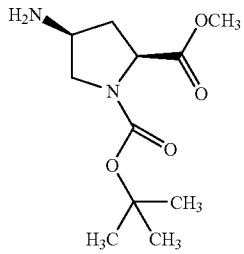 [SMILES: COC(=O)[C@@H]1C[C@H](N)CN1C(=O)OC(C)(C)C]

The title compound of example 22 is commercially available. (It could also be prepared from 4-trans-hydroxy-(L)-N-Boc-Proline: H. Marusawa et al., *Bioorg. Med. Chem.* 1399-1415, 2002).

EXAMPLE 22

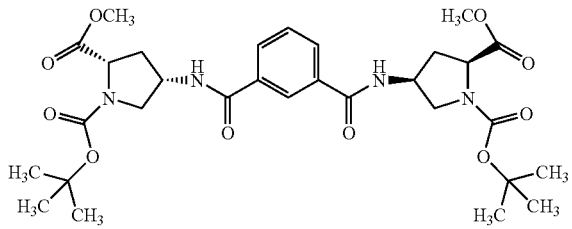 [SMILES: COC(=O)[C@@H]1C[C@H](NC(=O)c2cccc(C(=O)N[C@H]3C[C@@H](C(=O)OC)N(C(=O)OC(C)(C)C)C3)c2)CN1C(=O)OC(C)(C)C]

The title compound of Example 21 (2.5 g, 10.2 mmol) was dissolved in DCM (100 mL) at 0° C. TEA (2.13 mL, 15.3 mmol) was added and the mixture was stirred for 10 min, to which isophthaloyl dichloride (1.02 g, 5 mmol) was added. The reaction mixture was stirred for 1 hour at 0° C., then slowly warmed up to room temperature and stirred overnight. Water was added to quench the reaction. The two phases were separated and the aqueous phase extracted by DCM twice. The combined organic phase was washed by HCl solution (1M), saturated NaHCO$_3$ solution and brine. The organic phase was dried over sodium sulfate and concentrated under reduced pressure to give the title compound as a white solid. $^1$H NMR (CDCl$_3$): consistent with proposed structure.

EXAMPLE 23

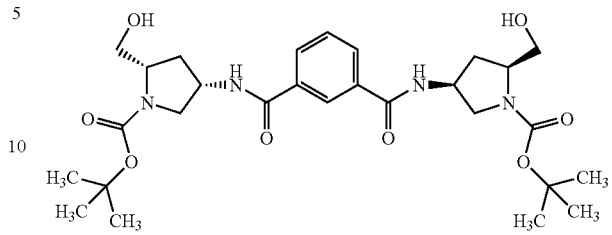

To a solution of the title compound of Example 22 (3.1 g, 5 mmol) in THF (100 mL) was added LiBH$_4$ (540 mg, 25 mmol) in two batches at 0° C. After the reaction mixture was stirred at 0° C. for 12 hours, 50 mL 1N HCl solution was slowly added to quench the reaction. The mixture was then extracted by EtOAc three times. The combined organic phase was washed by saturated NaHCO$_3$ solution and brine, dried over sodium sulfate and concentrated under reduced pressure to give the title compound as a white solid. $^1$H NMR (CDCl$_3$): consistent with proposed structure.

EXAMPLE 24

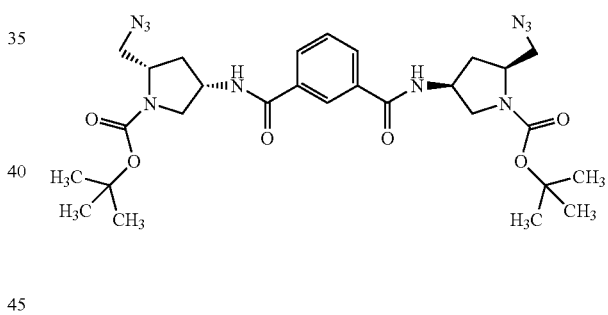

To a solution of the title compound of Example 23 (2.81 g, 5 mmol) in DCM (35 mL), was added TEA (1.84 mL, 13.2 mmol) at 0° C. MsCl (0.93 mL, 12 mmol) was slowly added and the resulting solution was stirred at 0° C. for 1 hours. 20 mL DCM was added. The mixture was washed by HCl solution (1 N), saturated NaHCO$_3$ solution and brine. The organic phase was dried over Na$_2$SO$_4$ and concentrated under reduced pressure to give the crude mesylate as an oil, which was used immediately without further purification. The oil was dissolved in DMSO (45 mL). NaN$_3$ (1.3 g, 20 mmol) was added. After heating at 90° C. for 4 hours, the solution was cooled to room temperature. Water (40 mL) was added and the mixture was extracted with EtOAc twice. The combined organic phase was washed by brine, dried over Na$_2$SO$_4$ and concentrated under reduced pressure. The residue was chromatographed on silica gel, eluting with 30% to 90% EtOAc/Hexane to give the title compound as a pale yellow solid.

$^1$H NMR (CDCl$_3$): consistent with proposed structure.

EXAMPLE 25

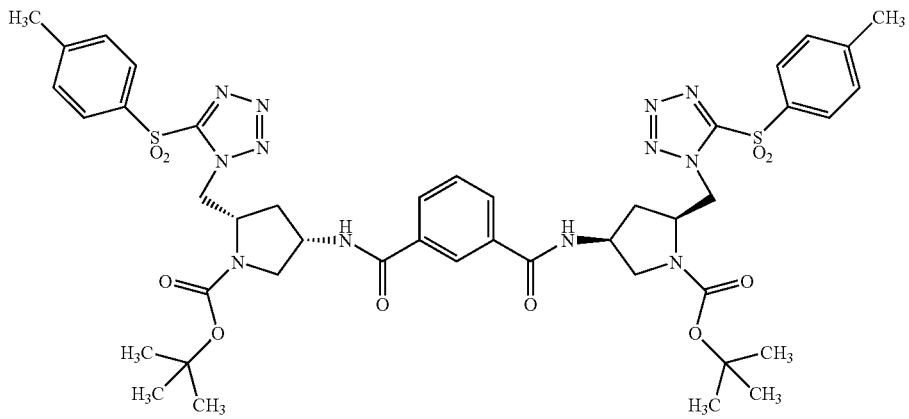

The title compound of Example 24 (1.5 g, 2.4 mmol) and toluene sulfonyl cyanide (888 mg, 4.9 mmol) were mixed in a sealed tube. The solids were then heated to 90° C. and melt to a dark brown color liquid. After stirring for 24 hours at 90° C., the mixture was cooled to room temperature. Add 3 mL DCM to dissolve the solids. The residue was chromatographed on silica gel, eluting with 30% to 95% EtOAc/Hexane to give the title compound. $^1$H NMR (CDCl$_3$): consistent with proposed structure.

EXAMPLE 26

Error! Objects Cannot be Created from Editing Field Codes

To a solution of the title compound of Example 25 (940 mg, 0.96 mmol) in CH$_3$CN (30 mL) was added K$_2$CO$_3$ (800 mg, 5.8 mmol) at room temperature. While stirring, the white suspension was added by PhSH (0.79 mL, 7.7 mmol). After stirring for 12 hours at room temperature, the reaction mixture was quenched by NaHCO$_3$ saturated solution. The two phases were separated and the aqueous phase was extracted by EtOAc twice. The combined organic phase was washed by brine, dried over Na$_2$SO$_4$ and concentrated under reduced pressure. The residue was chromatographed on silica gel, eluting with 30% to 95% EtOAc/Hexane to give the title compound as a white solid. $^1$H NMR (CDCl$_3$): consistent with proposed structure.

EXAMPLE 27

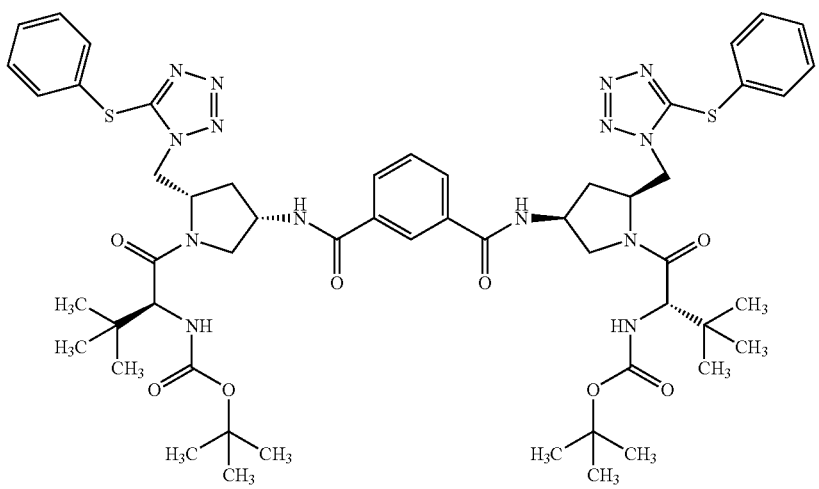 [SMILES: CC(C)(C)OC(=O)N[C@H](C(=O)N1C[C@@H](NC(=O)c2cccc(C(=O)N[C@H]3C[C@@H](Cn4nnnc4Sc4ccccc4)N(C(=O)[C@@H](NC(=O)OC(C)(C)C)C(C)(C)C)C3)c2)C[C@H]1Cn1nnnc1Sc1ccccc1)C(C)(C)C]

The title compound of Example 26 (165 mg, 0.19 mmol) in 0.2 mL DCM was treated with HCl/Dioxane (4M, 0.4 mL) using the general procedure B to deprotect the Boc group. The resulting amine salt and Boc-Tle-OH (86 mg, 0.37 mmol) was dissolved in DMF (4 mL) at 0° C. To the above solution was added HOBT (50 mg, 0.37 mmol) and DIPEA (147 µL, 0.84 mmol) in this order. After 5 minutes, EDC (72 mg, 0.37 mmol) was added. The reaction mixture was stirred for 1 hour at 0° C., then slowly warmed up to room temperature and stirred for 18 hours at room temperature. The reaction mixture was concentrated under vacuum. The residue was diluted with EtOAc and washed by HCl solution (1 N), saturated NaHCO$_3$ solution and brine. The organic phase was dried over Na$_2$SO$_4$ and concentrated under reduced pressure to give the desired product. $^1$H NMR (CDCl$_3$): consistent with proposed structure.

EXAMPLE 28

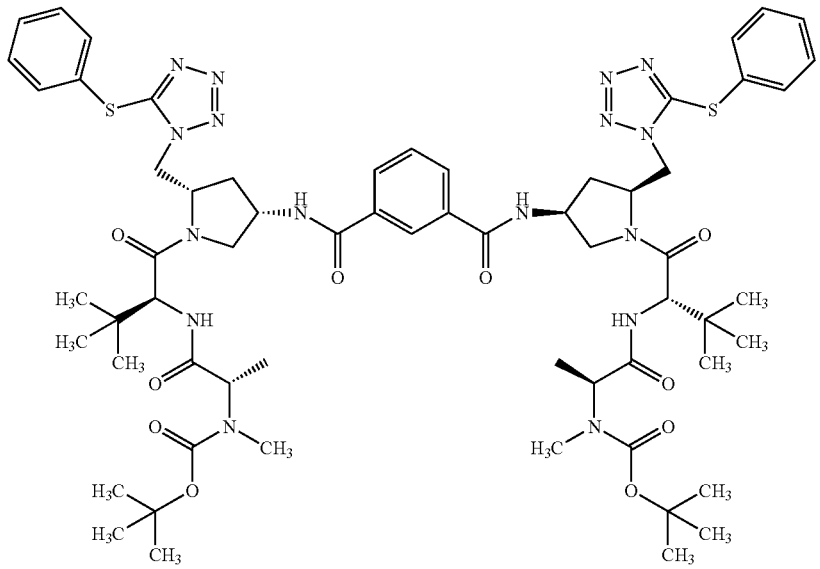 [SMILES: C[C@@H](C(=O)N[C@H](C(=O)N1C[C@@H](NC(=O)c2cccc(C(=O)N[C@H]3C[C@@H](Cn4nnnc4Sc4ccccc4)N(C(=O)[C@@H](NC(=O)[C@H](C)N(C)C(=O)OC(C)(C)C)C(C)(C)C)C3)c2)C[C@H]1Cn1nnnc1Sc1ccccc1)C(C)(C)C)N(C)C(=O)OC(C)(C)C]

The title compound of Example 27 was treated with HCl and then coupled to Boc-NMe-Ala-OH using a similar procedure as was used to prepare the title compound 14 to prepare the title compound 15. The crude product was chromatographed on silica gel, eluting with 30% to 95% EtOAc/Hexane to give the title compound as a white solid. $^1$H NMR (CDCl$_3$): consistent with proposed structure.

EXAMPLE 29

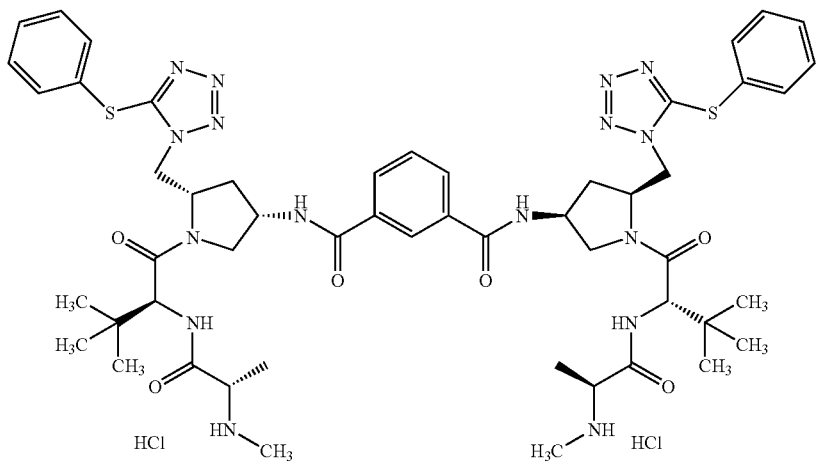 [SMILES: CN[C@@H](C)C(=O)N[C@H](C(=O)N1C[C@@H](NC(=O)c2cccc(C(=O)N[C@H]3C[C@@H](Cn4nnnc4Sc4ccccc4)N(C(=O)[C@@H](NC(=O)[C@H](C)NC)C(C)(C)C)C3)c2)C[C@H]1Cn1nnnc1Sc1ccccc1)C(C)(C)C ; Cl ; Cl]

The title compound of Example 28 was treated with HCl using the general procedure B to give the title compound as a white solid. $^1$H NMR (CDCl$_3$): consistent with proposed structure.

The following examples are included for illustrative purposes only and are not intended to represent or limit the scope of the subject matter claimed herein.

EXAMPLE 30

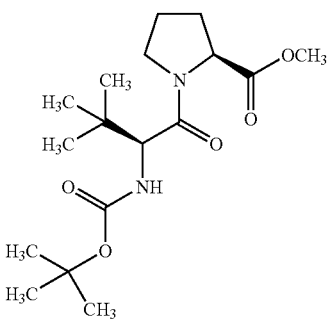 [SMILES: COC(=O)[C@@H]1CCCN1C(=O)[C@@H](NC(=O)OC(C)(C)C)C(C)(C)C]

(L)-Proline methyl ester was coupled to N-Boc-α-tert-butyl-glycine using the general procedure D to prepare the title compound. ¹H NMR (CDCl₃): consistent with proposed structure.

EXAMPLE 31

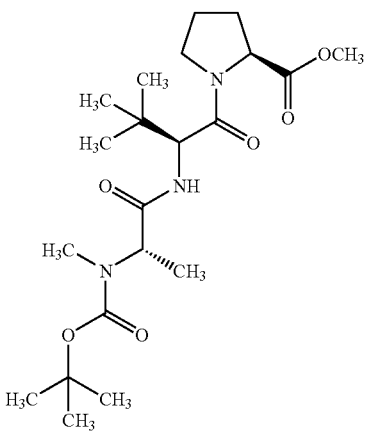 [SMILES: COC(=O)[C@@H]1CCCN1C(=O)[C@@H](NC(=O)[C@H](C)N(C)C(=O)OC(C)(C)C)C(C)(C)C]

The title compound of Example 30 was treated with HCl/Dioxane using the general procedure B to remove the BOC group. The resulting HCl salt was coupled to Boc-NMe-Ala-OH using the general procedure D to prepare the title compound. ¹H NMR (CDCl₃): consistent with proposed structure.

EXAMPLE 32

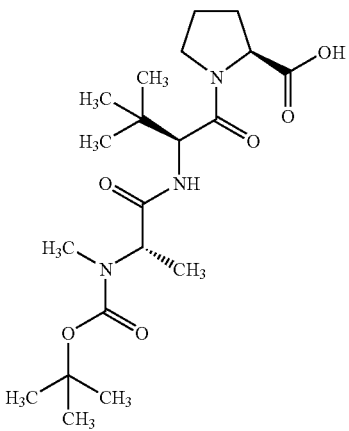 [SMILES: C[C@@H](C(=O)N[C@H](C(=O)N1CCC[C@H]1C(=O)O)C(C)(C)C)N(C)C(=O)OC(C)(C)C]

The title compound of Example 31 was treated with LiOH using the general procedure C to hydrolyze the methyl ester and give the title compound. ¹H NMR (CDCl₃): consistent with proposed structure.

EXAMPLE 33

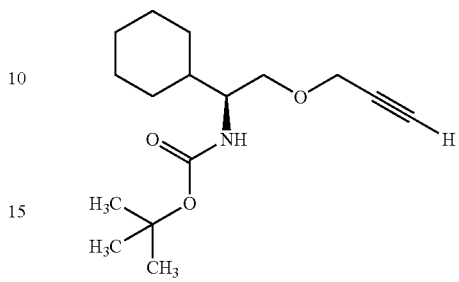

At 0° C., to a solution of Boc-L-cyclohexylglycinol (250 mg, 1.03 mmol) in 3 mL THF was added NaH (41 mg, 1.03 mmol). The suspension was stirred for 5 minutes and was added by the propargyl bromide solution (80% w % in toluene, 153 μL, 1.03 mmol). The reaction mixture was stirred for 1 hour at 0° C., then slowly warmed up to room temperature and stirred for 4 hours at room temperature. The reaction was quenched by HCl solution (0.5 N, 2 mL). The mixture was extracted by EtOAc twice. The combined organic phase was washed by saturated NaHCO₃ solution and brine, dried over Na₂SO₄ and concentrated under reduced pressure to give the title compound. ¹H NMR (CDCl₃): consistent with proposed structure.

EXAMPLE 34

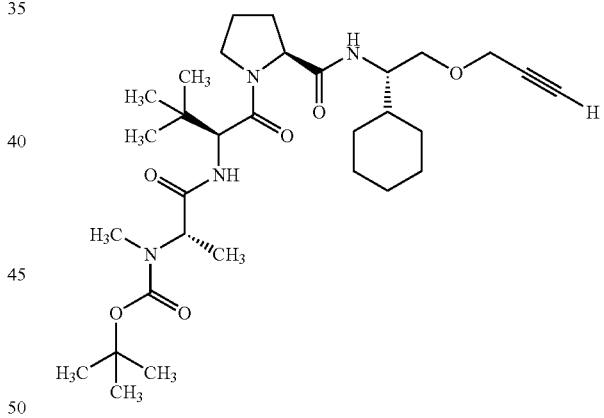

The title compound of Example 33 (287 mg, 1.03 mmol) in 1 mL DCM was treated with HCl/Dioxane (4M, 2 mL) using the general procedure B to remove the Boc group. The resulting HCl salt and the title compound 28 (387 mg, 0.94 mmol) was dissolved in DMF (10 mL) at 0° C. To the above solution were added HOBT (139 mg, 1.03 mmol) and DIPEA (404 μL, 2.32 mmol). After 5 minutes, EDC (197 mg, 1.03 mmol) was added. The reaction mixture was stirred for 1 hour at 0° C., then slowly warmed up to room temperature and stirred for 12 hours at room temperature. The reaction mixture was concentrated under vacuum. The residue was diluted with EtOAc and washed by HCl solution (1 N), saturated NaHCO₃ solution and brine. The organic phase was dried over Na₂SO₄ and concentrated under reduced pressure to give the title compound. ¹H NMR (CDCl₃): consistent with proposed structure.

EXAMPLE 35

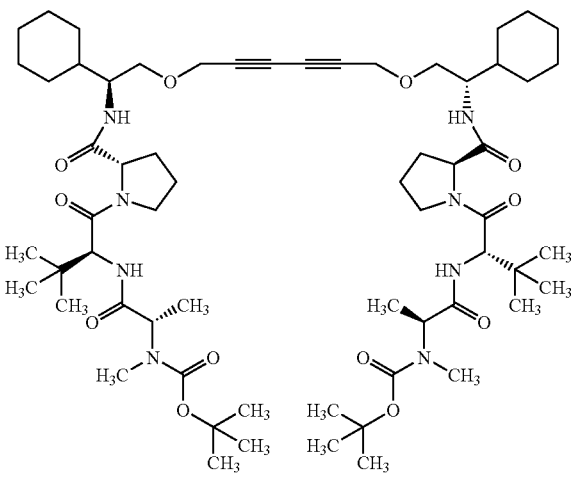 [SMILES: C[C@@H](C(=O)N[C@H](C(=O)N1CCC[C@H]1C(=O)N[C@H](COCC#CC#CCOC[C@@H](NC(=O)[C@@H]1CCCN1C(=O)[C@@H](NC(=O)[C@H](C)N(C)C(=O)OC(C)(C)C)C(C)(C)C)C1CCCCC1)C1CCCCC1)C(C)(C)C)N(C)C(=O)OC(C)(C)C]

The title compound of example 34 (290 mg, 0.5 mmol) was dissolved in 16 mL CH₃CN, to which Cu(OAc)₂ (91 mg, 0.5 mmol) was added. The suspension was heated to 90° C. and gently refluxed for 30 minutes. When all the starting material was consumed, the reaction mixture was cooled to room temperature, quenched by 2% NH₃.H₂O solution and extracted by EtOAc three times. The combined organic phase was dried over Na₂SO₄ and concentrated under reduced pressure. The crude product was chromatographed on silica gel, eluting with 50% EtOAc/Hexane and then pure EtOAc to give the title compound. $^1$H NMR (CDCl₃): consistent with proposed structure.

EXAMPLE 36

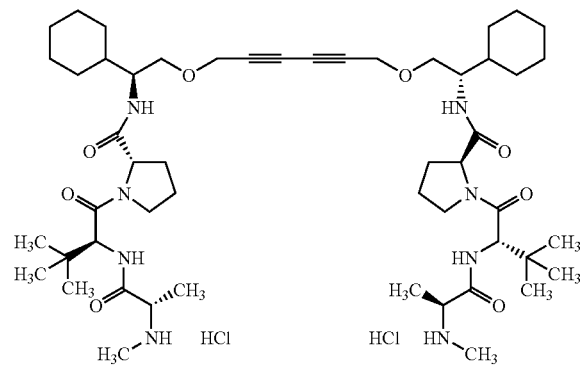 [SMILES: CN[C@@H](C)C(=O)N[C@H](C(=O)N1CCC[C@H]1C(=O)N[C@H](COCC#CC#CCOC[C@@H](NC(=O)[C@@H]1CCCN1C(=O)[C@@H](NC(=O)[C@H](C)NC)C(C)(C)C)C1CCCCC1)C1CCCCC1)C(C)(C)C ; Cl ; Cl]

The title compound of Example 35 (216 mg, 0.19 mmol) in 0.4 mL DCM was treated with HCl/Dioxane (4M, 0.8 mL) using the general procedure B to give the title compound. $^1$H NMR (CDCl₃): consistent with proposed structure.

EXAMPLE 37

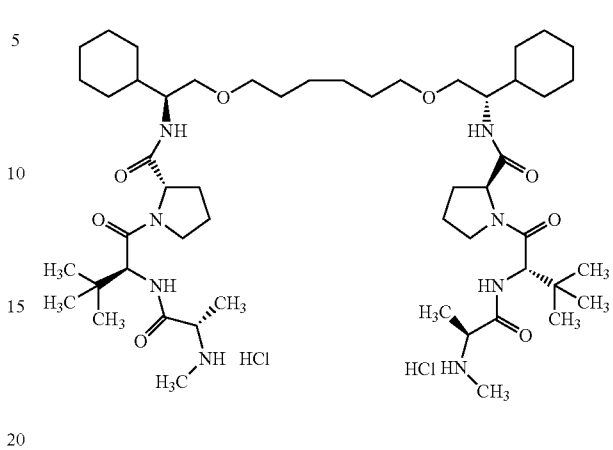

To a solution of the title compound of Example 36 (20 mg, 0.02 mmol) in 2 mL MeOH was added Pd/C (2 mg, 10% w/w) at room temperature under N₂ atmosphere. The mixture was charged with a hydrogen balloon and stirred for 12 hours at room temperature. After all the starting material had been consumed, the mixture was filtered through a Celite® pad and concentrated under reduced pressure to give the title compound. $^1$H NMR (CDCl₃): consistent with proposed structure.

EXAMPLE 38

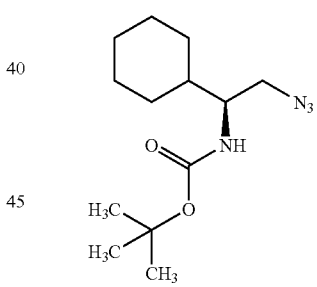

To a solution of the Boc-L-cyclohexylglycinol (1 g, 4.1 mmol) in DCM (15 mL) was added TEA (0.71 mL, 5.1 mmol) at 0° C. Methyl sulfonyl chloride (0.37 mL. 5.1 mmol) was added slowly and the solution was stirred at 0° C. for 3 hours. The reaction mixture was diluted with 15 mL DCM. The mixture was washed by HCl solution (1 N), saturated NaHCO₃ solution and brine. The organic phase was dried over Na₂SO₄ and concentrated under reduced pressure to give the crude mesylate as an oil, which was used immediately without further purification. The oil was dissolved in DMSO (20 mL), to which NaN₃ (540 mg, 8.2 mmol) was added. After heating at 70° C. for 6 hours, the solution was cooled to room temperature. Water (20 mL) was added and the mixture was extracted with EtOAc twice. The combined organic phase was washed by brine, dried over Na₂SO₄ and concentrated under reduced pressure to give the title compound. $^1$H NMR (CDCl₃): consistent with proposed structure.

EXAMPLE 39

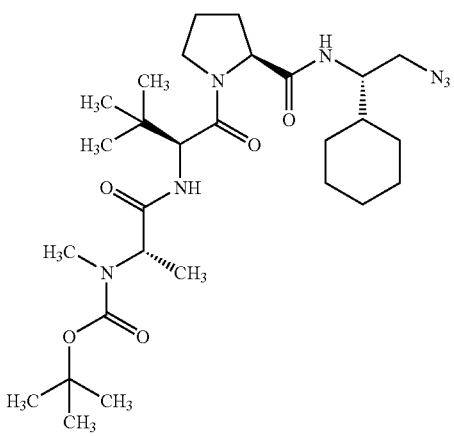 [SMILES: C[C@@H](C(=O)N[C@H](C(=O)N1CCC[C@H]1C(=O)N[C@H](CN=[N+]=[N-])C1CCCCC1)C(C)(C)C)N(C)C(=O)OC(C)(C)C]

The title compound of Example 38 (654 mg, 2.44 mmol) in 2.5 mL DCM was treated with HCl/Dioxane (4M, 5 mL) using the general procedure B to remove the Boc group. The resulting HCl salt and the title compound of Example 3 (919 mg, 2.22 mmol) was dissolved in DMF (40 mL) at 0° C. To the above solution were added HOBT (330 mg, 2.44 mmol) and DIPEA (956 µL, 5.49 mmol). After 5 minutes, EDC (468 mg, 2.44 mmol) was added. The reaction mixture was stirred for 1 hour at 0° C., then slowly warmed up to room temperature and stirred for 12 hours at room temperature. The reaction mixture was concentrated under vacuum. The residue was diluted with EtOAc and washed by HCl solution (1 N), saturated NaHCO$_3$ solution and brine. The organic phase was dried over Na$_2$SO$_4$ and concentrated under reduced pressure to give the title compound. $^1$H NMR (CDCl$_3$): consistent with proposed structure.

EXAMPLE 40

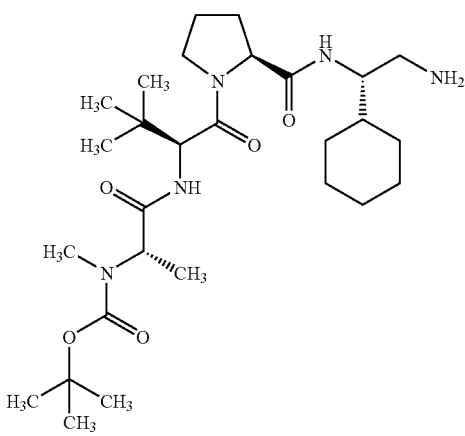 [SMILES: C[C@@H](C(=O)N[C@H](C(=O)N1CCC[C@H]1C(=O)N[C@H](CN)C1CCCCC1)C(C)(C)C)N(C)C(=O)OC(C)(C)C]

To a solution of the title compound of Example 39 (1.03 g, 1.83 mmol) in 18 mL MeOH was added Pd/C (103 mg, 10% w/w) at room temperature under N$_2$ atmosphere. The mixture was charged with a hydrogen balloon and stirred for 8 hours at room temperature. After all the starting material had been consumed, the mixture was filtered through a Celite® pad and concentrated under reduced pressure to give the title compound. $^1$H NMR (CDCl$_3$): consistent with proposed structure.

EXAMPLE 41

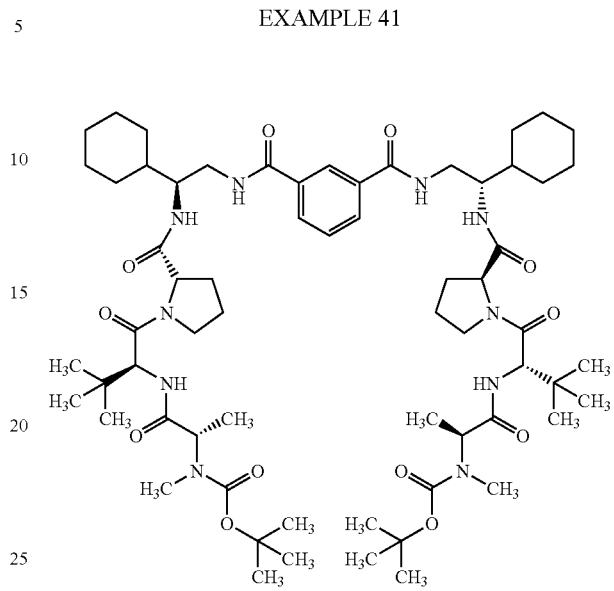

The title compound of Example 40 (250 mg, 0.44 mmol) was dissolved in DCM (8 mL) at 0° C. TEA (93 µL, 0.66 mmol) was added. The solution was stirred for 10 min, to which isophthaloyl dichloride (45 mg, 0.22 mmol) was added. The reaction mixture was stirred for 1 hour at 0° C., slowly warmed up to RT and stirred overnight. Water was added to quench the reaction. The two phases were separated and the aqueous phase was extracted by DCM twice. The combined organic phase was washed by HCl solution (1M), Saturated NaHCO$_3$ solution and brine. The organic phase was dried over sodium sulfate and concentrated under reduced pressure. The residue was chromatographed on silica gel, eluting with 50% Hexane/EtOAc, then pure EtOAc to give the title compound. $^1$H NMR (CDCl$_3$): consistent with proposed structure.

EXAMPLE 42

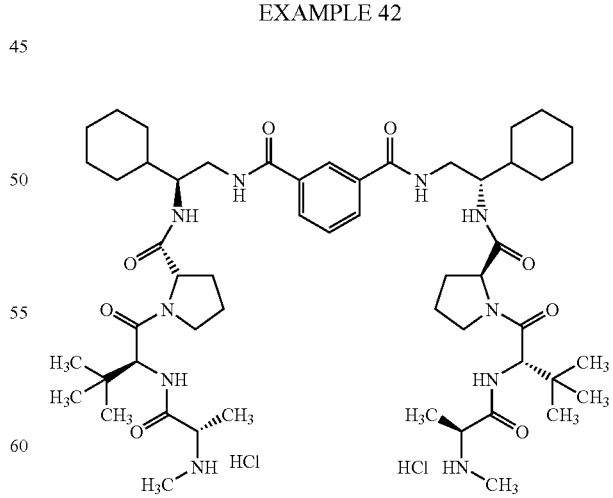

The title compound of Example 41 (69 mg, 0.057 mmol) in 0.1 mL DCM was treated with HCl/Dioxane (4M, 0.25 mL) using the general procedure B to give the title compound. $^1$H NMR (CDCl$_3$): consistent with proposed structure.

EXAMPLE 43

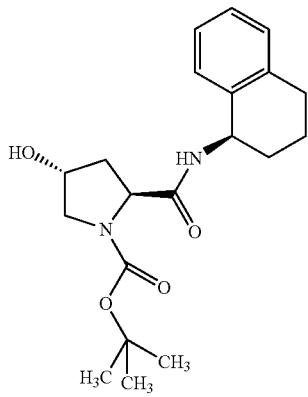 [SMILES: CC(C)(C)OC(=O)N1C[C@H](O)C[C@H]1C(=O)N[C@@H]1CCCc2ccccc21]

At 0° C., to a well-stirred mixture of 4-trans-hydroxy-(L)-N-Boc-Proline (10 g, 43.2 mmol) in 200 mL DMF was added HOBT (6.13 g, 45.4 mmol), DIPEA (11.9 mL, 68.1 mmol) and EDC (8.7 g, 45.4 mmol) in this order. After 10 minutes, (R)-tetrahydro-1-naphthylamine (6.5 mL, 45.4 mmol) was added. The mixture was stirred for 1 hour at 0° C., then slowly warmed up to room temperature and stirred for 12 hours at room temperature. The reaction mixture was concentrated under vacuum to remove the DMF. The residue was diluted with EtOAc (150 mL) and washed by HCl solution (1 N), saturated NaHCO$_3$ solution and brine. The organic phase was dried over Na$_2$SO$_4$ and concentrated under reduced pressure to give the title compound (crude yield 15.2 g). The crude was used directly in next step without purification. The product and relative purity was confirmed by LC-MS.

EXAMPLE 44

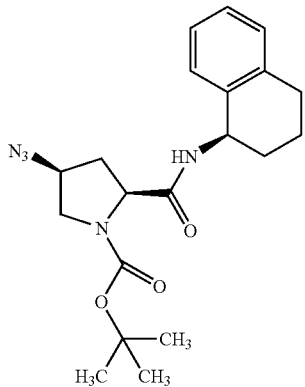 [SMILES: CC(C)(C)OC(=O)N1C[C@@H](N=[N+]=[N-])C[C@H]1C(=O)N[C@@H]1CCCc2ccccc21]

To a solution of the title compound of Example 43 (15.2 g, 42 mmol) in DCM (120 mL) was added TEA (7.7 mL, 55 mmol) at 0° C. Methyl sulfonyl chloride (3.92 mL. 50.6 mmol) was added slowly and the solution was stirred at 0° C. for 5 hours. 50 mL DCM was added. The mixture was washed by HCl solution (1 N), saturated NaHCO$_3$ solution and brine. The organic phase was dried over Na$_2$SO$_4$ and concentrated under reduced pressure to give the crude mesylate as an oil, which was used immediately without further purification. The oil was dissolved in DMSO (180 mL), to which NaN$_3$ (5.5 g, 84 mmol) was added. After heating at 90° C. for 8 hours, the solution was cooled to room temperature. Water (100 mL) was added and the mixture was extracted with EtOAc twice. The combined organic phase was washed by brine, dried over Na$_2$SO$_4$ and concentrated under reduced pressure to give the title compound (crude yield 15.2 g). The crude was used directly in next step without purification. The product and relative purity was confirmed by LC-MS.

EXAMPLE 45

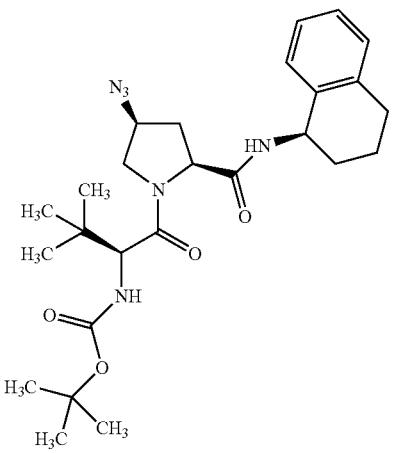 [SMILES: CC(C)(C)OC(=O)N[C@H](C(=O)N1C[C@@H](N=[N+]=[N-])C[C@H]1C(=O)N[C@@H]1CCCc2ccccc21)C(C)(C)C]

To a solution of the title compound of Example 44 (11.4 g, 29.5 mmol) in 30 mL DCM was added HCl/Dioxane (4N, 29.5 mL, 118 mmol) at room temperature. The solution was stirred at room temperature for 3 hours and monitored by LC-MS. After all the starting material had been consumed, the solvents and HCl were removed under reduced pressure to give the free amine salt (9.48 g).

The resulting amine salt (9.48 g) and N-Boc-α-tert-butyl-glycine (6.5 g, 28.1 mmol) was dissolved in 250 mL DMF at 0° C., to which HOBT (3.99 g, 29.5 mmol) and DIPEA (11.6 mL, 66.4 mmol) were added. After 5 minutes, EDC (5.66 g, 29.5 mmol) was added. The reaction mixture was stirred for 1 hour at 0° C., then slowly warmed up to room temperature and stirred for 12 hours at room temperature. The reaction mixture was concentrated under vacuum to remove the DMF. The residue was diluted with EtOAc (200 mL) and washed by HCl solution (1 N), saturated NaHCO$_3$ solution and brine. The organic phase was dried over Na$_2$SO$_4$ and concentrated under reduced pressure to give the title compound (crude yield 14.8 g). The crude was used directly in next step without purification. The product and relative purity was confirmed by LC-MS.

EXAMPLE 46

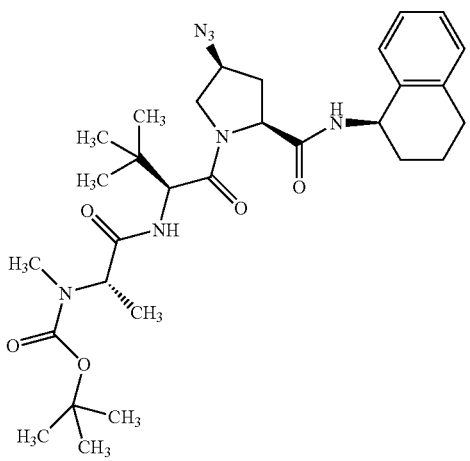 [SMILES: C[C@@H](C(=O)N[C@H](C(=O)N1C[C@@H](N=[N+]=[N-])C[C@H]1C(=O)N[C@@H]1CCCc2ccccc21)C(C)(C)C)N(C)C(=O)OC(C)(C)C]

To a solution of the title compound of Example 45 (14.8 g) in 30 mL DCM was added HCl/Dioxane (4N, 28.1 mL, 112 mmol) at room temperature. The solution was stirred at room temperature for 3 hours and monitored by LC-MS. After all the starting material had been consumed, the solvents and HCl were removed under reduced pressure to give the free amine salt.

The resulting amine salt and N-Boc-N-methyl-alanine (5.4 g, 26.8 mmol) was dissolved in 225 mL DMF at 0° C., to which HOBT (3.8 g, 28.1 mmol) and DIPEA (11 mL, 63.2 mmol) were added. After 5 minutes, EDC (5.4 g, 28.1 mmol) was added. The reaction mixture was stirred for 1 hour at 0° C., then slowly warmed up to room temperature and stirred for 12 hours at room temperature. The reaction mixture was concentrated under vacuum to remove the DMF. The residue was diluted with EtOAc (180 mL) and washed by HCl solution (1 N), saturated NaHCO₃ solution and brine. The organic phase was dried over Na₂SO₄ and concentrated under reduced pressure. The residue was chromatographed on silica gel, eluting with 30% to 95% EtOAc/Hexane gradually to give the title compound (14.9 g, 77.6% for 7 steps based on the beginning starting material 4-trans-hydroxy-(L)-N-Boc-Proline). The product and relative purity was confirmed by LC-MS. ¹H NMR (CDCl₃): consistent with proposed structure.

EXAMPLE 47

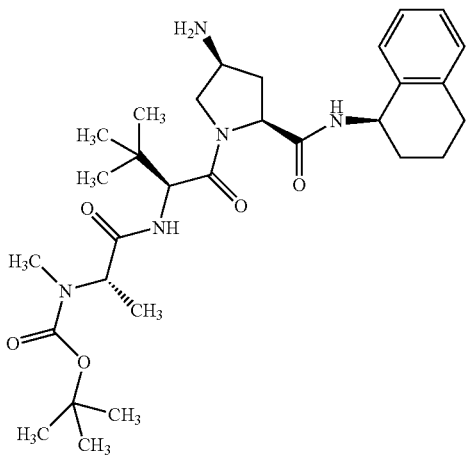 [SMILES: C[C@@H](C(=O)N[C@H](C(=O)N1C[C@@H](N)C[C@H]1C(=O)N[C@@H]1CCCc2ccccc21)C(C)(C)C)N(C)C(=O)OC(C)(C)C]

To a solution of the title compound of Example 46 (14.9 g, 25.6 mmol) in 100 mL MeOH, was added 10% Pd/C (1.49 g, 10% w/w) at room temperature under N₂ atmosphere. The reaction mixture was then vacuumed, charged with a hydrogen balloon and stirred for 8 hours at room temperature. After all the starting material has been consumed, the mixture was filtered through a CELITE® pad and concentrated under reduced pressure to give a white solid as the title compound (crude yield 14.0 g, 98%). The crude was used directly in next step without purification. The product and relative purity was confirmed by LC-MS. ¹H NMR (CDCl₃): consistent with proposed structure.

EXAMPLE 48

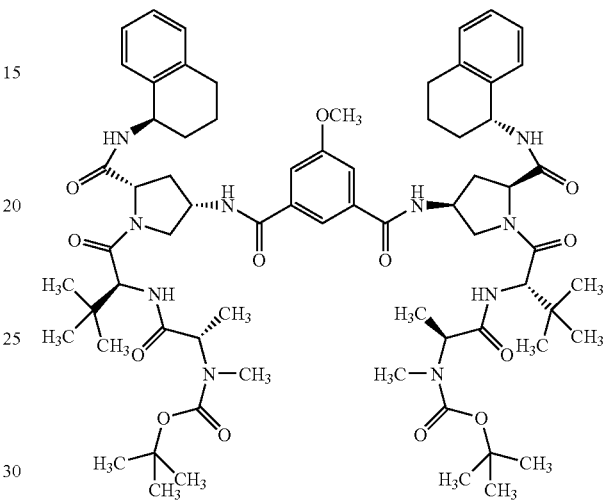

The title compound of Example 47 (2.0 g, 3.6 mmol) was dissolved in DMF (36 mL) at 0° C. HOBT (551 mg, 3.6 mmol) and 5-amino-isophthalic acid (352 mg, 1.8 mmol) were added, followed by the addition of DIPEA (0.94 mL, 5.4 mmol) and EDC (609 mg, 3.6 mmol). The reaction mixture was stirred for 1 hour at 0° C., and then slowly warmed up to room temperature and stirred overnight. DMF was removed under vacuum and the residue was diluted with 40 mL EtOAc. The resulting solution was washed by HCl solution (1M), saturated NaHCO₃ solution and brine. The organic phase was dried over sodium sulfate and concentrated under reduced pressure. The residue was chromatographed on silica gel, eluting with 50% to 95% EtOAc/Hexane, then 2% to 15% MeOH/DCM gradually to give the title compound (1.38 g with 95% purity and 364 mg with 90% purity, 71.8%). The product and relative purity was confirmed by LC-MS. ¹H NMR (CDCl₃): consistent with proposed structure.

EXAMPLE 49

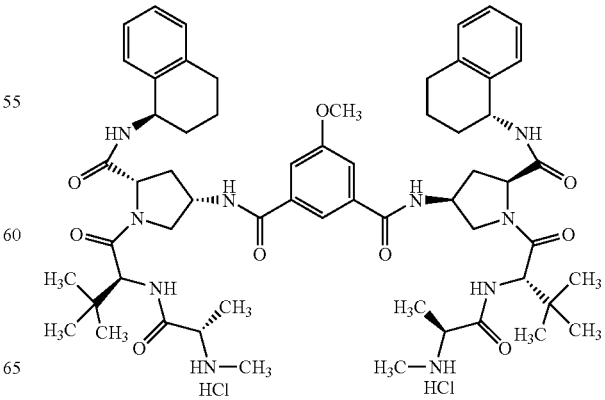

To a solution of the title compound of Example 48 (1.38 g, 1.08 mmol) in 10 mL DCM was added HCl/Dioxane (4N, 4.2 mL, 16.8 mmol) at room temperature. The solution was stirred at room temperature for 3 hours and monitored by LC-MS. After all the starting material had been consumed, the solvents and HCl were removed under reduced pressure to give the free amine salt as an pale yellow color solid, which was dissolved in 18 mL water. The above solution was filtered through a 0.45 μm syringe filter and lyophilized to give the title compound as an off white foam-like solid (1.24 g, 70.3% for 3 steps from title compound of Example 4). The product and relative purity was confirmed by LC-MS. $^1$H NMR (CDCl$_3$): consistent with proposed structure.

EXAMPLE 50

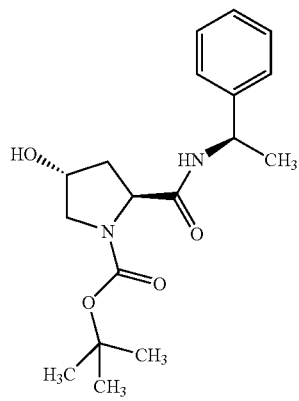 [SMILES: C[C@@H](NC(=O)[C@@H]1C[C@@H](O)CN1C(=O)OC(C)(C)C)c1ccccc1]

At 0° C., to a well-stirred mixture of 4-trans-hydroxy-(L)-N-Boc-Proline (11.56 g, 50 mmol) in 250 mL DMF was added HOBT (6.76 g, 50 mmol), DIPEA (13.1 mL, 75 mmol) and EDC (9.58 g, 50 mmol) in this order. After 10 minutes, D-α-methylbenzyl amine (6.36 mL, 50 mmol) was added. The mixture was stirred for 1 hour at 0° C., then slowly warmed up to room temperature and stirred for 12 hours at room temperature. The reaction mixture was concentrated under vacuum to remove the DMF. The residue was diluted with EtOAc (150 mL) and washed by HCl solution (1 N), saturated NaHCO$_3$ solution and brine. The organic phase was dried over Na$_2$SO$_4$ and concentrated under reduced pressure to give the title compound (crude yield 15.95 g). The crude was used directly in next step without purification. The product and relative purity was confirmed by LC-MS.

EXAMPLE 51

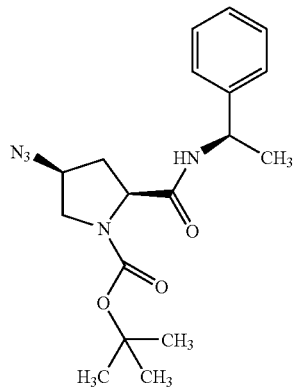 [SMILES: C[C@@H](NC(=O)[C@@H]1C[C@H](N=[N+]=[N-])CN1C(=O)OC(C)(C)C)c1ccccc1]

To a solution of the title compound of Example 50 (15.95 g, ~47.7 mmol) in DCM (150 mL) was added TEA (8.32 mL, 59.7 mmol) at 0° C. Methyl sulfonyl chloride (4.44 mL. 57.3 mmol) was added slowly and the solution was stirred at 0° C. for 5 hours. 50 mL DCM was added. The mixture was washed by HCl solution (1 N), saturated NaHCO$_3$ solution and brine. The organic phase was dried over Na$_2$SO$_4$ and concentrated under reduced pressure to give the crude mesylate as a white foam-like solid, which was used immediately without further purification. The solid was dissolved in DMSO (200 mL), to which NaN$_3$ (6.20 g, 95.4 mmol) was added. After heating at 90° C. for 8 hours, the solution was cooled to room temperature. Water (100 mL) was added and the mixture was extracted with EtOAc twice. The combined organic phase was washed by brine twice, dried over Na$_2$SO$_4$ and concentrated under reduced pressure to give the title compound (crude yield 17.54 g). The crude was used directly in next step without purification. The product and relative purity was confirmed by LC-MS.

EXAMPLE 52

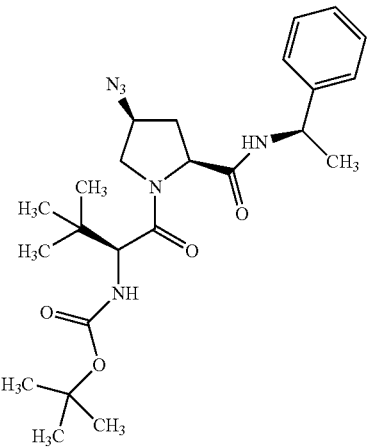 [SMILES: C[C@@H](NC(=O)[C@@H]1C[C@H](N=[N+]=[N-])CN1C(=O)[C@@H](NC(=O)OC(C)(C)C)C(C)(C)C)c1ccccc1]

To a solution of the title compound of Example 51 17.54 g, ~47.7 mmol) in 30 mL DCM was added HCl/Dioxane (4N, 35.8 mL, 140.3 mmol) at room temperature. The solution was stirred at room temperature for 4 hours and monitored by LC-MS. After all the starting material had been consumed, the solvents and HCl were removed under reduced pressure to give the free amine salt (15.89 g).

The resulting amine salt (2.48 g, ~7.44 mmol) and N-Boc-α-tert-butyl-glycine (1.94 g, 8.4 mmol) was dissolved in 75 mL DMF at 0° C., to which HOBT (1.14 g, 8.4 mmol) and DIPEA (3.3 mL, 18.9 mmol) were added. After 5 minutes, EDC (1.61 g, 8.4 mmol) was added. The reaction mixture was stirred for 1 hour at 0° C., then slowly warmed up to room temperature and stirred for 12 hours at room temperature. The reaction mixture was concentrated under vacuum to remove the DMF. The residue was diluted with EtOAc (50 mL) and washed by HCl solution (1 N), saturated NaHCO$_3$ solution and brine. The organic phase was dried over Na$_2$SO$_4$ and concentrated under reduced pressure to give the title compound (crude yield 4.0 g). The crude was used directly in next step without purification. The product and relative purity was confirmed by LC-MS.

EXAMPLE 53

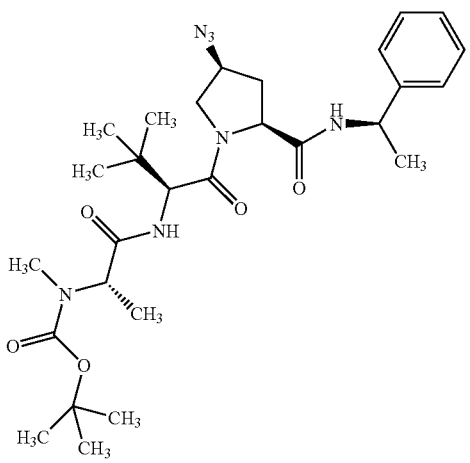 [SMILES: C[C@@H](NC(=O)[C@@H]1C[C@H](N=[N+]=[N-])CN1C(=O)[C@@H](NC(=O)[C@H](C)N(C)C(=O)OC(C)(C)C)C(C)(C)C)c1ccccc1]

To a solution of the title compound of Example 52 (4.0 g, 7.44 mmol) in 30 mL DCM was added HCl/Dioxane (4N, 5.6 mL, 22.4 mmol) at room temperature. The solution was stirred at room temperature for 3 hours and monitored by LC-MS. After all the starting material had been consumed, the solvents and HCl were removed under reduced pressure to give the free amine salt.

The resulting amine salt and N-Boc-N-methyl-alanine (1.67 g, 8.2 mmol) was dissolved in 74 mL DMF at 0° C., to which HOBT (1.11 g, 8.2 mmol) and DIPEA (3.2 mL, 18.4 mmol) were added. After 5 minutes, EDC (1.57 g, 8.2 mmol) was added. The reaction mixture was stirred for 1 hour at 0° C., then slowly warmed up to room temperature and stirred for 12 hours at room temperature. The reaction mixture was concentrated under vacuum to remove the DMF. The residue was diluted with EtOAc (50 mL) and washed by HCl solution (1 N), saturated NaHCO$_3$ solution and brine. The organic phase was dried over Na$_2$SO$_4$ and concentrated under reduced pressure. The residue was chromatographed on silica gel, eluting with 30% to 95% EtOAc/Hexane gradually to give the title compound (3.8 g, 87.4% for 7 steps based on the beginning starting material 4-trans-hydroxy-(L)-N-Boc-Proline). The product and relative purity was confirmed by LC-MS.

EXAMPLE 54

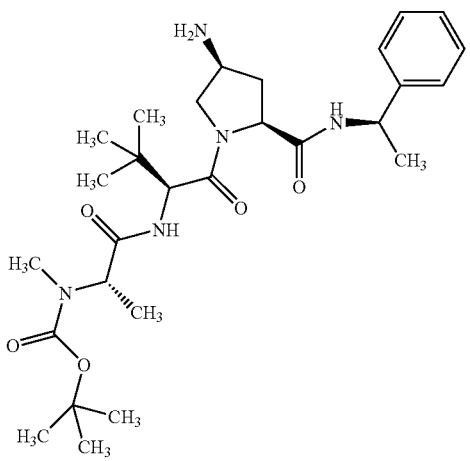 [SMILES: C[C@@H](NC(=O)[C@@H]1C[C@H](N)CN1C(=O)[C@@H](NC(=O)[C@H](C)N(C)C(=O)OC(C)(C)C)C(C)(C)C)c1ccccc1]

To a solution of the title compound of Example 53 (3.48 g, 6.2 mmol) in 100 mL MeOH, was added 10% Pd/C (348 mg, 10% w/w) at room temperature under N$_2$ atmosphere. The reaction mixture was then vacuumed, charged with a hydrogen balloon and stirred for 8 hours at room temperature. After all the starting material has been consumed, the mixture was filtered through a CELITE® pad and concentrated under reduced pressure to give a white solid as the title compound (crude yield 3.3 g, 100%). The crude was used directly in next step without purification. The product and relative purity was confirmed by LC-MS. $^1$H NMR (CDCl$_3$): consistent with proposed structure.

EXAMPLE 55

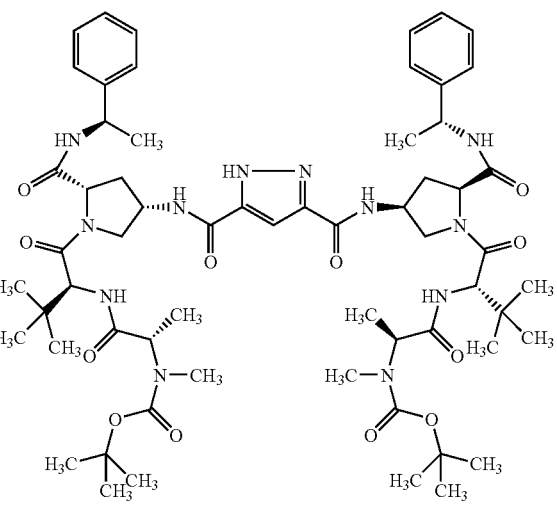

The title compound of Example 54 (2.445 g, 4.61 mmol) was dissolved in DMF (46 mL) at 0° C. HOBT (623 mg, 4.61 mmol) and 3,5-pyrazole dicarboxylic acid monohydrate (402 mg, 2.31 mmol) were added, followed by the addition of DIPEA (1.00 mL, 5.76 mmol) and EDC (884 mg, 4.61 mmol). The reaction mixture was stirred for 1 hour at 0° C., and then slowly warmed up to room temperature and stirred for 12 hours at room temperature. DMF was removed under vacuum and the residue was diluted with 30 mL EtOAc. The resulting solution was washed by HCl solution (1M), saturated NaHCO$_3$ solution and brine. The organic phase was dried over sodium sulfate and concentrated under reduced pressure. The residue was chromatographed on silica gel, eluting with 50% to 90% EtOAc/Hexane, then 2% to 10% MeOH/DCM gradually to give the title compound (1.756 g with 96% purity and 788 mg with 90% purity, 87.5%). The product and relative purity was confirmed by LCMS. $^1$H NMR (CDCl$_3$): consistent with proposed structure.

EXAMPLE 56

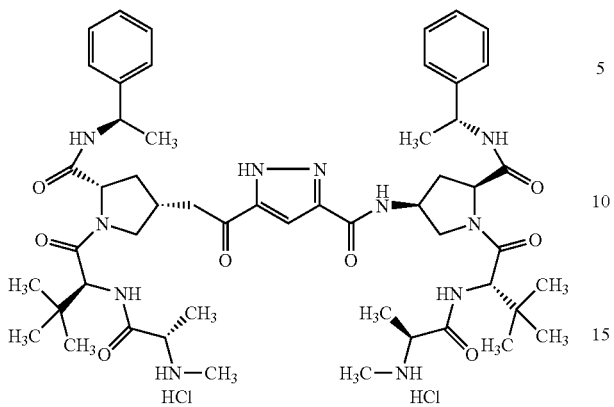

To a solution of the title compound of Example 55 (1.756 g, 1.48 mmol) in 5.9 mL DCM was added HCl/Dioxane (4N, 2.96 mL, 11.8 mmol) at room temperature. The solution was stirred at room temperature for 4 hours and monitored by LC-MS. After all the starting material had been consumed, the solvents and HCl were removed under reduced pressure to give the free amine salt as an white color solid, which was dissolved in 10 mL water. The above solution was filtered through a 0.45 μm syringe filter, rinsed with water twice and lyophilized to give the title compound as a white foam-like solid (1.51 g, 84.5% for 3 steps from title compound of Example 4). The product and relative purity was confirmed by LC-MS. $^1$H NMR (CDCl$_3$): consistent with proposed structure.

EXAMPLE 57

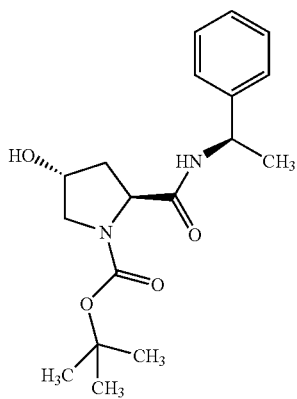 [SMILES: C[C@@H](NC(=O)[C@@H]1C[C@@H](O)CN1C(=O)OC(C)(C)C)c1ccccc1]

At 0° C., to a well-stirred mixture of 4-trans-hydroxy-(L)-N-Boc-Proline (11.56 g, 50 mmol) in 250 mL DMF was added HOBT (6.76 g, 50 mmol), DIPEA (13.1 mL, 75 mmol) and EDC (9.58 g, 50 mmol) in this order. After 10 minutes, D-α-methylbenzyl amine (6.36 mL, 50 mmol) was added. The mixture was stirred for 1 hour at 0° C., then slowly warmed up to room temperature and stirred for 12 hours at room temperature. The reaction mixture was concentrated under vacuum to remove the DMF. The residue was diluted with EtOAc (150 mL) and washed by HCl solution (1 N), saturated NaHCO$_3$ solution and brine. The organic phase was dried over Na$_2$SO$_4$ and concentrated under reduced pressure to give the title compound (crude yield 15.95 g). The crude was used directly in next step without purification. The product and relative purity was confirmed by LC-MS.

EXAMPLE 58

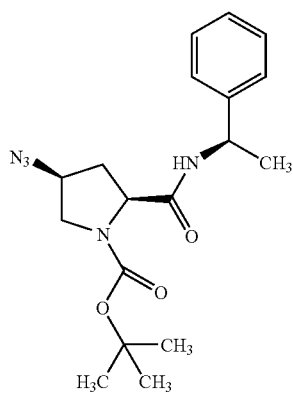 [SMILES: C[C@@H](NC(=O)[C@@H]1C[C@H](N=[N+]=[N-])CN1C(=O)OC(C)(C)C)c1ccccc1]

To a solution of the title compound of Example 57 (15.95 g, ~47.7 mmol) in DCM (150 mL) was added TEA (8.32 mL, 59.7 mmol) at 0° C. Methyl sulfonyl chloride (4.44 mL. 57.3 mmol) was added slowly and the solution was stirred at 0° C. for 5 hours. 50 mL DCM was added. The mixture was washed by HCl solution (1 N), saturated NaHCO$_3$ solution and brine. The organic phase was dried over Na$_2$SO$_4$ and concentrated under reduced pressure to give the crude mesylate as a white foam-like solid, which was used immediately without further purification. The solid was dissolved in DMSO (200 mL), to which NaN$_3$ (6.20 g, 95.4 mmol) was added. After heating at 90° C. for 8 hours, the solution was cooled to room temperature. Water (100 mL) was added and the mixture was extracted with EtOAc twice. The combined organic phase was washed by brine twice, dried over Na$_2$SO$_4$ and concentrated under reduced pressure to give the title compound (crude yield 17.54 g). The crude was used directly in next step without purification. The product and relative purity was confirmed by LC-MS.

EXAMPLE 59

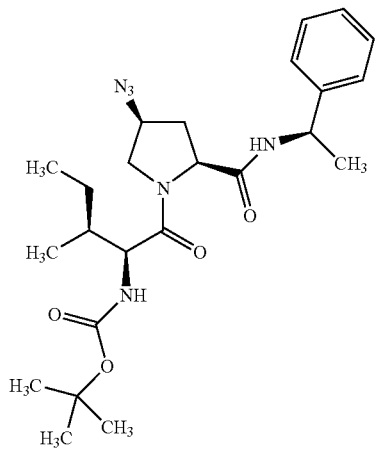 [SMILES: CC[C@H](C)[C@H](NC(=O)OC(C)(C)C)C(=O)N1C[C@@H](N=[N+]=[N-])C[C@H]1C(=O)N[C@H](C)c1ccccc1]

To a solution of the title compound of Example 58 (17.54 g, ~47.7 mmol) in 35 mL DCM was added HCl/Dioxane (4N, 35.8 mL, 140.3 mmol) at room temperature. The solution was stirred at room temperature for 4 hours and monitored by LC-MS. After all the starting material had been consumed, the solvents and HCl were removed under reduced pressure to give the free amine salt (15.89 g).

The resulting amine salt (1.605 g, ~4.82 mmol) and N-Boc-Isoleucine (1.26 g, 5.43 mmol) was dissolved in 54 mL DMF at 0° C., to which HOBT (831 mg, 5.43 mmol) and DIPEA (2.13 mL, 12.2 mmol) were added. After 5 minutes, EDC (1.04 g, 5.43 mmol) was added. The reaction mixture was stirred for 1 hour at 0° C., then slowly warmed up to room temperature and stirred for 12 hours at room temperature. The reaction mixture was concentrated under vacuum to remove the DMF. The residue was diluted with EtOAc (30 mL) and washed by HCl solution (1 N), saturated NaHCO$_3$ solution and brine. The organic phase was dried over Na$_2$SO$_4$ and concentrated under reduced pressure to give the title compound (crude yield 2.505 g). The crude was used directly in next step without purification. The product and relative purity was confirmed by LC-MS.

EXAMPLE 60

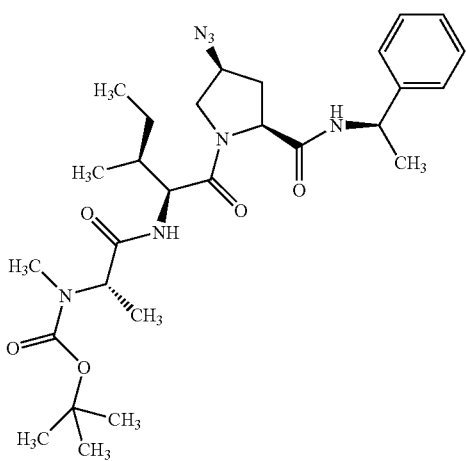 [SMILES: CC[C@H](C)[C@H](NC(=O)[C@H](C)N(C)C(=O)OC(C)(C)C)C(=O)N1C[C@@H](N=[N+]=[N-])C[C@H]1C(=O)N[C@H](C)c1ccccc1]

To a solution of the title compound of Example 59 (2.505 g, ~4.82 mmol) in 8 mL DCM was added HCl/Dioxane (4N, 4 mL, 16 mmol) at room temperature. The solution was stirred at room temperature for 3 hours and monitored by LC-MS. After all the starting material had been consumed, the solvents and HCl were removed under reduced pressure to give the free amine salt.

The resulting amine salt and N-Boc-N-methyl-alanine (1.08 g, 5.31 mmol) was dissolved in 53 mL DMF at 0° C., to which HOBT (813 mg, 5.31 mmol) and DIPEA (2.08 mL, 11.9 mmol) were added. After 5 minutes, EDC (1.02 g, 5.31 mmol) was added. The reaction mixture was stirred for 1 hour at 0° C., then slowly warmed up to room temperature and stirred for 12 hours at room temperature. The reaction mixture was concentrated under vacuum to remove the DMF. The residue was diluted with EtOAc (30 mL) and washed by HCl solution (1 N), saturated NaHCO$_3$ solution and brine. The organic phase was dried over Na$_2$SO$_4$ and concentrated under reduced pressure. The residue was chromatographed on silica gel, eluting with 30% to 95% EtOAc/Hexane gradually to give the title compound (2.23 g with 96% purity and 0.28 g with 87% purity, 84.8% for 7 steps based on the beginning starting material 4-trans-hydroxy-(L)-N-Boc-Proline). The product and relative purity was confirmed by LC-MS.

EXAMPLE 61

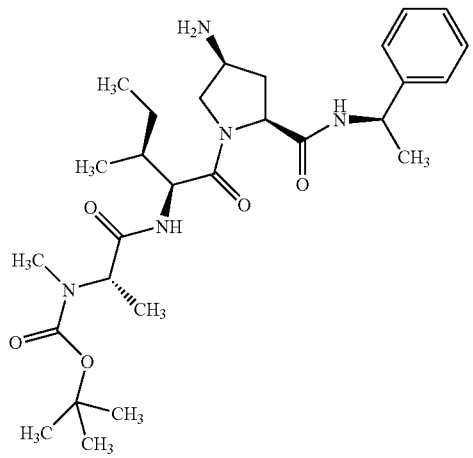 [SMILES: CC[C@H](C)[C@H](NC(=O)[C@H](C)N(C)C(=O)OC(C)(C)C)C(=O)N1C[C@@H](N)C[C@H]1C(=O)N[C@H](C)c1ccccc1]

To a solution of the title compound of Example 60 (2.23 g, 4.0 mmol) in 80 mL MeOH, was added 10% Pd/C (223 mg, 10% w/w) at room temperature under N$_2$ atmosphere. The reaction mixture was then vacuumed, charged with a hydrogen balloon and stirred for 8 hours at room temperature. After all the starting material has been consumed, the mixture was filtered through a CELITE® pad and concentrated under reduced pressure to give a white solid as the title compound (crude yield 1.98 g). The crude was used directly in next step without purification. The product and relative purity was confirmed by LC-MS. $^1$H NMR (CDCl$_3$): consistent with proposed structure.

EXAMPLE 62

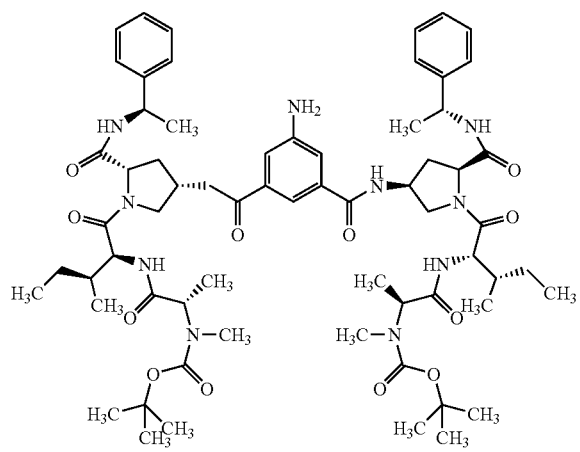 [SMILES: CC[C@H](C)[C@H](NC(=O)[C@H](C)N(C)C(=O)OC(C)(C)C)C(=O)N1C[C@@H](CC(=O)c2cc(N)cc(C(=O)N[C@H]3C[C@@H](C(=O)N[C@H](C)c4ccccc4)N(C(=O)[C@@H](NC(=O)[C@H](C)N(C)C(=O)OC(C)(C)C)[C@@H](C)CC)C3)c2)C[C@H]1C(=O)N[C@H](C)c1ccccc1]

The title compound of Example 61 (1.98 g, 3.73 mmol) was dissolved in DMF (37 mL) at 0° C. HOBT (566 mg, 3.73 mmol) and 5-amino-isophthalic acid (338 mg, 1.86 mmol) were added, followed by the addition of DIPEA (0.966 mL, 5.5 mmol) and EDC (709 mg, 3.73 mmol). The reaction mixture was stirred for 1 hour at 0° C., and then slowly warmed up to room temperature and stirred for 12 hours at room temperature. DMF was removed under vacuum and the residue was diluted with 30 mL EtOAc. The resulting solution was washed by HCl solution (1M), saturated NaHCO$_3$ solution and brine. The organic phase was dried over sodium sulfate and concentrated under reduced pressure. The residue was chromatographed on silica gel, eluting with 50% to 90% EtOAc/Hexane, then 2% to 15% MeOH/DCM gradually to give the title compound (1.17 g with 97% purity and 764 mg with 90% purity, 81.2%). The product and relative purity was confirmed by LC-MS. $^1$H NMR (CDCl$_3$): consistent with proposed structure.

EXAMPLE 63

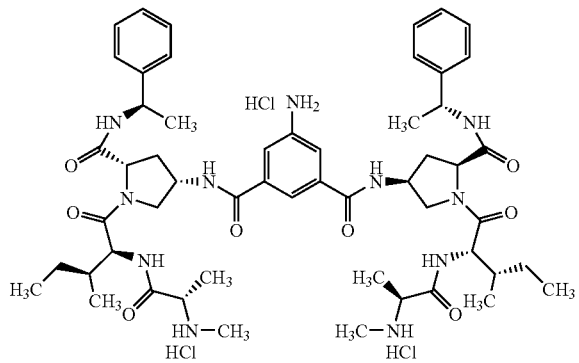 [SMILES: CC[C@H](C)[C@H](NC(=O)[C@H](C)NC)C(=O)N1C[C@@H](NC(=O)c2cc(N)cc(C(=O)N[C@H]3C[C@@H](C(=O)N[C@H](C)c4ccccc4)N(C(=O)[C@@H](NC(=O)[C@H](C)NC)[C@@H](C)CC)C3)c2)C[C@H]1C(=O)N[C@H](C)c1ccccc1 ; Cl ; Cl ; Cl]

To a solution of the title compound of Example 62 (1.17 g, 0.97 mmol) in 8 mL DCM was added HCl/Dioxane (4N, 3.9 mL, 15.6 mmol) at room temperature. The solution was stirred at room temperature for 4 hours and monitored by LC-MS. After all the starting material had been consumed, the solvents and HCl were removed under reduced pressure to give the free amine salt as an white color solid, which was dissolved in 8 mL water. The above solution was filtered through a 0.45 μm syringe filter, rinsed with water twice and lyophilized to give the title compound as a white foam-like solid (1.03 g, 70.9% for 3 steps from title compound of Example 4). The product and relative purity was confirmed by LC-MS. $^1$H NMR (CDCl$_3$): consistent with proposed structure.

EXAMPLE 64

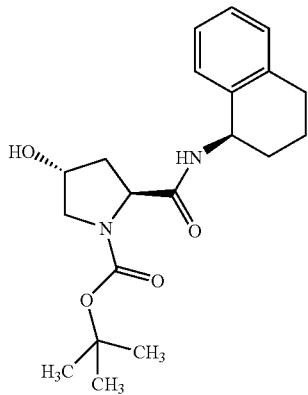 [SMILES: CC(C)(C)OC(=O)N1C[C@H](O)C[C@H]1C(=O)N[C@@H]1CCCc2ccccc21]

At 0° C., to a well-stirred mixture of 4-trans-hydroxy-(L)-N-Boc-Proline (10 g, 43.2 mmol) in 200 mL DMF was added HOBT (6.13 g, 45.4 mmol), DIPEA (11.9 mL, 68.1 mmol) and EDC (8.7 g, 45.4 mmol) in this order. After 10 minutes, (R)-tetrahydro-1-naphthylamine (6.5 mL, 45.4 mmol) was added. The mixture was stirred for 1 hour at 0° C., then slowly warmed up to room temperature and stirred for 12 hours at room temperature. The reaction mixture was concentrated under vacuum to remove the DMF. The residue was diluted with EtOAc (150 mL) and washed by HCl solution (1 N), saturated NaHCO$_3$ solution and brine. The organic phase was dried over Na$_2$SO$_4$ and concentrated under reduced pressure to give the title compound (crude yield 15.2 g). The crude was used directly in next step without purification. The product and relative purity was confirmed by LC-MS.

EXAMPLE 65

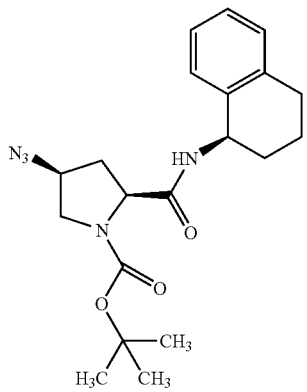 [SMILES: CC(C)(C)OC(=O)N1C[C@@H](N=[N+]=[N-])C[C@H]1C(=O)N[C@@H]1CCCc2ccccc21]

To a solution of the title compound of Example 64 (15.2 g, 42 mmol) in DCM (120 mL) was added TEA (7.7 mL, 55 mmol) at 0° C. Methyl sulfonyl chloride (3.92 mL. 50.6 mmol) was added slowly and the solution was stirred at 0° C. for 5 hours. 50 mL DCM was added. The mixture was washed by HCl solution (1 N), saturated NaHCO3 solution and brine. The organic phase was dried over Na$_2$SO$_4$ and concentrated under reduced pressure to give the crude mesylate as an oil, which was used immediately without further purification. The oil was dissolved in DMSO (180 mL), to which NaN$_3$ (5.5 g, 84 mmol) was added. After heating at 90° C. for 8 hours, the solution was cooled to room temperature. Water (100 mL) was added and the mixture was extracted with EtOAc twice. The combined organic phase was washed by brine, dried over Na$_2$SO$_4$ and concentrated under reduced pressure to give the title compound (crude yield 15.2 g). The crude was used directly in next step without purification. The product and relative purity was confirmed by LC-MS.

EXAMPLE 66

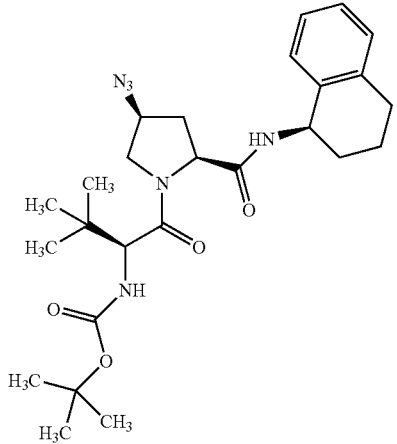 [SMILES: CC(C)(C)OC(=O)N[C@H](C(=O)N1C[C@@H](N=[N+]=[N-])C[C@H]1C(=O)N[C@@H]1CCCc2ccccc21)C(C)(C)C]

To a solution of the title compound of Example 65 (11.4 g, 29.5 mmol) in 30 mL DCM was added HCl/Dioxane (4N, 29.5 mL, 118 mmol) at room temperature. The solution was stirred at room temperature for 3 hours and monitored by LC-MS. After all the starting material had been consumed, the solvents and HCl were removed under reduced pressure to give the free amine salt (9.48 g).

The resulting amine salt (9.48 g) and N-Boc-α-tert-butylglycine (6.5 g, 28.1 mmol) was dissolved in 250 mL DMF at 0° C., to which HOBT (3.99 g, 29.5 mmol) and DIPEA (11.6 mL, 66.4 mmol) were added. After 5 minutes, EDC (5.66 g, 29.5 mmol) was added. The reaction mixture was stirred for 1 hour at 0° C., then slowly warmed up to room temperature and stirred for 12 hours at room temperature. The reaction mixture was concentrated under vacuum to remove the DMF. The residue was diluted with EtOAc (200 mL) and washed by HCl solution (1 N), saturated $NaHCO_3$ solution and brine. The organic phase was dried over $Na_2SO_4$ and concentrated under reduced pressure to give the title compound (crude yield 14.8 g). The crude was used directly in next step without purification. The product and relative purity was confirmed by LC-MS.

EXAMPLE 67

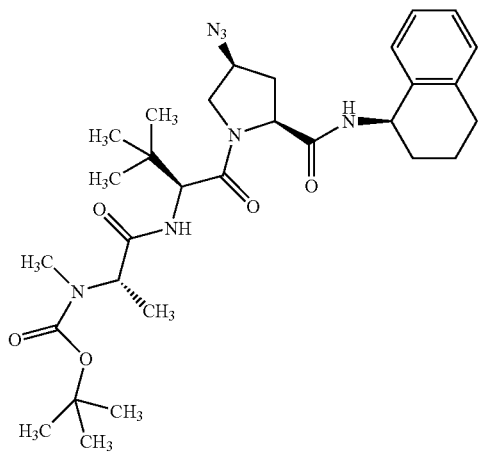 [SMILES: C[C@@H](C(=O)N[C@H](C(=O)N1C[C@@H](N=[N+]=[N-])C[C@H]1C(=O)N[C@@H]1CCCc2ccccc21)C(C)(C)C)N(C)C(=O)OC(C)(C)C]

To a solution of the title compound of Example 66 (14.8 g) in 30 mL DCM was added HCl/Dioxane (4N, 28.1 mL, 112 mmol) at room temperature. The solution was stirred at room temperature for 3 hours and monitored by LC-MS. After all the starting material had been consumed, the solvents and HCl were removed under reduced pressure to give the free amine salt.

The resulting amine salt and N-Boc-N-methyl-alanine (5.4 g, 26.8 mmol) was dissolved in 225 mL DMF at 0° C., to which HOBT (3.8 g, 28.1 mmol) and DIPEA (11 mL, 63.2 mmol) were added. After 5 minutes, EDC (5.4 g, 28.1 mmol) was added. The reaction mixture was stirred for 1 hour at 0° C., then slowly warmed up to room temperature and stirred for 12 hours at room temperature. The reaction mixture was concentrated under vacuum to remove the DMF. The residue was diluted with EtOAc (180 mL) and washed by HCl solution (1 N), saturated $NaHCO_3$ solution and brine. The organic phase was dried over $Na_2SO_4$ and concentrated under reduced pressure. The residue was chromatographed on silica gel, eluting with 30% to 95% EtOAc/Hexane gradually to give the title compound (14.9 g, 77.6% for 7 steps based on the beginning starting material 4-trans-hydroxy-(L)-N-Boc-Proline). The product and relative purity was confirmed by LC-MS. $^1$H NMR ($CDCl_3$): consistent with proposed structure.

EXAMPLE 68

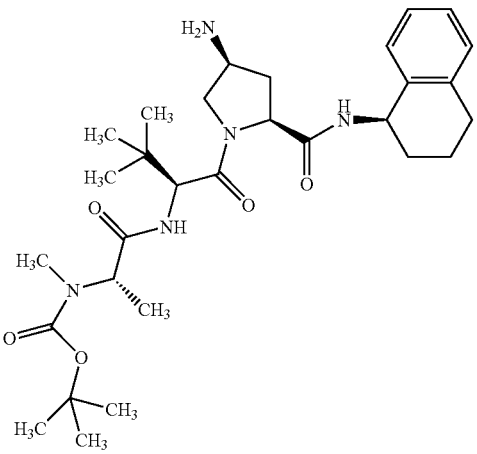 [SMILES: C[C@@H](C(=O)N[C@H](C(=O)N1C[C@@H](N)C[C@H]1C(=O)N[C@@H]1CCCc2ccccc21)C(C)(C)C)N(C)C(=O)OC(C)(C)C]

To a solution of the title compound of Example 67 (14.9 g, 25.6 mmol) in 100 mL MeOH, was added 10% Pd/C (1.49 g, 10% w/w) at room temperature under $N_2$ atmosphere. The reaction mixture was then vacuumed, charged with a hydrogen balloon and stirred for 8 hours at room temperature. After all the starting material has been consumed, the mixture was filtered through a CELITE® pad and concentrated under reduced pressure to give a white solid as the title compound (crude yield 14.0 g, 98%). The crude was used directly in next step without purification. The product and relative purity was confirmed by LC-MS. $^1$H NMR ($CDCl_3$): consistent with proposed structure.

EXAMPLE 69

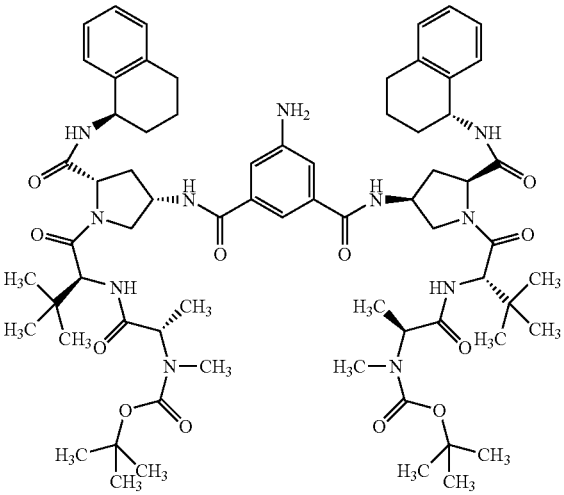

The title compound of Example 68 (3.29 g, 5.91 mmol) was dissolved in DMF (60 mL) at 0° C. HOBT (799 mg, 5.91 mmol) and 5-amino-isophthalic acid (535 mg, 2.95 mmol) were added, followed by the addition of DIPEA (2.3 mL, 13.3 mmol) and EDC (1.13 g, 5.91 mmol). The reaction mixture was stirred for 1 hour at 0° C., and then slowly warmed up to room temperature and stirred overnight. DMF was removed under vacuum and the residue was diluted with 100 mL EtOAc. The resulting solution was washed by HCl solution (1M), saturated NaHCO$_3$ solution and brine. The organic phase was dried over sodium sulfate and concentrated under reduced pressure. The residue was chromatographed on silica gel, eluting with 50% to 90% EtOAc/Hexane, then 2% to 10% MeOH/DCM gradually to give the title compound (3.17 g, 85.4%). The product and relative purity was confirmed by LC-MS. $^1$H NMR (CDCl$_3$): consistent with proposed structure.

EXAMPLE 70

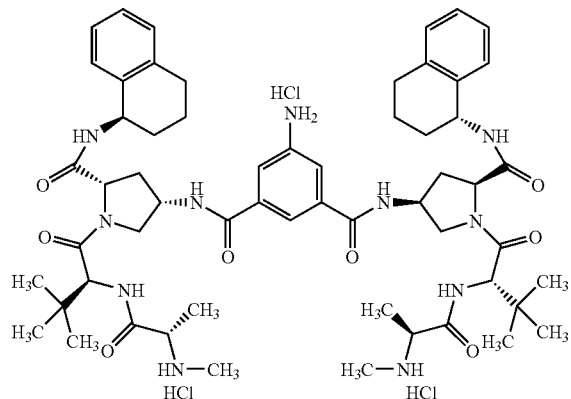 [SMILES: CN[C@@H](C)C(=O)N[C@H](C(=O)N1C[C@@H](NC(=O)c2cc(N)cc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@@H]1CCCc2ccccc21)C(C)(C)C ; Cl ; Cl ; Cl]

To a solution of the title compound of Example 69 (3.17 g, 2.52 mmol) in 10 mL DCM was added HCl/Dioxane (4N, 5 mL, 20 mmol) at room temperature. The solution was stirred at room temperature for 3 hours and monitored by LC-MS. After all the starting material had been consumed, the solvents and HCl were removed under reduced pressure to give the free amine salt as an pale yellow color solid, which was dissolved in 18 mL water. The above solution was filtered through a 0.45 μm syringe filter and lyophilized to give the title compound as an off white foam-like solid (2.81 g, 80.0% for 3 steps from title compound of Example 4). The product and relative purity was confirmed by LC-MS. $^1$H NMR (CDCl$_3$): consistent with proposed structure.

EXAMPLE 71

In Vitro IAP (BIR) Binding/Interaction Assay

Interaction between mimetics and IAPs was examined by GST-mediated pull-down assays. Approximately 0.4 mg of a recombinant IAP fragment (second and third BIR motifs of XIAP) is bound to 200 ml of glutathione resin as a GST-fusion protein and incubated with 0.5 mg of radiolabeled mimetics at room temperature. After extensive washing with an assay buffer containing 25 mM Tris, pH 8.0, 150 mM NaCl, and 2 mM dithiothreitol (DTT), the complex is eluted with 5 mM reduced glutathione and visualized by SDS-PAGE with Coomassie staining.

This assay demonstrates that the tested mimetics specifically bind IAP. Each assay includes as an internal reference the compound of formula:

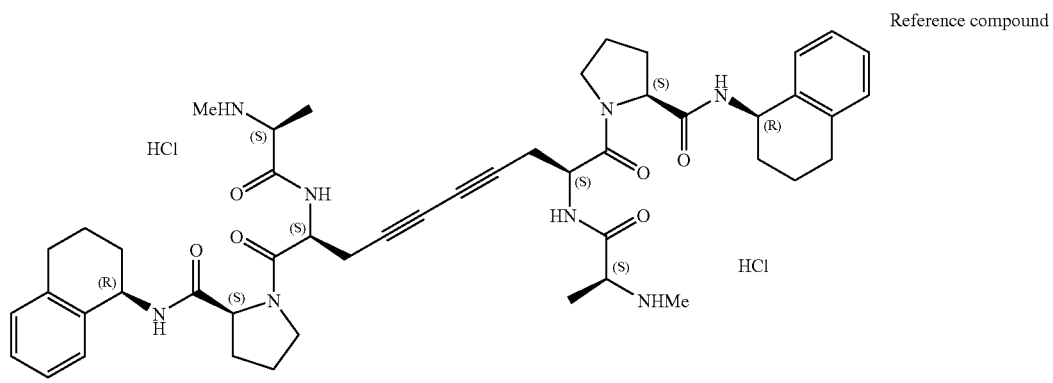

Reference compound

EXAMPLE 72

Fluorescent Polarization Assay

Increasing concentrations of Smac compounds are incubated with 2 nM of labeled peptide (fluorescein labeled 10mer peptide with AVPI 4 amino acids at its N terminus-Alexa Fluor 488) and truncated XIAP containing only BIR1, BIR2, and BIR3 domains at room temperature for 1 hour. Fluorescence reading, indicative of the bound portion of the labeled peptide, is measured in milipolarization units (mP). The more compound added, less fluorescein labeled peptide bind to the protein due to the competitive binding and less fluorescence signal is released.

Based on this principle, we obtain the $K_i$ value that evaluates compound's binding affinity.

EXAMPLE 73

In Vitro Caspase-3 Activation Assay

Caspase3 in most cell extracts can be activated by the addition of 1 mM dATP through the mitochondria caspase pathway. Hela S3 cells we use to make cell extract express higher XIAP, hence after addition of dATP in Hela S100, the induced caspase3 is blocked by IAPs. Taking advantage of this feature, we use 100 nM of synthetic Smac mimetic compound to test its ability to eliminate IAPs in the Hela S100 and fully induce Caspase3 activity. The In Vitro Caspase3 assay is carried out at 30° C., incubating 100 nM compounds with 30 ug of Hela S100, 1 mM dATP, 10 uM Caspase3 fluorogenic substrate (Caspase3 Substrate II, Fluorogenic, #235425 from Calbiochem). The readout is caspase-3 activity represented by relative fluorogenic unit, which is recorded kinetically. The slope in linear region of the curve for each compound is calculated.

Percent activity data is presented by comparing activity of the test compound with activity of the reference compound in Caspase-3 activation assay in vitro. The ratio of each synthetic compound's slope versus the slope of control reflects in vitro caspase-3 activation ability of compounds.

EXAMPLE 74

Cell Viability Assay in HCC461 Cells

HCC461 cells plated in 96 well plates at $5\times10^4$/ml cell density are treated with 50× synthetic Smac mimetic compounds (final concentration range between 30 uM and 0.001 uM). After 48 hrs incubation at 37° C. and 5% $CO_2$ viability of the cells are measured using Cell Proliferation Reagent WST-1 assay kit (Roche Cat #11 644 807 001).

WST-1 assay principle: The tetrazolium salts are cleaved to formazan by cellular enzymes. An expansion in the number of viable cells results in an increase in the overall activity of mitochondrial dehydrogenases in the samples. This augmentation in the enzyme activity leads to an increase in the amount of formazan dye formed, which directly correlates to the number of metabolically active cells in the culture. Quantification of the formazan dye produced by metabolically active cells by using a microplate (ELISA) reader at 420-480 nm.

EXAMPLE 75

Synergism of TRAIL and Smac Mimetic Compounds in PANC-1 Cells

PANC-1 cells plated in 96 well plates at $5\times10^4$/ml cell density are pre-treated with 100 nm compounds for 4 hrs at 37° C. and 5% $CO_2$. The cells are then treated with 50× TRAIL (final concentration range between 2400 ng/ml and 0.08 ng/ml). After 48 hrs incubation at 37° C. and 5% $CO_2$, viability of the cells are measured using Cell Proliferation Reagent WST-1 assay kit (Roche Cat #11 644 807 001). Comparison between viability of cells when treated with TRAIL alone versus when treated with TRAIL+100 nm Smac mimetic compound gives us synergism picture.

WST-1 assay principle: The tetrazolium salts are cleaved to formazan by cellular enzymes. An expansion in the number of viable cells results in an increase in the overall activity of mitochondrial dehydrogenases in the samples. This augmentation in the enzyme activity leads to an increase in the amount of formazan dye formed, which directly correlates to the number of metabolically active cells in the culture. Quantification of the formazan dye produced by metabolically active cells by using a microplate (ELISA) reader at 420-480 nm.

EXAMPLE 76

Representative Biodata

Representative bioassay data using assays described in Examples 71 and 73-75 are provided in Tables 1 and 2. Each table represents the data from a different experiment, using the reference compound described in Example 71 as an internal reference.

TABLE 1

Representative Biodata

| Compound No. | Ki (uM) in FP assay | % Activity at 100 nM | $IC_{50}$ (uM) in cell viability assay in HCC461 | Synergy with TRAIL in PANC-1 ng/ml | |
|---|---|---|---|---|---|
| | | | | $IC_{50}$ for TRAIL | $IC_{50}$ for TRAIL + 100 nm compound |
| Ref cpd | 0.35 | 100 | 0.082 | >2400 | 36.71 |
| 12 | 0.40 | 104 | 0.002 | >2400 | 24.14 |
| 13 | 0.30 | 108 | 0.026 | >2400 | 36.66 |
| 14 | 0.44 | 86 | 0.026 | >2400 | 26.55 |
| 15 | 0.45 | 116 | 0.009 | >2400 | 16.82 |
| 16 | 0.40 | 115 | 0.074 | >2400 | 26.57 |
| 17 | 0.50 | 92 | 0.019 | >2400 | 25.40 |
| 18 | 0.35 | 107 | 0.033 | >2400 | 13.75 |
| 19 | 0.45 | 120 | 0.007 | >2400 | 26.95 |
| 20 | | | 0.222 | >2400 | 1388.10 |
| 21 | | | 0.101 | >2400 | 36.12 |
| 22 | | | 0.263 | >2400 | >2400 |

TABLE 2

Representative Biodata

| Compound No. | Ki (uM) in FP assay | % Activity at 100 nM | $IC_{50}$ (uM) in cell viability assay in HCC461 | Synergy with TRAIL in PANC-1 ng/ml | |
|---|---|---|---|---|---|
| | | | | $IC_{50}$ for TRAIL | $IC_{50}$ for TRAIL + 100 nm compound |
| Ref cpd | 0.15 | | 0.063 | >2400 | 26.03 |
| 23 | 0.05 | | 0.002 | >2400 | 6.05 |
| 24 | 0.35 | | 0.021 | >2400 | 7.86 |
| 25 | 0.25 | | 0.024 | >2400 | 5.71 |
| 26 | 0.32 | | 0.023 | >2400 | 14.78 |
| 27 | 0.25 | | 0.082 | >2400 | 60.94 |
| 28 | 0.23 | | 0.002 | >2400 | 6.66 |
| 29 | 0.24 | | 0.005 | >2400 | 5.00 |
| 30 | 0.29 | | 0.008 | >2400 | 5.60 |
| 31 | 0.34 | | 0.003 | >2400 | 5.98 |
| 32 | 0.23 | | 0.015 | >2400 | 6.09 |

The compounds of Examples 6, 8, 10, 12, 14, 29, 36, 37, 42, 49, 56, 63, and 70 will mimic the activity of Smac, and are thus useful in the treatment of disorders that can be treated with Smac or a Smac mimetic, such as those disorders discussed herein.

Using methods similar to those described in the Examples, the compounds of Table 3 and Table 4 can readily be prepared and shown to be Smac mimetics.

TABLE 3
Dimeric Structures
| RECORD NUMBER | STRUCTURE |
|---|---|
| 1 | 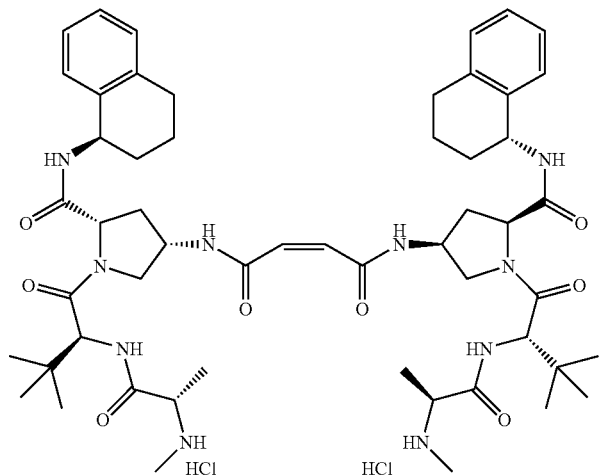 [SMILES: CN[C@@H](C)C(=O)N[C@H](C(=O)N1C[C@@H](NC(=O)/C=C\C(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl] |
| 2 | 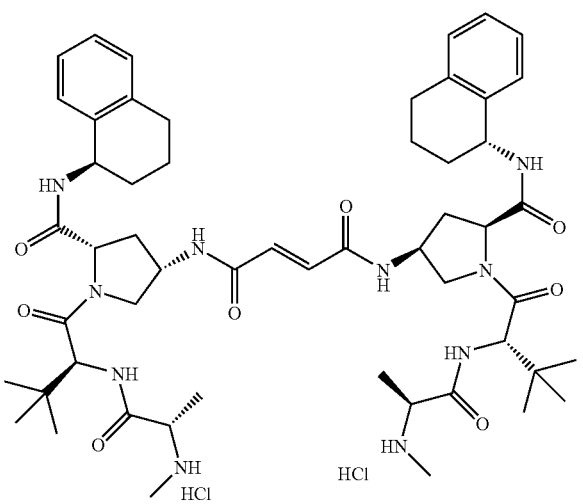 [SMILES: CN[C@@H](C)C(=O)N[C@H](C(=O)N1C[C@@H](NC(=O)/C=C/C(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl] |
| 3 | 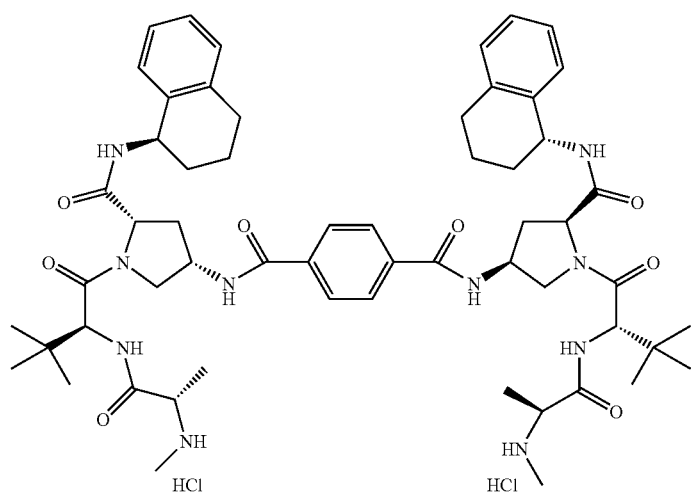 [SMILES: CN[C@@H](C)C(=O)N[C@H](C(=O)N1C[C@@H](NC(=O)c2ccc(C(=O)N[C@H]3C[C@@H](C(=O)N[C@@H]4CCCc5ccccc54)N(C(=O)[C@@H](NC(=O)[C@H](C)NC)C(C)(C)C)C3)cc2)C[C@H]1C(=O)N[C@@H]1CCCc2ccccc21)C(C)(C)C ; Cl ; Cl] |

US 8,642,554 B2
143                                                                 144
TABLE 3-continued
Dimeric Structures
| RECORD NUMBER | STRUCTURE |
|---|---|
| 4 (Example 10) | 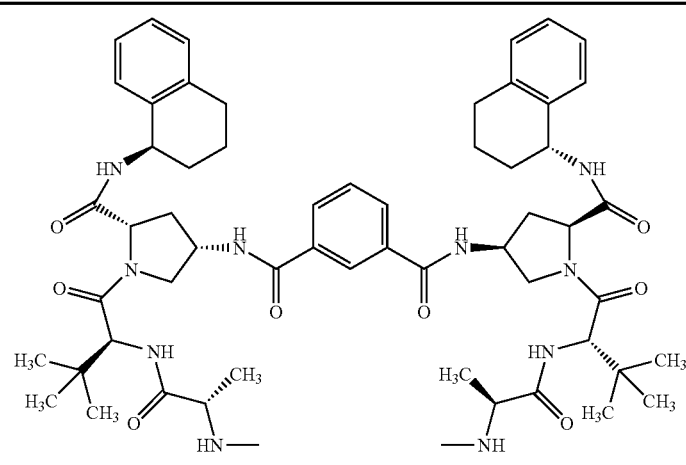 |
| 5 | 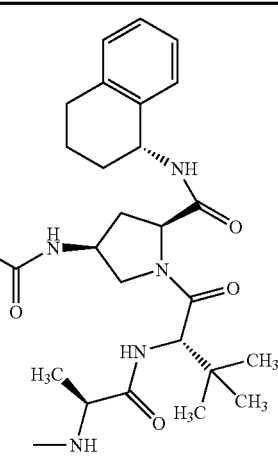 |
| 6 | 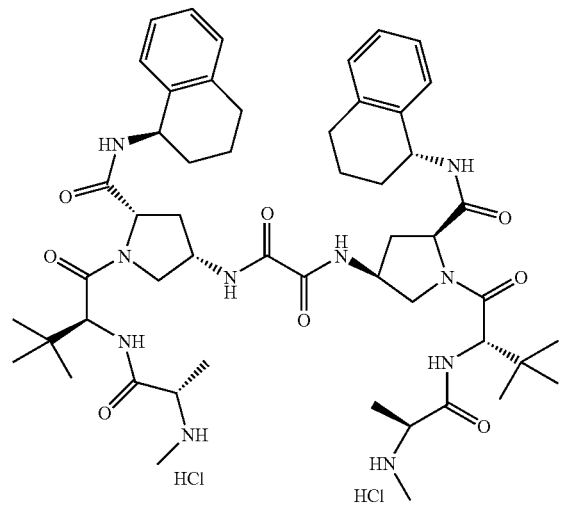 [SMILES: CN[C@@H](C)C(=O)N[C@H](C(=O)N1C[C@@H](NC(=O)C(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl] |

TABLE 3-continued
Dimeric Structures
| RECORD NUMBER | STRUCTURE |
|---|---|
| 7 | 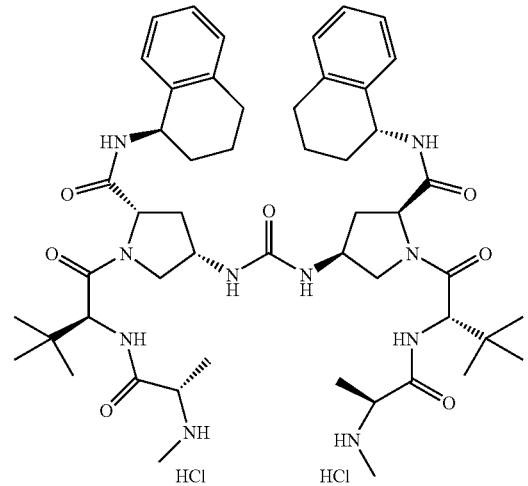 [SMILES: CN[C@@H](C)C(=O)N[C@H](C(=O)N1C[C@@H](NC(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl] |
| 8 | 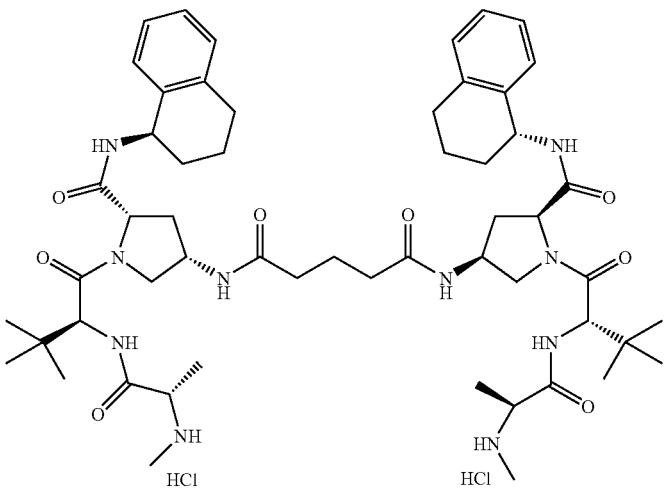 [SMILES: CN[C@@H](C)C(=O)N[C@H](C(=O)N1C[C@@H](NC(=O)CCCC(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl] |
| 9 | 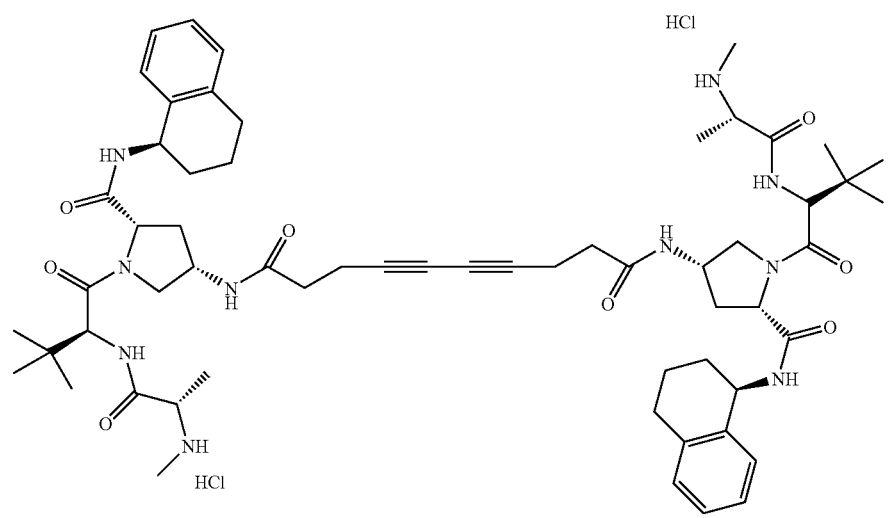 |

TABLE 3-continued
Dimeric Structures
| RECORD NUMBER | STRUCTURE |
|---|---|
| 10 | 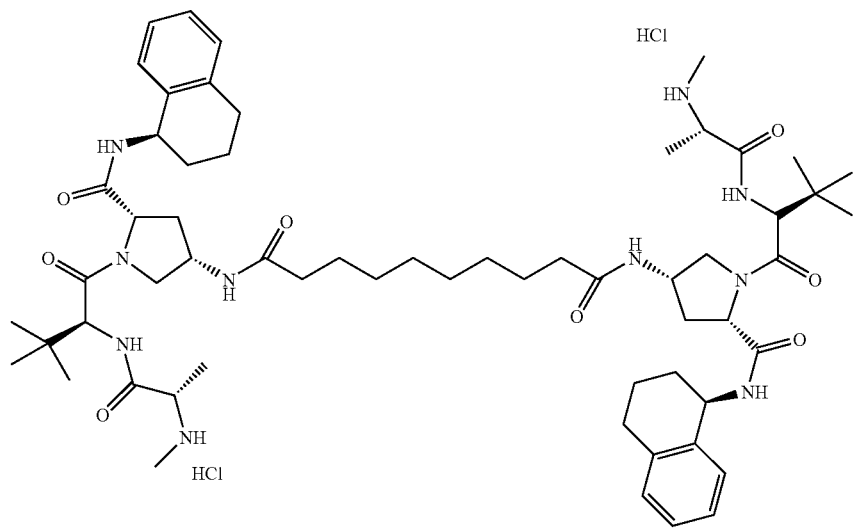 |
| 11 (Example 29) | 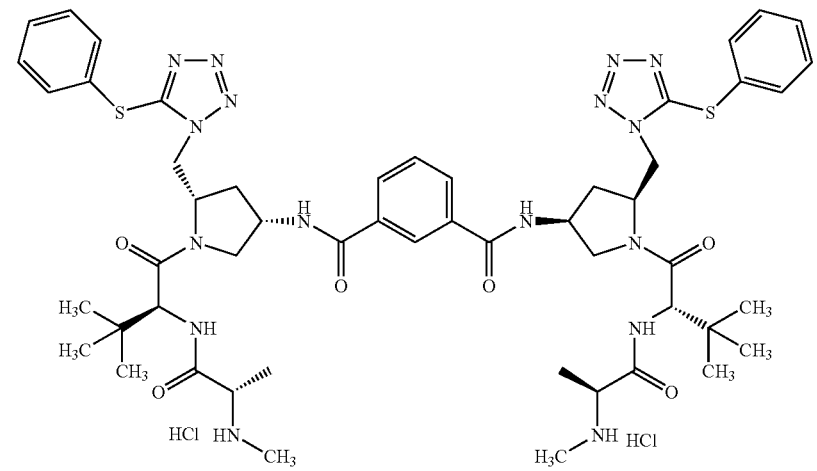 [SMILES: CN[C@@H](C)C(=O)N[C@H](C(=O)N1C[C@@H](NC(=O)c2cccc(C(=O)N[C@H]3C[C@@H](Cn4nnnc4Sc4ccccc4)N(C(=O)[C@@H](NC(=O)[C@H](C)NC)C(C)(C)C)C3)c2)C[C@H]1Cn1nnnc1Sc1ccccc1)C(C)(C)C ; Cl ; Cl] |
| 12 | 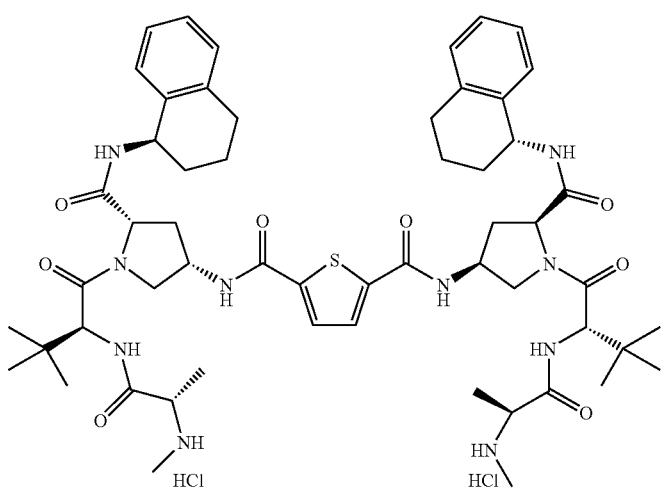 [SMILES: CN[C@@H](C)C(=O)N[C@H](C(=O)N1C[C@@H](NC(=O)c2ccc(C(=O)N[C@H]3C[C@@H](C(=O)N[C@@H]4CCCc5ccccc54)N(C(=O)[C@@H](NC(=O)[C@H](C)NC)C(C)(C)C)C3)s2)C[C@H]1C(=O)N[C@@H]1CCCc2ccccc21)C(C)(C)C ; Cl ; Cl] |

TABLE 3-continued
Dimeric Structures
| RECORD NUMBER | STRUCTURE |
|---|---|
| 13 | 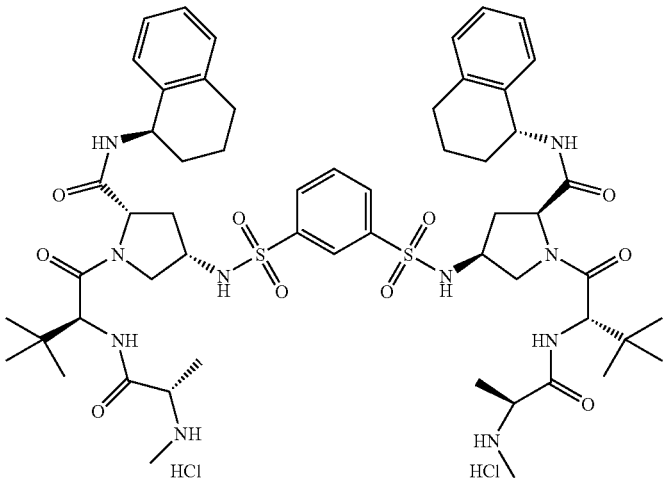 [SMILES: CN[C@@H](C)C(=O)N[C@H](C(=O)N1C[C@@H](NS(=O)(=O)c2cccc(S(=O)(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@@H]1CCCc2ccccc21)C(C)(C)C ; Cl ; Cl] |
| 14 | 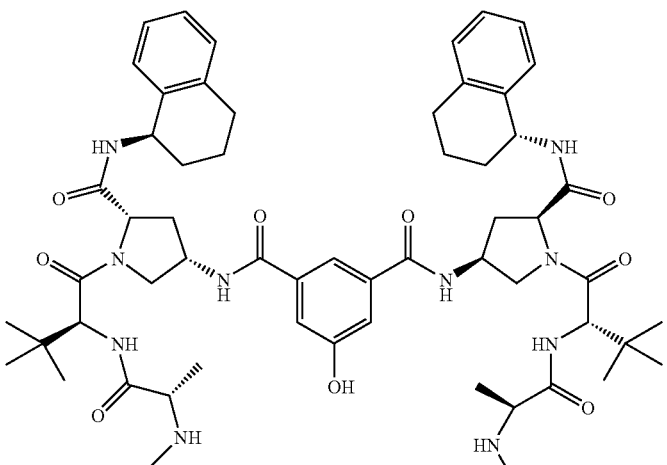 |
| 15 | 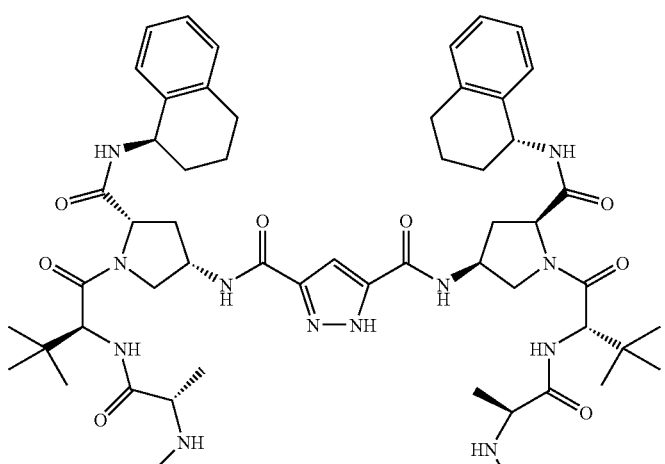 |

TABLE 3-continued
Dimeric Structures
| RECORD NUMBER | STRUCTURE |
|---|---|
| 16 | 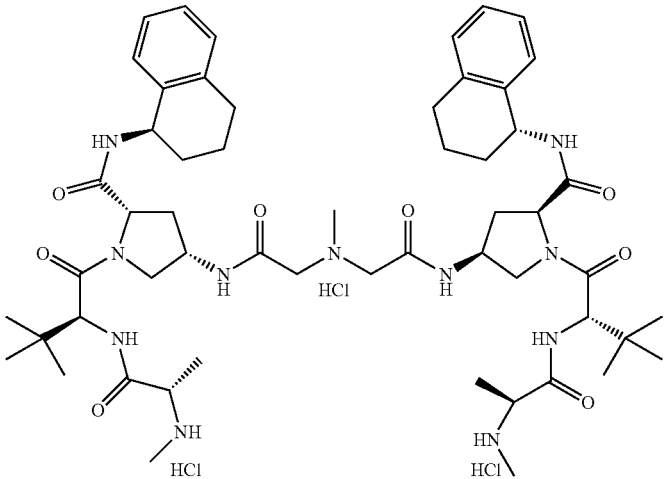 [SMILES: CN[C@@H](C)C(=O)N[C@H](C(=O)N1C[C@@H](NC(=O)CN(C)CC(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl ; Cl] |
| 17 | 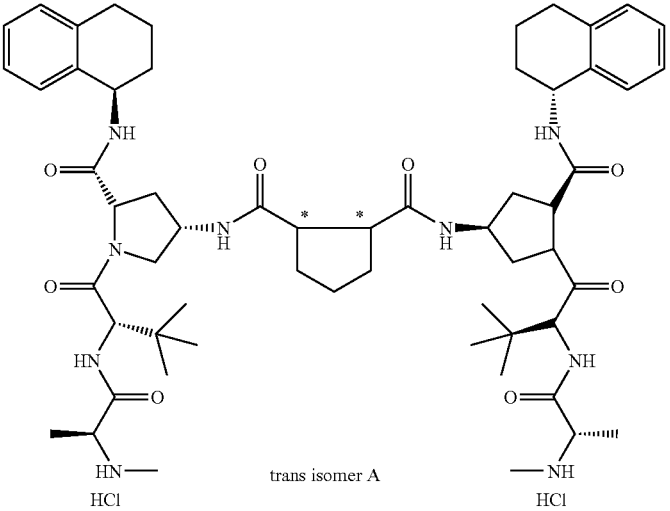<br>trans isomer A |
| 18 | 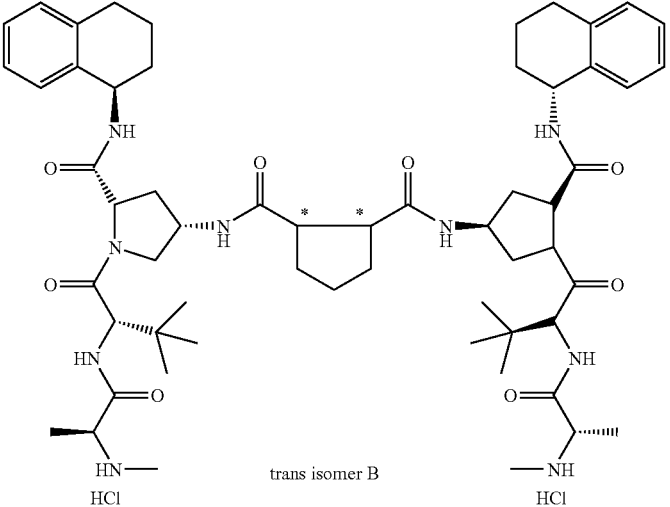<br>trans isomer B |

TABLE 3-continued
Dimeric Structures
| RECORD NUMBER | STRUCTURE |
|---|---|
| 19 | 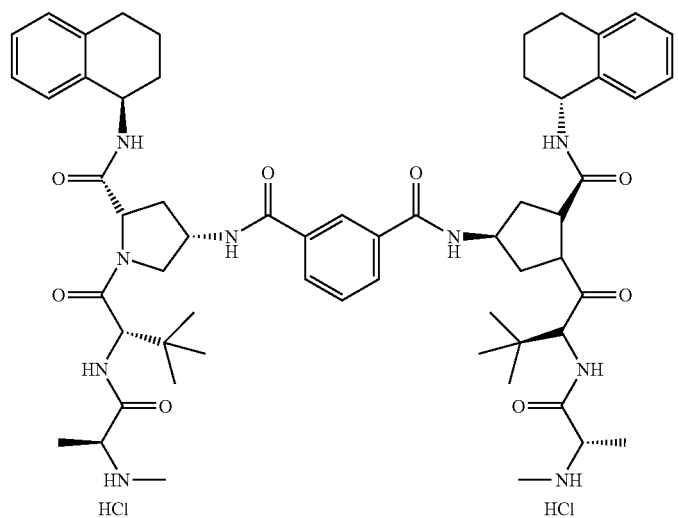 |
| 20 | 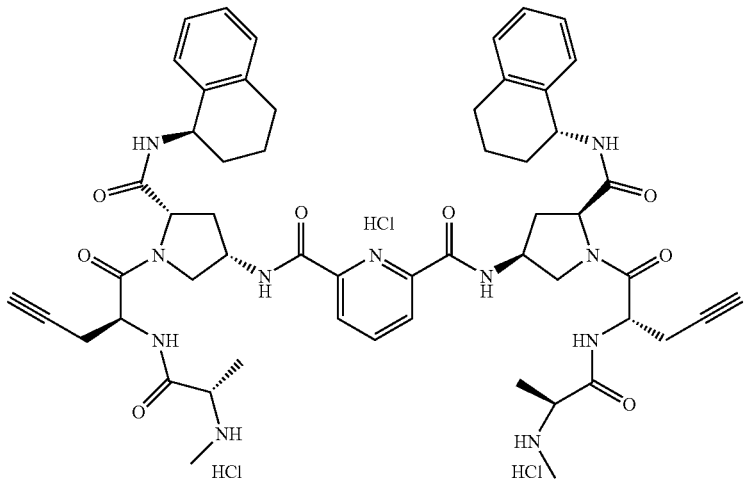 [SMILES: C#CC[C@H](NC(=O)[C@H](C)NC)C(=O)N1C[C@@H](NC(=O)c2cccc(C(=O)N[C@H]3C[C@@H](C(=O)N[C@@H]4CCCc5ccccc54)N(C(=O)[C@H](CC#C)NC(=O)[C@H](C)NC)C3)n2)C[C@H]1C(=O)N[C@@H]1CCCc2ccccc21 ; Cl ; Cl ; Cl] |
| 21 | 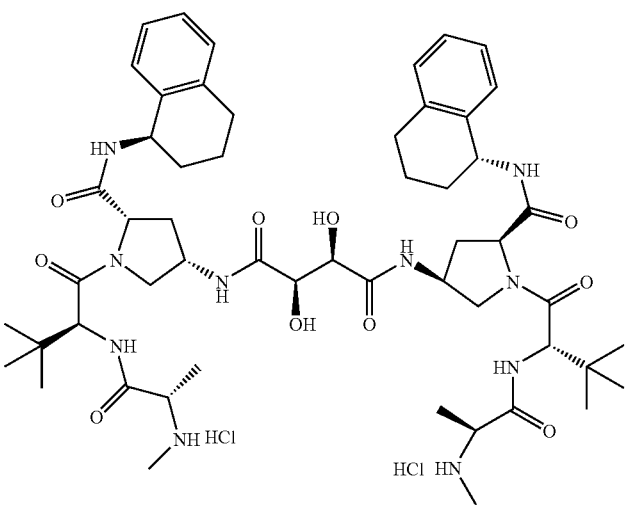 [SMILES: CN[C@@H](C)C(=O)N[C@H](C(=O)N1C[C@@H](NC(=O)[C@H](O)[C@@H](O)C(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl] |

TABLE 3-continued
Dimeric Structures
| RECORD NUMBER | STRUCTURE |
|---|---|
| 22 | 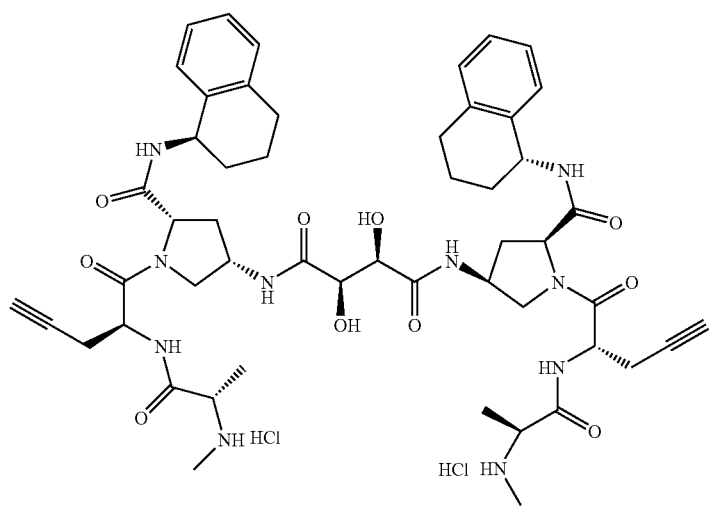 [SMILES: C#CC[C@H](NC(=O)[C@H](C)NC)C(=O)N1C[C@@H](NC(=O)[C@H](O)[C@@H](O)C(=O)N[C@H]2C[C@@H](C(=O)N[C@@H]3CCCc4ccccc43)N(C(=O)[C@H](CC#C)NC(=O)[C@H](C)NC)C2)C[C@H]1C(=O)N[C@@H]1CCCc2ccccc21 ; Cl ; Cl] |
| 23 | 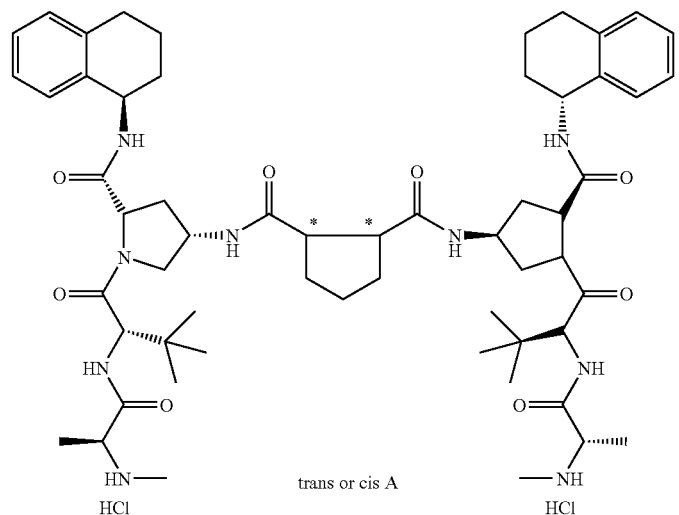 |

TABLE 3-continued
Dimeric Structures
| RECORD NUMBER | STRUCTURE |
|---|---|
| 24 | 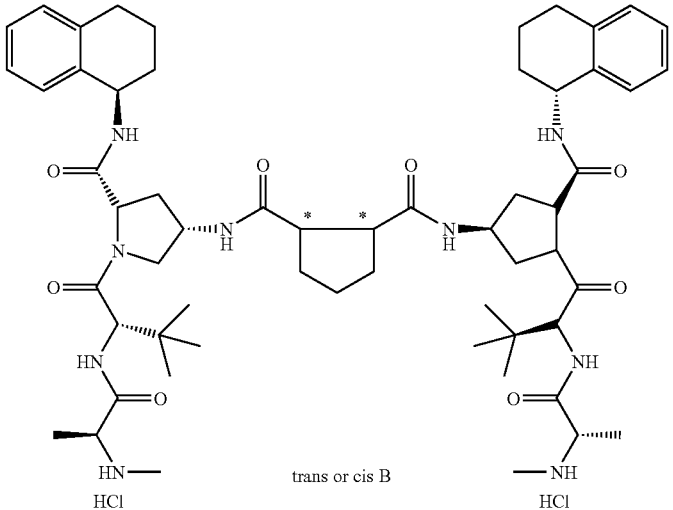 trans or cis B |
| 25 | 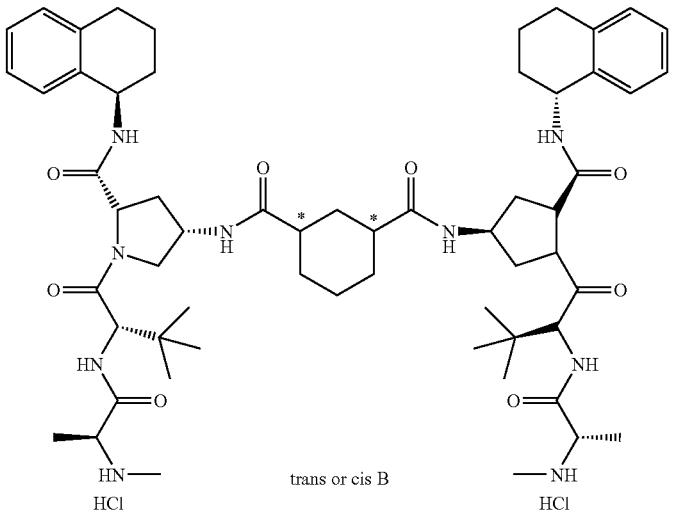 trans or cis B |
| 26 | 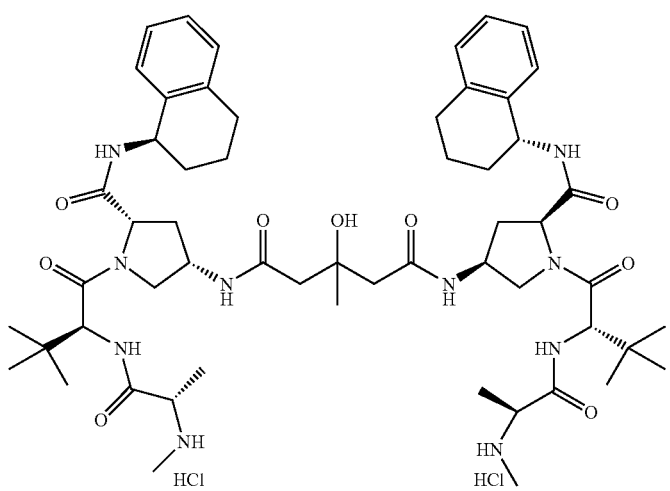 [SMILES: CN[C@@H](C)C(=O)N[C@H](C(=O)N1C[C@@H](NC(=O)CC(C)(O)CC(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl] |

TABLE 3-continued
Dimeric Structures
| RECORD NUMBER | STRUCTURE |
|---|---|
| 27 | 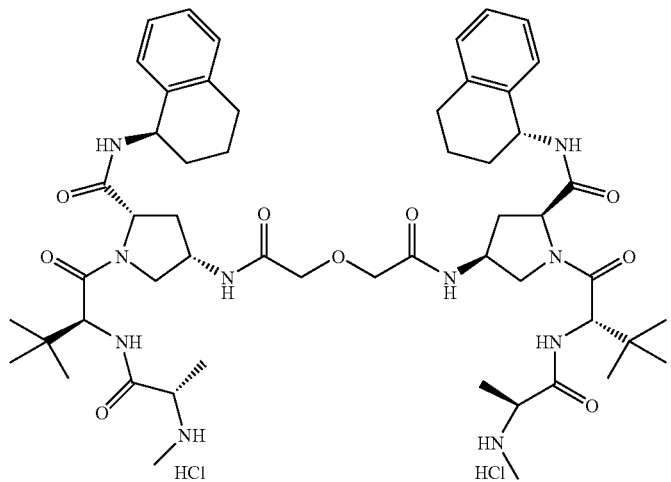 [SMILES: CN[C@@H](C)C(=O)N[C@H](C(=O)N1C[C@@H](NC(=O)COCC(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl] |
| 28 | 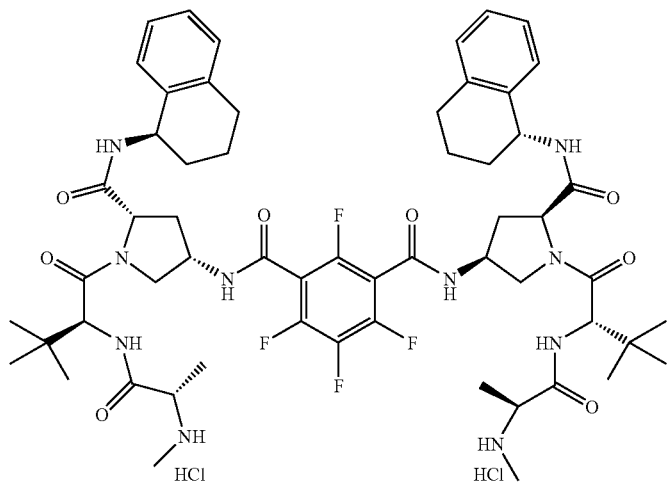 [SMILES: CN[C@@H](C)C(=O)N[C@H](C(=O)N1C[C@@H](NC(=O)c2c(F)c(F)c(F)c(C(=O)N[C@H]3C[C@@H](C(=O)N[C@@H]4CCCc5ccccc54)N(C(=O)[C@@H](NC(=O)[C@H](C)NC)C(C)(C)C)C3)c2F)C[C@H]1C(=O)N[C@@H]1CCCc2ccccc21)C(C)(C)C ; Cl ; Cl] |

TABLE 3-continued
Dimeric Structures
| RECORD NUMBER | STRUCTURE |
|---|---|
| 29 | 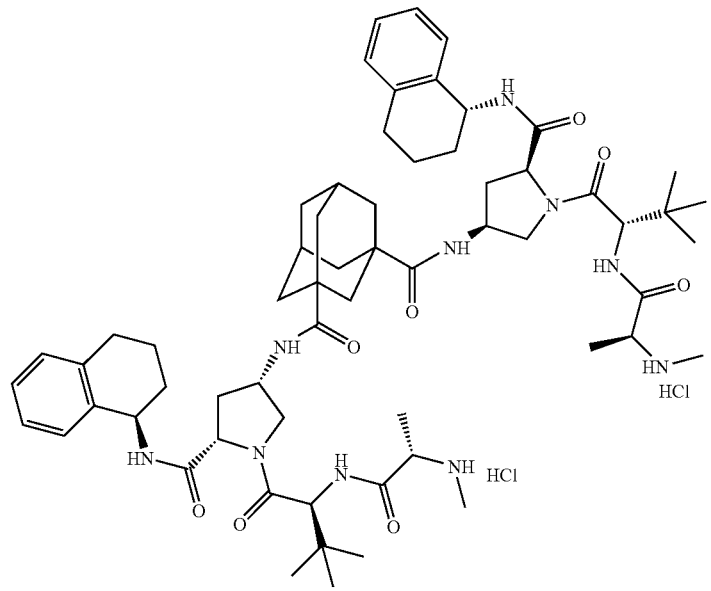 [SMILES: CN[C@@H](C)C(=O)N[C@H](C(=O)N1C[C@@H](NC(=O)C23CC4CC(C2)CC(C(=O)N[C@H]2C[C@@H](C(=O)N[C@@H]5CCCc6ccccc65)N(C(=O)[C@@H](NC(=O)[C@H](C)NC)C(C)(C)C)C2)(C4)C3)C[C@H]1C(=O)N[C@@H]1CCCc2ccccc21)C(C)(C)C ; Cl ; Cl] |
| 30 | 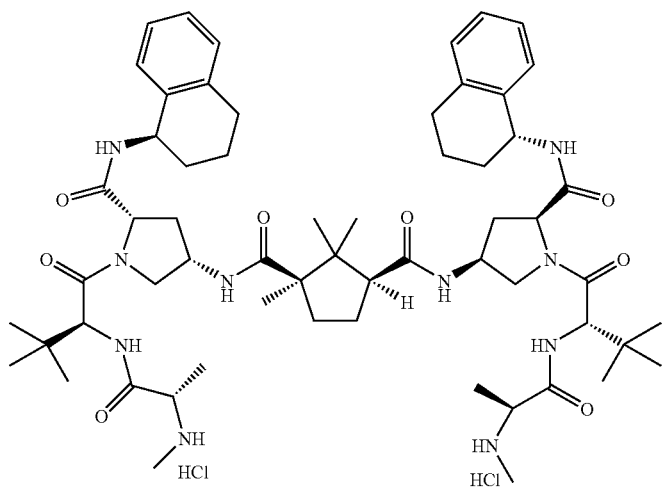 [SMILES: CN[C@@H](C)C(=O)N[C@H](C(=O)N1C[C@@H](NC(=O)[C@H]2CC[C@@](C)(C(=O)N[C@H]3C[C@@H](C(=O)N[C@@H]4CCCc5ccccc54)N(C(=O)[C@@H](NC(=O)[C@H](C)NC)C(C)(C)C)C3)C2(C)C)C[C@H]1C(=O)N[C@@H]1CCCc2ccccc21)C(C)(C)C ; Cl ; Cl] |

TABLE 3-continued
Dimeric Structures
| RECORD NUMBER | STRUCTURE |
|---|---|
| 31 | 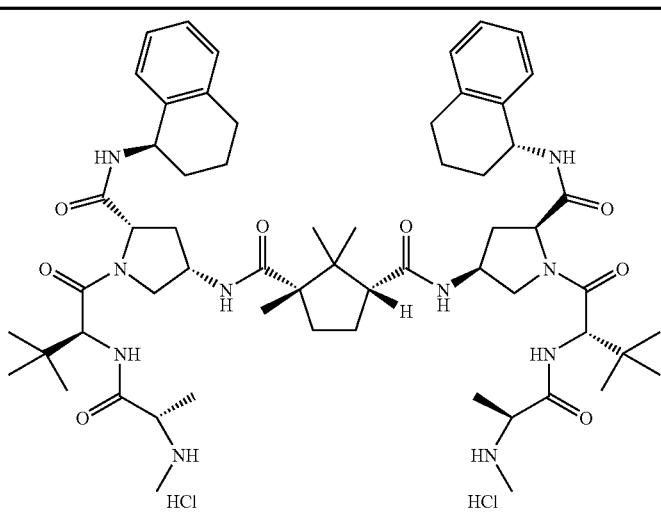 |
| 32 | 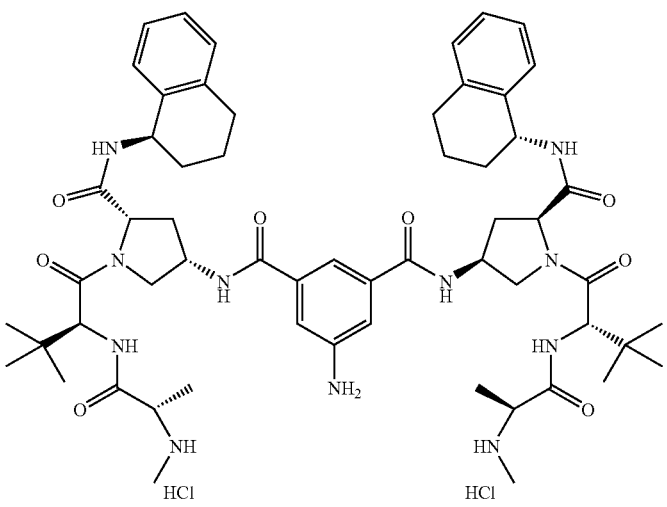 [SMILES: CN[C@@H](C)C(=O)N[C@H](C(=O)N1C[C@@H](NC(=O)c2cc(N)cc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@@H]1CCCc2ccccc21)C(C)(C)C ; Cl ; Cl] |
| 33 | 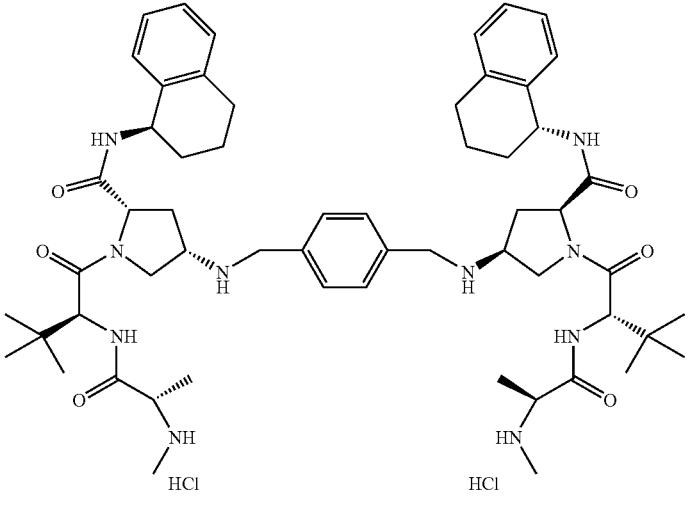 [SMILES: CN[C@@H](C)C(=O)N[C@H](C(=O)N1C[C@@H](NCc2ccc(CN[C@H]3C[C@@H](C(=O)N[C@@H]4CCCc5ccccc54)N(C(=O)[C@@H](NC(=O)[C@H](C)NC)C(C)(C)C)C3)cc2)C[C@H]1C(=O)N[C@@H]1CCCc2ccccc21)C(C)(C)C ; Cl ; Cl] |

TABLE 3-continued
Dimeric Structures
| RECORD NUMBER | STRUCTURE |
|---|---|
| 34 (Example 6) | 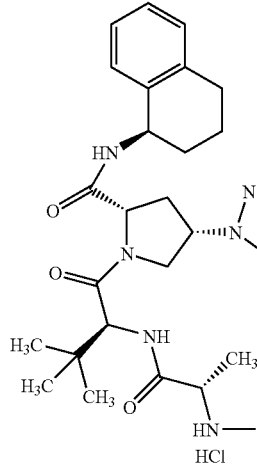 |
| 35 | 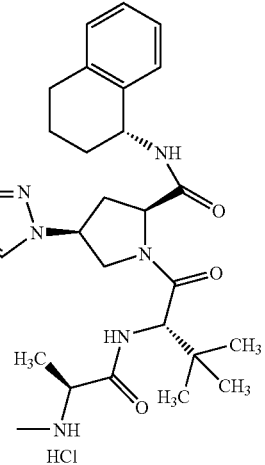 |
| 36 | 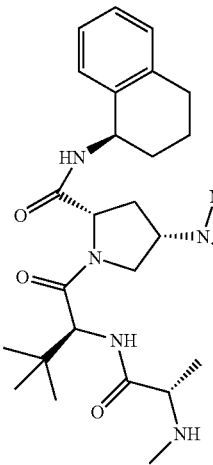 |

TABLE 3-continued
Dimeric Structures
| RECORD NUMBER | STRUCTURE |
|---|---|
| 37 | 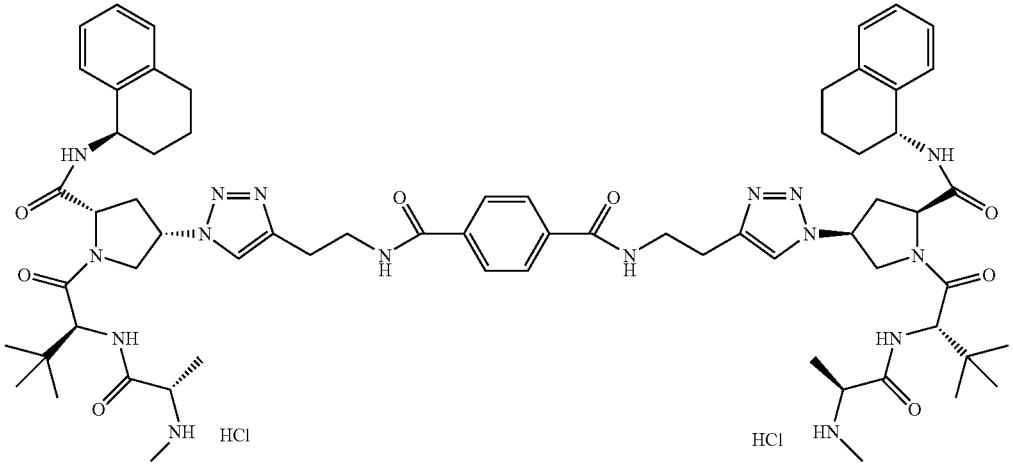 [SMILES: CN[C@@H](C)C(=O)N[C@H](C(=O)N1C[C@@H](n2cc(CCNC(=O)c3ccc(C(=O)NCCc4cn([C@H]5C[C@@H](C(=O)N[C@@H]6CCCc7ccccc76)N(C(=O)[C@@H](NC(=O)[C@H](C)NC)C(C)(C)C)C5)nn4)cc3)nn2)C[C@H]1C(=O)N[C@@H]1CCCc2ccccc21)C(C)(C)C ; Cl ; Cl] |
| 38 (Example 8) | 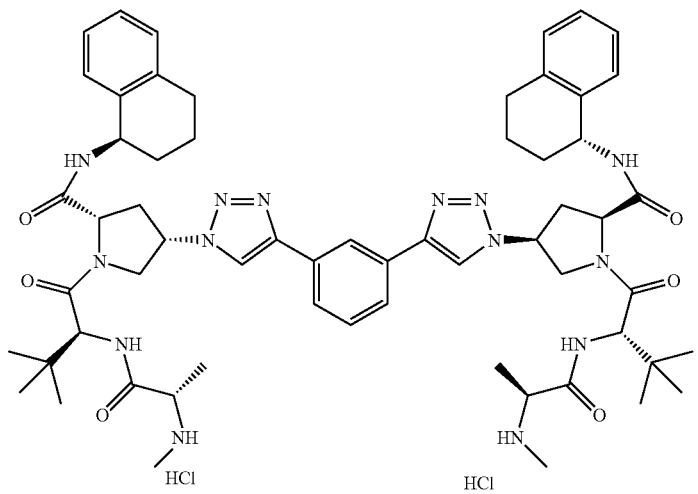 [SMILES: CN[C@@H](C)C(=O)N[C@H](C(=O)N1C[C@@H](n2cc(-c3cccc(-c4cn([C@H]5C[C@@H](C(=O)N[C@@H]6CCCc7ccccc76)N(C(=O)[C@@H](NC(=O)[C@H](C)NC)C(C)(C)C)C5)nn4)c3)nn2)C[C@H]1C(=O)N[C@@H]1CCCc2ccccc21)C(C)(C)C ; Cl ; Cl] |

TABLE 3-continued
Dimeric Structures
| RECORD NUMBER | STRUCTURE |
|---|---|
| 39 | 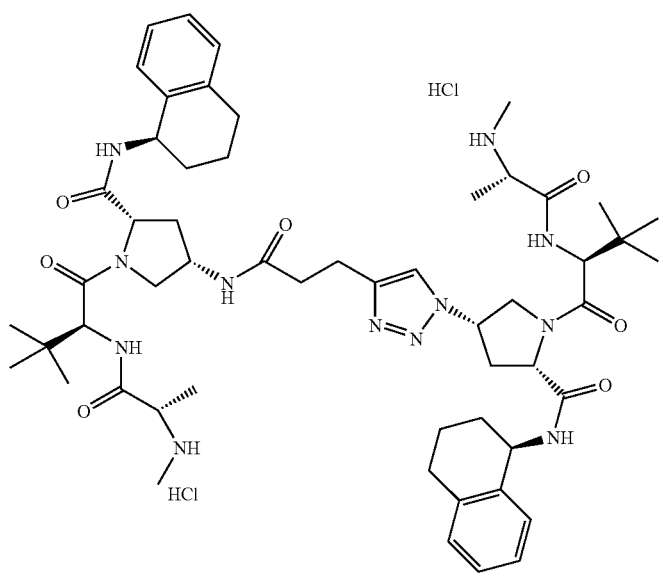 [SMILES: CN[C@@H](C)C(=O)N[C@H](C(=O)N1C[C@@H](NC(=O)CCc2cn([C@H]3C[C@@H](C(=O)N[C@@H]4CCCc5ccccc54)N(C(=O)[C@@H](NC(=O)[C@H](C)NC)C(C)(C)C)C3)nn2)C[C@H]1C(=O)N[C@@H]1CCCc2ccccc21)C(C)(C)C ; Cl ; Cl] |
| 40 | 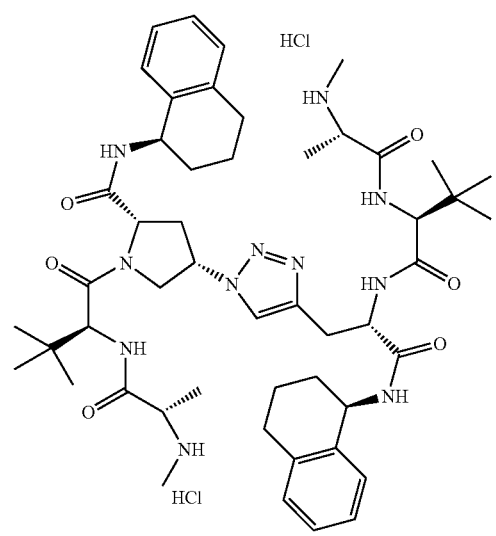 [SMILES: CN[C@@H](C)C(=O)N[C@H](C(=O)N[C@@H](Cc1cn([C@H]2C[C@@H](C(=O)N[C@@H]3CCCc4ccccc43)N(C(=O)[C@@H](NC(=O)[C@H](C)NC)C(C)(C)C)C2)nn1)C(=O)N[C@@H]1CCCc2ccccc21)C(C)(C)C ; Cl ; Cl] |

TABLE 3-continued
Dimeric Structures
| RECORD NUMBER | STRUCTURE |
|---|---|
| 41 | 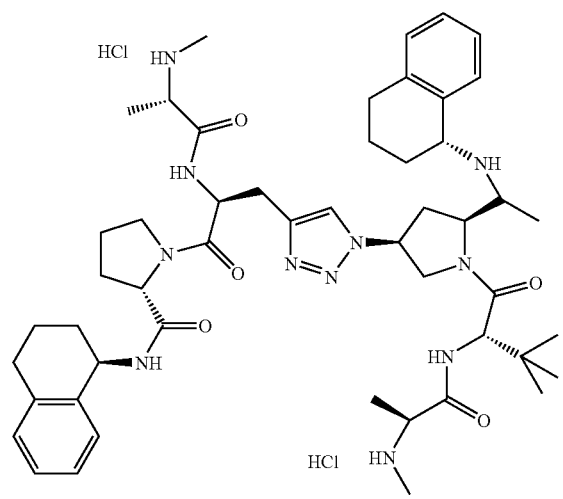 [SMILES: CN[C@@H](C)C(=O)N[C@@H](Cc1cn([C@H]2C[C@@H](C(C)N[C@@H]3CCCc4ccccc43)N(C(=O)[C@@H](NC(=O)[C@H](C)NC)C(C)(C)C)C2)nn1)C(=O)N1CCC[C@H]1C(=O)N[C@@H]1CCCc2ccccc21 ; Cl ; Cl] |
| 42 | 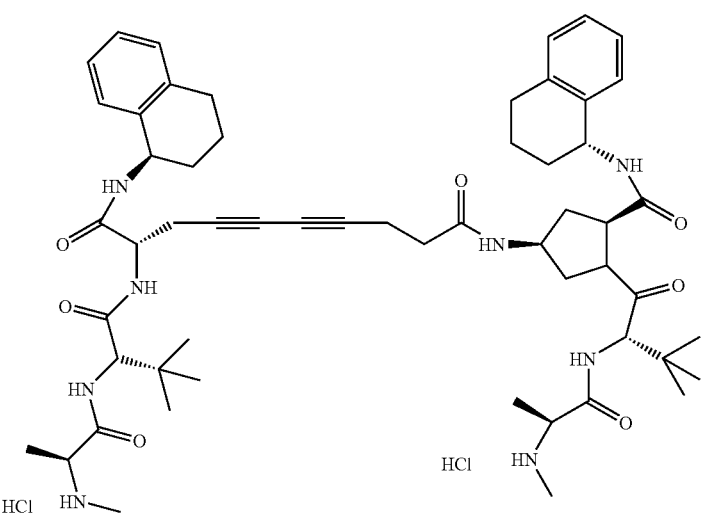 |

TABLE 3-continued
Dimeric Structures
| RECORD NUMBER | STRUCTURE |
|---|---|
| 43 | 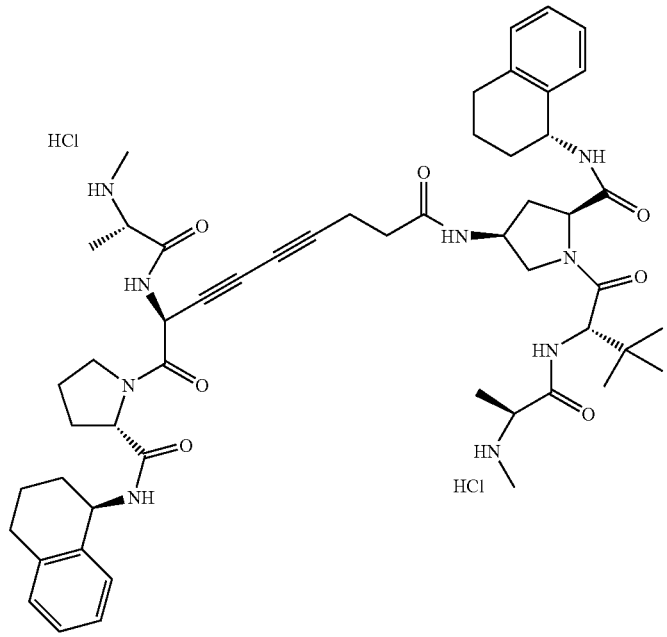 [SMILES: CN[C@@H](C)C(=O)N[C@@H](C#CC#CCCC(=O)N[C@H]1C[C@@H](C(=O)N[C@@H]2CCCc3ccccc32)N(C(=O)[C@@H](NC(=O)[C@H](C)NC)C(C)(C)C)C1)C(=O)N1CCC[C@H]1C(=O)N[C@@H]1CCCc2ccccc21 ; Cl ; Cl] |
| 44 | 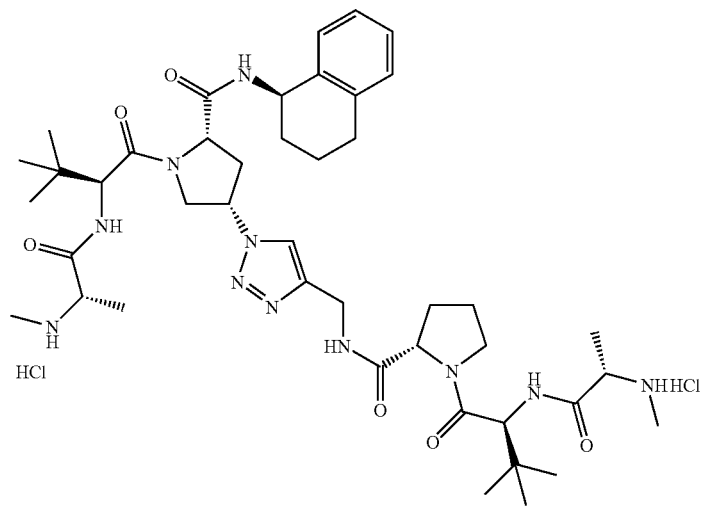 |

TABLE 3-continued
Dimeric Structures
| RECORD NUMBER | STRUCTURE |
|---|---|
| 45 | 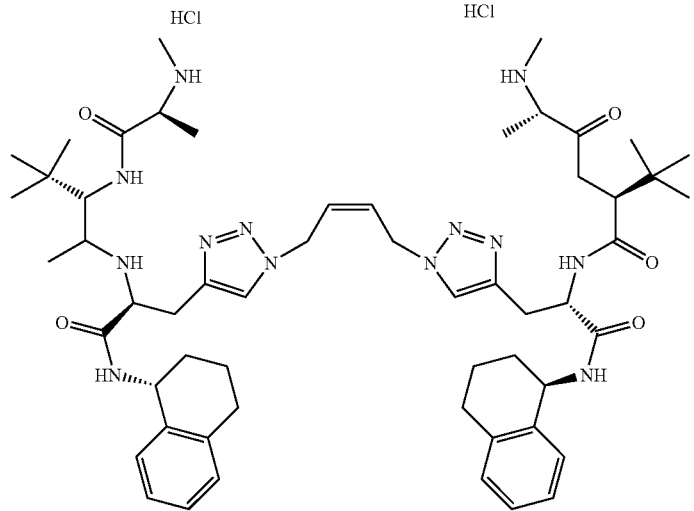 |
| 46 | 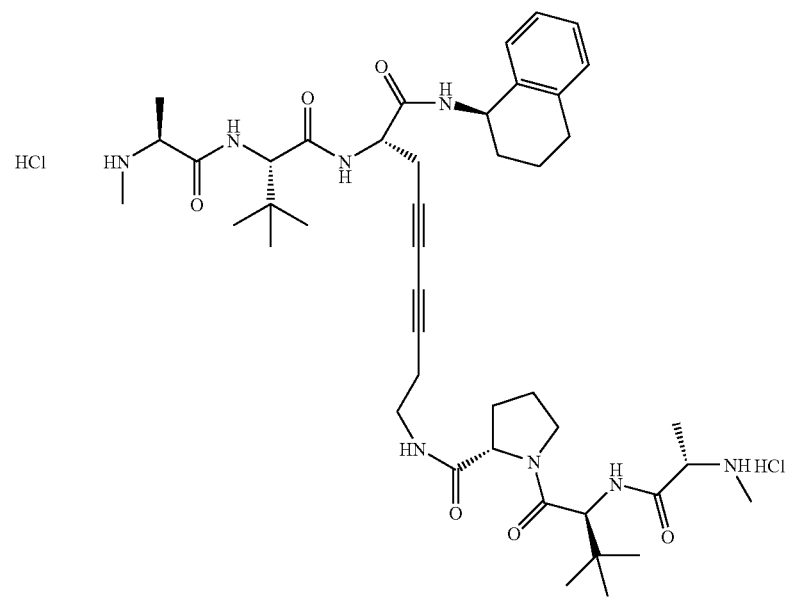 [SMILES: Cl ; CN[C@@H](C)C(=O)N[C@H](C(=O)N[C@@H](CC#CC#CCCNC(=O)[C@@H]1CCCN1C(=O)[C@@H](NC(=O)[C@H](C)NC)C(C)(C)C)C(=O)N[C@@H]1CCCc2ccccc21)C(C)(C)C ; Cl] |

TABLE 3-continued
Dimeric Structures
| RECORD NUMBER | STRUCTURE |
|---|---|
| 47 | 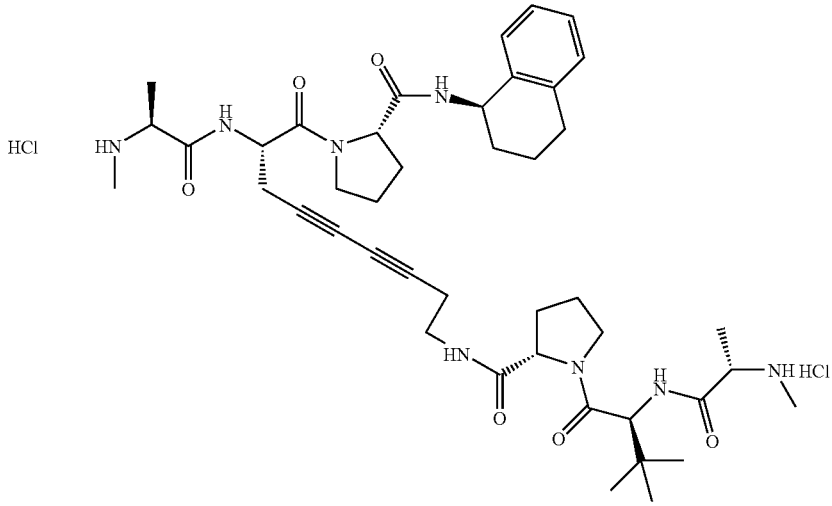 [SMILES: Cl ; CN[C@@H](C)C(=O)N[C@@H](CC#CC#CCCNC(=O)[C@@H]1CCCN1C(=O)[C@@H](NC(=O)[C@H](C)NC)C(C)(C)C)C(=O)N1CCC[C@H]1C(=O)N[C@@H]1CCCc2ccccc21 ; Cl] |
| 48 | 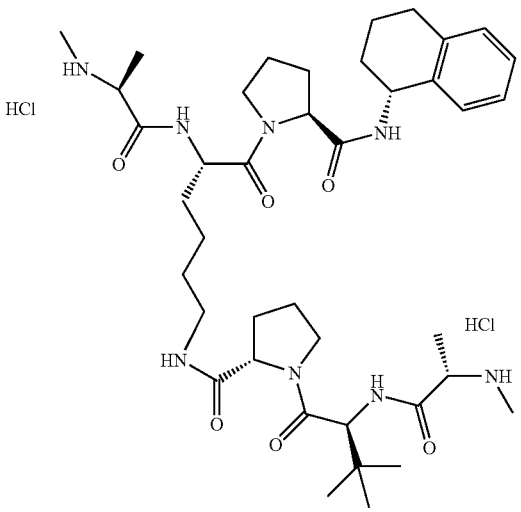 |
| 49 | 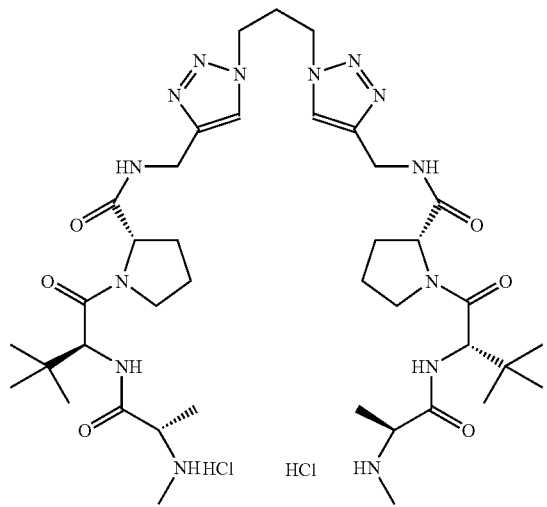 [SMILES: CN[C@@H](C)C(=O)N[C@H](C(=O)N1CCC[C@@H]1C(=O)NCc1cn(CCCn2cc(CNC(=O)[C@@H]3CCCN3C(=O)[C@@H](NC(=O)[C@H](C)NC)C(C)(C)C)nn2)nn1)C(C)(C)C ; Cl ; Cl] |

TABLE 3-continued

Dimeric Structures

| RECORD NUMBER | STRUCTURE |
|---|---|
| 50 | 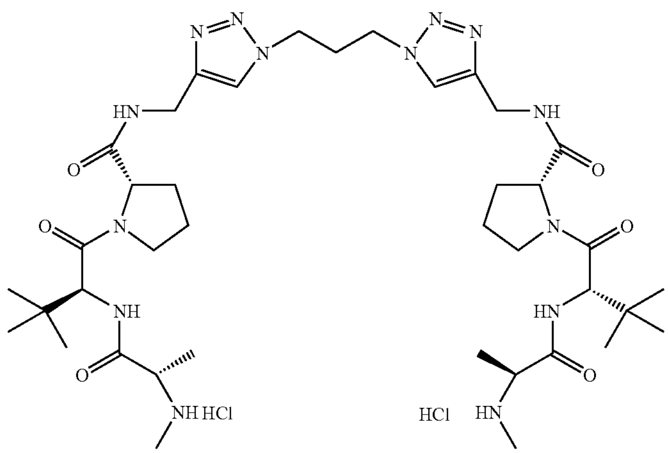 [SMILES: CN[C@@H](C)C(=O)N[C@H](C(=O)N1CCC[C@@H]1C(=O)NCc1cn(CCCn2cc(CNC(=O)[C@@H]3CCCN3C(=O)[C@@H](NC(=O)[C@H](C)NC)C(C)(C)C)nn2)nn1)C(C)(C)C ; Cl ; Cl] |
| 51 | 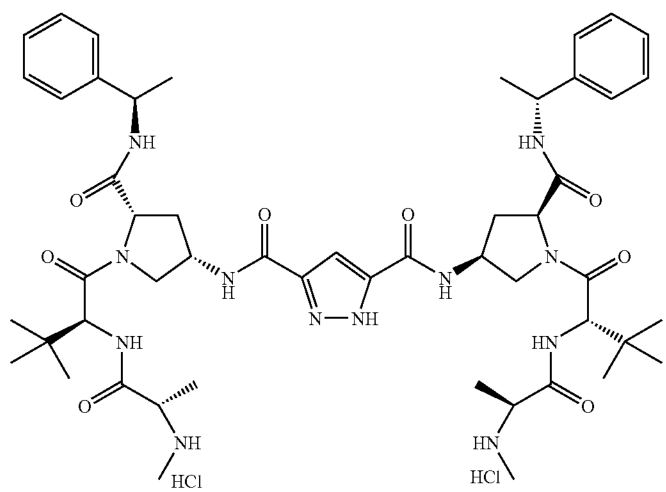 [SMILES: CN[C@@H](C)C(=O)N[C@H](C(=O)N1C[C@@H](NC(=O)c2cc(C(=O)N[C@H]3C[C@@H](C(=O)N[C@H](C)c4ccccc4)N(C(=O)[C@@H](NC(=O)[C@H](C)NC)C(C)(C)C)C3)[nH]n2)C[C@H]1C(=O)N[C@H](C)c1ccccc1)C(C)(C)C ; Cl ; Cl] |
| 52 | 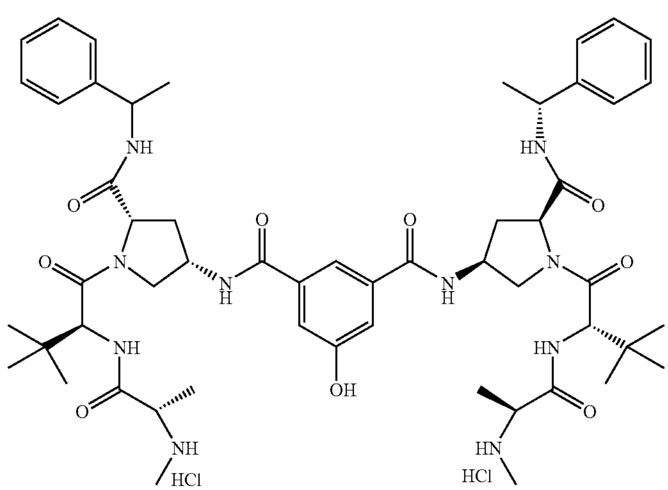 [SMILES: CN[C@@H](C)C(=O)N[C@H](C(=O)N1C[C@@H](NC(=O)c2cc(O)cc(C(=O)N[C@H]3C[C@@H](C(=O)N[C@H](C)c4ccccc4)N(C(=O)[C@@H](NC(=O)[C@H](C)NC)C(C)(C)C)C3)c2)C[C@H]1C(=O)NC(C)c1ccccc1)C(C)(C)C ; Cl ; Cl] |

TABLE 3-continued
Dimeric Structures
| RECORD NUMBER | STRUCTURE |
|---|---|
| 53 | 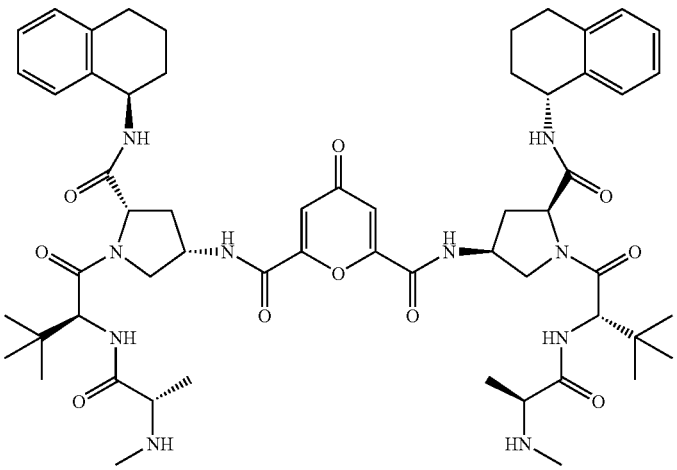 [SMILES: CN[C@@H](C)C(=O)N[C@H](C(=O)N1C[C@@H](NC(=O)c2cc(=O)cc(C(=O)N[C@H]3C[C@@H](C(=O)N[C@@H]4CCCc5ccccc54)N(C(=O)[C@@H](NC(=O)[C@H](C)NC)C(C)(C)C)C3)o2)C[C@H]1C(=O)N[C@@H]1CCCc2ccccc21)C(C)(C)C] |
| 54 | 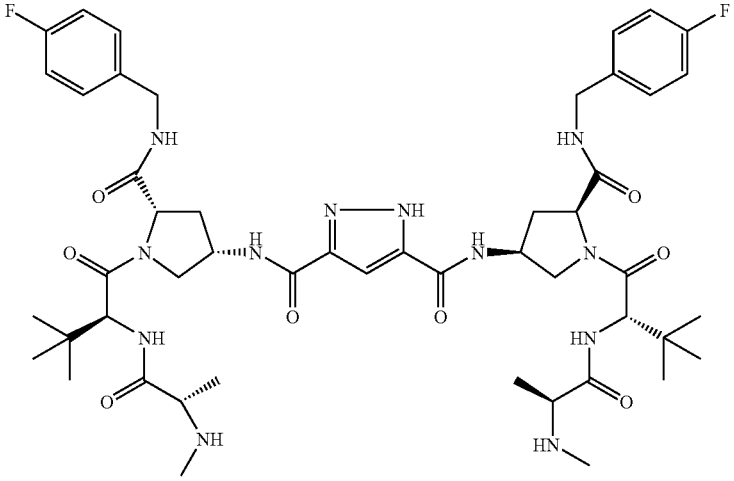 [SMILES: CN[C@@H](C)C(=O)N[C@H](C(=O)N1C[C@@H](NC(=O)c2cc(C(=O)N[C@H]3C[C@@H](C(=O)NCc4ccc(F)cc4)N(C(=O)[C@@H](NC(=O)[C@H](C)NC)C(C)(C)C)C3)[nH]n2)C[C@H]1C(=O)NCc1ccc(F)cc1)C(C)(C)C] |
| 55 | 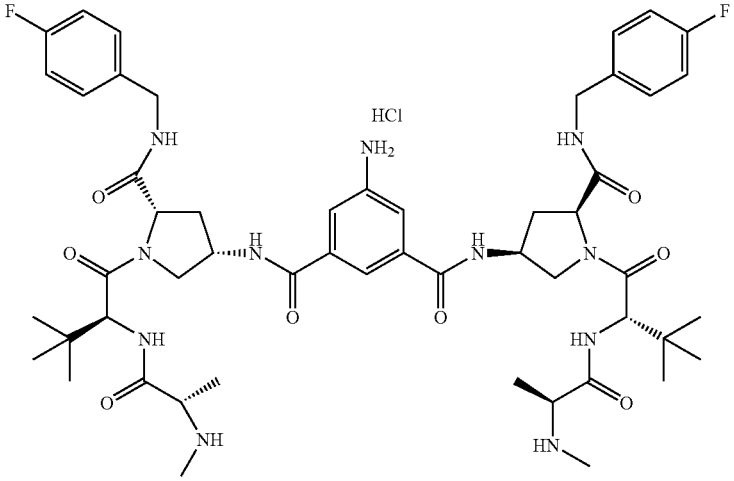 [SMILES: CN[C@@H](C)C(=O)N[C@H](C(=O)N1C[C@@H](NC(=O)c2cc(N)cc(C(=O)N[C@H]3C[C@@H](C(=O)NCc4ccc(F)cc4)N(C(=O)[C@@H](NC(=O)[C@H](C)NC)C(C)(C)C)C3)c2)C[C@H]1C(=O)NCc1ccc(F)cc1)C(C)(C)C ; Cl] |

TABLE 3-continued

Dimeric Structures

| RECORD NUMBER | STRUCTURE |
| --- | --- |
| 56 | 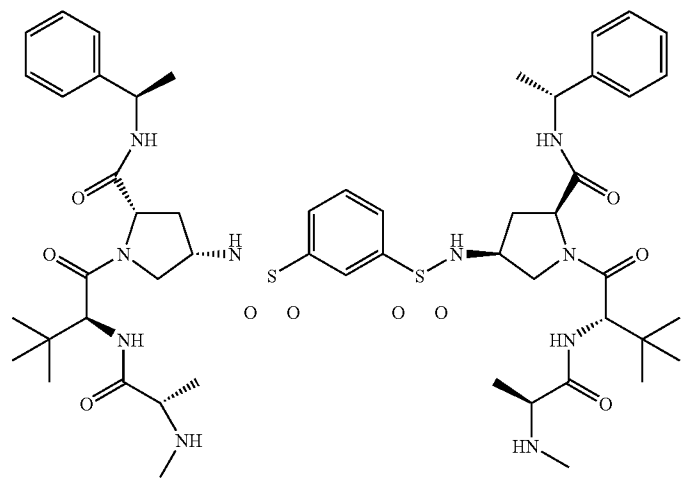 |
| 57 | 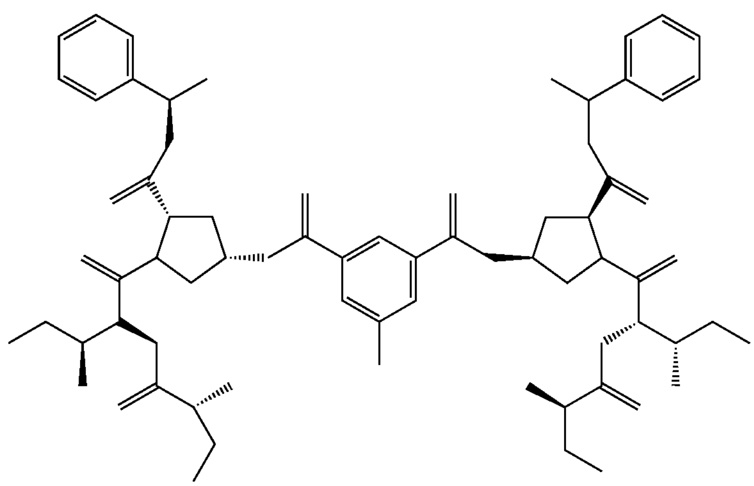 |
| 58 | 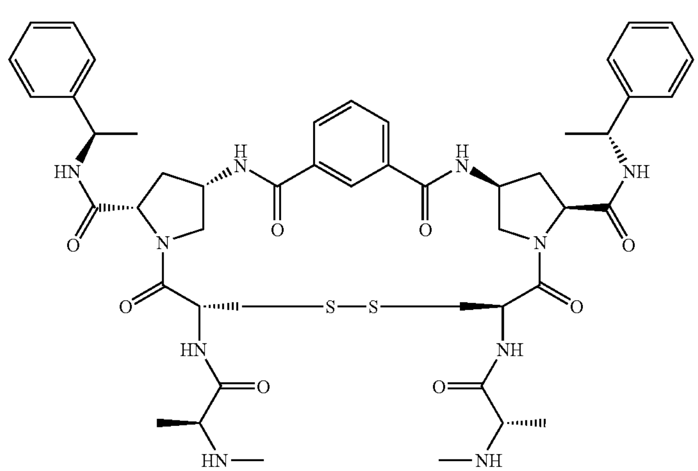 [SMILES: CN[C@@H](C)C(=O)N[C@H]1CSSC[C@H](NC(=O)[C@H](C)NC)C(=O)N2C[C@H](C[C@H]2C(=O)N[C@H](C)c2ccccc2)NC(=O)c2cccc(c2)C(=O)N[C@H]2C[C@@H](C(=O)N[C@H](C)c3ccccc3)N(C2)C1=O] |

TABLE 3-continued
Dimeric Structures
| RECORD NUMBER | STRUCTURE |
|---|---|
| 59 | 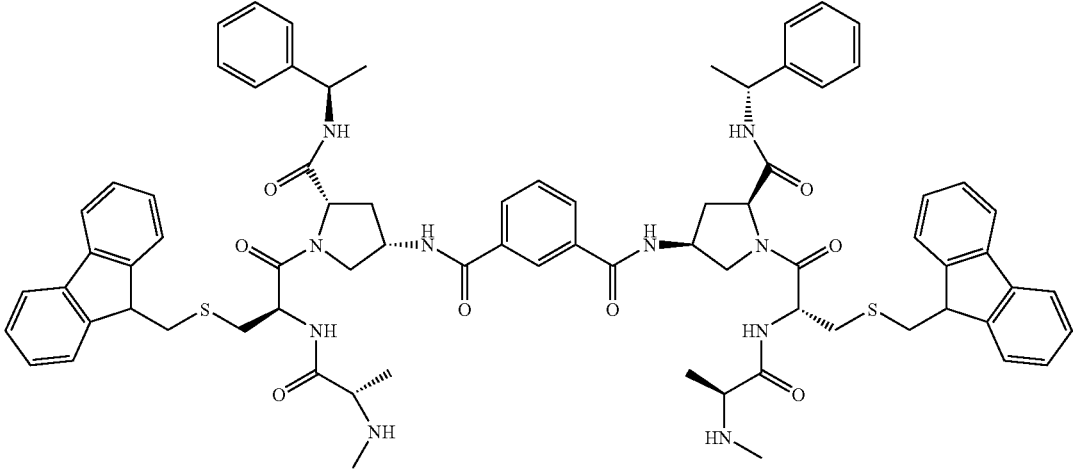 [SMILES: CN[C@@H](C)C(=O)N[C@@H](CSCC1c2ccccc2-c2ccccc21)C(=O)N1C[C@@H](NC(=O)c2cccc(C(=O)N[C@H]3C[C@@H](C(=O)N[C@H](C)c4ccccc4)N(C(=O)[C@H](CSCC4c5ccccc5-c5ccccc54)NC(=O)[C@H](C)NC)C3)c2)C[C@H]1C(=O)N[C@H](C)c1ccccc1] |
| 60 | 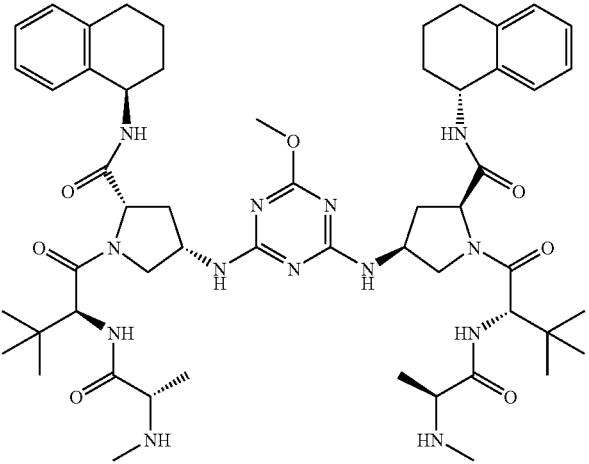 [SMILES: CN[C@@H](C)C(=O)N[C@H](C(=O)N1C[C@@H](Nc2nc(N[C@H]3C[C@@H](C(=O)N[C@@H]4CCCc5ccccc54)N(C(=O)[C@@H](NC(=O)[C@H](C)NC)C(C)(C)C)C3)nc(OC)n2)C[C@H]1C(=O)N[C@@H]1CCCc2ccccc21)C(C)(C)C] |
| 61 | 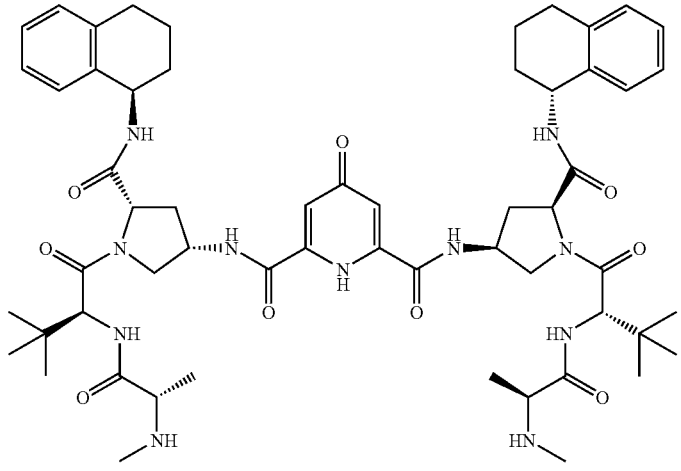 [SMILES: CN[C@@H](C)C(=O)N[C@H](C(=O)N1C[C@@H](NC(=O)c2cc(=O)cc(C(=O)N[C@H]3C[C@@H](C(=O)N[C@@H]4CCCc5ccccc54)N(C(=O)[C@@H](NC(=O)[C@H](C)NC)C(C)(C)C)C3)[nH]2)C[C@H]1C(=O)N[C@@H]1CCCc2ccccc21)C(C)(C)C] |

TABLE 3-continued

Dimeric Structures

| RECORD NUMBER | STRUCTURE |
|---|---|
| 62 | 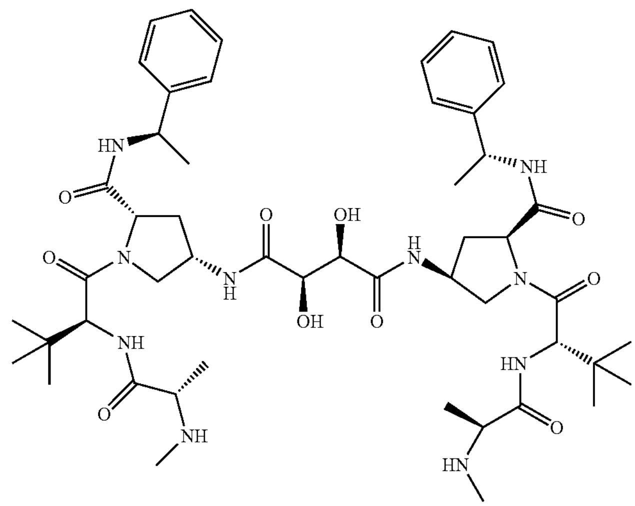 [SMILES: CN[C@@H](C)C(=O)N[C@H](C(=O)N1C[C@@H](NC(=O)[C@H](O)[C@@H](O)C(=O)N[C@H]2C[C@@H](C(=O)N[C@H](C)c3ccccc3)N(C(=O)[C@@H](NC(=O)[C@H](C)NC)C(C)(C)C)C2)C[C@H]1C(=O)N[C@H](C)c1ccccc1)C(C)(C)C] |
| 63 | 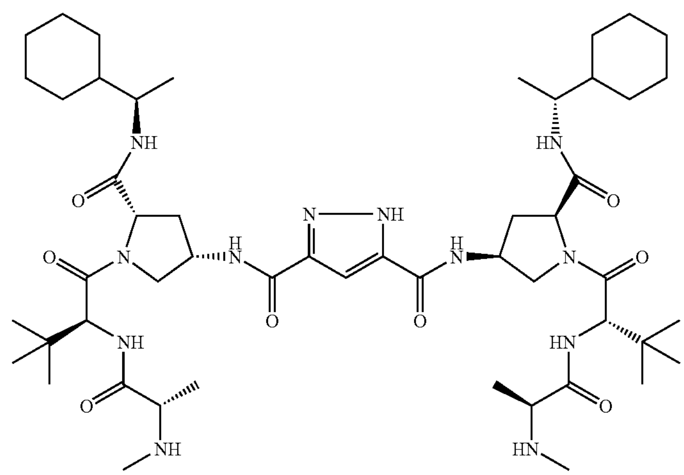 [SMILES: CN[C@@H](C)C(=O)N[C@H](C(=O)N1C[C@@H](NC(=O)c2cc(C(=O)N[C@H]3C[C@@H](C(=O)N[C@H](C)C4CCCCC4)N(C(=O)[C@@H](NC(=O)[C@H](C)NC)C(C)(C)C)C3)[nH]n2)C[C@H]1C(=O)N[C@H](C)C1CCCCC1)C(C)(C)C] |
| 64 | 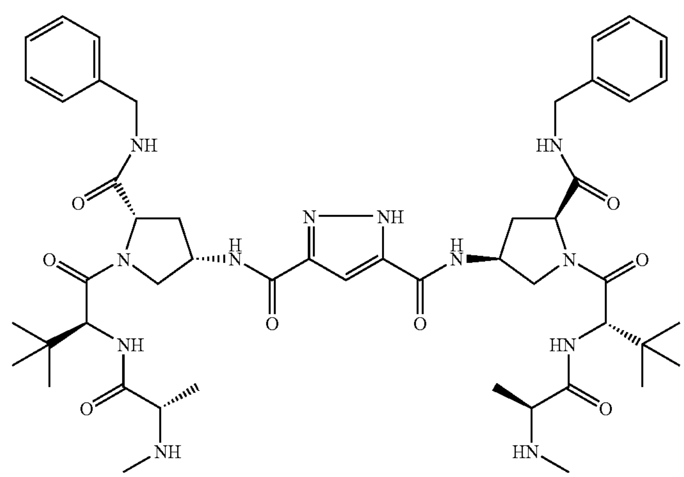 [SMILES: CN[C@@H](C)C(=O)N[C@H](C(=O)N1C[C@@H](NC(=O)c2cc(C(=O)N[C@H]3C[C@@H](C(=O)NCc4ccccc4)N(C(=O)[C@@H](NC(=O)[C@H](C)NC)C(C)(C)C)C3)[nH]n2)C[C@H]1C(=O)NCc1ccccc1)C(C)(C)C] |

TABLE 3-continued
Dimeric Structures
| RECORD NUMBER | STRUCTURE |
|---|---|
| 65 | 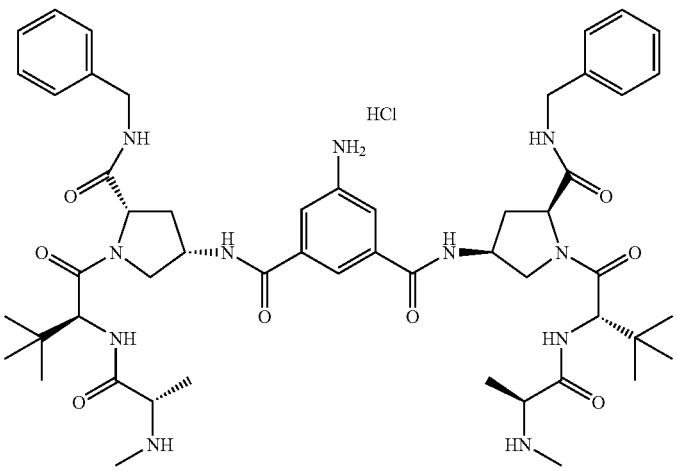 [SMILES: CN[C@@H](C)C(=O)N[C@H](C(=O)N1C[C@@H](NC(=O)c2cc(N)cc(C(=O)N[C@H]3C[C@@H](C(=O)NCc4ccccc4)N(C(=O)[C@@H](NC(=O)[C@H](C)NC)C(C)(C)C)C3)c2)C[C@H]1C(=O)NCc1ccccc1)C(C)(C)C ; Cl] |
| 66 | 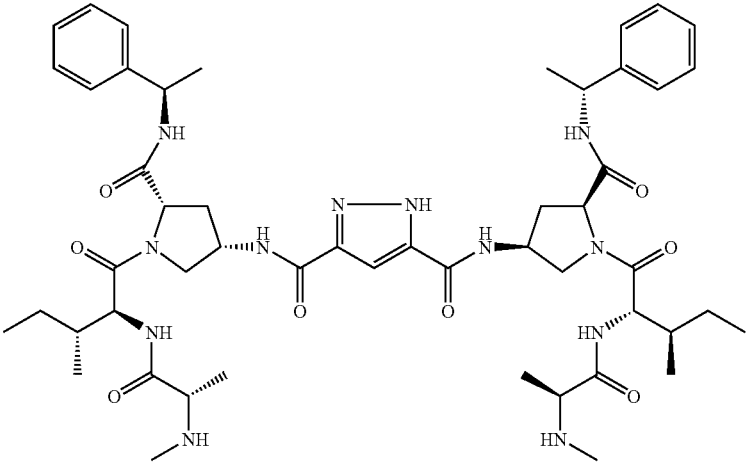 [SMILES: CC[C@@H](C)[C@H](NC(=O)[C@H](C)NC)C(=O)N1C[C@@H](NC(=O)c2cc(C(=O)N[C@H]3C[C@@H](C(=O)N[C@H](C)c4ccccc4)N(C(=O)[C@@H](NC(=O)[C@H](C)NC)[C@H](C)CC)C3)[nH]n2)C[C@H]1C(=O)N[C@H](C)c1ccccc1] |
| 67 | 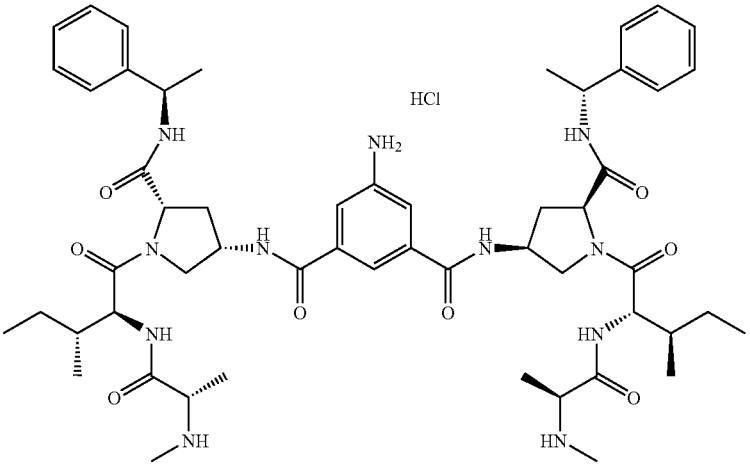 [SMILES: CC[C@@H](C)[C@H](NC(=O)[C@H](C)NC)C(=O)N1C[C@@H](NC(=O)c2cc(N)cc(C(=O)N[C@H]3C[C@@H](C(=O)N[C@H](C)c4ccccc4)N(C(=O)[C@@H](NC(=O)[C@H](C)NC)[C@H](C)CC)C3)c2)C[C@H]1C(=O)N[C@H](C)c1ccccc1 ; Cl] |

TABLE 3-continued
Dimeric Structures
| RECORD NUMBER | STRUCTURE |
|---|---|
| 68 | 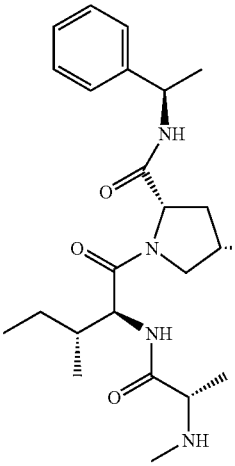 |
| 69 | 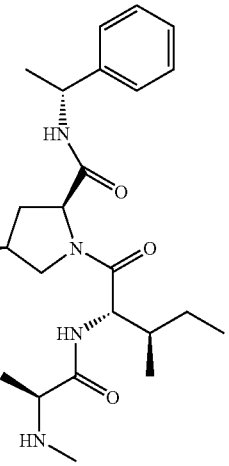 |
| 70 | 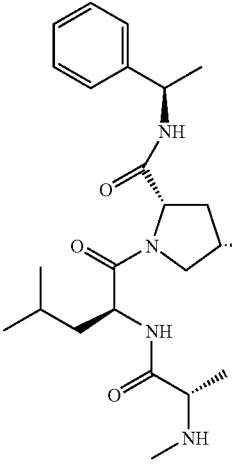 |

TABLE 3-continued
Dimeric Structures
| RECORD NUMBER | STRUCTURE |
|---|---|
| 71 | 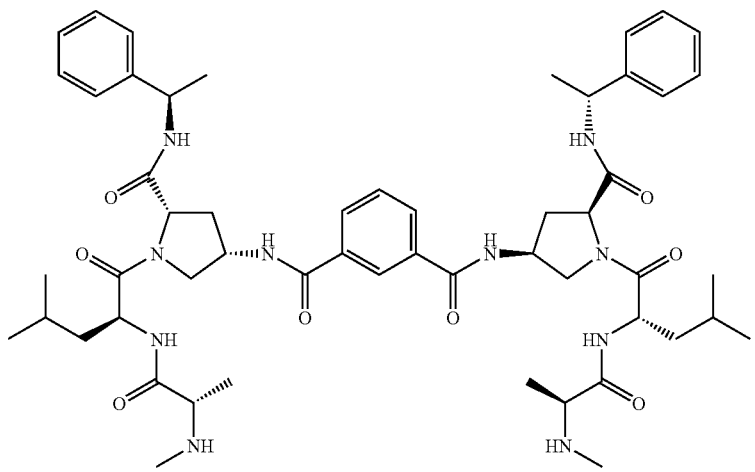 [SMILES: CN[C@@H](C)C(=O)N[C@@H](CC(C)C)C(=O)N1C[C@@H](NC(=O)c2cccc(C(=O)N[C@H]3C[C@@H](C(=O)N[C@H](C)c4ccccc4)N(C(=O)[C@H](CC(C)C)NC(=O)[C@H](C)NC)C3)c2)C[C@H]1C(=O)N[C@H](C)c1ccccc1] |
| 72 | 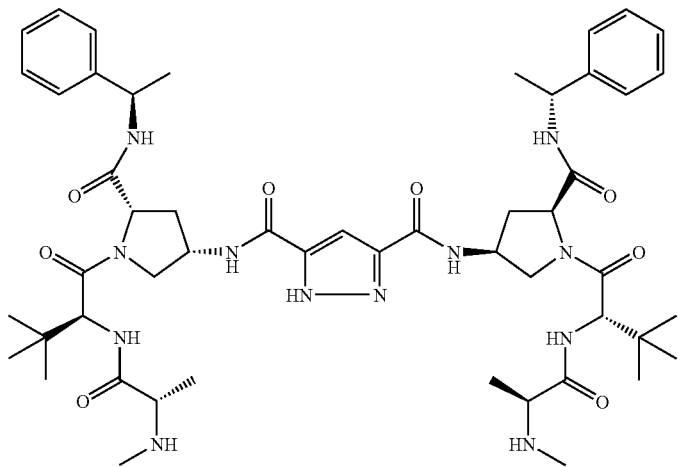 [SMILES: CN[C@@H](C)C(=O)N[C@H](C(=O)N1C[C@@H](NC(=O)c2cc(C(=O)N[C@H]3C[C@@H](C(=O)N[C@H](C)c4ccccc4)N(C(=O)[C@@H](NC(=O)[C@H](C)NC)C(C)(C)C)C3)[nH]n2)C[C@H]1C(=O)N[C@H](C)c1ccccc1)C(C)(C)C] |
| 73 | 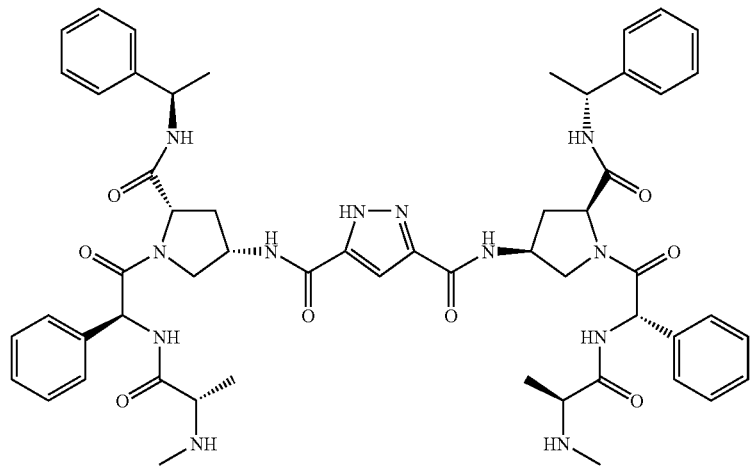 [SMILES: CN[C@@H](C)C(=O)N[C@H](C(=O)N1C[C@@H](NC(=O)c2cc(C(=O)N[C@H]3C[C@@H](C(=O)N[C@H](C)c4ccccc4)N(C(=O)[C@@H](NC(=O)[C@H](C)NC)c4ccccc4)C3)[nH]n2)C[C@H]1C(=O)N[C@H](C)c1ccccc1)c1ccccc1] |

TABLE 3-continued
Dimeric Structures
| RECORD NUMBER | STRUCTURE |
|---|---|
| 74 | 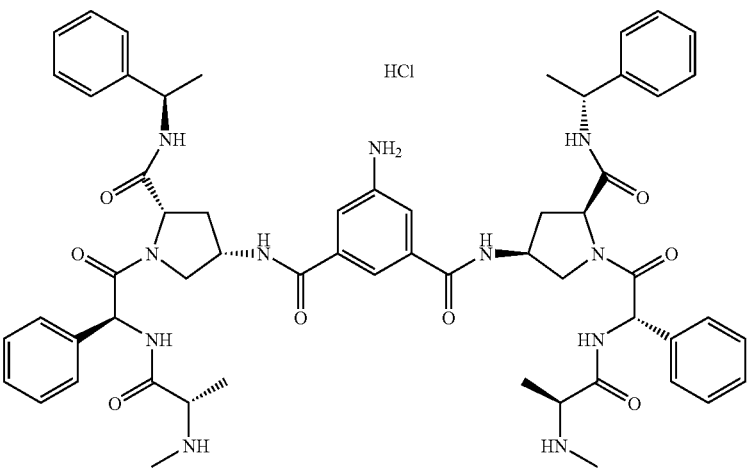 [SMILES: CN[C@@H](C)C(=O)N[C@H](C(=O)N1C[C@@H](NC(=O)c2cc(N)cc(C(=O)N[C@H]3C[C@@H](C(=O)N[C@H](C)c4ccccc4)N(C(=O)[C@@H](NC(=O)[C@H](C)NC)c4ccccc4)C3)c2)C[C@H]1C(=O)N[C@H](C)c1ccccc1)c1ccccc1 ; Cl] |
| 75 | 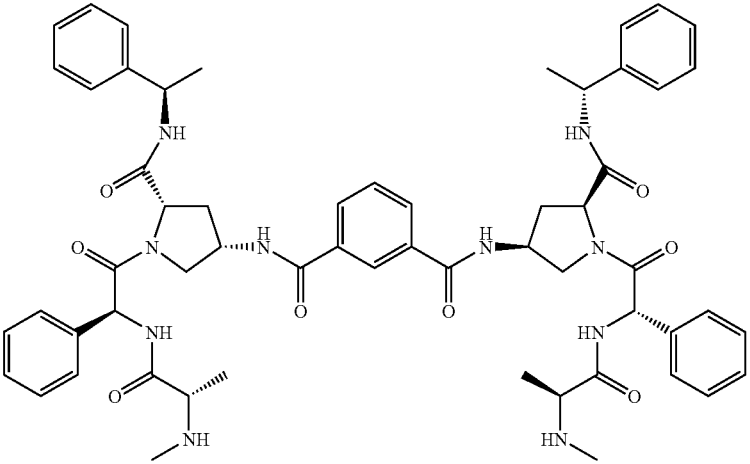 [SMILES: CN[C@@H](C)C(=O)N[C@H](C(=O)N1C[C@@H](NC(=O)c2cccc(C(=O)N[C@H]3C[C@@H](C(=O)N[C@H](C)c4ccccc4)N(C(=O)[C@@H](NC(=O)[C@H](C)NC)c4ccccc4)C3)c2)C[C@H]1C(=O)N[C@H](C)c1ccccc1)c1ccccc1] |
| 76 | 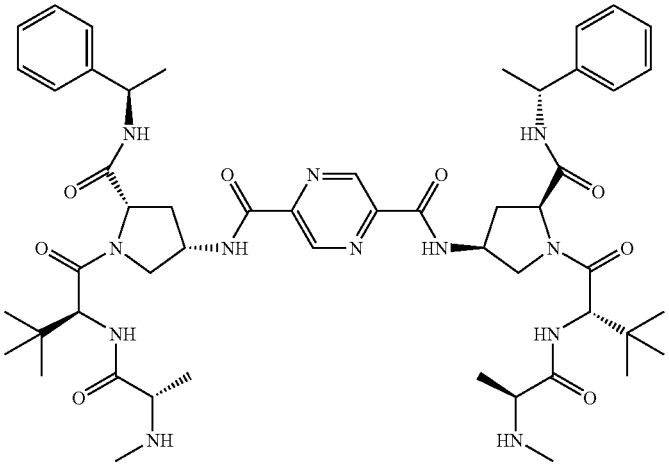 [SMILES: CN[C@@H](C)C(=O)N[C@H](C(=O)N1C[C@@H](NC(=O)c2cnc(C(=O)N[C@H]3C[C@@H](C(=O)N[C@H](C)c4ccccc4)N(C(=O)[C@@H](NC(=O)[C@H](C)NC)C(C)(C)C)C3)cn2)C[C@H]1C(=O)N[C@H](C)c1ccccc1)C(C)(C)C] |

TABLE 3-continued

Dimeric Structures

| RECORD NUMBER | STRUCTURE |
|---|---|
| 77 | 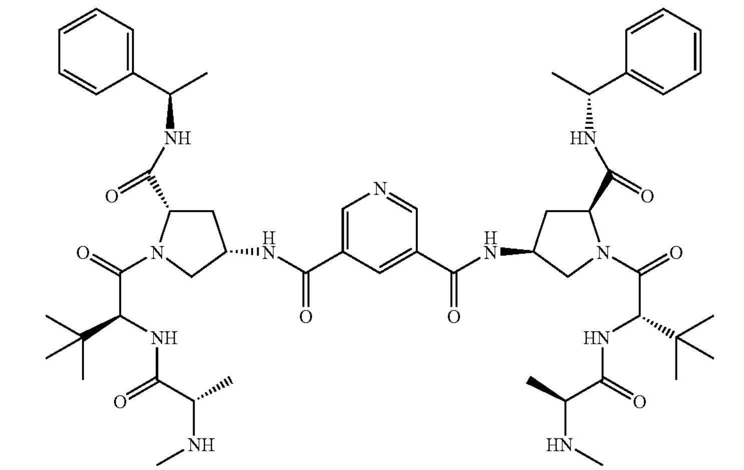 [SMILES: CN[C@@H](C)C(=O)N[C@H](C(=O)N1C[C@@H](NC(=O)c2cncc(C(=O)N[C@H]3C[C@@H](C(=O)N[C@H](C)c4ccccc4)N(C(=O)[C@@H](NC(=O)[C@H](C)NC)C(C)(C)C)C3)c2)C[C@H]1C(=O)N[C@H](C)c1ccccc1)C(C)(C)C] |
| 78 | 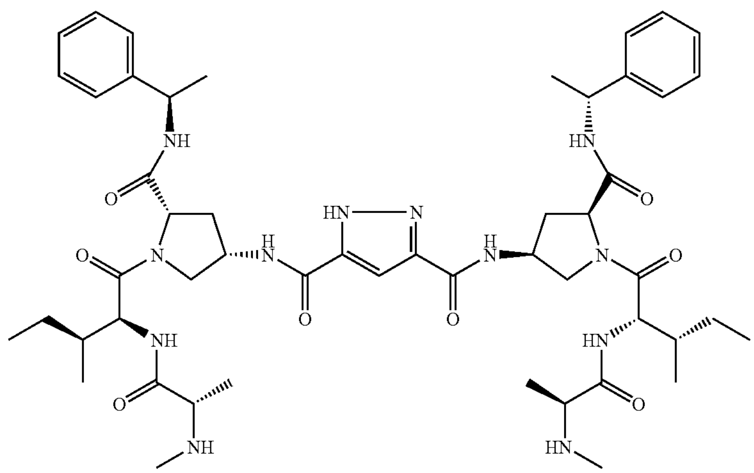 [SMILES: CC[C@H](C)[C@H](NC(=O)[C@H](C)NC)C(=O)N1C[C@@H](NC(=O)c2cc(C(=O)N[C@H]3C[C@@H](C(=O)N[C@H](C)c4ccccc4)N(C(=O)[C@@H](NC(=O)[C@H](C)NC)[C@@H](C)CC)C3)[nH]n2)C[C@H]1C(=O)N[C@H](C)c1ccccc1] |
| 79 | 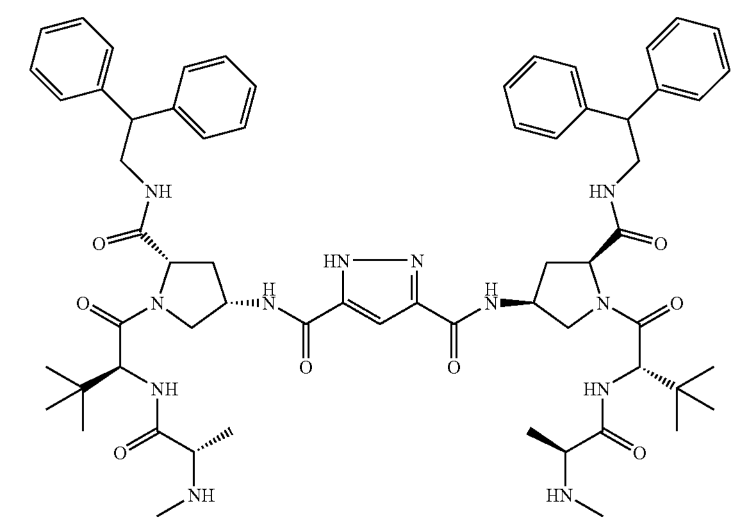 [SMILES: CN[C@@H](C)C(=O)N[C@H](C(=O)N1C[C@@H](NC(=O)c2cc(C(=O)N[C@H]3C[C@@H](C(=O)NCC(c4ccccc4)c4ccccc4)N(C(=O)[C@@H](NC(=O)[C@H](C)NC)C(C)(C)C)C3)[nH]n2)C[C@H]1C(=O)NCC(c1ccccc1)c1ccccc1)C(C)(C)C] |

TABLE 3-continued
Dimeric Structures
| RECORD NUMBER | STRUCTURE |
|---|---|
| 80 | 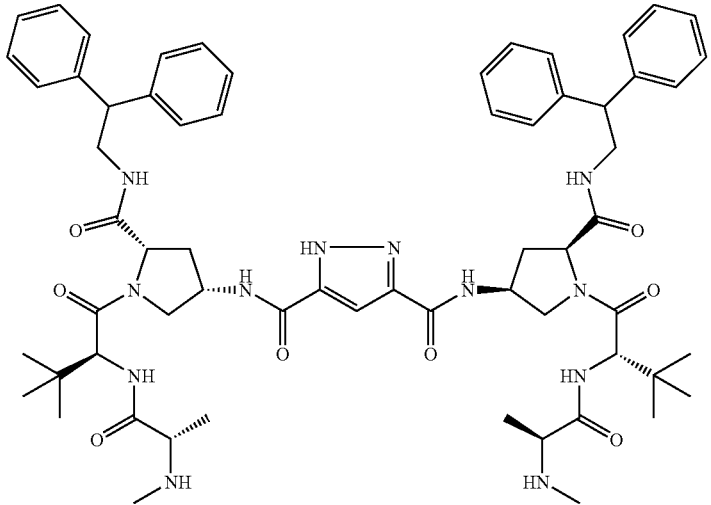 [SMILES: CN[C@@H](C)C(=O)N[C@H](C(=O)N1C[C@@H](NC(=O)c2cc(C(=O)N[C@H]3C[C@@H](C(=O)NCC(c4ccccc4)c4ccccc4)N(C(=O)[C@@H](NC(=O)[C@H](C)NC)C(C)(C)C)C3)[nH]n2)C[C@H]1C(=O)NCC(c1ccccc1)c1ccccc1)C(C)(C)C] |
| 81 | 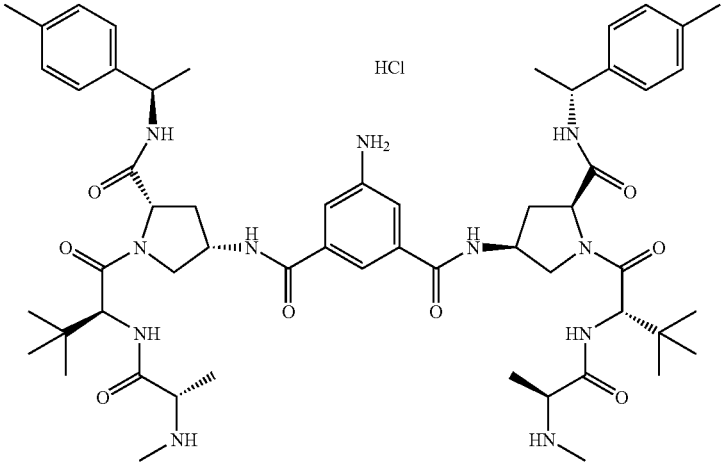 |
| 82 | 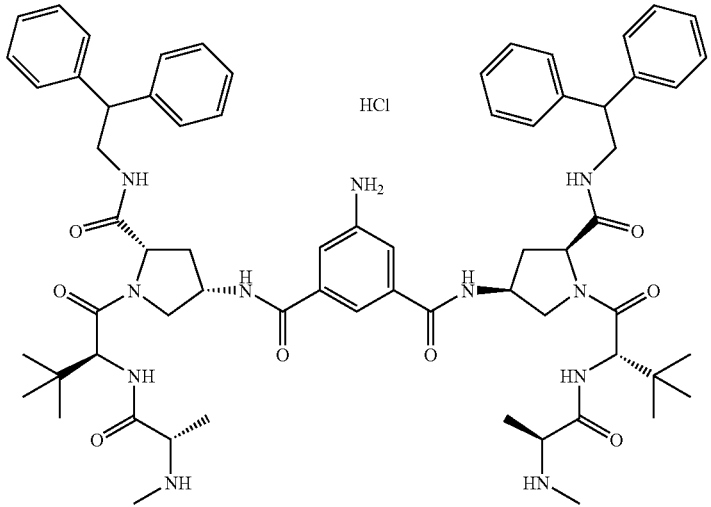 [SMILES: CN[C@@H](C)C(=O)N[C@H](C(=O)N1C[C@@H](NC(=O)c2cc(N)cc(C(=O)N[C@H]3C[C@@H](C(=O)NCC(c4ccccc4)c4ccccc4)N(C(=O)[C@@H](NC(=O)[C@H](C)NC)C(C)(C)C)C3)c2)C[C@H]1C(=O)NCC(c1ccccc1)c1ccccc1)C(C)(C)C ; Cl] |

TABLE 3-continued
Dimeric Structures
| RE-CORD NUMBER | STRUCTURE |
|---|---|
| 83 | 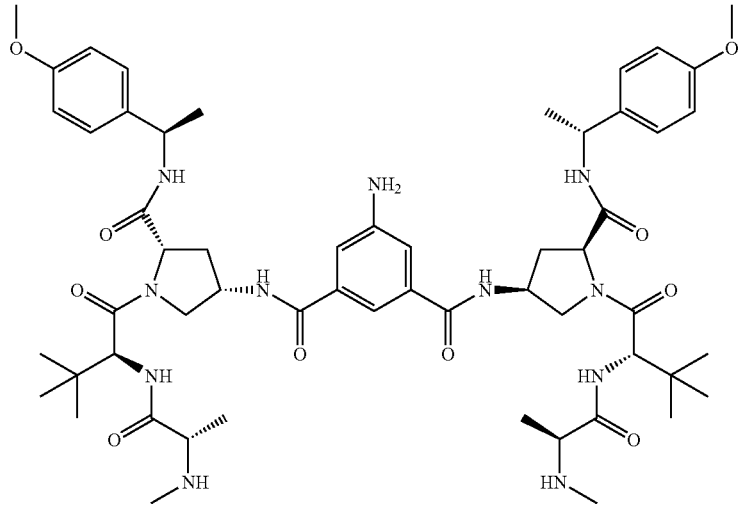 [SMILES: CN[C@@H](C)C(=O)N[C@H](C(=O)N1C[C@@H](NC(=O)c2cc(N)cc(C(=O)N[C@H]3C[C@@H](C(=O)N[C@H](C)c4ccc(OC)cc4)N(C(=O)[C@@H](NC(=O)[C@H](C)NC)C(C)(C)C)C3)c2)C[C@H]1C(=O)N[C@H](C)c1ccc(OC)cc1)C(C)(C)C] |
| 84 | 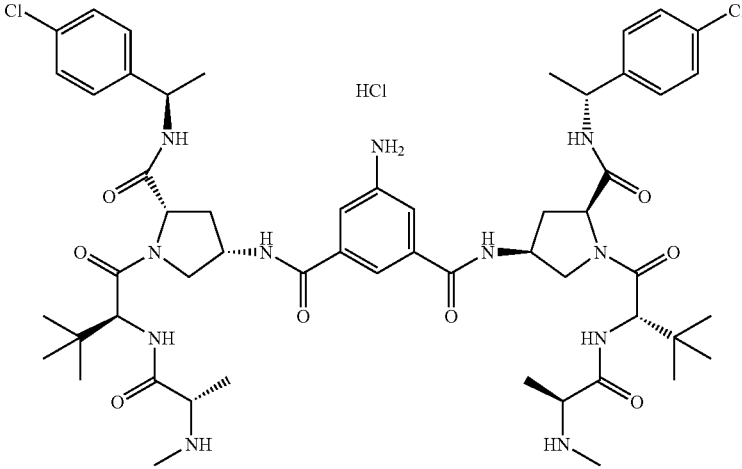 [SMILES: CN[C@@H](C)C(=O)N[C@H](C(=O)N1C[C@@H](NC(=O)c2cc(N)cc(C(=O)N[C@H]3C[C@@H](C(=O)N[C@H](C)c4ccc(Cl)cc4)N(C(=O)[C@@H](NC(=O)[C@H](C)NC)C(C)(C)C)C3)c2)C[C@H]1C(=O)N[C@H](C)c1ccc(Cl)cc1)C(C)(C)C ; Cl] |
| 85 | 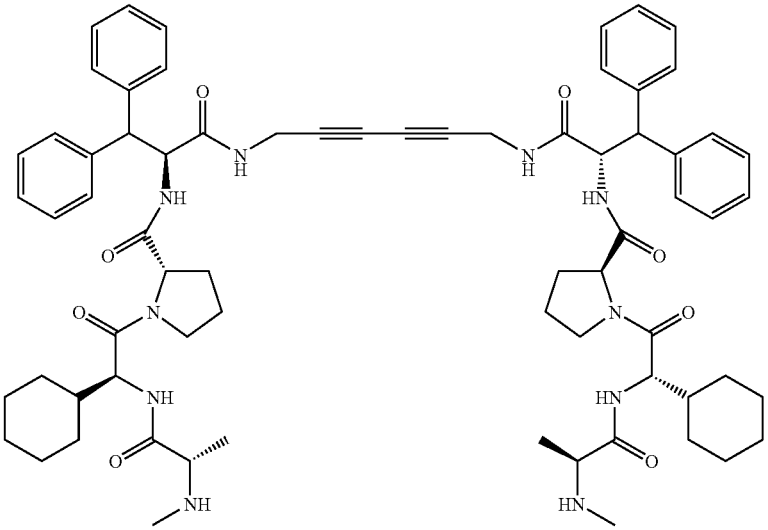 [SMILES: CN[C@@H](C)C(=O)N[C@H](C(=O)N1CCC[C@H]1C(=O)N[C@H](C(=O)NCC#CC#CCNC(=O)[C@@H](NC(=O)[C@@H]1CCCN1C(=O)[C@@H](NC(=O)[C@H](C)NC)C1CCCCC1)C(c1ccccc1)c1ccccc1)C(c1ccccc1)c1ccccc1)C1CCCCC1] |

TABLE 3-continued
Dimeric Structures
| RECORD NUMBER | STRUCTURE |
|---|---|
| 86 | 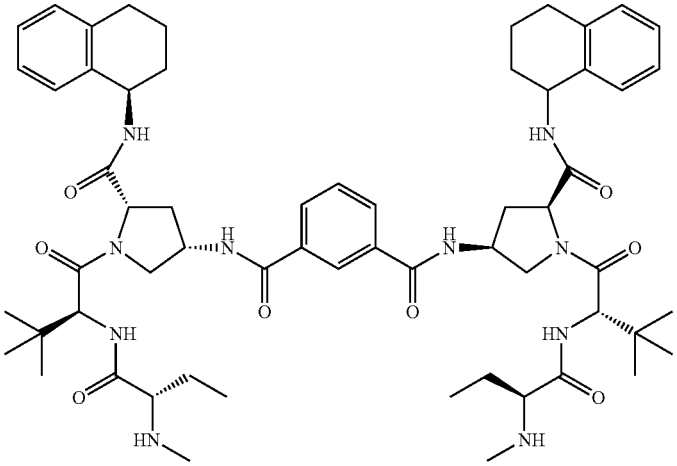 [SMILES: CC[C@H](NC)C(=O)N[C@H](C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](CC)NC)C(C)(C)C)C3)c2)C[C@H]1C(=O)NC1CCCc2ccccc21)C(C)(C)C] |
| 87 | 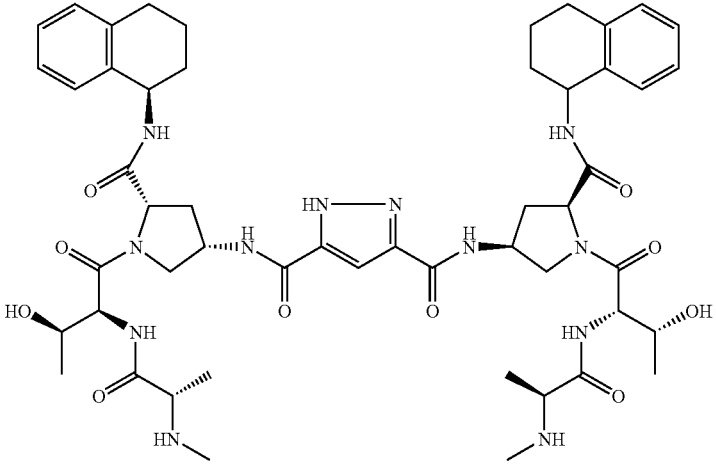 [SMILES: CN[C@@H](C)C(=O)N[C@H](C(=O)N1C[C@@H](NC(=O)c2cc(C(=O)N[C@H]3C[C@@H](C(=O)N[C@@H]4CCCc5ccccc54)N(C(=O)[C@@H](NC(=O)[C@H](C)NC)[C@@H](C)O)C3)[nH]n2)C[C@H]1C(=O)NC1CCCc2ccccc21)[C@@H](C)O] |
| 88 | 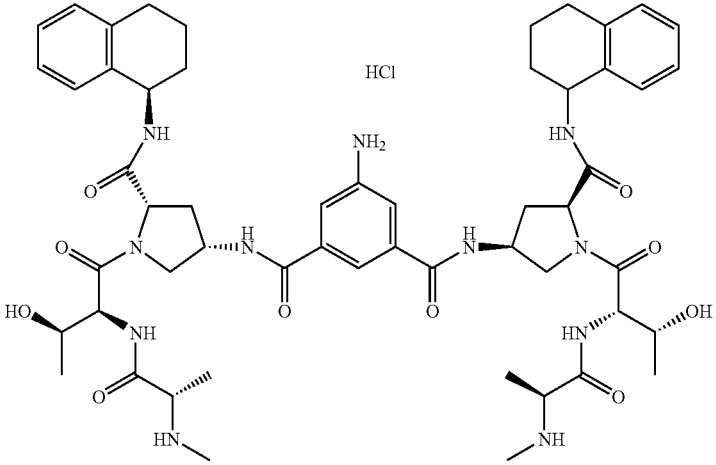 [SMILES: CN[C@@H](C)C(=O)N[C@H](C(=O)N1C[C@@H](NC(=O)c2cc(N)cc(C(=O)N[C@H]3C[C@@H](C(=O)N[C@@H]4CCCc5ccccc54)N(C(=O)[C@@H](NC(=O)[C@H](C)NC)[C@@H](C)O)C3)c2)C[C@H]1C(=O)NC1CCCc2ccccc21)[C@@H](C)O ; Cl] |

TABLE 3-continued

Dimeric Structures

| RECORD NUMBER | STRUCTURE |
|---|---|
| 89 | 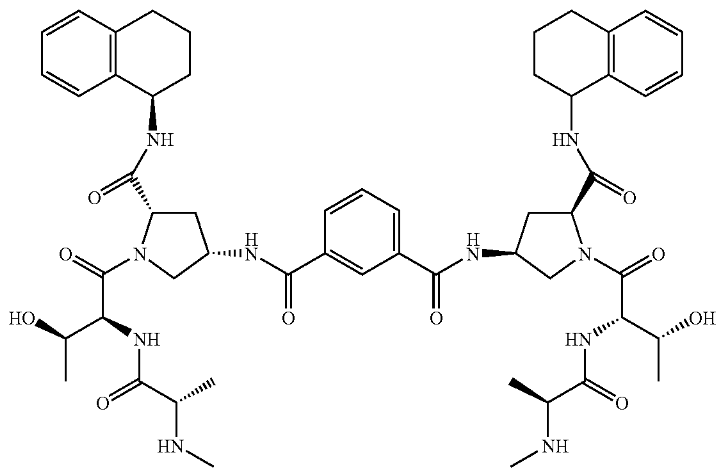 [SMILES: CN[C@@H](C)C(=O)N[C@H](C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)NC)[C@@H](C)O)C3)c2)C[C@H]1C(=O)NC1CCCc2ccccc21)[C@@H](C)O] |
| 90 | 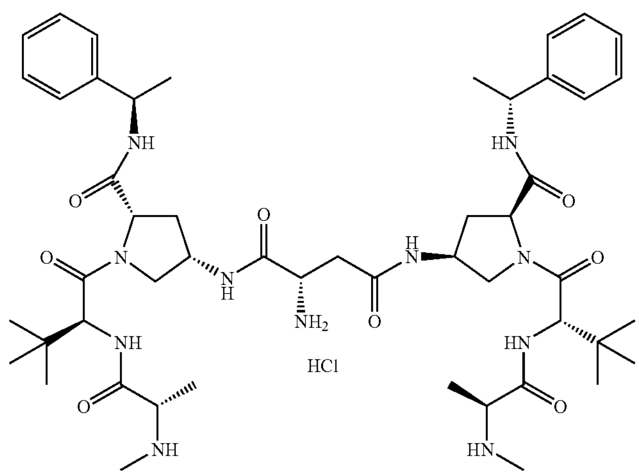 [SMILES: CN[C@@H](C)C(=O)N[C@H](C(=O)N1C[C@@H](NC(=O)C[C@H](N)C(=O)N[C@H]2C[C@@H](C(=O)N[C@H](C)c3ccccc3)N(C(=O)[C@@H](NC(=O)[C@H](C)NC)C(C)(C)C)C2)C[C@H]1C(=O)N[C@H](C)c1ccccc1)C(C)(C)C ; Cl] |
| 91 | 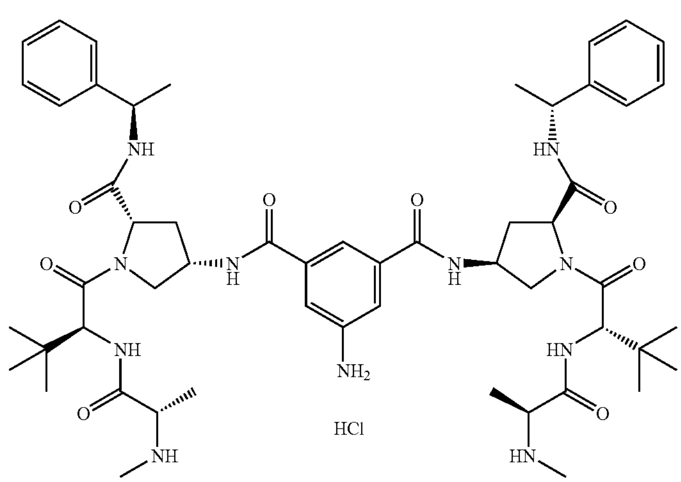 [SMILES: CN[C@@H](C)C(=O)N[C@H](C(=O)N1C[C@@H](NC(=O)c2cc(N)cc(C(=O)N[C@H]3C[C@@H](C(=O)N[C@H](C)c4ccccc4)N(C(=O)[C@@H](NC(=O)[C@H](C)NC)C(C)(C)C)C3)c2)C[C@H]1C(=O)N[C@H](C)c1ccccc1)C(C)(C)C ; Cl] |

TABLE 3-continued
Dimeric Structures
| RECORD NUMBER | STRUCTURE |
|---|---|
| 92 | 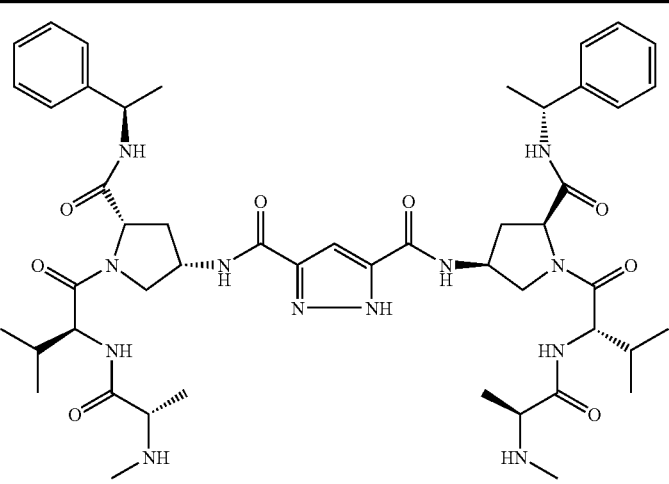 |
| 93 | 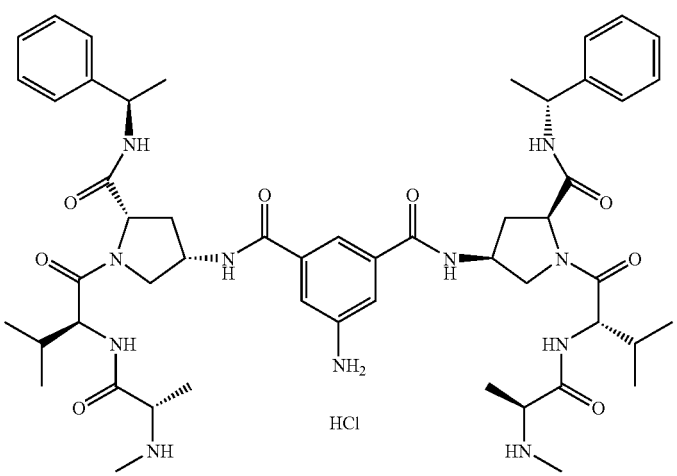 [SMILES: CN[C@@H](C)C(=O)N[C@H](C(=O)N1C[C@@H](NC(=O)c2cc(N)cc(C(=O)N[C@H]3C[C@@H](C(=O)N[C@H](C)c4ccccc4)N(C(=O)[C@@H](NC(=O)[C@H](C)NC)C(C)C)C3)c2)C[C@H]1C(=O)N[C@H](C)c1ccccc1)C(C)C ; Cl] |
| 94 | 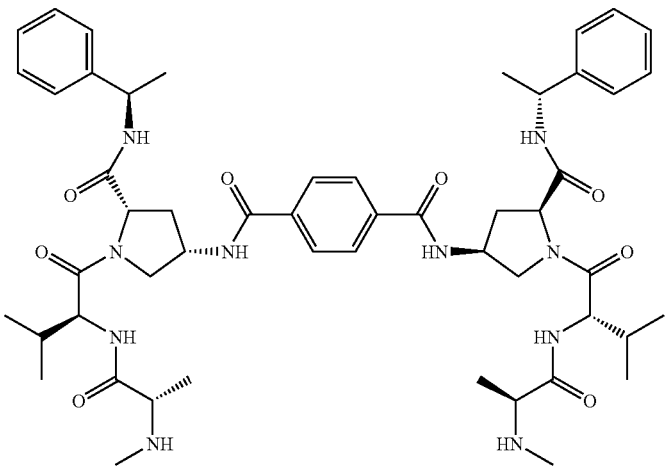 [SMILES: CN[C@@H](C)C(=O)N[C@H](C(=O)N1C[C@@H](NC(=O)c2ccc(C(=O)N[C@H]3C[C@@H](C(=O)N[C@H](C)c4ccccc4)N(C(=O)[C@@H](NC(=O)[C@H](C)NC)C(C)C)C3)cc2)C[C@H]1C(=O)N[C@H](C)c1ccccc1)C(C)C] |

TABLE 3-continued

Dimeric Structures

| RECORD NUMBER | STRUCTURE |
|---|---|
| 95 | 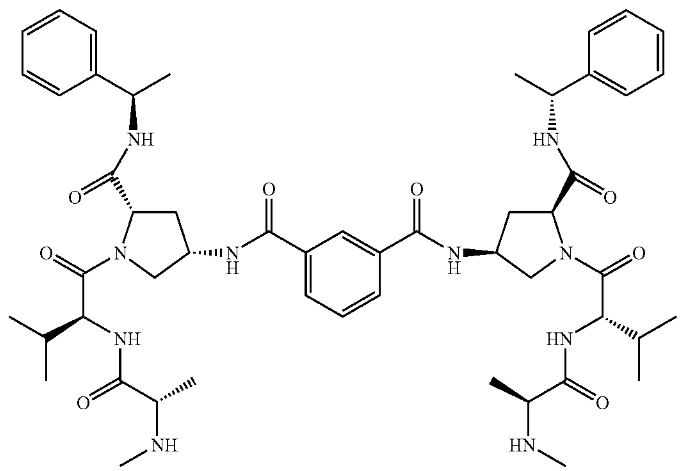 [SMILES: CN[C@@H](C)C(=O)N[C@H](C(=O)N1C[C@@H](NC(=O)c2cccc(C(=O)N[C@H]3C[C@@H](C(=O)N[C@H](C)c4ccccc4)N(C(=O)[C@@H](NC(=O)[C@H](C)NC)C(C)C)C3)c2)C[C@H]1C(=O)N[C@H](C)c1ccccc1)C(C)C] |
| 96 | 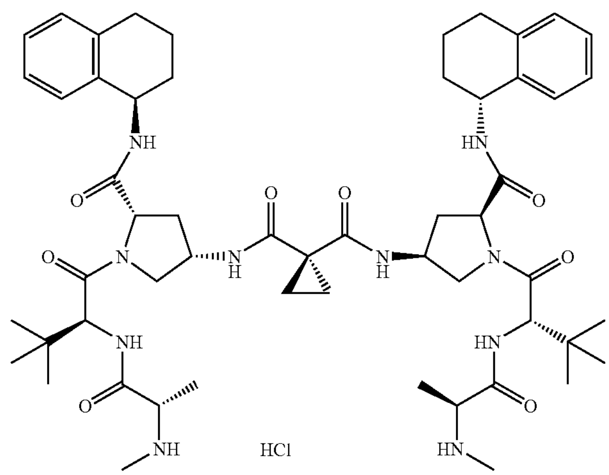 |
| 97 | 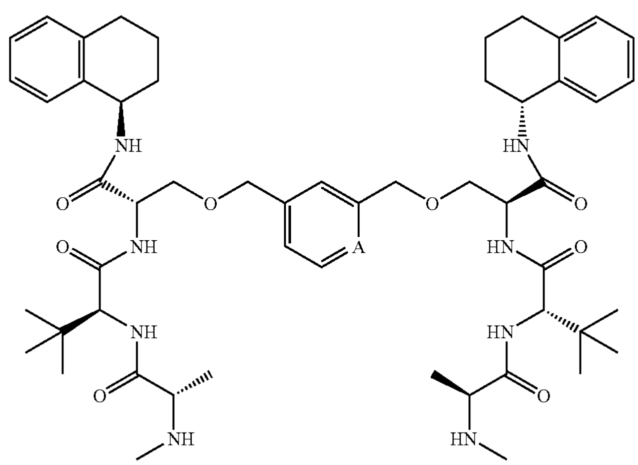 |

TABLE 3-continued

Dimeric Structures

| RECORD NUMBER | STRUCTURE |
|---|---|
| 98 | 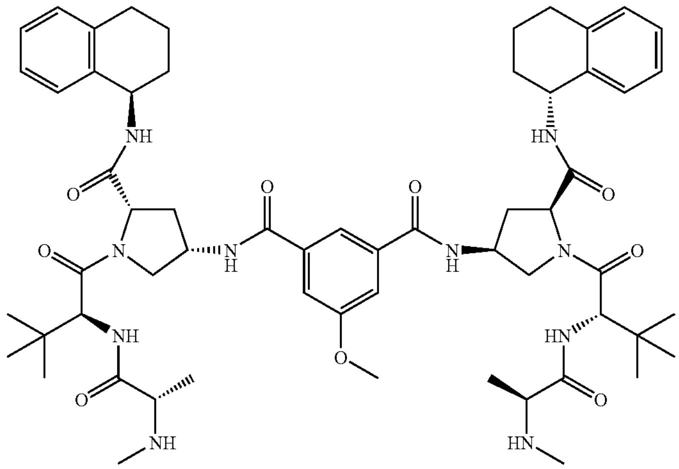 [SMILES: CN[C@@H](C)C(=O)N[C@H](C(=O)N1C[C@@H](NC(=O)c2cc(OC)cc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@@H]1CCCc2ccccc21)C(C)(C)C] |
| 99 | 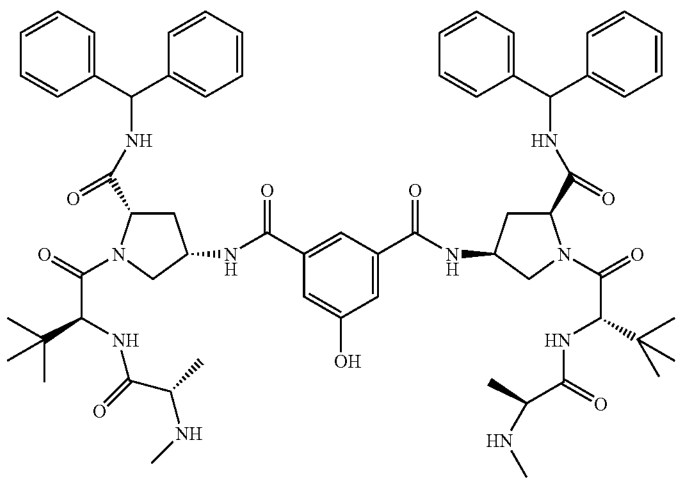 [SMILES: CN[C@@H](C)C(=O)N[C@H](C(=O)N1C[C@@H](NC(=O)c2cc(O)cc(C(=O)N[C@H]3C[C@@H](C(=O)NC(c4ccccc4)c4ccccc4)N(C(=O)[C@@H](NC(=O)[C@H](C)NC)C(C)(C)C)C3)c2)C[C@H]1C(=O)NC(c1ccccc1)c1ccccc1)C(C)(C)C] |
| 100 | 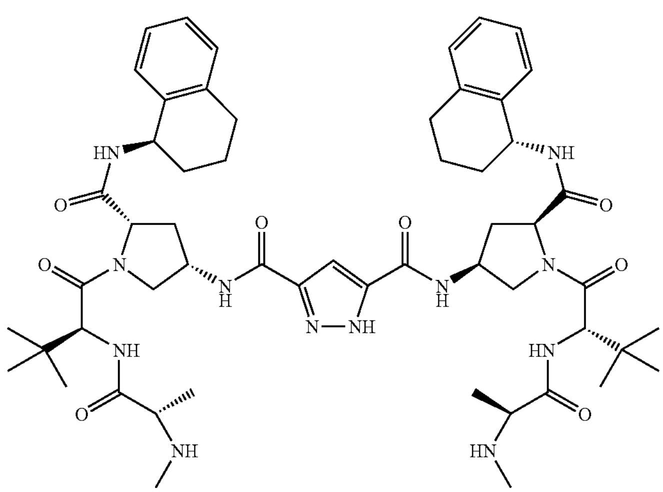 [SMILES: CN[C@@H](C)C(=O)N[C@H](C(=O)N1C[C@@H](NC(=O)c2cc(C(=O)N[C@H]3C[C@@H](C(=O)N[C@@H]4CCCc5ccccc54)N(C(=O)[C@@H](NC(=O)[C@H](C)NC)C(C)(C)C)C3)[nH]n2)C[C@H]1C(=O)N[C@@H]1CCCc2ccccc21)C(C)(C)C] |

TABLE 3-continued
Dimeric Structures
| RECORD NUMBER | STRUCTURE |
|---|---|
| 101 (Example 36) | 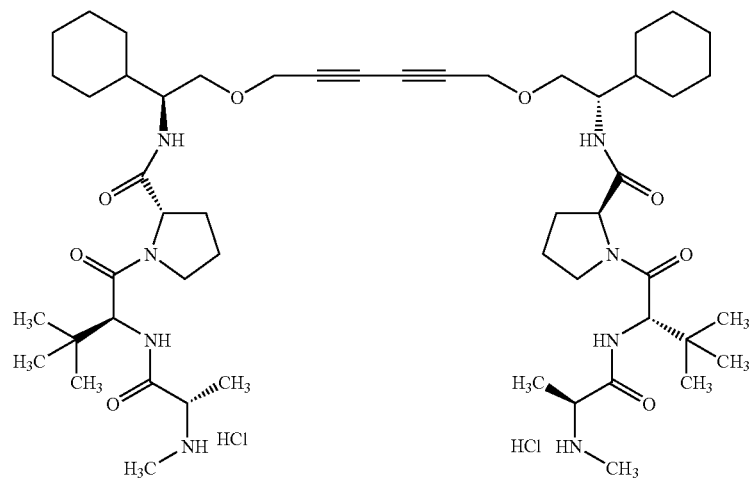 [SMILES: CN[C@@H](C)C(=O)N[C@H](C(=O)N1CCC[C@H]1C(=O)N[C@H](COCC#CC#CCOC[C@@H](NC(=O)[C@@H]1CCCN1C(=O)[C@@H](NC(=O)[C@H](C)NC)C(C)(C)C)C1CCCCC1)C1CCCCC1)C(C)(C)C ; Cl ; Cl] |
| 102 (Example 37) | 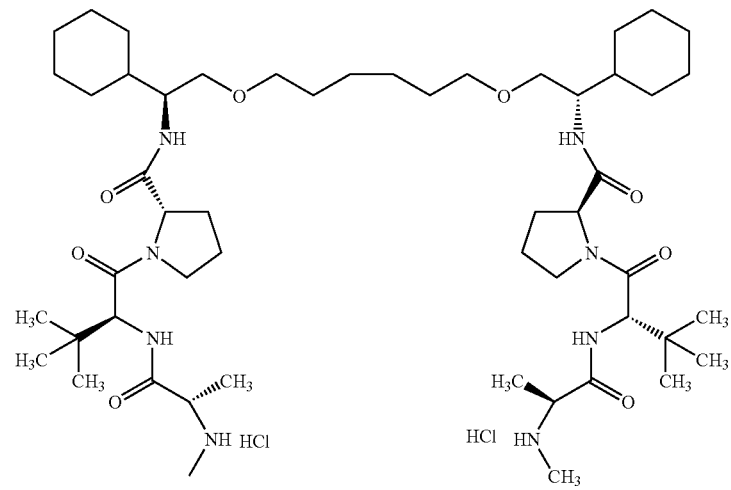 [SMILES: CN[C@@H](C)C(=O)N[C@H](C(=O)N1CCC[C@H]1C(=O)N[C@H](COCCCCCCOC[C@@H](NC(=O)[C@@H]1CCCN1C(=O)[C@@H](NC(=O)[C@H](C)NC)C(C)(C)C)C1CCCCC1)C1CCCCC1)C(C)(C)C ; Cl ; Cl] |
| 103 (Example 42) | 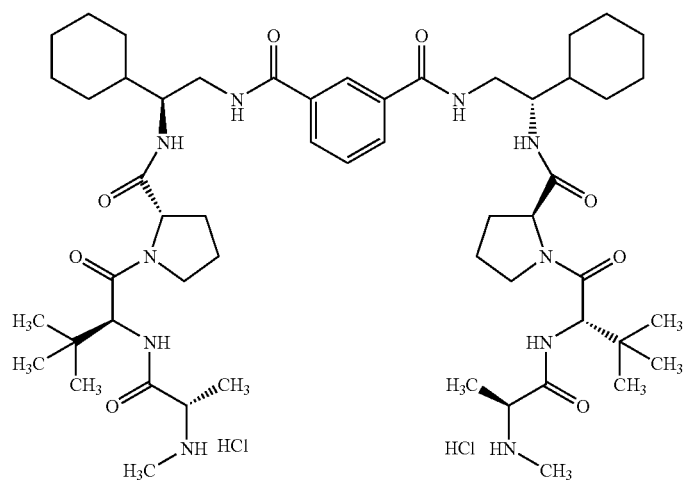 [SMILES: CN[C@@H](C)C(=O)N[C@H](C(=O)N1CCC[C@H]1C(=O)N[C@H](CNC(=O)c1cccc(C(=O)NC[C@@H](NC(=O)[C@@H]2CCCN2C(=O)[C@@H](NC(=O)[C@H](C)NC)C(C)(C)C)C2CCCCC2)c1)C1CCCCC1)C(C)(C)C ; Cl ; Cl] |

TABLE 3-continued
Dimeric Structures
| RE-CORD NUMBER | STRUCTURE |
|---|---|
| 104 (Example 49) | 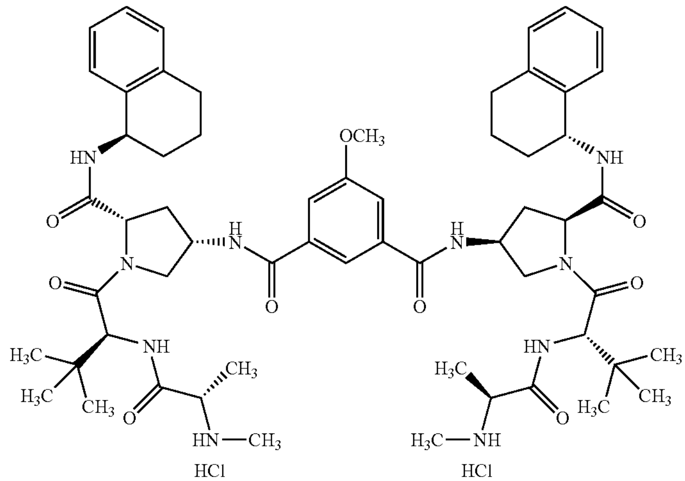 [SMILES: CN[C@@H](C)C(=O)N[C@H](C(=O)N1C[C@@H](NC(=O)c2cc(OC)cc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@@H]1CCCc2ccccc21)C(C)(C)C ; Cl ; Cl] |
TABLE 4
Trimeric Structures
| RECORD NUMBER | STRUCTURE |
|---|---|
| 105 (Example 12) | 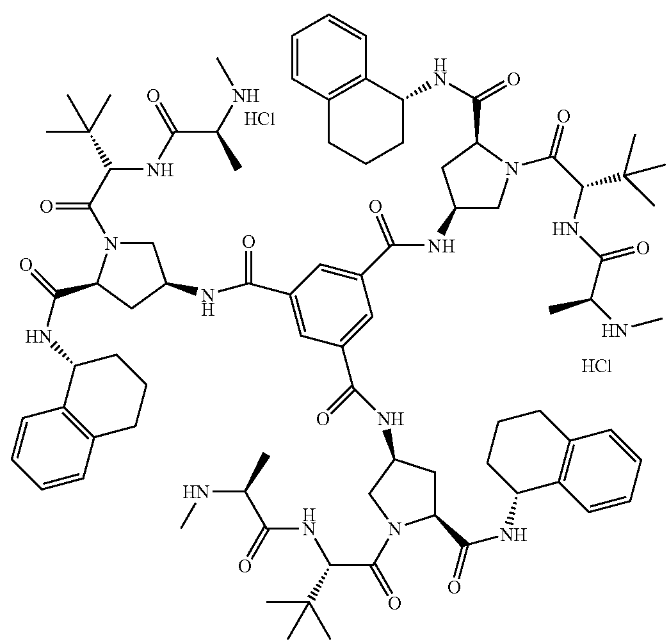 |
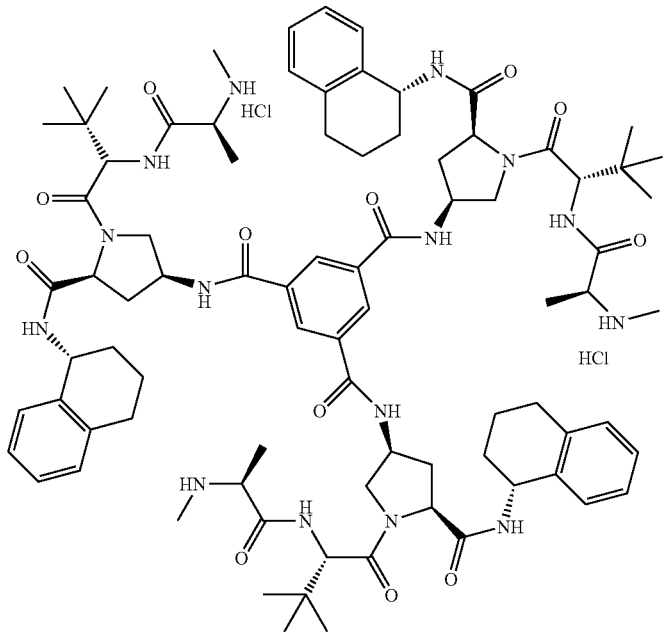

TABLE 4-continued

Trimeric Structures

| RECORD NUMBER | STRUCTURE |
|---|---|
| 106 | 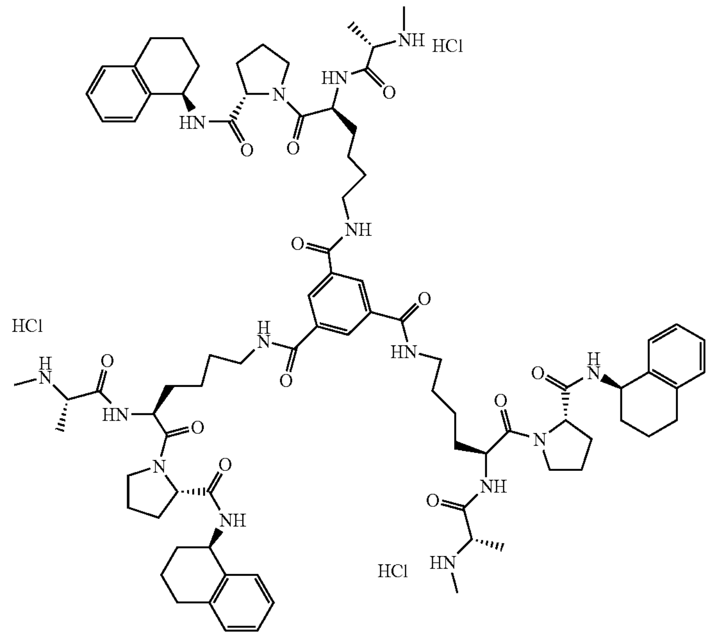 [SMILES: CN[C@@H](C)C(=O)N[C@@H](CCCCNC(=O)c1cc(C(=O)NCCCC[C@H](NC(=O)[C@H](C)NC)C(=O)N2CCC[C@H]2C(=O)N[C@@H]2CCCc3ccccc32)cc(C(=O)NCCCC[C@H](NC(=O)[C@H](C)NC)C(=O)N2CCC[C@H]2C(=O)N[C@@H]2CCCc3ccccc32)c1)C(=O)N1CCC[C@H]1C(=O)N[C@@H]1CCCc2ccccc21 ; Cl ; Cl ; Cl] |
| 107 | 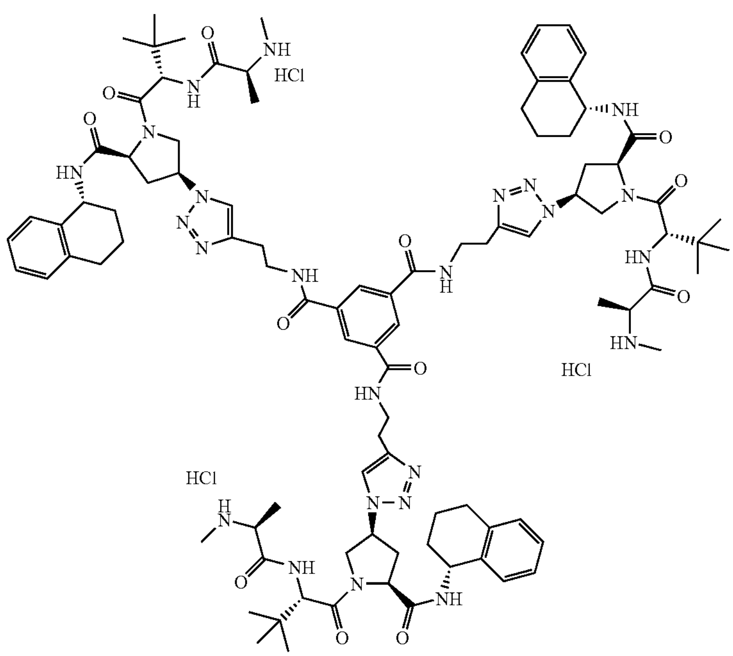 [SMILES: CN[C@@H](C)C(=O)N[C@H](C(=O)N1C[C@@H](n2cc(CCNC(=O)c3cc(C(=O)NCCc4cn([C@H]5C[C@@H](C(=O)N[C@@H]6CCCc7ccccc76)N(C(=O)[C@@H](NC(=O)[C@H](C)NC)C(C)(C)C)C5)nn4)cc(C(=O)NCCc4cn([C@H]5C[C@@H](C(=O)N[C@@H]6CCCc7ccccc76)N(C(=O)[C@@H](NC(=O)[C@H](C)NC)C(C)(C)C)C5)nn4)c3)nn2)C[C@H]1C(=O)N[C@@H]1CCCc2ccccc21)C(C)(C)C ; Cl ; Cl ; Cl] |

TABLE 5

| RECORD NUMBER | STRUCTURE |
| --- | --- |
| M-1 (Example 1) | 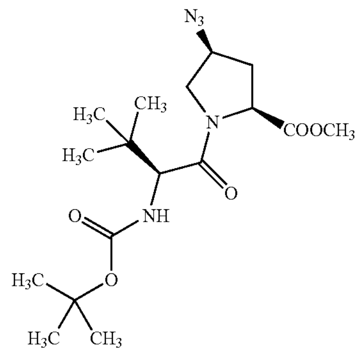 [SMILES: COC(=O)[C@@H]1C[C@H](N=[N+]=[N-])CN1C(=O)[C@@H](NC(=O)OC(C)(C)C)C(C)(C)C] |
| M-2 (Example 2) | 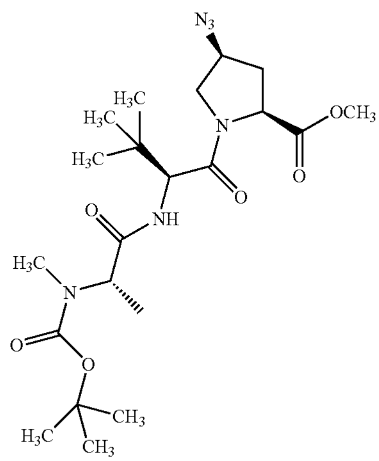 [SMILES: COC(=O)[C@@H]1C[C@H](N=[N+]=[N-])CN1C(=O)[C@@H](NC(=O)[C@H](C)N(C)C(=O)OC(C)(C)C)C(C)(C)C] |
| M-3 (Example 3) | 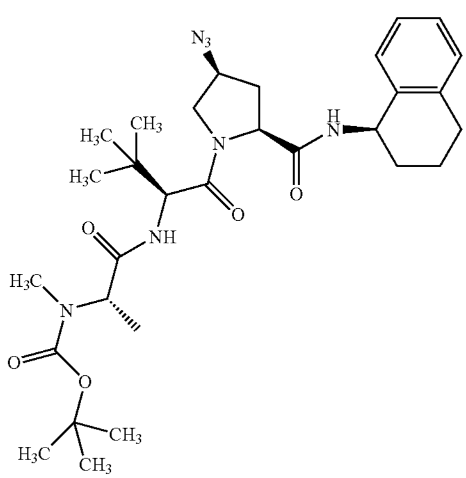 [SMILES: C[C@@H](C(=O)N[C@H](C(=O)N1C[C@@H](N=[N+]=[N-])C[C@H]1C(=O)N[C@@H]1CCCc2ccccc21)C(C)(C)C)N(C)C(=O)OC(C)(C)C] |

TABLE 5-continued
| RECORD NUMBER | STRUCTURE |
|---|---|
| M-4 (Example 4) | 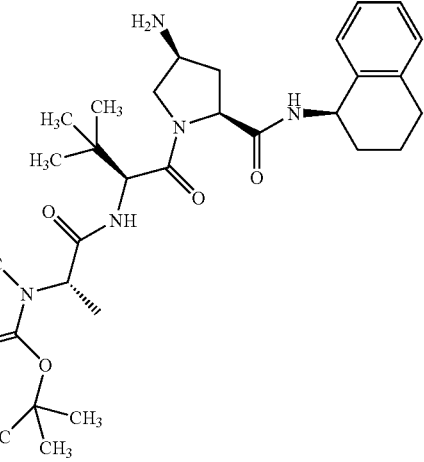 |
| M-5 (Example 15) | 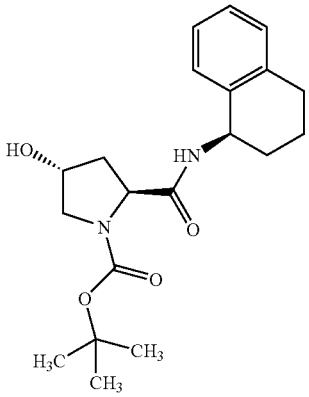 [SMILES: CC(C)(C)OC(=O)N1C[C@H](O)C[C@H]1C(=O)N[C@@H]1CCCc2ccccc21] |
| M-6 (Example 16) | 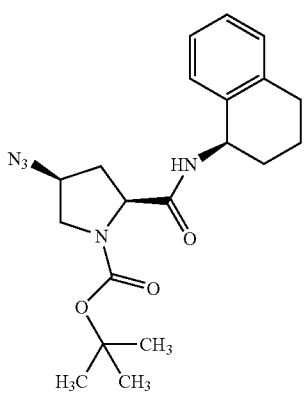 [SMILES: CC(C)(C)OC(=O)N1C[C@@H](N=[N+]=[N-])C[C@H]1C(=O)N[C@@H]1CCCc2ccccc21] |

TABLE 5-continued
| Monomers | |
|---|---|
| RECORD NUMBER | STRUCTURE |
| M-7 (Example 17) | 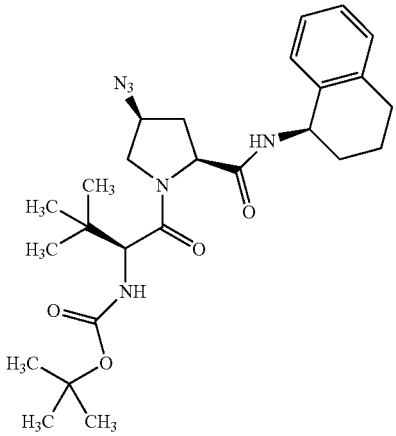 [SMILES: CC(C)(C)OC(=O)N[C@H](C(=O)N1C[C@@H](N=[N+]=[N-])C[C@H]1C(=O)N[C@@H]1CCCc2ccccc21)C(C)(C)C] |
| M-8 (Example 18) | 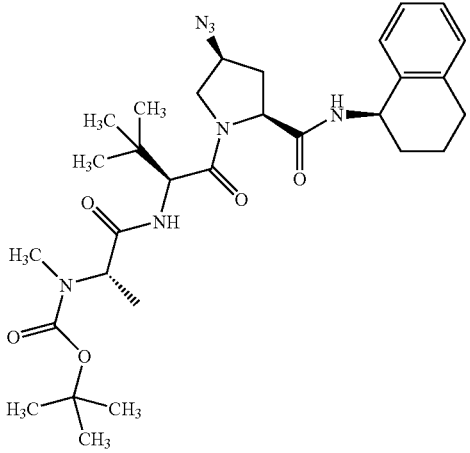 [SMILES: C[C@@H](C(=O)N[C@H](C(=O)N1C[C@@H](N=[N+]=[N-])C[C@H]1C(=O)N[C@@H]1CCCc2ccccc21)C(C)(C)C)N(C)C(=O)OC(C)(C)C] |
| M-9 (Example 19) | 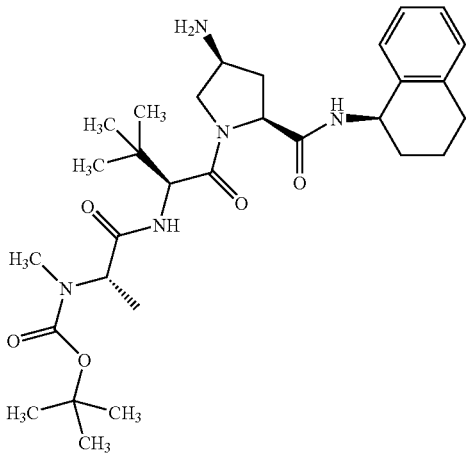 [SMILES: C[C@@H](C(=O)N[C@H](C(=O)N1C[C@@H](N)C[C@H]1C(=O)N[C@@H]1CCCc2ccccc21)C(C)(C)C)N(C)C(=O)OC(C)(C)C] |

TABLE 5-continued

| RECORD NUMBER | STRUCTURE |
|---|---|
| M-10 (Example 21) | 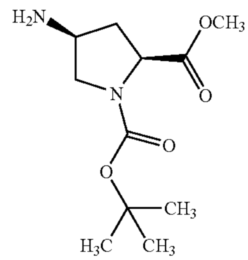 [SMILES: COC(=O)[C@@H]1C[C@H](N)CN1C(=O)OC(C)(C)C] |
| M-11 | 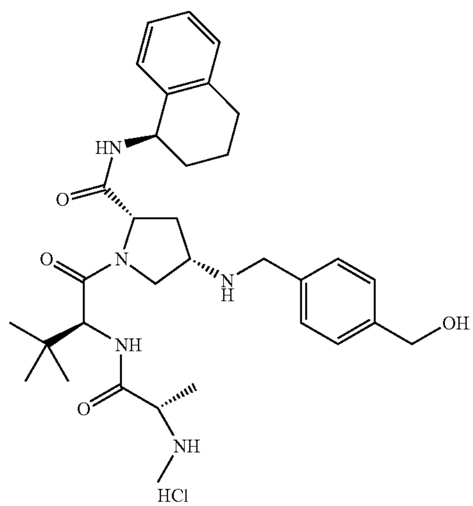 [SMILES: CN[C@@H](C)C(=O)N[C@H](C(=O)N1C[C@@H](NCc2ccc(CO)cc2)C[C@H]1C(=O)N[C@@H]1CCCc2ccccc21)C(C)(C)C ; Cl] |
| M-12 | 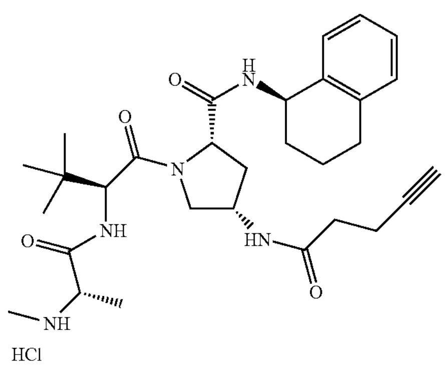 [SMILES: C#CCCC(=O)N[C@H]1C[C@@H](C(=O)N[C@@H]2CCCc3ccccc32)N(C(=O)[C@@H](NC(=O)[C@H](C)NC)C(C)(C)C)C1 ; Cl] |
| M-13 | 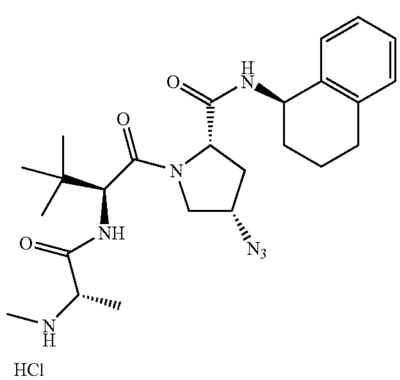 [SMILES: CN[C@@H](C)C(=O)N[C@H](C(=O)N1C[C@@H](N=[N+]=[N-])C[C@H]1C(=O)N[C@@H]1CCCc2ccccc21)C(C)(C)C ; Cl] |

TABLE 5-continued
| RECORD NUMBER | STRUCTURE |
|---|---|
| M-14 | 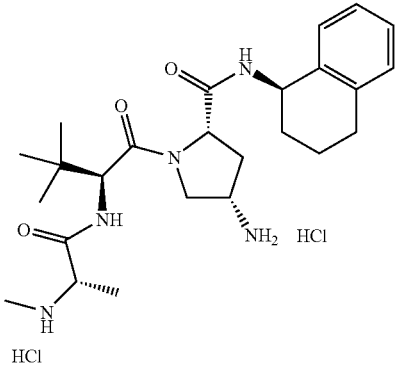 [SMILES: CN[C@@H](C)C(=O)N[C@H](C(=O)N1C[C@@H](N)C[C@H]1C(=O)N[C@@H]1CCCc2ccccc21)C(C)(C)C ; Cl ; Cl] |
| M-15 | 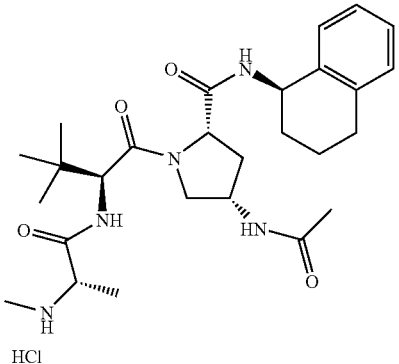 [SMILES: CN[C@@H](C)C(=O)N[C@H](C(=O)N1C[C@@H](NC(C)=O)C[C@H]1C(=O)N[C@@H]1CCCc2ccccc21)C(C)(C)C ; Cl] |
| M-16 | 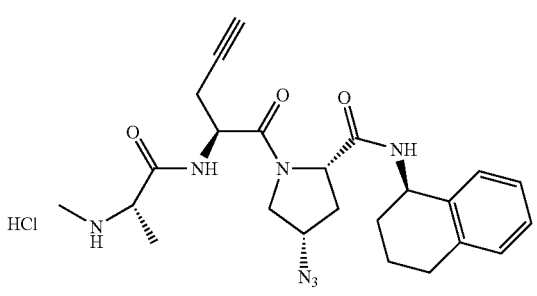 [SMILES: Cl ; C#CC[C@H](NC(=O)[C@H](C)NC)C(=O)N1C[C@@H](N=[N+]=[N-])C[C@H]1C(=O)N[C@@H]1CCCc2ccccc21] |
| M-17 (Example 33) | 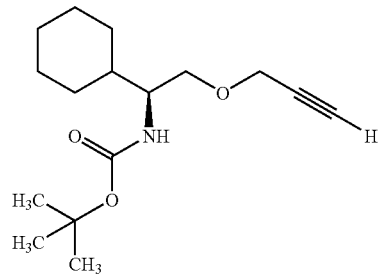 [SMILES: C#CCOC[C@@H](NC(=O)OC(C)(C)C)C1CCCCC1] |

TABLE 5-continued
| Monomers | |
|---|---|
| RECORD NUMBER | STRUCTURE |
| M-18 (Example 34) | 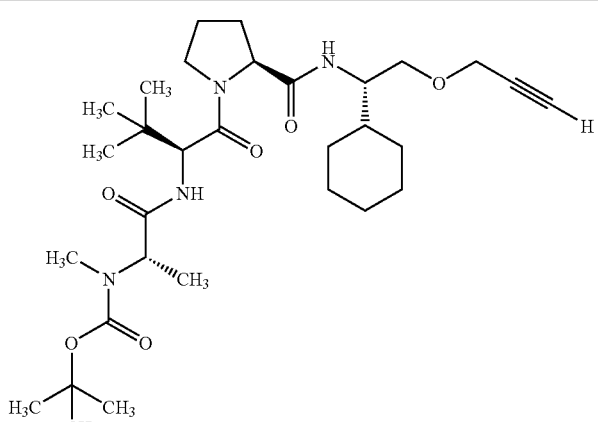 |
| M-19 | 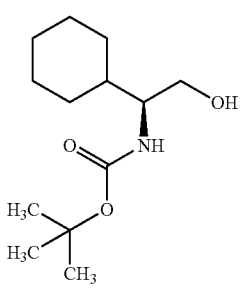 [SMILES: CC(C)(C)OC(=O)N[C@H](CO)C1CCCCC1] |
| M-20 | 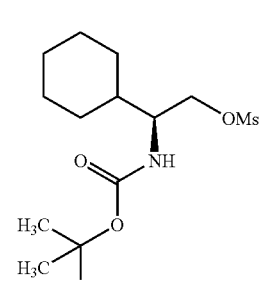 |
| M-21 (Example 38) | 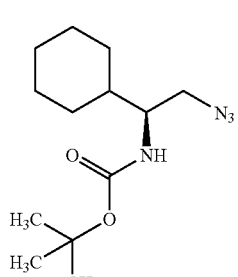 |

TABLE 5-continued

| Monomers | |
|---|---|
| RECORD NUMBER | STRUCTURE |
| M-22 (Example 39) | |
| M-23 (Example 40) | |
| M-24 | |

TABLE 5-continued
| Monomers | |
|---|---|
| RECORD NUMBER | STRUCTURE |
| M-25 | 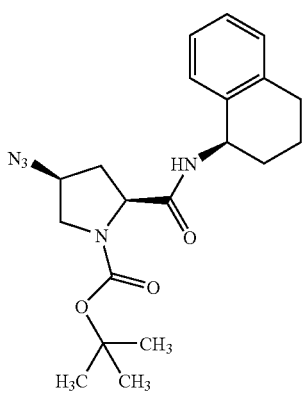 [SMILES: CC(C)(C)OC(=O)N1C[C@@H](N=[N+]=[N-])C[C@H]1C(=O)N[C@@H]1CCCc2ccccc21] |
| M-26 | 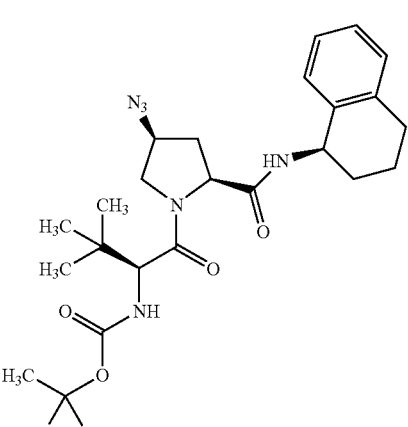 |
| M-27 | 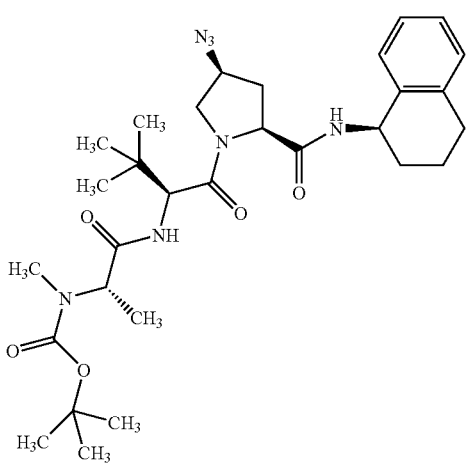 [SMILES: C[C@@H](C(=O)N[C@H](C(=O)N1C[C@@H](N=[N+]=[N-])C[C@H]1C(=O)N[C@@H]1CCCc2ccccc21)C(C)(C)C)N(C)C(=O)OC(C)(C)C] |

TABLE 5-continued

Monomers

| RECORD NUMBER | STRUCTURE |
|---|---|
| M-28 | 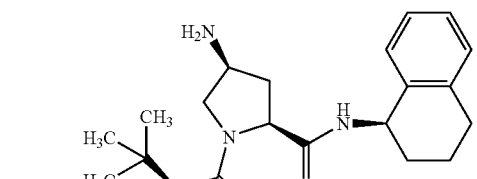 |

The following embodiments are provided as non-limiting examples only. The foregoing examples are provided only to illustrate the invention, which further includes those combinations and modifications that are apparent to one of ordinary skill from the present disclosures.

REPRESENTATIVE EMBODIMENTS

A1. A compound of formula (1):

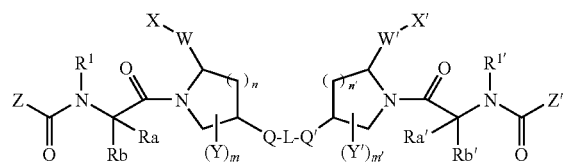

(1)

or a pharmaceutically acceptable salt or hydrate form thereof, wherein each $R_a$, $R_{a'}$, $R_b$ and $R_{b'}$ is independently H, or C1-C8 alkyl, C2-C8 alkenyl or C2-C8 alkynyl, or a heteroform of one of these, each of which may be optionally substituted; or is optionally substituted phenyl;

each Y and Y' independently represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl, and wherein two Y or Y' groups can cyclize to form a 3-6 membered ring that can be saturated, unsaturated or aromatic, and which ring may include a heteroatom selected from O, S and N as a ring member and may be optionally substituted;

each W and W' independently represents an optionally substituted C1-C6 alkylene or C1-C6 heteroalkylene;

each X and X' independently represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —O— or —$NR^2$—, where each $R^2$ is independently H, or optionally substituted C1-C8 alkyl, or optionally substituted C1-C8 heteroalkyl; or one or both of Q and Q' may be a bond when L comprises a ring;

each n and n' is independently 0-3;

each m and m' is independently 0-4;

each $R^1$ and $R^{1'}$ is independently H or optionally substituted C1-C8 alkyl;

each Z and Z' independently represents an optionally substituted C1-C6 aminoalkyl group; and L represents an optionally substituted C1-C24 hydrocarbyl linker, optionally containing from 1-8 heteroatoms selected from N, O and S, which linker is 1-18 atoms in length when counted along the shortest path between Q and Q'.

A2. The compound of embodiment A1, wherein L comprises a C1-C14 alkylene, C1-C14 heteroalkylene, C2-C14 alkenylene, C2-C14 heteroalkenylene, C2-C14 alkynylene, or a C2-C14 heteroalkynylene group, each of which may be optionally substituted.

A3. The compound of embodiment A2, wherein L is a C2-C14 alkynylene or a C2-C14 heteroalkynylene group.

A4. The compound of embodiment A1, wherein L comprises at least one optionally substituted carbocyclic, heterocyclic, aromatic or heteroaromatic ring that is part of or is fused to the linker which forms the shortest path between Q and Q'.

A5. The compound of embodiment A4, wherein said aromatic or heteroaromatic ring is an optionally substituted 5- or 6-membered aromatic or heteroaromatic ring.

A6. The compound of embodiment A5, wherein said optionally substituted 5- or 6-membered aromatic or heteroaromatic ring is selected from the group consisting of phenyl, pyridyl, pyrazinyl, triazinyl, pyrazolyl, and thiophenyl, each of which may be optionally substituted.

A7. The compound of embodiment A4, wherein L comprises at least one triazole ring.

A8. The compound of any one of embodiments A1 to A7, wherein each n and n' is 1, and each of m and m' is 0 or 1, and wherein Y and Y', if present, are the same.

A9. The compound of any one of embodiments A1 to A8, wherein each $R^1$ and $R^{1'}$ is H or methyl.

A10. The compound of any one of embodiments A1 to A9, wherein each Z and Z' is a 1-aminoalkyl group represented by the formula —$CH(R^3)NR^4_2$, where $R^3$ and each $R^4$ is independently H or C1-C4 alkyl.

A11. The compound of any one of embodiments A1 to A10, wherein each X and X' independently comprises an optionally substituted phenyl ring; or two phenyl rings, each of which may be optionally substituted; or a tetrahydronaphthyl, indanyl or fluorenyl ring system.

A12. The compound of any one of embodiments A1 to A11, wherein each W and W' represents —C(O)NR(CHR)$_p$—, where p is 0-2, and each R independently represents H, C1-C4 alkyl or C1-C4 heteroalkyl.

A13. The compound of any one of embodiments A1 to A12, wherein each Q and Q' is —$NR^2$—, where each $R^2$ is independently H or C1-C4 alkyl.

A14. The compound of any one of embodiments A1 to A12, wherein at least one of Q and Q' is a bond.

A15. The compound of embodiment A1, having the formula (3A):

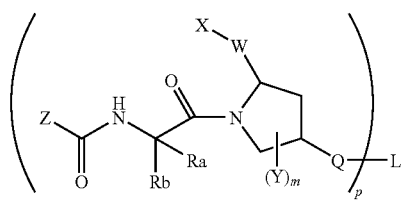

(3A)

or a pharmaceutically acceptable salt or hydrate form thereof, wherein $R_a$ is H and $R_b$ is $R^5$;

$R^5$ is H, or C1-C8 alkyl, C2-C8 alkenyl, C2-C8 alkynyl, or phenyl, each of which may be optionally substituted;

each Y represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl;

W represents an optionally substituted C1-C6 alkylene or C1-C6 heteroalkylene;

X represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

Q represents —O— or —$NR^2$—, where each $R^2$ is independently H, or optionally substituted C1-C8 alkyl, or optionally substituted C1-C8 heteroalkyl; or Q may be a bond when L comprises a ring;

m is 0-4;

p is 2-3;

Z represents an optionally substituted C1-C6 aminoalkyl group of the formula —$CH(R^3)NR^4_2$;

$R^3$ is H, or an optionally substituted C1-C8 alkyl or optionally substituted C1-C8 heteroalkyl, and $R^3$ can cyclize with $R^4$ on an adjacent nitrogen atom to form an optionally substituted azacyclic group having 5-10 ring members, which azacyclic group may be saturated, unsaturated or aromatic, and may contain 1-2 additional heteroatoms selected from N, O and S as a ring member;

each $R^4$ is independently H, or an optionally substituted C1-C8 alkyl or optionally substituted C1-C8 heteroalkyl, and the two $R^4$ groups on one nitrogen can cyclize to form an optionally substituted azacyclic group having 5-10 ring members, which azacyclic group may be saturated, unsaturated or aromatic, and may contain 1-2 additional heteroatoms selected from N, O and S as a ring member; and L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

A 16. The compound of embodiment A 15, having the formula (4):

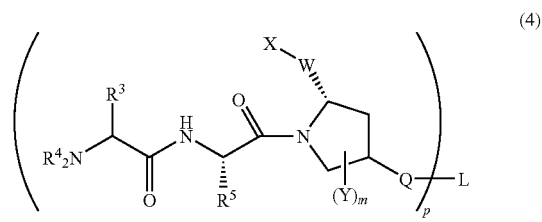

(4)

or a pharmaceutically acceptable salt or hydrate form thereof, wherein $R^5$ is H, or C1-C8 alkyl, C2-C8 alkenyl, C2-C8 alkynyl, or phenyl, each of which may be optionally substituted;

each Y represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl;

W represents an optionally substituted C1-C6 alkylene or C1-C6 heteroalkylene;

X represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

Q represents —O— or —$NR^2$—, where each $R^2$ is independently H, optionally substituted C1-C8 alkyl or optionally substituted C1-C8 heteroalkyl; or Q may be a bond when L comprises a ring;

m is 0-4;

p is 2 or 3;

$R^3$ is H, or an optionally substituted C1-C8 alkyl or optionally substituted C1-C8 heteroalkyl, and $R^3$ can cyclize with $R^4$ on an adjacent nitrogen atom to form an optionally substituted azacyclic group having 5-10 ring members, which azacyclic group may be saturated, unsaturated or aromatic, and may contain 1-2 additional heteroatoms selected from N, O and S as a ring member;

each $R^4$ is independently H, or an optionally substituted C1-C8 alkyl or optionally substituted C1-C8 heteroalkyl, and the two $R^4$ groups on one nitrogen can cyclize to form an optionally substituted azacyclic group having 5-10 ring members, which azacyclic group may be saturated, unsaturated or aromatic, and may contain 1-2 additional heteroatoms selected from N, O and S as a ring member; and L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

A17. The compound of embodiment A15, having the formula (5):

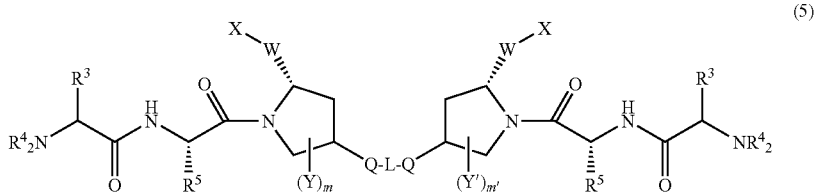

(5)

or a pharmaceutically acceptable salt or hydrate form thereof, $R^5$ is H, or C1-C8 alkyl, C2-C8 alkenyl, C2-C8 alkynyl, or phenyl, each of which may be optionally substituted;

each Y represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl;

W represents an optionally substituted C1-C6 alkylene or C1-C6 heteroalkylene; X represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

Q represents —O— or —$NR^2$—, where each $R^2$ is independently H, optionally substituted C1-C8 alkyl or optionally substituted C1-C8 heteroalkyl; or Q may be a bond when L comprises a ring;

m is 0-4;

$R^3$ is H, or an optionally substituted C1-C8 alkyl or optionally substituted C1-C8 heteroalkyl, and $R^3$ can cyclize with $R^4$ on an adjacent nitrogen atom to form an optionally substituted azacyclic group having 5-10 ring members, which azacyclic group may be saturated, unsaturated or aromatic, and may contain 1-2 additional heteroatoms selected from N, O and S as a ring member;

each $R^4$ is independently H, or an optionally substituted C1-C8 alkyl or C1-C8 heteroalkyl group, and the two $R^4$ groups on one nitrogen can cyclize to form an optionally substituted azacyclic group having 5-10 ring members, which azacyclic group may be saturated, unsaturated or aromatic, and may contain 1-2 additional heteroatoms selected from N, O and S as a ring member;

L represents a C1-C14 alkylene, C1-$C_{14}$ alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

A18. The compound of embodiment A15, A16 or A17, wherein $R^3$ is selected from methyl, ethyl, n-propyl, isopropyl, cyclopropyl, n-butyl, isobutyl, sec-butyl, and tert-butyl.

A19. The compound of any one of embodiments A15 to A18, wherein each $R^4$ is independently H or methyl.

A20. A compound selected from the group consisting of the compounds in Tables 3 and 4, or a pharmaceutically acceptable salt thereof.

A21. A compound of formula (6):

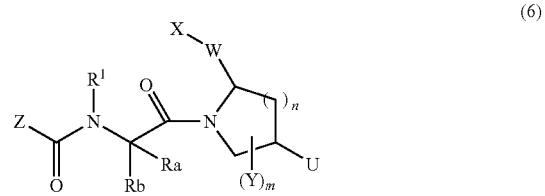

(6)

or a pharmaceutically acceptable salt or hydrate form thereof, wherein $R_a$ and $R_b$ are independently H, or C1-C8 alkyl, C2-C8 alkenyl or C2-C8 alkynyl, or a heteroform of one of these, each of which may be optionally substituted;

each Y independently represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl, and wherein two Y groups can cyclize to form a 3-6 membered ring that can be saturated, unsaturated or aromatic, and which ring may include a heteroatom selected from O, S and N as a ring member and may be optionally substituted;

W represents an optionally substituted C1-C6 alkylene or C1-C6 heteroalkylene;

X represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

n is 0-3;

m is 0-4;

$R^1$ is H or optionally substituted C1-C8 alkyl;

U represents —$OR^8$, —$OC(O)R^8$, —$OSO_2R^8$, C=O, —$OC(O)OR^8$, —$COOR^8$, —$NR^8_2$, azido or halo, where each $R^8$ is independently H, or C1-C8 alkyl, C1-C8 alkenyl, C1-C8 alkynyl, C5-C12 aryl, C5-C21 arylalkyl, or a heteroform of one of these, each of which may be optionally substituted; or C1-C8 alkyl, C2-C8 alkenyl, C2-C8 alkynyl, C5-C12 aryl or C5-C21 arylalkyl, or a heteroform of one of these, each of which may be optionally substituted; and Z is an optionally substituted C1-C6 aminoalkyl group wherein the amine may be in a protected or unprotected form.

A22. A method of making a compound of formula (1) as in embodiment A1, comprising reacting a first monomer of formula (6) with a second monomer of formula (6), wherein for each of said first monomer and said second monomer, U comprises at least one functional group that can be used to connect said first monomer and said second monomer, either directly or indirectly, to provide a compound of formula (1).

A23. A pharmaceutical composition comprising a compound of formula (1) as in embodiment A1, and at least one pharmaceutically acceptable excipient.

A24. The pharmaceutical composition of embodiment A23, further comprising at least one additional therapeutic agent.

A25. The pharmaceutical composition of embodiment A24, wherein the additional therapeutic agent is selected from the group consisting of TRAIL, etoposide, a TRAIL receptor antibody, an Hsp90 inhibitor, TNF-α, and TNF-β.

A26. A method to treat cancer, inflammation, or an autoimmune disorder, comprising administering to a subject in need of such treatment an effective amount of a compound of any one of embodiments A1 to A20.

A27. The method of embodiment A26, wherein the subject is treated with an additional therapeutic agent selected from the group consisting of TRAIL, etoposide, a TRAIL receptor antibody, an Hsp90 inhibitor, TNF-α, and TNF-β.

A28. A compound of formula (I):

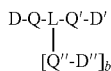

(I)

D-Q-L-Q'-D'
|
[Q''-D'']$_b$ or a pharmaceutically acceptable salt or hydrate form thereof, wherein b is 0 or 1;

each Q, Q' and Q", if present, independently represents —O— or —NR$^2$—, where each R$^2$ is independently H, optionally substituted C1-C8 alkyl or optionally substituted C1-C8 heteroalkyl; or —CH$_2$—, —CH(OR)—, —CH(R)—, —CH$_2$O—, —CH(R)O— or —(CH$_2$)$_4$NH—, wherein R is H, C$_1$-C$_4$ alkyl or C$_1$-C$_4$ heteroalkyl; or one or more of Q, Q' and Q" may be a bond when L comprises a ring;

L represents an optionally substituted C1-C24 hydrocarbyl linker, optionally containing from 1-8 heteroatoms selected from N, O and S, which linker is 1-18 atoms in length when counted along the shortest path between Q and Q', or Q and Q", or Q' and Q"; and each D, D' and D", if present, is independently selected from the group consisting of

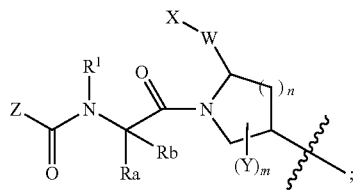

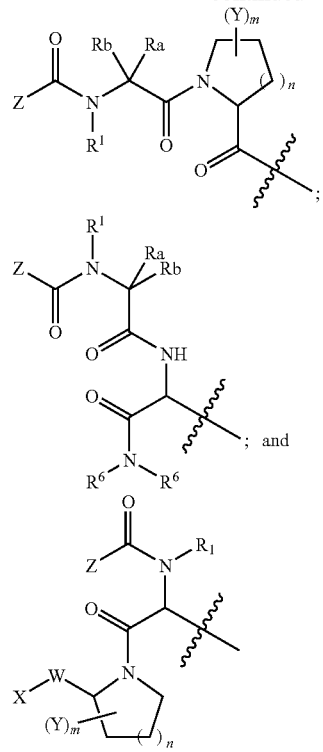

wherein each R$_a$ and R$_b$ is independently H, or C1-C8 alkyl, C2-C8 alkenyl or C2-C8 alkynyl, or a heteroform of one of these, each of which may be optionally substituted; or is optionally substituted phenyl;

each R$^1$ is independently H or optionally substituted C1-C8 alkyl;

each Z independently represents an optionally substituted C1-C6 aminoalkyl group;

each Y, where present, independently represents C1-C8 alkyl, =O, OR, NR$_2$, OC(O)R, NRC(O)R, NRSO$_2$R or COOR, wherein each R is independently H, C1-C8 alkyl or C1-C8 heteroalkyl, and wherein two Y groups can cyclize to form a 3-6 membered ring that can be saturated, unsaturated or aromatic, and which ring may include a heteroatom selected from O, S and N as a ring member and may be optionally substituted;

each W, where present, independently represents an optionally substituted C1-C6 alkylene or C1-C6 heteroalkylene;

each X, where present, independently represents an optionally substituted C5-C20 ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

each n, where present, is independently 0-3;

each m, where present, is independently 0-4; and each R$^6$, where present, is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring;

with the proviso that, when b is 0, D and D' are not the same and both of the formula

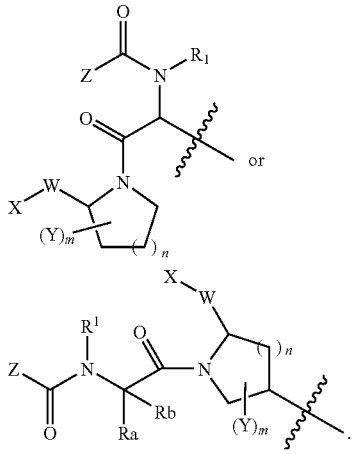

or

B1. A compound of formula (I):

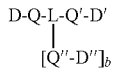   (I)

or a pharmaceutically acceptable salt or hydrate form thereof, wherein b is 0 or 1;

each Q, Q' and Q", if present, independently represents —O— or —NR$^2$—, where each R$^2$ is independently H, optionally substituted C1-C8 alkyl or optionally substituted C1-C8 heteroalkyl; or —CH$_2$—, —CH(OR)—, —CH(R)—, —CH$_2$O—, —CH(R)O— or —(CH$_2$)$_4$NH—, wherein R is H, C$_1$-C$_4$ alkyl or C$_1$-C$_4$ heteroalkyl; or one or more of Q, Q' and Q" may be a bond when L comprises a ring;

L represents an optionally substituted C1-C24 hydrocarbyl linker, optionally containing from 1-8 heteroatoms selected from N, O and S, which linker is 1-18 atoms in length when counted along the shortest path between Q and Q', or Q and Q", or Q' and Q"; and each D, D' and D", if present, is independently selected from the group consisting of

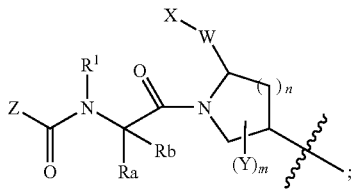

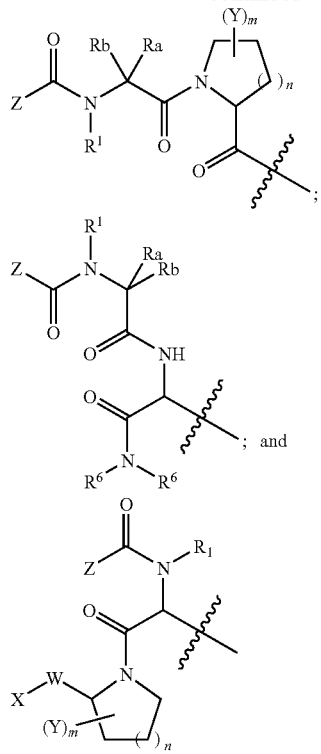

wherein each R$_a$ and R$_b$ is independently H, or C1-C8 alkyl, C2-C8 alkenyl or C2-C8 alkynyl, or a heteroform of one of these, each of which may be optionally substituted; or is optionally substituted phenyl;

each R$^1$ is independently H or optionally substituted C1-C8 alkyl;

each Z independently represents an optionally substituted C1-C6 aminoalkyl group;

each Y, where present, independently represents C1-C8 alkyl, =O, OR, NR$_2$, OC(O)R, NRC(O)R, NRSO$_2$R or COOR, wherein each R is independently H, C1-C8 alkyl or C1-C8 heteroalkyl, and wherein two Y groups can cyclize to form a 3-6 membered ring that can be saturated, unsaturated or aromatic, and which ring may include a heteroatom selected from O, S and N as a ring member and may be optionally substituted;

each W, where present, independently represents an optionally substituted C1-C6 alkylene or C1-C6 heteroalkylene;

each X, where present, independently represents an optionally substituted C$_5$-C$_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

each n, where present, is independently 0-3;

each m, where present, is independently 0-4; and each R$^6$, where present, is independently H, C1-C8 alkyl, C5-C12 aryl or C5-C12 arylalkyl, or a heteroform of one of these, each of which may be optionally substituted; or is a C8-C14 bicyclic or tricyclic ring system comprising a 5- or 6-membered saturated or partially unsaturated ring fused to a C5-C6 aryl or C5-C6 heteroaryl ring, which ring system may be attached to nitrogen through any available position on the saturated or aromatic ring;

with the proviso that, when b is 0, D and D' are not the same and both of the formula

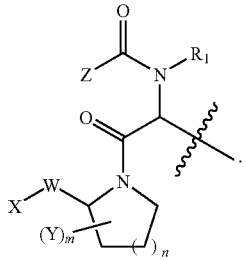

B2. The compound of embodiment B1, having the formula (1):

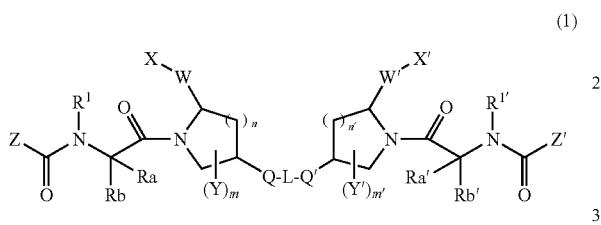

(1)

or a pharmaceutically acceptable salt or hydrate form thereof, wherein each $R_a$, $R_{a'}$, $R_b$ and $R_{b'}$ is independently H, or C1-C8 alkyl, C2-C8 alkenyl or C2-C8 alkynyl, or a heteroform of one of these, each of which may be optionally substituted; or is optionally substituted phenyl;

each Y and Y' independently represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl, and wherein two Y or Y' groups can cyclize to form a 3-6 membered ring that can be saturated, unsaturated or aromatic, and which ring may include a heteroatom selected from O, S and N as a ring member and may be optionally substituted;

each W and W' independently represents an optionally substituted C1-C6 alkylene or C1-C6 heteroalkylene;

each X and X' independently represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —O— or —$NR^2$—, where each $R^2$ is independently H, or optionally substituted C1-C8 alkyl, or optionally substituted C1-C8 heteroalkyl; or one or both of Q and Q' may be a bond when L comprises a ring;

each n and n' is independently 0-3;

each m and m' is independently 0-4;

each $R^1$ and $R^{1'}$ is independently H or optionally substituted C1-C8 alkyl;

each Z and Z' independently represents an optionally substituted C1-C6 aminoalkyl group; and L represents an optionally substituted C1-C24 hydrocarbyl linker, optionally containing from 1-8 heteroatoms selected from N, O and S, which linker is 1-18 atoms in length when counted along the shortest path between Q and Q'.

B3. The compound of embodiment B1 or B2, wherein each n and n' is 1, and each of m and m' is 0 or 1, and wherein Y and Y', if present, are the same.

B4. The compound of embodiment B1, B2 or B3, wherein each $R^1$ and $R^{1'}$ is H or methyl.

B5. The compound of any one of embodiments B1 to B4, wherein each Z and Z' is a 1-aminoalkyl group represented by the formula —$CH(R^3)NR^4_2$, where $R^3$ and each $R^4$ is independently H or C1-C4 alkyl.

B6. The compound of embodiment B2, having the formula (3A):

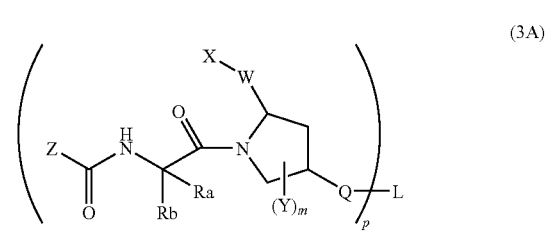

(3A)

or a pharmaceutically acceptable salt or hydrate form thereof, wherein $R_a$ is H and $R_b$ is $R^5$;

$R^5$ is H, or C1-C8 alkyl, C2-C8 alkenyl, C2-C8 alkynyl, or phenyl, each of which may be optionally substituted;

each Y represents C1-C8 alkyl, =O, OR, $NR_2$, OC(O)R, NRC(O)R, $NRSO_2R$ or COOR, wherein each R is independently H, C1-C8 alkyl or C1-C8 heteroalkyl;

W represents an optionally substituted C1-C6 alkylene or C1-C6 heteroalkylene;

X represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

Q represents —O— or —$NR^2$—, where each $R^2$ is independently H, or optionally substituted C1-C8 alkyl, or optionally substituted C1-C8 heteroalkyl; or Q may be a bond when L comprises a ring;

m is 0-4;

p is 2-3;

Z represents an optionally substituted C1-C6 aminoalkyl group of the formula —$CH(R^3)NR^4_2$;

$R^3$ is H, or an optionally substituted C1-C8 alkyl or optionally substituted C1-C8 heteroalkyl, and $R^3$ can cyclize with $R^4$ on an adjacent nitrogen atom to form an optionally substituted azacyclic group having 5-10 ring members, which azacyclic group may be saturated, unsaturated or aromatic, and may contain 1-2 additional heteroatoms selected from N, O and S as a ring member;

each R⁴ is independently H, or an optionally substituted C1-C8 alkyl or optionally substituted C1-C8 heteroalkyl, and the two R⁴ groups on one nitrogen can cyclize to form an optionally substituted azacyclic group having 5-10 ring members, which azacyclic group may be saturated, unsaturated or aromatic, and may contain 1-2 additional heteroatoms selected from N, O and S as a ring member; and L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

B7. The compound of embodiment B6, having the formula (4):

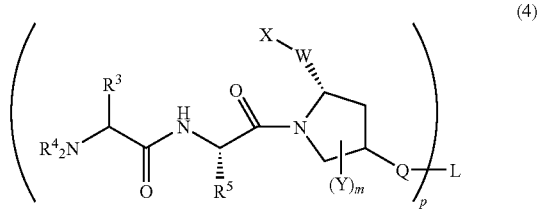

or a pharmaceutically acceptable salt or hydrate form thereof, wherein R⁵ is H, or C1-C8 alkyl, C2-C8 alkenyl, C2-C8 alkynyl, or phenyl, each of which may be optionally substituted;

each Y represents C1-C8 alkyl, =O, OR, NR₂, OC(O)R, NRC(O)R, NRSO₂R or COOR, wherein each R is independently H, C1-C8 alkyl or C1-C8 heteroalkyl;

W represents an optionally substituted C1-C6 alkylene or C1-C6 heteroalkylene;

X represents an optionally substituted C₅-C₂₀ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

Q represents —O— or —NR²—, where each R² is independently H, optionally substituted C1-C8 alkyl or optionally substituted C1-C8 heteroalkyl; or Q may be a bond when L comprises a ring;

m is 0-4;

p is 2 or 3;

R³ is H, or an optionally substituted C1-C8 alkyl or optionally substituted C1-C8 heteroalkyl, and R³ can cyclize with R⁴ on an adjacent nitrogen atom to form an optionally substituted azacyclic group having 5-10 ring members, which azacyclic group may be saturated, unsaturated or aromatic, and may contain 1-2 additional heteroatoms selected from N, O and S as a ring member;

each R⁴ is independently H, or an optionally substituted C1-C8 alkyl or optionally substituted C1-C8 heteroalkyl, and the two R⁴ groups on one nitrogen can cyclize to form an optionally substituted azacyclic group having 5-10 ring members, which azacyclic group may be saturated, unsaturated or aromatic, and may contain 1-2 additional heteroatoms selected from N, O and S as a ring member; and L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

B8. The compound of embodiment B6, having the formula (5):

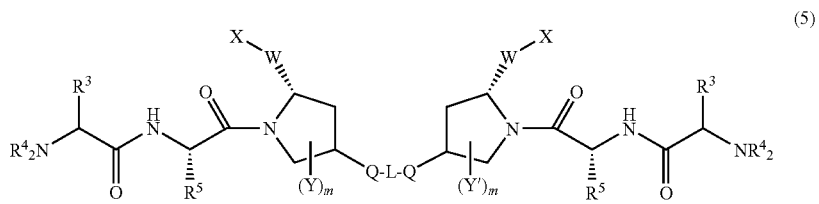

or a pharmaceutically acceptable salt or hydrate form thereof,

R⁵ is H, or C1-C8 alkyl, C2-C8 alkenyl, C2-C8 alkynyl, or phenyl, each of which may be optionally substituted;

each Y represents C1-C8 alkyl, =O, OR, NR₂, OC(O)R, NRC(O)R, NRSO₂R or COOR, wherein each R is independently H, C1-C8 alkyl or C1-C8 heteroalkyl;

W represents an optionally substituted C1-C6 alkylene or C1-C6 heteroalkylene; X represents an optionally substituted C₅-C₂₀ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

Q represents —O— or —NR²—, where each R² is independently H, optionally substituted C1-C8 alkyl or optionally substituted C1-C8 heteroalkyl; or Q may be a bond when L comprises a ring;

m is 0-4;

R³ is H, or an optionally substituted C1-C8 alkyl or optionally substituted C1-C8 heteroalkyl, and R³ can cyclize with R⁴ on an adjacent nitrogen atom to form an optionally substituted azacyclic group having 5-10 ring members, which azacyclic group may be saturated, unsaturated or aromatic, and may contain 1-2 additional heteroatoms selected from N, O and S as a ring member;

each R⁴ is independently H, or an optionally substituted C1-C8 alkyl or C1-C8 heteroalkyl group, and the two R⁴ groups on one nitrogen can cyclize to form an optionally substituted azacyclic group having 5-10 ring members, which azacyclic group may be saturated, unsaturated or aromatic, and may contain 1-2 additional heteroatoms selected from N, O and S as a ring member;

L represents a C1-C14 alkylene, C1-C14 alkenylene, C1-C14 alkynylene, C5-C12 arylene, C5-C21 arylalkylene, C5-C21 arylalkenylene, or C5-C21 arylalkynylene linker, or a heteroform of one of these, each of which may be optionally substituted.

B9. The compound of any one of embodiments B1 to B5, wherein each X and X' independently comprises an optionally substituted phenyl ring; or two phenyl rings, each of which may be optionally substituted; or a tetrahydronaphthyl, indanyl or fluorenyl ring system.

B10. The compound of any one of embodiments B1 to B5, wherein each W and W' represents —C(O)NR(CHR)$_p$—, where p is 0-2, and each R independently represents H, C1-C4 alkyl or C1-C4 heteroalkyl.

B11. The compound of any one of embodiments B1 to B5, wherein each Q and Q' is —NR$^2$—, where each R$^2$ is independently H or C1-C4 alkyl.

B12. The compound of any one of embodiments B1 to B5, wherein at least one of Q and Q' is a bond.

B13. The compound of any one of embodiments B1 to B12, wherein L comprises at least one optionally substituted carbocyclic, heterocyclic, aromatic or heteroaromatic ring that is part of or is fused to the linker which forms the shortest path between Q and Q'.

B14. The compound of embodiment B13, wherein said aromatic or heteroaromatic ring is an optionally substituted 5- or 6-membered aromatic or heteroaromatic ring.

B15. The compound of embodiment B14, wherein said optionally substituted 5- or 6-membered aromatic or heteroaromatic ring is selected from the group consisting of phenyl, pyridyl, pyrazinyl, triazinyl, pyrazolyl, and thiophenyl, each of which may be optionally substituted.

B16. The compound of any one of embodiments B1 to B14, wherein L comprises at least one triazole ring.

B17. The compound of any one of embodiments B1 to B12, wherein L comprises a C1-C14 alkylene, C1-C14 heteroalkylene, C2-C14 alkenylene, C2-C14 heteroalkenylene, C2-C14 alkynylene, or a C2-C14 heteroalkynylene group, each of which may be optionally substituted.

B18. The compound of embodiment B17, wherein L is a C2-C14 alkynylene or a C2-C14 heteroalkynylene group.

B19. The compound of embodiment B7 or B8, wherein R$^3$ is selected from methyl, ethyl, n-propyl, isopropyl, cyclopropyl, n-butyl, isobutyl, sec-butyl, and tert-butyl.

B20. The compound of embodiment B7, B8, or B19, wherein each R$^4$ is independently H or methyl.

B21. A compound selected from the group consisting of the compounds in Tables 3 and 4, or a pharmaceutically acceptable salt thereof.

B22. A pharmaceutical composition comprising a compound of any of the preceding embodiments, and at least one pharmaceutically acceptable excipient.

B23. The pharmaceutical composition of embodiment B22, further comprising at least one additional therapeutic agent.

B24. The pharmaceutical composition of embodiment B23, wherein the additional therapeutic agent is selected from the group consisting of TRAIL, etoposide, a TRAIL receptor antibody, an Hsp90 inhibitor, TNF-α, and TNF-β.

B25. A method to treat cancer, inflammation, or an autoimmune disorder, comprising administering to a subject in need of such treatment an effective amount of a compound as defined in any one of embodiments B1 to B21.

B26. The method of embodiment B25, wherein the subject is treated with an additional therapeutic agent selected from the group consisting of TRAIL, etoposide, a TRAIL receptor antibody, an Hsp90 inhibitor, TNF-α, and TNF-β.

B27. A compound of formula (6):

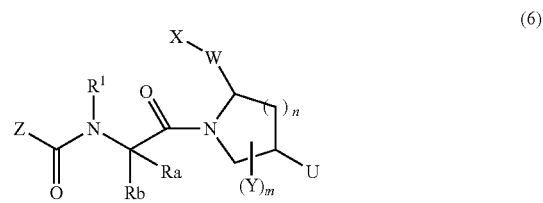

or a pharmaceutically acceptable salt or hydrate form thereof, wherein R$_a$ and R$_b$ are independently H, or C1-C8 alkyl, C2-C8 alkenyl or C2-C8 alkynyl, or a heteroform of one of these, each of which may be optionally substituted;

each Y independently represents C1-C8 alkyl, =O, OR, NR$_2$, OC(O)R, NRC(O)R, NRSO$_2$R or COOR, wherein each R is independently H, C1-C8 alkyl or C1-C8 heteroalkyl, and wherein two Y groups can cyclize to form a 3-6 membered ring that can be saturated, unsaturated or aromatic, and which ring may include a heteroatom selected from O, S and N as a ring member and may be optionally substituted;

W represents an optionally substituted C1-C6 alkylene or C1-C6 heteroalkylene;

X represents an optionally substituted C$_5$-C$_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W, provided that each X comprises at least one aryl or heteroaryl ring;

n is 0-3;

m is 0-4;

R$^1$ is H or optionally substituted C1-C8 alkyl;

U represents —OR$^8$, —OC(O)R$^8$, —OSO$_2$R$^8$, C=O, —OC(O)OR$^8$, —COOR$^8$, —NR$^8{}_2$, azido or halo, where each R$^8$ is independently H, or C1-C8 alkyl, C1-C8 alkenyl, C1-C8 alkynyl, C5-C12 aryl, C5-C21 arylalkyl, or a heteroform of one of these, each of which may be optionally substituted; or C1-C8 alkyl, C2-C8 alkenyl, C2-C8 alkynyl, C5-C12 aryl or C5-C21 arylalkyl, or a heteroform of one of these, each of which may be optionally substituted; and Z is an optionally substituted C1-C6 aminoalkyl group wherein the amine may be in a protected or unprotected form.

B28. A method of making a compound of formula (1) as in embodiment B2, comprising reacting a first monomer of formula (6) with a second monomer of formula (6), wherein for each of said first monomer and said second monomer, U comprises at least one functional group that can be used to connect said first monomer and said second monomer, either directly or indirectly, to provide a compound of formula (1).

B29. A dimeric or trimeric SMAC mimetic compound for use in the treatment or amelioration of cancer, inflammation, or an autoimmune disorder,
wherein the dimeric or trimeric SMAC mimetic compound is a compound as defined in any one of embodiments B1 to B21.

B30. A pharmaceutical composition comprising a dimeric or trimeric SMAC mimetic compound, useful for the treatment or amelioration of cancer, inflammation, or an autoimmune disorder, and at least one pharmaceutically acceptable excipient,
wherein the dimeric or trimeric SMAC mimetic compound is a compound as defined in any one of embodiments B1 to B21.

B30-1. The pharmaceutical composition of embodiment B30, wherein the dimeric or trimeric SMAC mimetic compound is a compound as defined in any one of embodiments B2 to B21.

B31. The pharmaceutical composition of embodiment B30, further comprising at least one additional therapeutic agent.

B32. The pharmaceutical composition of embodiment B31, wherein the additional therapeutic agent is selected from the group consisting of TRAIL, etoposide, a TRAIL receptor antibody, an Hsp90 inhibitor, TNF-α, and TNF-β.

The invention claimed is:

1. A compound having the dimeric structure:

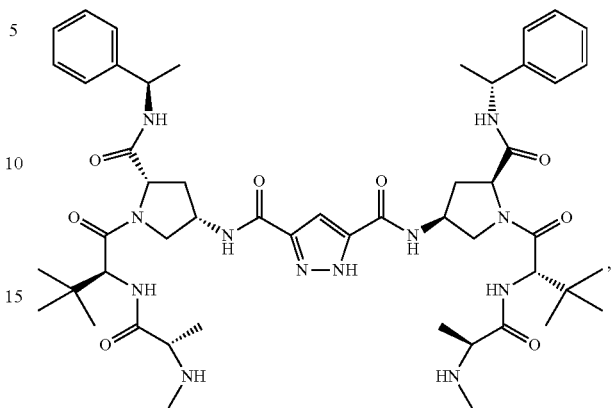

or a pharmaceutically acceptable salt thereof.

2. A pharmaceutical composition comprising a compound of claim 1 and at least one additional therapeutic agent selected from the group consisting of TNF-related apoptosis-inducing ligand (TRAIL), etoposide, a TRAIL receptor antibody, an Hsp90 inhibitor, TNF-α, and TNF-β.

3. A pharmaceutical composition comprising a compound of claim 1 and TNF-related apoptosis-inducing ligand (TRAIL).

* * * * *